United States Patent
Sakagami et al.

(10) Patent No.: US 8,889,674 B2
(45) Date of Patent: Nov. 18, 2014

(54) PIPERIDINE AND PYRROLIDINE DERIVATIVES HAVING NPY Y5 RECEPTOR ANTAGONISM

(75) Inventors: Masahiro Sakagami, Osaka (JP); Hitomi Araki, Osaka (JP); Hiroshi Hashizume, Osaka (JP); Hiroshi Yari, Osaka (JP); Kenji Takaya, Osaka (JP)

(73) Assignee: Shionogi & Co., Ltd., Osaka-shi (JP)

( * ) Notice: Subject to any disclaimer, the term of this patent is extended or adjusted under 35 U.S.C. 154(b) by 0 days.

(21) Appl. No.: 13/254,750

(22) PCT Filed: Mar. 5, 2010

(86) PCT No.: PCT/JP2010/053662
§ 371 (c)(1),
(2), (4) Date: Sep. 2, 2011

(87) PCT Pub. No.: WO2010/101246
PCT Pub. Date: Sep. 10, 2010

(65) Prior Publication Data
US 2011/0319412 A1   Dec. 29, 2011

(30) Foreign Application Priority Data
Mar. 5, 2009   (JP) .................. 2009-052063

(51) Int. Cl.
| A61K 31/454 | (2006.01) |
| A61K 31/4545 | (2006.01) |
| A61K 31/5377 | (2006.01) |
| C07D 471/04 | (2006.01) |
| C07D 401/12 | (2006.01) |
| C07D 207/16 | (2006.01) |
| C07D 413/12 | (2006.01) |
| C07D 403/12 | (2006.01) |
| C07D 417/12 | (2006.01) |
| C07D 401/14 | (2006.01) |
| C07D 401/06 | (2006.01) |
| C07D 413/06 | (2006.01) |
| C07D 211/62 | (2006.01) |
| C07D 405/06 | (2006.01) |
| C07D 401/04 | (2006.01) |

(52) U.S. Cl.
CPC ............ *C07D 207/16* (2013.01); *C07D 471/04* (2013.01); *C07D 401/12* (2013.01); *C07D 413/12* (2013.01); *C07D 403/12* (2013.01); *C07D 417/12* (2013.01); *C07D 401/14* (2013.01); *C07D 401/06* (2013.01); *C07D 413/06* (2013.01); *C07D 211/62* (2013.01); *C07D 405/06* (2013.01); *C07D 401/04* (2013.01)
USPC ........ 514/235.2; 514/300; 514/318; 514/322; 514/323; 514/326

(58) Field of Classification Search
None
See application file for complete search history.

(56) References Cited

U.S. PATENT DOCUMENTS

| 6,054,590 A | 4/2000 | Poindexter et al. |
| 6,063,934 A | 5/2000 | Poindexter et al. |
| 6,096,745 A | 8/2000 | Poindexter et al. |
| 6,444,687 B1 | 9/2002 | Stamford et al. |
| 6,514,977 B1 * | 2/2003 | Anantanarayan et al. .......... 514/254.01 |
| 6,699,891 B1 | 3/2004 | Kawanishi et al. |
| 6,958,333 B1 * | 10/2005 | Hayama et al. ............ 514/230.2 |
| 7,265,130 B2 | 9/2007 | Kawanishi et al. |
| 7,534,892 B2 | 5/2009 | Nakatani |
| 7,781,461 B2 | 8/2010 | Kawanishi et al. |
| 2003/0114465 A1 | 6/2003 | Stamford et al. |
| 2003/0191112 A1 | 10/2003 | Dorwald |
| 2003/0225060 A1 | 12/2003 | Ujjainwalla et al. |
| 2004/0058920 A1 | 3/2004 | Jover et al. |
| 2004/0067941 A1 | 4/2004 | Torrens-Jover et al. |
| 2004/0176462 A1 | 9/2004 | Kawanishi et al. |
| 2004/0180964 A1 | 9/2004 | Kawanishi et al. |
| 2004/0220191 A1 | 11/2004 | Schwink et al. |

(Continued)

FOREIGN PATENT DOCUMENTS

| EP | 1 249 233 A1 | 10/2002 |
| JP | 2000 510164 | 8/2000 |

(Continued)

OTHER PUBLICATIONS

Grundy et al. Circulation 112 (2005), pp. 2735-2753.*

(Continued)

*Primary Examiner* — Alicia L Otton
(74) *Attorney, Agent, or Firm* — Oblon, Spivak, McClelland, Maier & Neustadt, L.L.P.

(57) ABSTRACT

The present invention discloses novel piperidine and pyrrolidine derivatives having NPY Y5 receptor antagonistic activity. Specifically, the present invention discloses a compound represented by the formula (I), a pharmaceutically acceptable salt or a solvate thereof:

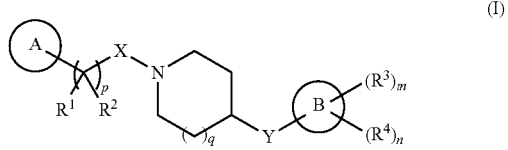

(I)

wherein
A is substituted or unsubstituted monocyclic aryl or monocyclic heterocyclyl; X is a single bond or C(=O); Y is a single bond, $CR^5R^6NR^7$ or $C(=O)NR^7$; $R^1$ and $R^2$ are independently hydrogen or substituted or unsubstituted alkyl; $R^3$ is substituted or unsubstituted aryl or heterocyclyl; $R^4$ is halogen, substituted or unsubstituted alkyl, alkoxy, aryloxy or heterocyclyloxy, etc.; p is an integer of 0 to 2; q is 0 or 1; m is 0 or 1; n is an integer of 0 to 5; and B is aromatic carbocycle, monocyclic heterocycle or bicyclic fused hetero ring.

2 Claims, No Drawings

(56) References Cited

U.S. PATENT DOCUMENTS

| | | |
|---|---|---|
| 2004/0266821 A1 | 12/2004 | Ujjainwalla et al. |
| 2006/0128701 A1 | 6/2006 | Jover et al. |
| 2007/0015762 A1 | 1/2007 | Kawanishi et al. |
| 2007/0015807 A1 | 1/2007 | Aslanian et al. |
| 2007/0037752 A1 | 2/2007 | Ansorge et al. |
| 2007/0054939 A1* | 3/2007 | Guedat et al. ............ 514/316 |
| 2007/0142394 A1* | 6/2007 | Solomon et al. ......... 514/253.01 |
| 2007/0287710 A1 | 12/2007 | Nakatani |
| 2008/0064632 A1 | 3/2008 | Amatruda et al. |
| 2009/0023710 A1 | 1/2009 | Vicker et al. |
| 2009/0163545 A1 | 6/2009 | Goldfarb |
| 2009/0203712 A1 | 8/2009 | Yano |
| 2009/0233910 A1 | 9/2009 | Botez et al. |
| 2010/0004295 A1 | 1/2010 | Kouyama |
| 2010/0063027 A1 | 3/2010 | Okuno et al. |
| 2010/0093692 A1 | 4/2010 | Aslanian et al. |
| 2010/0267945 A1 | 10/2010 | Okuno et al. |
| 2010/0273841 A1 | 10/2010 | Okuno et al. |
| 2010/0273842 A1 | 10/2010 | Okuno et al. |
| 2010/0292500 A1 | 11/2010 | Kawanishi et al. |
| 2011/0028468 A1 | 2/2011 | Sakagami et al. |
| 2011/0039802 A1 | 2/2011 | Kawanishi et al. |

FOREIGN PATENT DOCUMENTS

| | | | |
|---|---|---|---|
| JP | 2001-139574 | 5/2001 | |
| JP | 2001-172257 | 6/2001 | |
| JP | 2002 507611 | 3/2002 | |
| JP | 2003 517479 | 5/2003 | |
| JP | 2003-523941 | 8/2003 | |
| JP | 2004-509108 | 3/2004 | |
| JP | 2004 529105 | 9/2004 | |
| JP | 2004-315511 | 11/2004 | |
| JP | 2005 507906 | 3/2005 | |
| JP | 2005 529866 | 10/2005 | |
| JP | 2006 517563 | 7/2006 | |
| JP | 2008 504278 | 2/2008 | |
| JP | 2008 514616 | 5/2008 | |
| JP | 2008 179612 | 8/2008 | |
| JP | 2008 538749 | 11/2008 | |
| JP | 2008 546784 | 12/2008 | |
| WO | WO 98/24766 * | 6/1998 | ........... C07D 213/73 |
| WO | WO 98/35957 A1 | 8/1998 | |
| WO | WO 99/48888 A1 | 9/1999 | |
| WO | 01 37826 | 5/2001 | |
| WO | WO 01/44201 A1 | 6/2001 | |
| WO | WO 01/64675 A1 | 9/2001 | |
| WO | WO 02/22592 A2 | 3/2002 | |
| WO | WO 02/22592 A3 | 3/2002 | |
| WO | WO 02/068388 A2 | 9/2002 | |
| WO | WO 02/068388 A3 | 9/2002 | |
| WO | WO 02/096902 A1 | 12/2002 | |
| WO | WO 03/028641 A2 | 4/2003 | |
| WO | WO 03/028641 A3 | 4/2003 | |
| WO | WO 03/031432 A1 | 4/2003 | |
| WO | WO 03/084952 A1 | 10/2003 | |
| WO | WO 2005/014593 A1 | 2/2005 | |
| WO | WO 2005/037257 A2 | 4/2005 | |
| WO | WO 2006/001318 A1 | 1/2006 | |
| WO | WO 2006/002349 A1 | 1/2006 | |
| WO | WO 2006/036770 A2 | 4/2006 | |
| WO | WO 2006/036770 A3 | 4/2006 | |
| WO | WO 2006/116355 A1 | 11/2006 | |
| WO | WO 2007/001975 A1 | 1/2007 | |
| WO | 2007 075555 | 7/2007 | |
| WO | 2007 125952 | 11/2007 | |
| WO | 2007 146761 | 12/2007 | |
| WO | WO 2007/144394 A2 | 12/2007 | |
| WO | WO 2007/144394 A3 | 12/2007 | |
| WO | WO 2008/026563 A1 | 3/2008 | |
| WO | WO 2008/026564 A1 | 3/2008 | |
| WO | WO 2008/057775 A2 | 5/2008 | |
| WO | WO 2008/057775 A3 | 5/2008 | |
| WO | WO 2008/072061 A1 | 6/2008 | |
| WO | 2008 108957 | 9/2008 | |
| WO | 2008 108958 | 9/2008 | |
| WO | 2008/141976 | 11/2008 | |
| WO | WO 2008/138939 * | 11/2008 | ........... C07D 401/14 |
| WO | WO 2009/004356 A1 | 1/2009 | |
| WO | WO 2009/054434 A1 | 4/2009 | |
| WO | WO 2009/131096 A1 | 10/2009 | |

OTHER PUBLICATIONS

Molnar, D. "New drug policy in childhood obesity," 2005, International Journal of Obesity, 29:S62-S65.*

U.S. Appl. No. 13/254,702, filed Sep. 2, 2011, Yoshida, et al.

International Search Report issued May 25, 2010 in PCT/JP10/053662 filed Mar. 5, 2010.

International Preliminary Report on Patentability and Written Opinion of the International Searching Authority issued Sep. 15, 2011, in Patent Application No. PCT/JP2010/053662, filed Mar. 5, 2010.

Lars Grundemar et al., "Neuropeptide Y Effector Systems: Perspectives for Drug Development", Trends in Pharmaceutical Sciences, vol. 15, May 1994, pp. 153-159.

Ambikaipakan Balasubramaniam, "Neuropeptide Y Family of Hormones: Receptor Subtypes and Antagonists", vol. 18, No. 3, 1997, pp. 445-457.

Seiichiro Tabuchi et al., "Novel Potent Antagonists of Human Neuropeptide Y Y5 Receptor. Part 1: 2-Oxobenzothiazolin-3-Acetic Acid Derivatives", Bioorganic & Medicinal Chemistry Letters, vol. 12, 2002, pp. 1171-1175.

Hiromichi Itani, "Novel Potent Antagonists of Human Neuropeptide Y Y5 Receptors. Part 3: 7-Methoxy-1-Hydroxy-1-Substituted Tetraline Derivatives", Bioorganic & Medicinal Chemistry Letters, vol. 12, 2002, pp. 799-802.

Lars Grundemar et al., "Neuropeptide Y Effector Systems: Perspectives for Drug Development", Trends in Pharmacological Sciences, vol. 15, May 1994, pp. 153-159.

Catalina Betancur et al., "Nonpeptide Antagonists of Neuropeptide Receptors: Tools for Research and Therapy", Trends in Pharmacological Sciences, vol. 18, 1997, pp. 372-386.

Ambikaipakan Balasubramaniam, "Neuropeptide Y Family of Hormones: Receptor Subtypes and Antagonists", Peptides, vol. 18, No. 3, 1997, pp. 445-457.

Kevin W. Gillman et al., "Synthesis and evaluation of 5,5-diphenylimidazolones as potent human neuropeptide Y5 receptor antagonists", Bioorganic & Medicinal Chemistry, 2006, vol. 14, No. 16, pp. 5517-5526.

Office Action issued Jun. 18, 2014 in Japanese Patent Application No. 2011-502821.

* cited by examiner

PIPERIDINE AND PYRROLIDINE DERIVATIVES HAVING NPY Y5 RECEPTOR ANTAGONISM

TECHNICAL FIELD

The present invention relates to a novel piperidine and pyrrolidine derivatives having NPY Y5 receptor antagonistic activity.

BACKGROUND ART

Neuropeptide Y (hereinafter referred to as NPY) is a peptide which consists of 36 amino acid residues and was isolated from porcine brain in 1982. NPY is widely distributed in the central nervous system and peripheral tissues of humans and animals.

It has been reported that NPY possesses a stimulating activity of food intake, an anti-seizure activity, a learning-promoting activity, an anti-anxiety activity, an anti-stress activity etc. in central nervous system, and it may be pivotally involved in the central nervous system diseases such as depression, Alzheimer-type dementia and Parkinson's disease. NPY is thought to be associated with circulatory disorders, since it induces a contraction of smooth muscles such as blood vessels or cardiac muscles in the peripheral tissues. Furthermore, NPY is also known to be involved in the metabolic diseases such as obesity, diabetes and hormone abnormalities (Non-patent Document 1). Therefore, an NPY receptor antagonist is expected as a medicine for preventing or treating various diseases involved in the NPY receptor like the above.

As to NPY receptor, Y1, Y2, Y3, Y4, Y5, and Y6 subtypes have been identified (Non-patent Document 2). It has been suggested that Y5 receptor is at least involved in the feeding behavior and its antagonist is expected as an anti-obesity agent (Non-patent Document 3).

As a NPY Y5 receptor antagonist, JP2001-139574 (Patent Document 1), Bioorganic & Medicinal Chemistry Letters (2002), 12 (8), 1171-1175 (Non-Patent Document 4) and Bioorganic & Medicinal Chemistry Letters (2002), 12 (5), 799-802 (Non-Patent Document 5) disclose benzothiazolyl derivatives, WO2005/014593 (Patent Document 2) discloses thiazole derivatives, WO02/096902 (Patent Document 3) discloses carbazole derivatives, JP2004-509108 (Patent Document 4) discloses a compound having a cyclic structure connected to phenyl group via urea bond, JP2001-172257 (Patent Document 5), WO01/37826 (Patent Document 7) and WO2006/001318 (Patent Document 8) disclose sulfonamide compounds, WO01/64675 (Patent Document 6) discloses compounds having a fused tricyclic hetero ring, WO2009/131096 (Patent Document 15) discloses compounds having a monocyclic or bicyclic aromatic hetero ring, WO2007/125952 (Patent Document 9) and WO2009/054434 (Patent Document 14) disclose amine derivatives, WO2008/026563 (Patent Document 10) discloses hydrazine amide derivatives, WO2008/026564 (Patent Document 11) discloses urea derivatives. These compounds differ from the compound of the invention in structure.

Also, compounds having a similar structure to the compound of the present invention are disclosed in WO2003/028641 (Patent Document 12), JP2004-315511 (Patent Document 13), US2009/0163545 (Patent Document 16), WO2009/004356 (Patent Document 17), WO2008/057775 (Patent Document 18), WO2007/144394 (Patent Document 19), WO2005/037257 (Patent Document 20), WO2006/116355 (Patent Document 21), etc. However, these documents do not describe NPY Y5 receptor antagonism, and thus, do not suggest the present invention.

[Patent Document 1] JP2001-139574
[Patent Document 2] WO2005/014593
[Patent Document 3] WO02/096902
[Patent Document 4] JP2004-509108
[Patent Document 5] JP2001-172257
[Patent Document 6] WO01/64675
[Patent Document 7] WO01/37826
[Patent Document 8] WO2006/001318
[Patent Document 9] WO2007/125952
[Patent Document 10] WO2008/026563
[Patent Document 11] WO2008/026564
[Patent Document 12] WO2003/028641
[Patent Document 13] JP2004-315511
[Patent Document 14] WO2009/054434
[Patent Document 15] WO2009/131096
[Patent Document 16] US2009/0163545
[Patent Document 17] WO2009/004356
[Patent Document 18] WO2008/057775
[Patent Document 19] WO2007/144394
[Patent Document 20] WO2005/037257
[Patent Document 21] WO2006/116355
[Non-Patent Document 1] Trends in Pharmacological Sciences, Vol. 15, 153 (1994)
[Non-Patent Document 3] Trends in Pharmacological Sciences, Vol. 18, 372 (1997)
[Non-Patent Document 4] Peptides, Vol. 18, 445 (1997)
[Non-Patent Document 5] Bioorganic & Medicinal Chemistry Letters (2002), 12 (8), 1171-1175
[Non-Patent Document 6] Bioorganic & Medicinal Chemistry Letters (2002), 12 (5), 799-802

DISCLOSURE OF INVENTION

Problems to be Solved by the Invention

The objection of the present invention is to provide excellent new compounds having NPY Y5 receptor antagonistic activity.

Means for Solving the Problem

The present invention provides the followings.
[1] A compound of the formula (I):

[Chemical Formula 1]

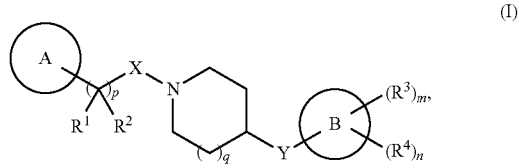

a pharmaceutically acceptable salt or solvate thereof, wherein
A is substituted or unsubstituted aryl or substituted or unsubstituted heterocyclyl;
X is a single bond or C(=O);
Y is a single bond, $CR^5R^6NR^7$ or $C(=O)NR^7$ in which $R^5$, $R^6$ and $R^7$ are independently hydrogen or substituted or unsubstituted alkyl;
$R^1$ and $R^2$ are independently hydrogen or substituted or unsubstituted alkyl;

R³ is substituted or unsubstituted aryl or substituted or unsubstituted heterocyclyl;

R⁴ is each independently selected from the group consisting of:

halogen, cyano, nitro, nitroso, azido, oxo, substituted or unsubstituted alkyl, substituted or unsubstituted alkenyl, substituted or unsubstituted alkynyl, substituted or unsubstituted cycloalkyl, substituted or unsubstituted cycloalkenyl; hydroxy, substituted or unsubstituted alkoxy, substituted or unsubstituted alkenyloxy, substituted or unsubstituted cycloalkyloxy, substituted or unsubstituted cycloalkenyloxy, substituted or unsubstituted aryloxy, substituted or unsubstituted heterocyclyloxy; mercapto, substituted or unsubstituted alkylthio, substituted or unsubstituted alkenylthio, substituted or unsubstituted cycloalkylthio, substituted or unsubstituted cycloalkenylthio, substituted or unsubstituted arylthio, substituted or unsubstituted heterocyclylthio; carboxy, substituted or unsubstituted alkoxycarbonyl, substituted or unsubstituted alkenyloxycarbonyl, substituted or unsubstituted cycloalkyloxycarbonyl, substituted or unsubstituted cycloalkenyloxycarbonyl, substituted or unsubstituted aryloxycarbonyl, substituted or unsubstituted heterocyclyloxycarbonyl, substituted or unsubstituted carbamoyl; formyl, substituted or unsubstituted alkylcarbonyl, substituted or unsubstituted alkenylcarbonyl, substituted or unsubstituted cycloalkylcarbonyl, substituted or unsubstituted cycloalkenylcarbonyl, substituted or unsubstituted arylcarbonyl, substituted or unsubstituted heterocyclylcarbonyl; sulfino, sulfo, substituted or unsubstituted alkylsulfonyl, substituted or unsubstituted alkenylsulfonyl, substituted or unsubstituted cycloalkylsulfonyl, substituted or unsubstituted cycloalkenylsulfonyl, substituted or unsubstituted arylsulfonyl, substituted or unsubstituted heterocyclylsulfonyl, substituted or unsubstituted alkylsulfinyl, substituted or unsubstituted alkenylsulfinyl, substituted or unsubstituted cycloalkylsulfinyl, substituted or unsubstituted cycloalkenylsulfinyl, substituted or unsubstituted arylsulfinyl, substituted or unsubstituted heterocyclylsulfinyl, substituted or unsubstituted sulfamoyl; and substituted or unsubstituted amino;

p is an integer of 0 to 2, with the proviso that P is not 0 when X is a single bond;

q is 0 or 1;

m is 0 or 1;

n is an integer of 0 to 5;

B is aromatic carbocycle, monocyclic heterocycle or fused bicyclic hetero ring;

provided that a compound wherein A is substituted dihydrobenzothiazolyl and a compound wherein B is quinazoline is excluded.

[2] The compound, pharmaceutically acceptable salt or solvate thereof according to [1] wherein X is C(=O); Y is a single bond or C(=O)NH.

[3] The compound, pharmaceutically acceptable salt or solvate thereof according to [2] wherein X is C(=O); Y is C(=O)NH; and p is 0.

[4] The compound, pharmaceutically acceptable salt or solvate thereof according to [2] wherein X is C(=O); Y is C(=O)NH; and p is 1.

[5] The compound, pharmaceutically acceptable salt or solvate thereof according to [2] wherein X is C(=O); Y is a single bond; and p is 0.

[6] The compound, pharmaceutically acceptable salt or solvate thereof according to [2] wherein X is C(=O); Y is a single bond; and p is 1.

[7] The compound, pharmaceutically acceptable salt or solvate thereof according to any one of [1] to [6] wherein A is substituted or unsubstituted monocyclic aryl or substituted or unsubstituted monocyclic heterocyclyl.

[8] The compound, pharmaceutically acceptable salt or solvate thereof according to [7] wherein A is substituted or unsubstituted phenyl, substituted or unsubstituted pyridyl, substituted or unsubstituted pyrrolidyl, substituted or unsubstituted tetrahydrofuryl, substituted or unsubstituted pyrrolyl, substituted or unsubstituted isoxazolyl or substituted or unsubstituted oxadiazolyl.

[9] The compound, pharmaceutically acceptable salt or solvate thereof according to [7] or [8] wherein A has a substituent.

[10] The compound, pharmaceutically acceptable salt or solvate thereof according to [9] wherein A has a substituent at least either one of the positions adjacent to the position of attachment.

[11] The compound, pharmaceutically acceptable salt or solvate thereof according to [10] wherein the substituent(s) is one or more selected from alkyl, haloalkyl, alkoxyalkyl, alkylcarbonyl, phenoxy, halophenoxy or oxo.

[12] The compound, pharmaceutically acceptable salt or solvate thereof according to any one of [1] to [11] wherein B is benzene, pyrazole, thiazole, imidazole, pyridine, benzimidazole, indole, pyrrolopyridine, indazole, dihydrobenzoxazole or indoline.

[13] The compound, pharmaceutically acceptable salt or solvate thereof according to any one of [1] to [12] wherein m is 1.

[14] The compound, pharmaceutically acceptable salt or solvate thereof according to [13] wherein R³ is substituted or unsubstituted phenyl, substituted or unsubstituted thiazolyl, substituted or unsubstituted pyridyl, substituted or unsubstituted pyrimidyl or substituted or unsubstituted morpholino.

[15] The compound, pharmaceutically acceptable salt or solvate thereof according to any one of [1] to [12] wherein m is 0; and n is 1.

[16] The compound, pharmaceutically acceptable salt or solvate thereof according to [15] wherein Y is a single bond.

[17] The compound, pharmaceutically acceptable salt or solvate thereof according to [15] or [16] wherein R⁴ is halogen, oxo, substituted or unsubstituted alkyl, substituted or unsubstituted alkoxy, substituted or unsubstituted aryloxy, substituted or unsubstituted heterocyclyloxy, substituted or unsubstituted arylthio or arylsulfinyl.

[18] A pharmaceutical composition comprising the compound, pharmaceutically acceptable salt or solvate thereof according to any one of [1] to [17] as an active ingredient.

[19] A NPY Y5 receptor antagonist comprising the compound, pharmaceutically acceptable salt or solvate thereof according to any one of [1] to [17] as an active ingredient.

[20] A pharmaceutical composition having NPY Y5 receptor antagonist activity comprising a compound of the formula (I), a pharmaceutically acceptable salt or solvate thereof:

[Chemical Formula 2]

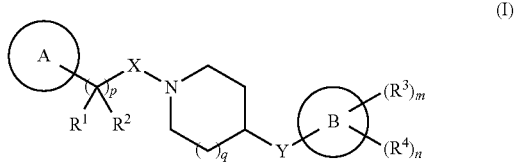

(I)

wherein
A is substituted or unsubstituted monocyclic aryl or substituted or unsubstituted monocyclic heterocyclyl;
X is a single bond or C(=O);
the group of the formula:

[Chemical Formula 3]

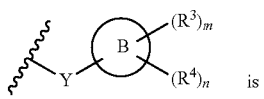 is

[Chemical Formula 4]

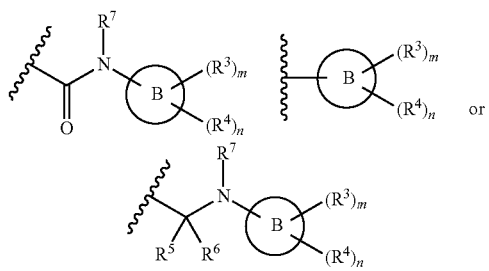

in which $R^5$, $R^6$ and $R^7$ are independently hydrogen or substituted or unsubstituted alkyl;
$R^1$ and $R^2$ are independently hydrogen or substituted or unsubstituted alkyl;
$R^3$ is substituted or unsubstituted aryl or substituted or unsubstituted heterocyclyl;
$R^4$ is each independently selected from the group consisting of:
halogen, cyano, nitro, nitroso, azido, oxo, substituted or unsubstituted alkyl, substituted or unsubstituted alkenyl, substituted or unsubstituted alkynyl, substituted or unsubstituted cycloalkyl, substituted or unsubstituted cycloalkenyl;
hydroxy, substituted or unsubstituted alkoxy, substituted or unsubstituted alkenyloxy, substituted or unsubstituted cycloalkyloxy, substituted or unsubstituted cycloalkenyloxy, substituted or unsubstituted aryloxy, substituted or unsubstituted heterocyclyloxy;
mercapto, substituted or unsubstituted alkylthio, substituted or unsubstituted alkenylthio, substituted or unsubstituted cycloalkylthio, substituted or unsubstituted cycloalkenylthio, substituted or unsubstituted arylthio, substituted or unsubstituted heterocyclylthio;
carboxy, substituted or unsubstituted alkoxycarbonyl, substituted or unsubstituted alkenyloxycarbonyl, substituted or unsubstituted cycloalkyloxycarbonyl, substituted or unsubstituted cycloalkenyloxycarbonyl, substituted or unsubstituted aryloxycarbonyl, substituted or unsubstituted heterocyclyloxycarbonyl, substituted or unsubstituted carbamoyl;
formyl, substituted or unsubstituted alkylcarbonyl, substituted or unsubstituted alkenylcarbonyl, substituted or unsubstituted cycloalkylcarbonyl, substituted or unsubstituted cycloalkenylcarbonyl, substituted or unsubstituted arylcarbonyl, substituted or unsubstituted heterocyclylcarbonyl;
sulfino, sulfo, substituted or unsubstituted alkylsulfonyl, substituted or unsubstituted alkenylsulfonyl, substituted or unsubstituted cycloalkylsulfonyl, substituted or unsubstituted cycloalkenylsulfonyl, substituted or unsubstituted arylsulfonyl, substituted or unsubstituted heterocyclylsulfonyl, substituted or unsubstituted alkylsulfinyl, substituted or unsubstituted alkenylsulfinyl, substituted or unsubstituted cycloalkylsulfinyl, substituted or unsubstituted cycloalkenylsulfinyl, substituted or unsubstituted arylsulfinyl, substituted or unsubstituted heterocyclylsulfinyl, substituted or unsubstituted sulfamoyl; and
substituted or unsubstituted amino;
p is an integer of 0 to 2, with the proviso that p is not 0 when X is a single bond;
q is 0 or 1;
m is 0 or 1;
n is an integer of 0 to 5;
B is aromatic carbocycle, monocyclic heterocycle or fused bicyclic hetero ring;
provided that a compound wherein B is quinazoline is excluded.

[21] The pharmaceutical composition having NPY Y5 receptor antagonist activity according to [20] wherein X is C(=O); a group of the formula:

[Chemical Formula 5]

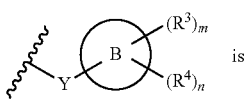 is

[Chemical Formula 6]

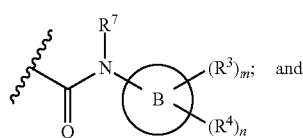; and p is

[22] The pharmaceutical composition having NPY Y5 receptor antagonist activity according to [20] wherein X is C(=O); a group of the formula:

[Chemical Formula 7]

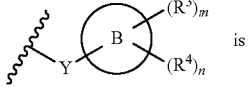 is

[Chemical Formula 8]

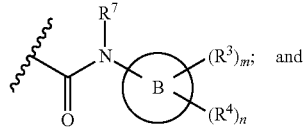; and p is 1.

[23] The pharmaceutical composition having NPY Y5 receptor antagonist activity according to [20] wherein X is C(=O); a group of the formula:

[Chemical Formula 9]

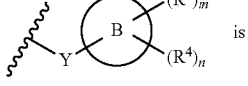 is

[Chemical Formula 10]

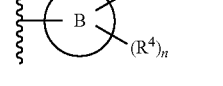; and p is 0.

[24] The pharmaceutical composition having NPY Y5 receptor antagonist activity according to [20] wherein X is C(=O); a group of the formula:

[Chemical Formula 11]

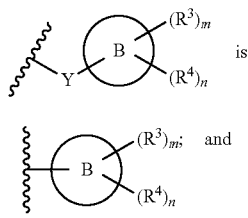

is

[Chemical Formula 12]

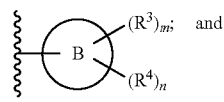
and p is 1.

[25] The pharmaceutical composition having NPY Y5 receptor antagonist activity according to [20] wherein A is substituted or unsubstituted phenyl, substituted or unsubstituted pyridyl, substituted or unsubstituted pyrrolidyl, substituted or unsubstituted tetrahydrofuryl, substituted or unsubstituted pyrrolyl, substituted or unsubstituted isoxazolyl or substituted or unsubstituted oxadiazolyl.

[26] The pharmaceutical composition having NPY Y5 receptor antagonist activity according to [25] wherein A has a substituent.

[27] The pharmaceutical composition having NPY Y5 receptor antagonist activity according to [26] wherein A has a substituent at least either one of the positions adjacent to the position of attachment.

[28] The pharmaceutical composition having NPY Y5 receptor antagonist activity according to [27] wherein the substituent(s) is one or more selected from cyano, alkyl, haloalkyl, alkoxyalkyl, alkylcarbonyl, phenoxy, halophenoxy or oxo.

[29] The pharmaceutical composition having NPY Y5 receptor antagonist activity according to any one of [20] to [28] wherein B is benzene, pyrazole, thiazole, imidazole, pyridine, benzimidazole, indole, pyrrolopyridine, indazole, dihydrobenzoxazole or indoline.

[30] The pharmaceutical composition having NPY Y5 receptor antagonist activity according to any one of [20] to [28] wherein m is 1.

[31] The pharmaceutical composition having NPY Y5 receptor antagonist activity according to [30] wherein $R^3$ is substituted or unsubstituted phenyl, substituted or unsubstituted thiazolyl, substituted or unsubstituted pyridyl, substituted or unsubstituted pyrimidyl or substituted or unsubstituted morpholino.

[32] The pharmaceutical composition having NPY Y5 receptor antagonist activity according to any one of [20] to [29] wherein m is 0; and n is 1.

[33] The pharmaceutical composition having NPY Y5 receptor antagonist activity according to [32] wherein the group of the formula:

[Chemical Formula 13]

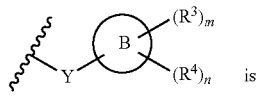
is

[Chemical Formula 14]

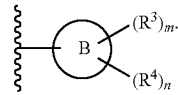

[34] The pharmaceutical composition having NPY Y5 receptor antagonist activity according to [32] or [33] wherein $R^4$ is halogen, oxo, substituted or unsubstituted alkyl, substituted or unsubstituted alkoxy, substituted or unsubstituted aryloxy, substituted or unsubstituted heterocyclyloxy, substituted or unsubstituted arylthio or arylsulfinyl.

[35] The pharmaceutical composition having NPY Y5 receptor antagonist activity according to any one of [20] to [34] for use in the prevention or treatment of obesity or obesity-related diseases, or weight control in obesity.

[36] A compound of the formula (II):

[Chemical Formula 15]

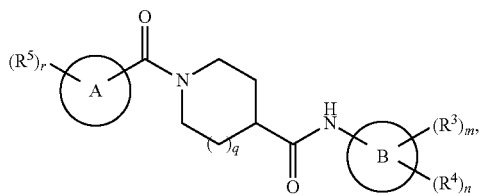

(II)

a pharmaceutically acceptable salt or solvate thereof, wherein
A is phenyl, pyridyl, pyrrolidyl, tetrahydrofuryl, pyrrolyl or isoxazolyl;
$R^5$ is a group each independently selected from halogen, cyano, oxo, alkyl, haloalkyl, alkoxy, alkoxyalkyl or alkylcarbonyl;
$R^3$ is substituted or unsubstituted phenyl, substituted or unsubstituted thiazolyl, substituted or unsubstituted pyridyl, substituted or unsubstituted pyrimidyl or substituted or unsubstituted morpholino;
$R^4$ is halogen, oxo, substituted or unsubstituted alkyl, substituted or unsubstituted alkoxy, substituted or unsubstituted aryloxy, substituted or unsubstituted heterocyclyloxy, substituted or unsubstituted arylthio or arylsulfinyl;
q is 0 or 1;
m is 0 or 1;
n is an integer of 0 to 5;
r is an integer of 0 to 3;
B is benzene, pyrazole, thiazole, pyridine, indole, indazole or dihydrobenzoxazole.

[37] A compound of the formula (III):

[Chemical Formula 16]

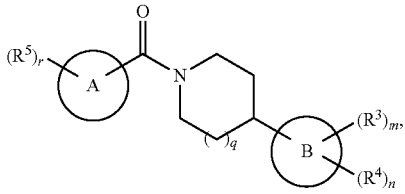

(III)

a pharmaceutically acceptable salt or solvate thereof, wherein
A is phenyl or pyrrolidyl;
$R^5$ is a group selected each independently from halogen, cyano, oxo, alkyl, haloalkyl, alkoxy, alkoxyalkyl or alkylcarbonyl;
$R^3$ is substituted or unsubstituted phenyl, substituted or unsubstituted pyridyl, substituted or unsubstituted morpholino;
$R^4$ is halogen, oxo, substituted or unsubstituted alkyl or substituted or unsubstituted alkoxy;
q is 0 or 1;
m is 0 or 1;
n is an integer of 0 to 5;
r is an integer of 0 to 3;
B is pyrazole, imidazole, benzimidazole, indole, pyrrolopyridine, indazole or indoline.

[38] A pharmaceutical composition comprising a compound, a pharmaceutically acceptable salt or solvate thereof according to [36] or [37].

[39] Use of a compound, a pharmaceutically acceptable salt or solvate thereof according to any one of [1] to [38], for the manufacture of a NPY Y5 receptor antagonist.

[40] Use of a compound, a pharmaceutically acceptable salt or solvate thereof according to any one of [1] to [38], for the manufacture of a pharmaceutical composition for use in the prevention or treatment of obesity or obesity-related diseases, or weight control in obesity.

[41] Use of a compound, a pharmaceutically acceptable salt or solvate thereof according to any one of [1] to [38] for the manufacture of an anorectic agent.

[42] A compound, a pharmaceutically acceptable salt or solvate thereof according to any one of [1] to [38] for use in the prevention or treatment of a disease involving an NPY Y5 receptor.

[43] A compound, a pharmaceutically acceptable salt or solvate thereof according to any one of [1] to [38] for use in the prevention or treatment of obesity or obesity-related diseases, or weight control in obesity.

[44] A method for the prevention or treatment of a disease involving an NPY Y5 receptor, which comprises a step of administrating a compound, a pharmaceutically acceptable salt or solvate thereof according to any one of [1] to [38].

[45] A method for the prevention or treatment of obesity or obesity-related diseases, or weight control in obesity which comprises a step of administrating a compound, a pharmaceutically acceptable salt or solvate thereof according to any one of [1] to [38].

Effect of the Invention

A compound of the present invention having the formula (I) has an antagonistic activity against NPY Y5 receptor. Furthermore, a compound of the present invention is useful for a medicament and has any or all of the excellent features listed below.
 a) Good pharmacokinetic such as high transportability to brain.
 b) High selectivity for Y5 receptor.
 c) High metabolic stability.
 d) Weak CYP enzyme (e.g., CYP1A2, CYP2C9, CYP3A4, etc.) inhibition.
 e) Less induction of a drug-metabolizing enzyme.
 f) Low toxicity, such as less anemia-inducing activity.
 g) Good pharmacokinetics, such as high bioavailability and adequate drug clearance.
 h) High water-solubility.

The compound of the invention has transportability to brain particularly higher than that of other derivatives having a NPY Y5 antagonistic activity. Furthermore, the compound of the invention wherein X is C(=O) and p is 0 in the above formula has particular high metabolic stability.

The compound of the present invention exhibits NPY Y5 receptor antagonistic activity and are very useful as a medicament, especially for the treatment and/or prevention of diseases involving NPY Y5, such as feeding disorder, obesity, hyperorexia, sexual disorder, impaired fertility, depression, epileptic seizure, hypertension, cerebral hemorrhage, congestive heart failure or sleep disorders, etc. Also, the compound of the present invention exhibits efficient anorectic activity, and thus, very useful in weight control in obesity, reduction of body weight, maintaining of weight after weight reduction. Moreover, the compound of the invention is useful for the treatment and/or prevention of the diseases in which obesity acts as a risk factor, such as diabetes, hypertension, dyslipidemia, atherosclerosis and acute coronary syndrome.

BEST MODE FOR CARRYING OUT THE INVENTION

As used herein, the term "halogen" includes fluorine, chlorine, bromine and iodine. In particular, fluorine and chlorine are preferable.

The term "alkyl" which is used alone or in combination with the other term means a straight or branched chain alkyl and includes, for example, methyl, ethyl, n-propyl, isopropyl, n-butyl, isobutyl, sec-butyl, tert-butyl, n-pentyl, isopentyl, neo-pentyl, n-hexyl, isohexyl, n-heptyl, isoheptyl, n-octyl, isooctyl, n-nonyl, n-decyl, n-undecyl, n-dodecyl, n-tridecyl, n-tetradecyl and n-pentadecyl etc.

The term "alkenyl" includes a straight or branched chain alkenyl having one or more double bonds in the above "alkyl" containing 2 to 10 carbon atoms, preferably 2 to 8 carbon atoms, and more preferably 3 to 6 carbon atoms. The alkenyl includes, for example, vinyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl, etc.

The term "alkynyl" means a straight or branched chain alkynyl having one or more triple bonds in the above "alkyl" and containing 2 to 8 carbon atoms and includes, for example, ethynyl, 1-propynyl, 2-propynyl, 1-buthynyl, 2-buthynyl, 3-buthynyl, etc.

The term "an aromatic carbocycle" is a mono- or polycyclic aromatic carbocyclic ring and includes, for example, benzene ring, naphthalene ring, anthracene ring, phenanthrene ring and indene ring, etc. In particular, benzene ring and naphthalene ring are preferable.

The term "aryl" is a group obtained by removing a hydrogen from the above aromatic carbocycle and includes, for example, phenyl, naphthyl, anthryl and phenanthryl and indenyl, etc.

The term "heterocyclyl" includes a heterocyclic group having one or more heteroatoms selected from O, S and N in the ring and includes 5- or 6-membered heteroaryl such as pyrrolyl, imidazolyl, pyrazolyl, pyridyl, pyridazinyl, pyrimidinyl, pyrazinyl, triazolyl, triazinyl, tetrazolyl, isoxazolyl, oxazolyl, oxadiazolyl, isothiazolyl, thiazolyl, thiadiazolyl, furyl, thienyl, etc; fused bicyclic heterocyclic groups such as indolyl, isoindolyl, indazolyl, indolizinyl, indolinyl, isoindolinyl, quinolyl, isoquinolyl, cinnolinyl, phthalazinyl, quinazolinyl, naphthyridinyl, quinoxalinyl, purinyl, pteridinyl, benzopyranyl, benzimidazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, triazolopyridyl, imidazothiazolyl, pyrazinopyridazinyl, quinazolinyl, quinolyl, isoquinolyl, naphthyridinyl, dihydropyridyl, tetrahydroquinolyl, tetrahydrobenzothienyl, etc; tricyclic fused heterocyclic groups such as carbazolyl, acrydinyl, xanthenyl, phenothiadinyl, phenoxathiinyl, phenoxadinyl, dibenzofuryl, etc; non-aromatic heterocyclic groups such as dioxanyl, thiiranyl, oxiranyl, oxathioranyl, azetidinyl, thianyl, pyrrolidyl, pyrrolinyl, imidazolidinyl, imidazolinyl, pyrazolidinyl, pyrazolinyl, piperidyl, piperadinyl, morpholinyl, morpholino, thiomorpholinyl, thiomorpholino, dihydropyridyl, tetrahydrofuryl, tetrahydropyranyl, tetrahydrothiazolyl and tetrahydroisothiazolyl, etc.

The term "cycloalkyl" includes a cyclic alkyl group having 3 to 8 carbon atoms, and preferably 5 or 6 carbon atoms, such as cyclopropyl, cyclobutyl, cyclopentyl, cyclohexyl, cycloheptyl, cyclooctyl, etc.

The term "cycloalkenyl" includes a group having one or more double bonds at any position in the above "cycloalkyl" ring, such as cyclopropenyl, cyclobutenyl, cyclopentenyl, cyclohexenyl and cyclohexadienyl, etc.

The term "alkoxy" means the above "alkyl" attached through an oxygen atom and includes, for example, methoxy, ethoxy, n-propoxy, isopropoxy, n-butoxy, isobutoxy, sec-butoxy, tert-butoxy, n-pentyloxy, n-hexyloxy, n-heptyloxy, n-octyloxy, etc. Especially, a straight or branched chain alkoxy having 1 to 4 carbon atoms, such as methoxy, ethoxy, n-propoxy, isopropoxy, n-butoxy, isobutoxy, sec-butoxy and tert-butoxy are preferable.

The term "monocyclic heterocycle" includes a 5- or 6-membered monocyclic heterocyclic ring having one or more heteroatoms selected from O, S and N in the ring. Specifically, it includes aromatic heterocycles such as furan, thiophene, pyrrole, pyrazole, imidazole, oxazole, oxadiazole, isoxazole, triazole, isothiazole, thiadiazole, pyran, thiopyran, pyridine, pyridazine, pyrimidine, pyradine, triazole, triadine, etc; non-aromatic heterocycles such as dihydropyridine, dihydropyridazine, dihydropyradine, dioxane, oxathiolane, thiane, pyrroline, pyrazolidine, piperidine, piperadine, morpholine, pirrolidine, imidazolidine, isoxazolidine, isothiazolidine, tetrahydropyran, thiomorpholine, etc.

Substituent groups for "monocyclic heterocycle" includes the above alkyl, alkenyl, hydroxy, halogen, carboxy, alkoxycarbonyl, alkoxy, mercapto, alkylthio, alkylsulfonyl, aryl or heterocycle, etc., and one or more positions may be substituted.

The term "fused bicyclic heterocycle" includes those wherein the above "monocyclic heterocycle" is fused with a monocyclic carbocycle (e.g., a ring derived from the above aromatic carbocycle or cycloalkyl, a ring derived from cycloalkenyl, etc.) or fused with a monocyclic heterocycle as defined above. For example, it includes indole, isoindole, indazole, indolizine, indoline, isoindole, quinoline, isoquinoline, cinnoline, phtharadine, quinazole, naphthyridine, quinoxaline, purine, pteridin, benzopyran, benzimidazole, benzisoxazole, benzoxazole, benzoxadiazole, benzisothiazole, benzothiazole, benzothiadiazole, benzofurin, isobenzofurin, benzothiene, benzotriazole, imidazopyridine, triazolopyridine, imidazothiazole, pyrazinopyridazine, quinazole, quinoline, isoquinoline, naphthyridine, dihydropyridine, tetrahydroquinoline, tetrahydrobenzothiene, pyrrolopyridine, dihydrobenzoxazole, etc.

The alkyl moiety in "alkylthio", "alkylcarbonyl", "alkylsulfonyl", "alkoxyalkyl" and "alkylsuifinyl" is the same as those in the above "alkyl".

The alkenyl moiety in "alkenyloxy", "alkenylthio", "alkenylcarbonyl", "alkenylsulfonyl" and "alkenylsulfinyl" is the same as those in the above "alkenyl".

The alkenyloxy moiety in "alkenyloxycarbonyl" is the same as those in the above "alkenyloxy".

The aryl moiety in "aryloxy", "arylthio", "arylcarbonyl", "arylsulfonyl" and "arylsulfinyl" is the same as those in the above "aryl".

The aryloxy moiety in "aryloxycarbonyl" is the same as those in the above "aryloxy".

The heterocyclyl moiety in "heterocyclyloxy", "heterocyclylthio", "heterocyclyloxycarbonyl", "heterocyclylcarbonyl", "heterocyclylsulfonyl" and "heterocyclylsulfinyl" is the same as those in the above "heterocyclyl".

The cycloalkyl moiety in "cycloalkyloxy", "cycloalkylthio", "cycloalkylcarbonyl", "cycloalkylsulfonyl" and "cycloalkylsulfinyl" is the same as those in the above "cycloalkyl".

The cycloalkyloxy moiety in "cycloalkyloxycarbonyl" is the same as those in the above "cycloalkyloxy".

The cycloalkenyl moiety in "cycloalkenyloxy", "cycloalkenylthio", "cycloalkenylcarbonyl", "cycloalkenylsulfonyl" and "cycloalkenylsulfinyl" is the same as those in the above "cycloalkenyl".

The cycloalkenyloxy moiety in "cycloalkenyloxycarbonyl" is the same as those in the above "cycloalkenyloxy".

The alkoxy moiety in "alkoxycarbonyl" and "alkoxyalkyl" is the same as those in the above "alkoxy".

Substituent groups for "substituted or unsubstituted alkyl", "substituted or unsubstituted alkenyl", "substituted or unsubstituted alkynyl", "substituted or unsubstituted alkoxy", "substituted or unsubstituted alkenyloxy", "substituted or unsubstituted cycloalkyl", "substituted or unsubstituted cycloalkyloxy", "substituted or unsubstituted cycloalkenyl", "substituted or unsubstituted cycloalkenyloxy", "substituted or unsubstituted aryl", "substituted or unsubstituted aryloxy", "substituted or unsubstituted heterocyclyl", "substituted or unsubstituted heterocyclyloxy", "substituted or unsubstituted alkylthio", "substituted or unsubstituted alkenylthio", "substituted or unsubstituted cycloalkylthio", "substituted or unsubstituted cycloalkenylthio", "substituted or unsubstituted arylthio", "substituted or unsubstituted heterocyclylthio", "substituted or unsubstituted alkoxycarbonyl", "substituted or unsubstituted alkenyloxycarbonyl", "substituted or unsubstituted cycloalkyloxycarbonyl", "substituted or unsubstituted cycloalkenyloxycarbonyl", "substituted or unsubstituted aryloxycarbonyl", "substituted or unsubstituted heterocyclyloxycarbonyl", "substituted or unsubstituted alkylcarbonyl", "substituted or unsubstituted alkenylcarbonyl", "substituted or unsubstituted cycloalkylcarbonyl", "substituted or unsubstituted cycloalkenylcarbonyl", "substituted or unsubstituted arylcarbonyl", "substituted or unsubstituted heterocyclylcarbonyl", "substituted or unsubstituted alkylsulfonyl", "substituted or unsubstituted alkenylsulfonyl", "substituted or unsubstituted cycloalkylsulfonyl", "substituted or unsubstituted cycloalkenylsulfonyl", "substituted or unsubstituted arylsulfonyl", "substituted or unsubstituted heterocyclylsulfonyl", "substituted or unsubstituted alkylsulfinyl", "substituted or unsubstituted alkenylsulfinyl", "substituted or unsubstituted cycloalkylsulfinyl", "substituted or unsubstituted cycloalkenylsulfinyl", "substituted or unsubstituted arylsulfinyl" and "substituted or unsubstituted heterocyclylsulfinyl" includes, for example, hydroxy, carboxy, halogen, halogenated alkyl (e.g., $CF_3$, $CH_2CF_3$, $CH_2CCl_3$), alkyl (e.g., methyl, ethyl, isopropyl, tert-butyl), alkenyl (e.g., vinyl), alkynyl (e.g., ethynyl), cycloalkyl (e.g., cyclopropyl), cycloalkenyl (e.g., cyclopropenyl), alkoxy (e.g., methoxy, ethoxy, propoxy, butoxy), halogenated alkoxy (e.g., $OCF_3$), alkenyloxy (e.g., vinyloxy, allyloxy), alkoxyalkyl (e.g., methoxymethyl, methoxyethyl), alkoxycarbonyl (e.g., methoxycarbonyl, ethoxycarbonyl, tert-butoxycarbonyl), nitro, nitroso, substituted or unsubstituted amino (e.g., alkylamino (e.g., methylamino, ethylamino, dimethylamino), acylamino (e.g., acetylamino, benzoylamino), aralkylamino (e.g., benzylamino, tritylamino), hydroxyamino, alkoxycarbonylamino, alkylsulfonylamino, carbamoylamino, heterocyclylcarbonylamino, arylsulfonylamino), azide, aryl (e.g., phenyl), aralkyl (e.g., benzyl), cyano, isocyano, isocyanato, thiocyanato, isothiocyanato, mercapto, alkylthio (e.g., methylthio), alkylsulfonyl (e.g., methanesulfonyl, ethanesulfonyl), substituted or unsubstituted carbamoyl (e.g., alkylcarbamoyl (e.g., methylcarbamoyl, ethylcarbamoyl, dimethylcarbamoyl), alkylsulfonylcarbamoyl), sulfamoyl, acyl (e.g., formyl, acetyl), formyloxy, haloformyl, oxalo, thioformyl, thiocarboxy, dithiocarboxy, thiocarbamoyl, sulfino, sulfo, sulfonyl, sulfinyl, sulfoamino, hydrazino, azide, ureido, amidino, guanidino, phthalimide, oxo, heteroaryl, heterocyclyl, alkylene, alkylenedioxy (—O—$CH_2$—O—, —O—$CH_2$—$CH_2$—O—, —O—$CH_2$—$CH_2$—$CH_2$—O— etc.), alkenylene, cycloalkylene, cycloalkenylene, arylene, heterocyclyldiyl, heteroarylene, heterocyclylcarbonyl, aryloxy (e.g., phenoxy), haloaryloxy (e.g., halophenoxy), aryloxycarbonyl, arylsulfonyl and arylthio, etc.

Substituent groups for "substituted or unsubstituted amino", "substituted or unsubstituted carbamoyl" and "substituted or unsubstituted sulfamoyl" includes alkyl, alkenyl, aryl, heteroaryl, alkylcarbonyl, arylcarbonyl, heteroarylcarbonyl, heterocyclylcarbonyl, alkoxycarbonyl, aryloxycarbonyl, heteroaryloxycarbonyl, heterocyclyloxycarbonyl, sulfamoyl, alkylsulfonyl, carbamoyl, cycloalkylsulfonyl, arylsulfonyl, heteroarylsulfonyl, heterocyclylsulfonyl, acyl, hydroxy, sulfinyl, etc.

The compound of the present invention includes any formable and pharmaceutically acceptable salts thereof. Examples of "pharmaceutically acceptable salt" include salts with mineral acids such as hydrochloric acid, sulfuric acid, nitric acid and phosphoric acid, salts with organic acids such as para-toluenesulfonic acid, methanesulfonic acid, oxalic acid and citric acid, salts with organic bases such as ammonium, trimethylammonium and triethylammonium, salts with alkaline metals such as sodium and potassium, salts with alkaline earth metals such as calcium and magnesium, etc.

The compound of the present invention includes solvates of a compound of the formula (I). Hydrate is preferable, and arbitrary numbers of water molecules may coordinate to the compound of the present invention.

In addition, the compound of the present invention includes a prodrug thereof. Such prodrug is a derivative of the compound of the present invention having a group which can be chemically or metabolically degraded, and is a compound which serves as a pharmaceutically active compound of the present invention in vivo by solvolysis, or under physiological condition. A method of selecting a suitable prodrug derivative and a process for producing a suitable prodrug derivative are described, for example, in Design of Prodrugs, Elsevier, Amsterdam 1985.

For example, when the compound (I) of the present invention has carboxy group, a prodrug such as an ester derivative obtained by the reaction of the carboxy group of the compound (I) and a suitable alcohol or an amide derivative obtained by the reaction of the carboxy group of the compound (I) and a suitable amine is exemplified.

For example, when the compound (I) of the present invention has hydroxy group, a prodrug such as an acyloxy derivative obtained by the reaction of the hydroxy group of the compound (I) and suitable acyl halide or suitable acid anhydride is exemplified.

For example, when the compound (I) of the present invention has amino group, a prodrug such as an amide derivative obtained by the reaction of the amino group of the compound (I) and suitable acid halide or suitable mixed acid anhydride is exemplified.

When the compound (I) of the present invention has an asymmetric carbon atom, racemates, enantiomeric pairs and all steric isomers (geometrical isomer, epimer, enantiomer and the like) thereof are included. In addition, when the compound of the formula (I) has one or more double bonds and can exist in E-form or Z-form, these forms are included.

In addition, one or more hydrogen, carbon or other atoms of a compound of the formula (I) can be replaced by an isotope of the hydrogen, carbon or other atoms. The compounds of formula (I) include all radiolabeled forms of compounds of the formula (I). Such "radiolabeled" "radiolabeled form" and the like of a compound of formula (I), each of which is encompassed by the invention, is useful as a research and/or diagnostic tool in metabolism pharmacokinetic studies and in binding assays. Examples of isotopes that can be incorporated into a compound of the formula (I) of the present invention include isotopes of hydrogen, carbon, nitrogen, oxygen, phosphorous, sulfur, fluorine and chlorine, such as $^2H$, $3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Radiolabeled compounds of the invention can be prepared by methods known in the art. For example, tritiated compounds of formula (I) can be prepared by introducing tritium into the particular compound of Formula (I), for example, by catalytic dehalogenation with tritium. This method may include reacting a suitably halogen-substituted precursor of a compound of Formula (I) with tritium gas in the presence of a suitable catalyst, for example, Pd/C, in the presence or absence of a base. Other suitable methods for preparing tritiated compounds can be found in Isotopes in the Physical and Biomedical Sciences, Vol. 1, Labeled Compounds (Part A), Chapter 6 (1987). $^{14}C$-labeled compounds can be prepared by employing starting materials having a $^{14}C$ carbon.

Particularly preferred compounds of the formula (I) are as follows.

In the formula (I),
(A1) A is substituted or unsubstituted phenyl (hereinafter referred to as "A is A1"),
(A2) A is substituted or unsubstituted pyridyl, substituted or unsubstituted pyrrolidyl, substituted or unsubstituted tetrahydrofuryl, substituted or unsubstituted pyrrolyl, substituted or unsubstituted isoxazolyl or substituted or unsubstituted oxadiazolyl (hereinafter referred to as "A is A2"),
(B1) B is benzene (hereinafter referred to as "B is B1"),
(B2) B is pyrazole, thiazole, imidazole or pyridine (hereinafter referred to as "B is B2"),
(B3) B is benzimidazole, indole, pyrrolopyridine, indazole, dihydrobenzoxazole or indoline (hereinafter referred to as "B is B3"),
(M1) m is 0 (hereinafter referred to as "m is M1"),
(M2) m is 1 (hereinafter referred to as "m is M2"),
(N1) n is 0 (hereinafter referred to as "n is N1"),
(N2) n is 1 (hereinafter referred to as "n is N2"),
(P1) p is 0 (hereinafter referred to as "p is P1"),
(P2) p is 1 (hereinafter referred to as "p is P2"),
(Q1) q is 0 (hereinafter referred to as "q is Q1"),
(Q2) q is 1 (hereinafter referred to as "q is Q2"), (R3a) R³ is substituted or unsubstituted phenyl (hereinafter referred to as "R³ is R3a"),
(R3b) R³ is substituted or unsubstituted thiazolyl, substituted or unsubstituted pyridyl, substituted or unsubstituted pyrimidyl or substituted or unsubstituted morpholino (hereinafter referred to as "R³ is R3b"),
(R4a) R⁴ is halogen, oxo, substituted or unsubstituted alkyl (hereinafter referred to as "R⁴ is R4a"),
(R4b) R⁴ is substituted or unsubstituted alkoxy, substituted or unsubstituted aryloxy, substituted or unsubstituted heterocyclyoxy (hereinafter referred to as
"R4 is R4b"),
(R4c) R⁴ is substituted or unsubstituted arylthio or arylsulfinyl (hereinafter referred to as "R⁴ is R4c"),
(X1) X is a single bond (hereinafter referred to as "X is X1"),
(X2) X is C(=O) (hereinafter referred to as "X is X2"),
(Y1) Y is a single bond (hereinafter referred to as "Y is Y1"),
(Y2) Y is C(=O)NH (hereinafter referred to as "Y is Y2"),
(Y3) Y is CH₂NH (hereinafter referred to as "Y is Y3"),
(Z) The compounds wherein the combinations of A, B, m, n, p, q, R³, R⁴, X and Y, i.e., (A, B, m, n, p, q, R³, R⁴, X, Y), are as follows:
(A1, B1, M1, N1, P1, Q1, R3a, R4a, X1, Y1), (A1, B1, M1, N1, P1, Q1, R3a, R4a, X1, Y2), (A1, B1, M1, N1, P1, Q1, R3a, R4a, X1, Y3), (A1, B1, M1, N1, P1, Q1, R3a, R4a, X2, Y1), (A1, B1, M1, N1, P1, Q1, R3a, R4a, X2, Y2), (A1, B1, M1, N1, P1, Q1, R3a, R4a, X2, Y3), (A1, B1, M1, N1, P1, Q1, R3a, R4b, X1, Y1), (A1, B1, M1, N1, P1, Q1, R3a, R4b, X1, Y2), (A1, B1, M1, N1, P1, Q1, R3a, R4b, X1, Y3), (A1, B1, M1, N1, P1, Q1, R3a, R4b, X2, Y1), (A1, B1, M1, N1, P1, Q1, R3a, R4b, X2, Y2), (A1, B1, M1, N1, P1, Q1, R3a, R4b, X2, Y3), (A1, B1, M1, N1, P1, Q1, R3a, R4c, X1, Y1), (A1, B1, M1, N1, P1, Q1, R3a, R4c, X1, Y2), (A1, B1, M1, N1, P1, Q1, R3a, R4c, X1, Y3), (A1, B1, M1, N1, P1, Q1, R3a, R4c, X2, Y1), (A1, B1, M1, N1, P1, Q1, R3a, R4c, X2, Y2), (A1, B1, M1, N1, P1, Q1, R3a, R4c, X2, Y3), (A1, B1, M1, N1, P1, Q1, R3b, R4a, X1, Y1), (A1, B1, M1, N1, P1, Q1, R3b, R4a, X1, Y2), (A1, B1, N1, N1, P1, Q1, R3b, R4a, X1, Y3), (A1, B1, N1, N1, P1, Q1, R3b, R4a, X2, Y1), (A1, B1, M1, N1, P1, Q1, R3b, R4a, X2, Y2), (A1, B1, M1, N1, P1, Q1, R3b, R4a, X2, Y3), (A1, B1, M1, N1, P1, Q1, R3b, R4b, X1, Y1), B1, M1, N1, P1, Q1, R3b, R4b, X1, Y2), (A1, B1, M1, N1, P1, Q1, R3b, R4b, X1, Y3), (A1, B1, M1, N1, P1, Q1, R3b, R4b, X2, Y1), (A1, B1, M1, N1, P1, Q1, R3b, R4b, X2, Y2), (A1, B1, M1, N1, P1, Q1, R3b, R4b, X2, Y3), (A1, B1, M1, N1, P1, Q1, R3b, R4c, X1, Y1), (A1, B1, M1, N1, P1, Q1, R3b, R4c, X1, Y2), (A1, B1, M1, N1, P1, Q1, R3b, R4c, X1, Y3), (A1, B1, M1, N1, P1, Q1, R3b, R4c, X2, Y1), (A1, B1, M1, N1, P1, Q1, R3b, R4c, X2, Y2), (A1, B1, M1, N1, P1, Q1, R3b, R4c, X2, Y3), (A1, B1, M1, N1, P1, Q2, R3a, R4a, X1, Y1), (A1, B1, M1, N1, P1, Q2, R3a, R4a, X1, Y2), (A1, B1, M1, N1, P1, Q2, R3a, R4a, X1, Y3), (A1, B1, M1, N1, P1, Q2, R3a, R4a, X2, Y1), (A1, B1, M1, N1, P1, Q2, R3a, R4a, X2, Y2), (A1, B1, M1, N1, P1, Q2, R3a, R4a, X2, Y3), (A1, B1, M1, N1, P1, Q2, R3a, R4b, X1, Y1), (A1, B1, M1, N1, P1, Q2, R3a, R4b, X1, Y2), (A1, B1, M1, N1, P1, Q2, R3a, R4b, X1, Y3), (A1, B1, M1, N1, P1, Q2, R3a, R4b, X2, Y1), (A1, B1, M1, N1, P1, Q2, R3a, R4b, X2, Y2), (A1, B1, M1, N1, P1, Q2, R3a, R4b, X2, Y3), (A1, B1, M1, N1, P1, Q2, R3a, R4c, X1, Y1), (A1, B1, M1, N1, P1, Q2, R3a, R4c, X1, Y2), (A1, B1, M1, N1, P1, Q2, R3a, R4c, X1, Y3), (A1, B1, M1, N1, P1, Q2, R3a, R4c, X2, Y1), (A1, B1, M1, N1, P1, Q2, R3a, R4c, X2, Y2), (A1, B1, M1, N1, P1, Q2, R3a, R4c, X2, Y3), (A1, B1, M1, N1, P1, Q2, R3b, R4a, X1, Y1), (A1, B1, M1, N1, P1, Q2, R3b, R4a, X1, Y2), (A1, B1, M1, N1, P1, Q2, R3b, R4a, X1, Y3), (A1, B1, M1, N1, P1, Q2, R3b, R4a, X2, Y1), (A1, B1, M1, N1, P1, Q2, R3b, R4a, X2, Y2), (A1, B1, M1, N1, P1, Q2, R3b, R4a, X2, Y3), (A1, B1, M1, N1, P1, Q2, R3b, R4b, X1, Y1), (A1, B1, M1, N1, P1, Q2, R3b, R4b, X1, Y2), (A1, B1, M1, N1, P1, Q2, R3b, R4b, X1, Y3), (A1, B1, M1, N1, P1, Q2, R3b, R4b, X2, Y1), (A1, B1, M1, N1, P1, Q2, R3b, R4b, X2, Y2), (A1, B1, M1, N1, P1, Q2, R3b, R4b, X2, Y3), (A1, B1, M1, N1, P1, Q2, R3b, R4c, X1, Y1), (A1, B1, M1, N1, P1, Q2, R3b, R4c, X1, Y2), (A1, B1, M1, N1, P1, Q2, R3b, R4c, X1, Y3), (A1, B1, M1, N1, P1, Q2, R3b, R4c, X2, Y1), (A1, B1, M1, N1, P1, Q2, R3b, R4c, X2, Y2), (A1, B1, M1, N1, P1, Q2, R3b, R4c, X2, Y3), (A1, B1, M1, N1, P2, Q1, R3a, R4a, X1, Y1), (A1, B1, M1, N1, P2, Q1, R3a, R4a, X1, Y2), (A1, B1, M1, N1, P2, Q1, R3a, R4a, X1, Y3), (A1, B1, M1, N1, P2, Q1, R3a, R4a, X2, Y1), (A1, B1, M1, N1, P2, Q1, R3a, R4a, X2, Y2), (A1, B1, M1, N1, P2, Q1, R3a, R4a, X2, Y3), (A1, B1, M1, N1, P2, Q1, R3a, R4b, X1, Y1), (A1, B1, M1, N1, P2, Q1, R3a, R4b, X1, Y2),
(A1, B1, M1, N1, P2, Q1, R3a, R4b, X1, Y3), (A1, B1, M1, N1, P2, Q1, R3a, R4b, X2, Y1), (A1, B1, M1, N1, P2, Q1, R3a, R4b, X2, Y2), (A1, B1, M1, N1, P2, Q1, R3a, R4b, X2, Y3), (A1, B1, M1, N1, P2, Q1, R3a, R4c, X1, Y1), (A1, B1, M1, N1, P2, Q1, R3a, R4c, X1, Y2), (A1, B1, M1, N1, P2, Q1, R3a, R4c, X1, Y3), (A1, B1, M1, N1, P2, Q1, R3a, R4c, X2, Y1), (A1, B1, M1, N1, P2, Q1, R3a, R4c, X2, Y2), (A1, B1, M1, N1, P2, Q1, R3a, R4c, X2, Y3), (A1, B1, M1, N1, P2, Q1, R3b, R4a, X1, Y1), (A1, B1, M1, N1, P2, Q1, R3b, R4a, X1, Y2), (A1, B1, M1, N1, P2, Q1, R3b, R4a, X1, Y3), (A1, B1, M1, N1, P2, Q1, R3b, R4a, X2, Y1), (A1, B1, M1, N1, P2, Q1, R3b, R4a, X2, Y2), (A1, B1, M1, N1, P2, Q1, R3b, R4a, X2, Y3), (A1, B1, M1, N1, P2, Q1, R3b, R4b, X1, Y1), (A1, B1, M1, N1, P2, Q1, R3b, R4b, X1, Y2), (A1, B1, M1, N1, P2, Q1, R3b, R4b, X1, Y3), (A1, B1, M1, N1, P2, Q1, R3b, R4b, X2, Y1) (A1, B1, M1, N1, P2, Q1, R3b, R4b, X2, Y2), (A1, B1, M1, N1, P2, Q1, R3b, R4b, X2, Y3), (A1, B1, M1, N1, P2, Q1, R3b, R4c, X1, Y1), (A1, B1, M1, N1, P2, Q1, R3b, R4c, X1, Y2), (A1, B1, M1, N1, P2, Q1, R3b, R4c, X1, Y3), (A1, B1, M1, N1, P2, Q1, R3b, R4c, X2, Y1), (A1, B1, M1, N1, P2, Q1, R3b, R4c, X2, Y2), (A1, B1, M1, N1, P2, Q1, R3b, R4c, X2, Y3), (A1, B1, M1, N1, P2, Q2, R3a, R4a, X1, Y1), (A1, B1, M1, N1, P2, Q2, R3a, R4a, X1, Y2), (A1, B1, M1, N1, P2, Q2, R3a, R4a, X1, Y3), (A1, B1, M1, N1, P2, Q2, R3a, R4a, X2, Y1), (A1, B1, M1, N1, P2, Q2, R3a, R4a, X2, Y2), (A1, B1, M1, N1, P2, Q2, R3a, R4a, X2, Y3), (A1, B1, M1, N1, P2, Q2, R3a, R4b, X1, Y1), (A1, B1, M1, N1, P2, Q2, R3a, R4b, X1, Y2), (A1, B1, M1, N1, P2, Q2, R3a, R4b, X1, Y3), (A1, B1, M1, N1, P2, Q2, R3a, R4b, X2, Y1), (A1, B1, M1, N1, P2, Q2, R3a, R4b, X2, Y2), (A1, B1, M1, N1, P2, Q2, R3a, R4b, X2, Y3), (A1, B1, M1, N1, P2, Q2, R3a, R4c, X1, Y1), (A1, B1, M1, N1, P2, Q2, R3a, R4c, X1, Y2), (A1, B1, M1, N1, P2, Q2, R3a, R4c, X1, Y3), (A1, B1, M1, N1, P2, Q2, R3a, R4c, X2, Y1), (A1, B1, M1, N1, P2, Q2, R3a, R4c, X2, Y2), (A1, B1, M1, N1, P2, Q2, R3a, R4c, X2, Y3), (A1, B1, M1, N1, P2, Q2, R3b, R4a, X1, Y1), (A1, B1, M1, N1, P2, Q2, R3b, R4a, X1, Y2), (A1, B1, M1, N1, P2, Q2, R3b, R4a, X1, Y3), (A1, B1, M1, N1, P2, Q2, R3b, R4a, X2, Y1), (A1, B1, M1, N1, P2, Q2, R3b, R4a, X2, Y2), (A1, B1, M1, N1, P2, Q2, R3b, R4a, X2, Y3), (A1, B1, M1, N1, P2, Q2, R3b, R4b, X1, Y1), (A1, B1, M1, N1, P2, Q2, R3b, R4b, X1, Y2), (A1, B1, M1, N1, P2, Q2, R3b, R4b, X1, Y3), (A1, B1, M1, N1, P2, Q2, R3b, R4b, X2, Y1), (A1, B1, M1, N1, P2, Q2, R3b, R4b, X2, Y2), (A1, B1, M1, N1, P2, Q2, R3b, R4b, X2, Y3), (A1, B1, M1, N1, P2, Q2, R3b, R4c, X1, Y1), (A1, B1, M1, N1, P2, Q2, R3b, R4c, X1, Y2), (A1, B1, M1, N1, P2, Q2, R3b, R4c, X1, Y3), (A1, B1, M1, N1, P2, Q2, R3b, R4c, X2, Y1), (A1, B1, M1, N1, P2, Q2, R3b, R4c, X2, Y2), (A1, B1, M1, N1, P2, Q2, R3b, R4c, X2, Y3), (A1, B1, M1, N2, P1, Q1, R3a, R4a, X1, Y1), (A1, B1, M1, N2, P1, Q1, R3a, R4a, X1, Y2), (A1, B1, M1, N2, P1, Q1, R3a, R4a, X1, Y3), (A1, B1, M1, N2, P1, Q1, R3a, R4a, X2, Y1), (A1, B1, M1, N2, P1, Q1, R3a, R4a, X2, Y2), (A1, B1, M1, N2, P1, Q1, R3a, R4a, X2, Y3), (A1, B1, M1, N2, P1, Q1, R3a, R4b, X1, Y1), (A1, B1, M1, N2, P1, Q1, R3a, R4b, X1, Y2), (A1, B1, M1, N2, P1, Q1, R3a, R4b, X1, Y3), (A1, B1, M1, N2, P1, Q1, R3a, R4b, X2, Y1), (A1, B1, M1, N2, P1, Q1, R3a, R4b, X2, Y2), (A1, B1, M1, N2, P1, Q1, R3a, R4b, X2, Y3), (A1, B1, M1, N2, P1, Q1, R3a, R4c, X1, Y1), (A1, B1, M1, N2, P1, Q1, R3a, R4c, X1, Y2), (A1, B1, M1, N2, P1, Q1, R3a, R4c, X1, Y3), (A1, B1, M1, N2, P1, Q1, R3a, R4c, X2, Y1), (A1, B1, M1, N2, P1, Q1, R3a, R4c, X2, Y2), (A1, B1, M1, N2, P1, Q1, R3a, R4c, X2, Y3), (A1, B1, M1, N2, P1, Q1, R3b, R4a, X1, Y1), (A1, B1, M1, N2, P1, Q1, R3b, R4a, X1, Y2), (A1, B1, M1, N2, P1, Q1, R3b, R4a, X1, Y3), (A1, B1, M1, N2, P1, Q1, R3b, R4a, X2, Y1), (A1, B1, M1, N2, P1, Q1, R3b, R4a, X2, Y2), (A1, B1, M1, N2, P1, Q1, R3b, R4a, X2, Y3), (A1, B1, M1, N2, P1, Q1, R3b, R4b, X1, Y1), (A1, B1, M1, N2, P1, Q1, R3b, R4b, X1, Y2), (A1, B1, M1, N2, P1, Q1, R3b, R4b, X1, Y3), (A1, B1, M1, N2, P1, Q1, R3b, R4b, X2, Y1), (A1, B1, M1, N2, P1, Q1, R3b, R4b, X2, Y2), (A1, B1, M1, N2, P1, Q1, R3b, R4b, X2, Y3), (A1, B1, M1, N2, P1, Q1, R3b, R4c, X1, Y1), (A1, B1, M1, N2, P1, Q1, R3b, R4c, X1, Y2), (A1, B1, M1, N2, P1, Q1, R3b, R4c, X1, Y3), (A1, B1, M1, N2, P1, Q1, R3b, R4c, X2, Y1), (A1, B1, M1, N2, P1, Q1, R3b, R4c, X2, Y2), (A1, B1, M1, N2, P1, Q1, R3b, R4c, X2, Y3), (A1, B1, M1, N2, P1, Q2, R3a, R4a, X1, Y1), (A1, B1, M1, N2, P1, Q2, R3a, R4a, X1, Y2), (A1, B1, M1, N2, P1, Q2, R3a, R4a, X1, Y3), (A1, B1, M1, N2, P1, Q2, R3a, R4a, X2, Y1), (A1, B1, M1, N2, P1, Q2, R3a, R4a, X2, Y2), (A1, B1, M1, N2, P1, Q2, R3a, R4a, X2, Y3), (A1, B1, M1, N2, P1, Q2, R3a, R4b, X1, Y1), (A1, B1, M1, N2, P1, Q2, R3a, R4b, X1, Y2), (A1, B1, M1, N2, P1, Q2, R3a, R4b, X1, Y3), (A1, B1, M1, N2, P1, Q2, R3a, R4b, X2, Y1), (A1, B1, M1, N2, P1, Q2, R3a, R4b, X2, Y2), (A1, B1, M1, N2, P1, Q2, R3a, R4b, X2, Y3) (A1, B1, M1, N2, P1, Q2, R3a, R4c, X1, Y1), (A1, B1, M1, N2, P1, Q2, R3a, R4c, X1, Y2), (A1, B1, M1, N2, P1, Q2, R3a, R4c, X1, Y3), (A1, B1, M1, N2, P1, Q2, R3a, R4c, X2, Y1), (A1, B1, M1, N2, P1, Q2, R3a, R4c, X2, Y2), (A1, B1, M1, N2, P1, Q2, R3a, R4c, X2, Y3), (A1, B1, M1, N2, P1, Q2, R3b, R4a, X1, Y1), (A1, B1, M1, N2, P1, Q2, R3b, R4a, X1, Y2), (A1, B1, M1, N2, P1, Q2, R3b, R4a, X1, Y3), (A1, B1, M1, N2, P1, Q2, R3b, R4a, X2, Y1), (A1, B1, M1, N2, P1, Q2, R3b, R4a, X2, Y2), (A1, B1, M1, N2, P1, Q2, R3b, R4a, X2, Y3), (A1, B1, M1, N2, P1, Q2, R3b, R4b, X1, Y1), (A1, B1, M1, N2, P1, Q2, R3b, R4b, X1, Y2) (A1, B1, M1, N2, P1, Q2, R3b, R4b, X1, Y3), (A1, B1, M1, N2, P1, Q2, R3b, R4b, X2, Y1), (A1, B1, M1, N2, P1, Q2, R3b, R4b, X2, Y2), (A1, B1, M1, N2, P1, Q2, R3b, R4b, X2, Y3), (A1, B1, M1, N2, P1, Q2, R3b, R4c, X1, Y1) (A1, B1, M1, N2, P1, Q2, R3b, R4c, X1, Y2), (A1, B1, M1, N2, P1, Q2, R3b, R4c, X1, Y3), (A1, B1, M1, N2, P1, Q2, R3b, R4c, X2, Y1) (A1, B1, M1, N2, P1, Q2, R3b, R4c, X2, Y2), (A1, B1, M1, N2, P1, Q2, R3b, R4c, X2, Y3), (A1, B1, M1, N2, P2, Q1, R3a, R4a, X1, Y1), (A1, B1, M1, N2, P2, Q1, R3a, R4a, X1, Y2), (A1, B1, M1, N2, P2, Q1, R3a, R4a, X1, Y3) (A1, B1, M1, N2, P2, Q1, R3a, R4a, X2, Y1) (A1, B1, M1, N2, P2, Q1, R3a, R4a, X2, Y2), (A1, B1, M1, N2, P2, Q1, R3a, R4a, X2, Y3), (A1, B1, M1, N2, P2, Q1, R3a, R4b, X1, Y1), (A1, B1, M1, N2, P2, Q1, R3a, R4b, X1, Y2), (A1, B1, M1, N2, P2, Q1, R3a, R4b, X1, Y3), (A1, B1, M1, N2, P2, Q1, R3a, R4b, X2, Y1), (A1, B1, M1, N2, P2, Q1, R3a, R4b, X2, Y2), (A1, B1, M1, N2, P2, Q1, R3a, R4b, X2, Y3), (A1, B1, M1, N2, P2, Q1, R3a, R4c, X1, Y1), (A1, B1, M1, N2, P2, Q1, R3a, R4c, X1, Y2), (A1, B1, M1, N2, P2, Q1, R3a, R4c, X1, Y3), (A1, B1, M1, N2, P2, Q1, R3a, R4c, X2, Y1), (A1, B1, M1, N2, P2, Q1, R3a, R4c, X2, Y2), (A1, B1, M1, N2, P2, Q1, R3a, R4c, X2, Y3), (A1, B1, M1, N2, P2, Q1, R3b, R4a, X1, Y2), (A1, B1, M1, N2, P2, Q1, R3b, R4a, X1, Y3), (A1, B1, M1, N2, P2, Q1, R3b, R4a, X2, Y1), (A1, B1, M1, N2, P2, Q1, R3b, R4a, X2, Y2), (A1, B1, M1, N2, P2, Q1, R3b, R4a, X2, Y3), (A1, B1, M1, N2, P2, Q1, R3b, R4b, X1, Y1), (A1, B1, M1, N2, P2, Q1, R3b, R4b, X1, Y2), (A1, B1, M1, N2, P2, Q1, R3b, R4b, X1, Y3), (A1, B1, M1, N2, P2, Q1, R3b, R4b, X2, Y1), (A1, B1, M1, N2, P2, Q1, R3b, R4b, X2, Y2), (A1, B1, M1, N2, P2, Q1, R3b, R4b, X2, Y3), (A1, B1, M1, N2, P2, Q1, R3b, R4c, X1, Y1), (A1, B1, M1, N2, P2, Q1, R3b, R4c, X1, Y2), (A1, B1, M1, N2, P2, Q1, R3b, R4c, X1, Y3), (A1, B1, M1, N2, P2, Q1, R3b, R4c, X2, Y1), (A1, B1, M1, N2, P2, Q1, R3b, R4c, X2, Y2), (A1, B1, M1, N2, P2, Q1, R3b, R4c, X2, Y3), (A1, B1, M1, N2, P2, Q2, R3a, R4a, X1, Y1), (A1, B1, M1, N2, P2, Q2, R3a, R4a, X1, Y2), (A1, B1, M1, N2, P2, Q2, R3a, R4a, X1, Y3), (A1, B1, M1, N2, P2, Q2, R3a, R4a, X2, Y1), (A1, B1, M1, N2, P2, Q2, R3a, R4a, X2, Y2), (A1, B1, M1, N2, P2, Q2, R3a, R4a, X2, Y3), (A1, B1, M1, N2, P2, Q2, R3a, R4b, X1, Y1), (A1, B1, M1, N2, P2, Q2, R3a, R4b, X1, Y2), (A1, B1, M1, N2, P2, Q2, R3a, R4b, X1, Y3), (A1, B1, M1, N2, P2, Q2, R3a, R4b, X2, Y1), (A1, B1, M1, N2, P2, Q2, R3a, R4b, X2, Y2), (A1, B1, M1, N2, P2, Q2, R3a, R4b, X2, Y3), (A1, B1, M1, N2, P2, Q2, R3a, R4c, X1, Y1), (A1, B1, M1, N2, P2, Q2, R3a, R4c, X1, Y2), (A1, B1, M1, N2, P2, Q2, R3a, R4c, X1, Y3), (A1, B1, M1, N2, P2, Q2, R3a, R4c, X2, Y1), (A1, B1, M1, N2, P2, Q2, R3a, R4c, X2, Y2), (A1, B1, M1, N2, P2, Q2, R3a, R4c, X2, Y3), (A1, B1, M1, N2, P2, Q2, R3b, R4a, X1, Y1), (A1, B1, M1, N2, P2, Q2, R3b, R4a, X1, Y2), (A1, B1, M1, N2, P2, Q2, R3b, R4a, X1, Y3), (A1, B1, M1, N2, P2, Q2, R3b, R4a, X2, Y1), (A1, B1, M1, N2, P2, Q2, R3b, R4a, X2, Y2), (A1, B1, M1, N2, P2, Q2, R3b, R4a, X2, Y3), (A1, B1, M1, N2, P2, Q2, R3b, R4b, X1, Y1), (A1, B1, M1, N2, P2, Q2, R3b, R4b, X1, Y2), (A1, B1, M1, N2, P2, Q2, R3b, R4b, X1, Y3), (A1, B1, M1, N2, P2, Q2, R3b, R4b, X2, Y1), (A1, B1, M1, N2, P2, Q2, R3b, R4b, X2, Y2), (A1, B1, M1, N2, P2, Q2, R3b, R4b, X2, Y3), (A1, B1, M1, N2, P2, Q2, R3b, R4c, X1, Y1), (A1, B1, M1, N2, P2, Q2, R3b, R4c, X1, Y2), (A1, B1, M1, N2, P2, Q2, R3b, R4c, X1, Y3), (A1, B1, M1, N2, P2, Q2, R3b, R4c, X2, Y1), (A1, B1, M1, N2, P2, Q2, R3b, R4c, X2, Y2), (A1, B1, M1, N2, P2, Q2, R3b, R4c, X2, Y3), (A1, B1, M2, N1, P1, Q1, R3a, R4a, X1, Y1), (A1, B1, M2, N1, P1, Q1, R3a, R4a, X1, Y2), (A1, B1, M2, N1, P1, Q1, R3a, R4a, X1, Y3), (A1, B1, M2, N1, P1, Q1, R3a, R4a, X2, Y1), (A1, B1, M2, N1, P1, Q1, R3a, R4a, X2, Y2), (A1, B1, M2, N1, P1, Q1, R3a, R4a, X2, Y3), (A1, B1, M2, N1, P1, Q1, R3a, R4b, X1, Y1), (A1, B1, M2, N1, P1, Q1, R3a, R4b, X1, Y2), (A1, B1, M2, N1, P1, Q1, R3a, R4b, X1, Y3), (A1, B1, M2, N1, P1, Q1, R3a, R4b, X2, Y1), (A1, B1, M2, N1, P1, Q1, R3a, R4b, X2, Y2), (A1, B1, M2, N1, P1, Q1, R3a, R4b, X2, Y3), (A1, B1, M2, N1, P1, Q1, R3a, R4c, X1, Y1), (A1, B1, M2, N1, P1, Q1, R3a, R4c, X1, Y2), (A1, B1, M2, N1, P1, Q1, R3a, R4c, X1, Y3), (A1, B1, M2, N1, P1, Q1, R3a, R4c, X2, Y1), (A1, B1, M2, N1, P1, Q1, R3a, R4c, X2, Y2), (A1, B1, M2, N1, P1, Q1, R3a, R4c, X2, Y3), (A1, B1, M2, N1, P1, Q1, R3b, R4a, X1, Y1), (A1, B1, M2, N1, P1, Q1, R3b, R4a, X1, Y2), (A1, B1, M2, N1, P1, Q1, R3b, R4a, X1, Y3), (A1, B1, M2, N1, P1, Q1, R3b, R4a, X2, Y1), (A1, B1, M2, N1, P1, Q1, R3b, R4a, X2, Y2), (A1, B1, M2, N1, P1, Q1, R3b, R4a, X2, Y3), (A1, B1, M2, N1, P1, Q1, R3b, R4b, X1, Y1), (A1, B1, M2, N1, P1, Q1, R3b, R4b, X1, Y2), (A1, B1, M2, N1, P1, Q1, R3b, R4b, X1, Y3), (A1, B1, M2, N1, P1, Q1, R3b, R4b, X2, Y1), (A1, B1, M2, N1, P1, Q1, R3b, R4b, X2, Y2), (A1, B1, M2, N1, P1, Q1, R3b, R4b, X2, Y3), (A1, B1, M2, N1, P1, Q1, R3b, R4c, X1, Y1), (A1, B1, M2, N1, P1, Q1, R3b, R4c, X1, Y2), (A1, B1, M2, N1, P1, Q1, R3b, R4c, X1, Y3), (A1, B1, M2, N1, P1, Q1, R3b, R4c, X2, Y1), (A1, B1, M2, N1, P1, Q1, R3b, R4c, X2, Y2), (A1, B1, M2, N1, P1, Q1, R3b, R4c, X2, Y3), (A1, B1, M2, N1, P1, Q2, R3a, R4a, X1, Y1), (A1, B1, M2, N1, P1, Q2, R3a, R4a, X1, Y2), (A1, B1, M2, N1, P1, Q2, R3a, R4a, X1, Y3), (A1, B1, M2, N1, P1, Q2, R3a, R4a, X2, Y1), (A1, B1, M2, N1, P1, Q2, R3a, R4a, X2, Y2), (A1, B1, M2, N1, P1, Q2, R3a, R4a, X2, Y3), (A1, B1, M2, N1, P1, Q2, R3a, R4b, X1, Y1), (A1, B1, M2, N1, P1, Q2, R3a, R4b, X1, Y2) (A1, B1, M2, N1, P1, Q2, R3a, R4b, X1, Y3), (A1, B1, M2, N1, P1, Q2, R3a, R4b, X2, Y1), (A1, B1, M2, N1, P1, Q2, R3a, R4b, X2, Y2), (A1, B1, M2, N1, P1, Q2, R3a, R4b, X2, Y3), (A1, B1, M2, N1, P1, Q2, R3a, R4c, X1, Y1), (A1, B1, M2, N1, P1, Q2, R3a, R4c, X1, Y2), (A1, B1, M2, N1, P1, Q2, R3a, R4c, X1, Y3), (A1, B1, M2, N1, P1, Q2, R3a, R4c, X2, Y1), (A1, B1, M2, N1, P1, Q2, R3a, R4c, X2, Y2), (A1, B1, M2, N1, P1, Q2, R3a, R4c, X2, Y3), (A1, B1, M2, N1, P1, Q2, R3b, R4a, X1, Y1), (A1, B1, M2, N1, P1, Q2, R3b, R4a, X1, Y2), (A1, B1, M2, N1, P1, Q2, R3b, R4a, X1, Y3), (A1, B1, M2, N1, P1, Q2, R3b, R4a, X2, Y1), (A1, B1, M2, N1, P1, Q2, R3b, R4a, X2, Y2), (A1, B1, M2, N1, P1, Q2, R3b, R4a, X2, Y3), (A1, B1, M2, N1, P1, Q2, R3b, R4b, X1, Y1), (A1, B1, M2, N1, P1, Q2, R3b, R4b, X1, Y2), (A1, B1, M2, N1, P1, Q2, R3b, R4b, X1, Y3), (A1, B1, M2, N1, P1, Q2, R3b, R4b, X2, Y1), (A1, B1, M2, N1, P1, Q2, R3b, R4b, X2, Y2), (A1, B1, M2, N1, P1, Q2, R3b, R4b, X2, Y3), (A1, B1, M2, N1, P1, Q2, R3b, R4c, X1, Y1), (A1, B1, M2, N1, P1, Q2, R3b, R4c, X1, Y2), (A1, B1, M2, N1, P1, Q2, R3b, R4c, X1, Y3), (A1, B1, M2, N1, P1, Q2, R3b, R4c, X2, Y1), (A1, B1, M2, N1, P1, Q2, R3b, R4c, X2, Y2), (A1, B1, M2, N1, P1, Q2, R3b, R4c, X2, Y3), (A1, B1, M2, N1, P2, Q1, R3a, R4a, X1, Y1), (A1, B1, M2, N1, P2, Q1, R3a, R4a, X1, Y2), (A1, B1, M2, N1, P2, Q1, R3a, R4a, X1, Y3), (A1, B1, M2, N1, P2, Q1, R3a, R4a, X2, Y1), (A1, B1, M2, N1, P2, Q1, R3a, R4a, X2, Y2), (A1, B1, M2, N1, P2, Q1, R3a, R4a, X2, Y3), (A1, B1, M2, N1, P2, Q1, R3a, R4b, X1, Y1), (A1, B1, M2, N1, P2, Q1, R3a, R4b, X1, Y2), (A1, B1, M2, N1, P2, Q1, R3a, R4b, X1, Y3), (A1, B1, M2, N1, P2, Q1, R3a, R4b, X2, Y1), (A1, B1, M2, N1, P2, Q1, R3a, R4b, X2, Y2), (A1, B1, M2, N1, P2, Q1, R3a, R4b, X2, Y3), (A1, B1, M2, N1, P2, Q1, R3a, R4c, X1, Y1), (A1, B1, M2, N1, P2, Q1, R3a, R4c, X1, Y2), (A1, B1, M2, N1, P2, Q1, R3a, R4c, X1, Y3), (A1, B1, M2, N1, P2, Q1, R3a, R4c, X2, Y1), (A1, B1, M2, N1, P2, Q1, R3a, R4c, X2, Y2), (A1, B1, M2, N1, P2, Q1, R3a, R4c, X2, Y3), (A1, B1, M2, N1, P2, Q1, R3b, R4a, X1, Y1), (A1, B1, M2, N1, P2, Q1, R3b, R4a, X1, Y2), (A1, B1, M2, N1, P2, Q1, R3b, R4a, X1, Y3), (A1, B1, M2, N1, P2, Q1, R3b, R4a, X2, Y1), (A1, B1, M2, N1, P2, Q1, R3b, R4a, X2, Y2), (A1, B1, M2, N1, P2, Q1, R3b, R4a, X2, Y3), (A1, B1, M2, N1, P2, Q1, R3b, R4b, X1, Y1), (A1, B1, M2, N1, P2, Q1, R3b, R4b, X1, Y2), (A1, B1, M2, N1, P2, Q1, R3b, R4b, X1, Y3), (A1, B1, M2, N1, P2, Q1, R3b, R4b, X2, Y1), (A1, B1, M2, N1, P2, Q1, R3b, R4b, X2, Y2), (A1, B1, M2, N1, P2, Q1, R3b, R4b, X2, Y3), (A1, B1, M2, N1, P2, Q1, R3b, R4c, X1, Y1), (A1, B1, M2, N1, P2, Q1, R3b, R4c, X1, Y2), (A1, B1, M2, N1, P2, Q1, R3b, R4c, X1, Y3), (A1, B1, M2, N1, P2, Q1, R3b, R4c, X2, Y1), (A1, B1, M2, N1, P2, Q1, R3b, R4c, X2, Y2), (A1, B1, M2, N1, P2, Q1, R3b, R4c, X2, Y3), (A1, B1, M2, N1, P2, Q2, R3a, R4a, X1, Y1), (A1, B1, M2, N1, P2, Q2, R3a, R4a, X1, Y2), (A1, B1, M2, N1, P2, Q2, R3a, R4a, X1, Y3), (A1, B1, M2, N1, P2, Q2, R3a, R4a, X2, Y1), (A1, B1, M2, N1, P2, Q2, R3a, R4a, X2, Y2), (A1, B1, M2, N1, P2, Q2, R3a, R4a, X2, Y3), (A1, B1, M2, N1, P2, Q2, R3a, R4b, X1, Y1), (A1, B1, M2, N1, P2, Q2, R3a, R4b, X1, Y2), (A1, B1, M2, N1, P2, Q2, R3a, R4b, X1, Y3), (A1, B1, M2, N1, P2, Q2, R3a, R4b, X2, Y1), (A1, B1, M2, N1, P2, Q2, R3a, R4b, X2, Y2), (A1, B1, M2, N1, P2, Q2, R3a, R4b, X2, Y3), (A1, B1, M2, N1, P2, Q2, R3a, R4c, X1, Y1), (A1, B1, M2, N1, P2, Q2, R3a, R4c, X1, Y2), (A1, B1, M2, N1, P2, Q2, R3a, R4c, X1, Y3), (A1, B1, M2, N1, P2, Q2, R3a, R4c, X2, Y1), (A1, B1, M2, N1, P2, Q2, R3a, R4c, X2, Y2), (A1, B1, M2, N1, P2, Q2, R3a, R4c, X2, Y3), (A1, B1, M2, N1, P2, Q2, R3b, R4a, X1, Y1), (A1, B1, M2, N1, P2, Q2, R3b, R4a, X1, Y2), (A1, B1, M2, N1, P2, Q2, R3b, R4a, X1, Y3), (A1, B1, M2, N1, P2, Q2, R3b, R4a, X2, Y1), (A1, B1, M2, N1, P2, Q2, R3b, R4a, X2, Y2), (A1, B1, M2, N1, P2, Q2, R3b, R4a, X2, Y3), (A1, B1, M2, N1, P2, Q2, R3b, R4b, X1, Y1), (A1, B1, M2, N1, P2, Q2, R3b, R4b, X1, Y2), (A1, B1, M2, N1, P2, Q2, R3b, R4b, X1, Y3), (A1, B1, M2, N1, P2, Q2, R3b, R4b, X2, Y1), (A1, B1, M2, N1, P2, Q2, R3b, R4b, X2, Y2), (A1, B1, M2, N1, P2, Q2, R3b, R4b, X2, Y3), (A1, B1, M2, N1, P2, Q2, R3b, R4c, X1, Y1), (A1, B1, M2, N1, P2, Q2, R3b, R4c, X1, Y2), (A1, B1, M2, N1, P2, Q2, R3b, R4c, X1, Y3), (A1, B1, M2, N1, P2, Q2, R3b, R4c, X2, Y1), (A1, B1, M2, N1, P2, Q2, R3b, R4c, X2, Y2), (A1, B1, M2, N1, P2, Q2, R3b, R4c, X2, Y3), (A1, B1, M2, N2, P1, Q1, R3a, R4a, X1, Y1), (A1, B1, M2, N2, P1, Q1, R3a, R4a, X1, Y2), (A1, B1, M2, N2, P1, Q1, R3a, R4a, X1, Y3), (A1, B1, M2, N2, P1, Q1, R3a, R4a, X2, Y1), (A1, B1, M2, N2, P1, Q1, R3a, R4a, X2, Y2), (A1, B1, M2, N2, P1, Q1, R3a, R4a, X2, Y3), (A1, B1, M2, N2, P1, Q1, R3a, R4b, X1, Y1), (A1, B1, M2, N2, P1, Q1, R3a, R4b, X1, Y2), (A1, B1, M2, N2, P1, Q1, R3a, R4b, X1, Y3), (A1, B1, M2, N2, P1, Q1, R3a, R4b, X2, Y1), (A1, B1, M2, N2, P1, Q1, R3a, R4b, X2, Y2), (A1, B1, M2, N2, P1, Q1, R3a, R4b, X2, Y3), (A1, B1, M2, N2, P1, Q1, R3a, R4c, X1, Y1), (A1, B1, M2, N2, P1, Q1, R3a, R4c, X1, Y2), (A1, B1, M2, N2, P1, Q1, R3a, R4c, X1, Y3), (A1, B1, M2, N2, P1, Q1, R3a, R4c, X2, Y1), (A1, B1, M2, N2, P1, Q1, R3a, R4c, X2, Y2), (A1, B1, M2, N2, P1, Q1, R3a, R4c, X2, Y3), (A1, B1, M2, N2, P1, Q1, R3b, R4a, X1, Y1), (A1, B1, M2, N2, P1, Q1, R3b, R4a, X1, Y2), (A1, B1, M2, N2, P1, Q1, R3b, R4a, X1, Y3), (A1, B1, M2, N2, P1, Q1, R3b, R4a, X2, Y1), (A1, B1, M2, N2, P1, Q1, R3b, R4a, X2, Y2), (A1, B1, M2, N2, P1, Q1, R3b, R4a, X2, Y3), (A1, B1, M2, N2, P1, Q1, R3b, R4b, X1, Y1), (A1, B1, M2, N2, P1, Q1, R3b, R4b, X1, Y2), (A1, B1, M2, N2, P1, Q1, R3b, R4b, X1, Y3), (A1, B1, M2, N2, P1, Q1, R3b, R4b, X2, Y1), (A1, B1, M2, N2, P1, Q1, R3b, R4b, X2, Y2), (A1, B1, M2, N2, P1, Q1, R3b, R4b, X2, Y3), (A1, B1, M2, N2, P1, Q1, R3b, R4c, X1, Y1), (A1, B1, M2, N2, P1, Q1, R3b, R4c, X1, Y2), (A1, B1, M2, N2, P1, Q1, R3b, R4c, X1, Y3), (A1, B1, M2, N2, P1, Q1, R3b, R4c, X2, Y1), (A1, B1, M2, N2, P1, Q1, R3b, R4c, X2, Y2), (A1, B1, M2, N2, P1, Q1, R3b, R4c, X2, Y3), (A1, B1, M2, N2, P1, Q2, R3a, R4a, X1, Y1), (A1, B1, M2, N2, P1, Q2, R3a, R4a, X1, Y2), (A1, B1, M2, N2, P1, Q2, R3a, R4a, X1, Y3), (A1, B1, M2, N2, P1, Q2, R3a, R4a, X2, Y1), (A1, B1, M2, N2, P1, Q2, R3a, R4a, X2, Y2), (A1, B1, M2, N2, P1, Q2, R3a, R4a, X2, Y3), (A1, B1, M2, N2, P1, Q2, R3a, R4b, X1, Y1), (A1, B1, M2, N2, P1, Q2, R3a, R4b, X1, Y2), (A1, B1, M2, N2, P1, Q2, R3a, R4b, X1, Y3), (A1, B1, M2, N2, P1, Q2, R3a, R4b, X2, Y1), (A1, B1, M2, N2, P1, Q2, R3a, R4b, X2, Y2), (A1, B1, M2, N2, P1, Q2, R3a, R4b, X2, Y3), (A1, B1, M2, N2, P1, Q2, R3a, R4c, X1, Y1), (A1, B1, M2, N2, P1, Q2, R3a, R4c, X1, Y2), (A1, B1, M2, N2, P1, Q2, R3a, R4c, X1, Y3), (A1, B1, M2, N2, P1, Q2, R3a, R4c, X2, Y1), (A1, B1, M2, N2, P1, Q2, R3a, R4c, X2, Y2), (A1, B1, M2, N2, P1, Q2, R3a, R4c, X2, Y3), (A1, B1, M2, N2, P1, Q2, R3b, R4a, X1, Y1), (A1, B1, M2, N2, P1, Q2, R3b, R4a, X1, Y2), (A1, B1, M2, N2, P1, Q2, R3b, R4a, X1, Y3), (A1, B1, M2, N2, P1, Q2, R3b, R4a, X2, Y1), (A1, B1, M2, N2, P1, Q2, R3b, R4a, X2, Y2), (A1, B1, M2, N2, P1, Q2, R3b, R4a, X2, Y3), (A1, B1, M2, N2, P1, Q2, R3b, R4b, X1, Y1), (A1, B1, M2, N2, P1, Q2, R3b, R4b, X1, Y2), (A1, B1, M2, N2, P1, Q2, R3b, R4b, X1, Y3), (A1, B1, M2, N2, P1, Q2, R3b, R4b, X2, Y1), (A1, B1, M2, N2, P1, Q2, R3b, R4b, X2, Y2), (A1, B1, M2, N2, P1, Q2, R3b, R4b, X2, Y3), (A1, B1, M2, N2, P1, Q2, R3b, R4c, X1, Y1), (A1, B1, M2, N2, P1, Q2, R3b, R4c, X1, Y2), (A1, B1, M2, N2, P1, Q2, R3b, R4c, X1, Y3), (A1, B1, M2, N2, P1, Q2, R3b, R4c, X2, Y1), (A1, B1, M2, N2, P1, Q2, R3b, R4c, X2, Y2), (A1, B1, M2, N2, P1, Q2, R3b, R4c, X2, Y3), (A1, B1, M2, N2, P2, Q1, R3a, R4a, X1, Y1), (A1, B1, M2, N2, P2, Q1, R3a, R4a, X1, Y2), (A1, B1, M2, N2, P2, Q1, R3a, R4a, X1, Y3), (A1, B1, M2, N2, P2, Q1, R3a, R4a, X2, Y1), (A1, B1, M2, N2, P2, Q1, R3a, R4a, X2, Y2), (A1, B1, M2, N2, P2, Q1, R3a, R4a, X2, Y3), (A1, B1, M2, N2, P2, Q1, R3a, R4b, X1, Y1), (A1, B1, M2, N2, P2, Q1, R3a, R4b, X1, Y2), (A1, B1, M2, N2, P2, Q1, R3a, R4b, X1, Y3), (A1, B1, M2, N2, P2, Q1, R3a, R4b, X2, Y1), (A1, B1, M2, N2, P2, Q1, R3a, R4b, X2, Y2), (A1, B1, M2, N2, P2, Q1, R3a, R4b, X2, Y3), (A1, B1, M2, N2, P2, Q1, R3a, R4c, X1, Y1), (A1, B1, M2, N2, P2, Q1, R3a, R4c, X1, Y2), (A1, B1, M2, N2, P2, Q1, R3a, R4c, X1, Y3), (A1, B1, M2, N2, P2, Q1, R3a, R4c, X2, Y1), (A1, B1, M2, N2, P2, Q1, R3a, R4c, X2, Y2), (A1, B1, M2, N2, P2, Q1, R3a, R4c, X2, Y3), (A1, B1, M2, N2, P2, Q1, R3b, R4a, X1, Y1), (A1, B1, M2, N2, P2, Q1, R3b, R4a, X1, Y2), (A1, B1, M2, N2, P2, Q1, R3b, R4a, X1, Y3), (A1, B1, M2, N2, P2, Q1, R3b, R4a, X2, Y1), (A1, B1, M2, N2, P2, Q1, R3b, R4a, X2, Y2), (A1, B1, M2, N2, P2, Q1, R3b, R4a, X2, Y3), (A1, B1, M2, N2, P2, Q1, R3b, R4b, X1, Y1), (A1, B1, M2, N2, P2, Q1, R3b, R4b, X1, Y2), (A1, B1, M2, N2, P2, Q1, R3b, R4b, X1, Y3), (A1, B1, M2, N2, P2, Q1, R3b, R4b, X2, Y1), (A1, B1, M2, N2, P2, Q1, R3b, R4b, X2, Y2), (A1, B1, M2, N2, P2, Q1, R3b, R4b, X2, Y3), (A1, B1, M2, N2, P2, Q1, R3b, R4c, X1, Y1), (A1, B1, M2, N2, P2, Q1, R3b, R4c, X1, Y2), (A1, B1, M2, N2, P2, Q1, R3b, R4c, X1, Y3), (A1, B1, M2, N2, P2, Q1, R3b, R4c, X2, Y1), (A1, B1, M2, N2, P2, Q1, R3b, R4c, X2, Y2), (A1, B1, M2, N2, P2, Q1, R3b, R4c, X2, Y3), (A1, B1, M2, N2, P2, Q2, R3a, R4a, X1, Y1), (A1, B1, M2, N2, P2, Q2, R3a, R4a, X1, Y2), (A1, B1, M2, N2, P2, Q2, R3a, R4a, X1, Y3), (A1, B1, M2, N2, P2, Q2, R3a, R4a, X2, Y1), (A1, B1, M2, N2, P2, Q2, R3a, R4a, X2, Y2), (A1, B1, M2, N2, P2, Q2, R3a, R4a, X2, Y3), (A1, B1, M2, N2, P2, Q2, R3a, R4b, X1, Y1), (A1, B1, M2, N2, P2, Q2, R3a, R4b, X1, Y2), (A1, B1, M2, N2, P2, Q2, R3a, R4b, X1, Y3), (A1, B1, M2, N2, P2, Q2, R3a, R4b, X2, Y1), (A1, B1, M2, N2, P2, Q2, R3a, R4b, X2, Y2), (A1, B1, M2, N2, P2, Q2, R3a, R4b, X2, Y3), (A1, B1, M2, N2, P2, Q2, R3a, R4c, X1, Y1), (A1, B1, M2, N2, P2, Q2, R3a, R4c, X1, Y2), (A1, B1, M2, N2, P2, Q2, R3a, R4c, X1, Y3), (A1, B1, M2, N2, P2, Q2, R3a, R4c, X2, Y1), (A1, B1, M2, N2, P2, Q2, R3a, R4c, X2, Y2), (A1, B1, M2, N2, P2, Q2, R3a, R4c, X2, Y3), (A1, B1, M2, N2, P2, Q2, R3b, R4a, X1, Y1), (A1, B1, M2, N2, P2, Q2, R3b, R4a, X1, Y2), (A1, B1, M2, N2, P2, Q2, R3b, R4a, X1, Y3), (A1, B1, M2, N2, P2, Q2, R3b, R4a, X2, Y1), (A1, B1, M2, N2, P2, Q2, R3b, R4a, X2, Y2), (A1, B1, M2, N2, P2, Q2, R3b, R4a, X2, Y3), (A1, B1, M2, N2, P2, Q2, R3b, R4b, X1, Y1), (A1, B1, M2, N2, P2, Q2, R3b, R4b, X1, Y2), (A1, B1, M2, N2, P2, Q2, R3b, R4b, X1, Y3), (A1, B1, M2, N2, P2, Q2, R3b, R4b, X2, Y1), (A1, B1, M2, N2, P2, Q2, R3b, R4b, X2, Y2), (A1, B1, M2, N2, P2, Q2, R3b, R4b, X2, Y3), (A1, B1, M2, N2, P2, Q2, R3b, R4c, X1, Y1), (A1, B1, M2, N2, P2, Q2, R3b, R4c, X1, Y2), (A1, B1, M2, N2, P2, Q2, R3b, R4c, X1, Y3), (A1, B1, M2, N2, P2, Q2, R3b, R4c, X2, Y1), (A1, B1, M2, N2, P2, Q2, R3b, R4c, X2, Y2), (A1, B1, M2, N2, P2, Q2, R3b, R4c, X2, Y3), (A1, B2, M1, N1, P1, Q1, R3a, R4a, X1, Y1), (A1, B2, M1, N1, P1, Q1, R3a, R4a, X1, Y2), (A1, B2, M1, N1, P1, Q1, R3a, R4a, X1, Y3), (A1, B2, M1, N1, P1, Q1, R3a, R4a, X2, Y1), (A1, B2, M1, N1, P1, Q1, R3a, R4a, X2, Y2), (A1, B2, M1, N1, P1, Q1, R3a, R4a, X2, Y3), (A1, B2, M1, N1, P1, Q1, R3a, R4b, X1, Y1), (A1, B2, M1, N1, P1, Q1, R3a, R4b, X1, Y2), (A1, B2, M1, N1, P1, Q1, R3a, R4b, X1, Y3), (A1, B2, M1, N1, P1, Q1, R3a, R4b, X2, Y1), (A1, B2, M1, N1, P1, Q1, R3a, R4b, X2, Y2), (A1, B2, M1, N1, P1, Q1, R3a, R4b, X2, Y3), (A1, B2, M1, N1, P1, Q1, R3a, R4c, X1, Y1), (A1, B2, M1, N1, P1, Q1, R3a, R4c, X1, Y3), (A1, B2, M1, N1, P1, Q1, R3a, R4c, X2, Y1), (A1, B2, M1, N1, P1, Q1, R3a, R4c, X2, Y2), (A1, B2, M1, N1, P1, Q1, R3a, R4c, X2, Y3), (A1, B2, M1, N1, P1, Q1, R3b, R4a, X1, Y1), (A1, B2, M1, N1, P1, Q1, R3b, R4a, X1, Y2), (A1, B2, M1, N1, P1, Q1, R3b, R4a, X1, Y3), (A1, B2, M1, N1, P1, Q1, R3b, R4a, X2, Y1), (A1, B2, M1, N1, P1, Q1, R3b, R4a, X2, Y2), (A1, B2, M1, N1, P1, Q1, R3b, R4a, X2, Y3), (A1, B2, M1, N1, P1, Q1, R3b, R4b, X1, Y1), (A1, B2, M1, N1, P1, Q1, R3b, R4b, X1, Y2), (A1, B2, M1, N1, P1, Q1, R3b, R4b, X1, Y3), (A1, B2, M1, N1, P1, Q1, R3b, R4b, X2, Y1), (A1, B2, M1, N1, P1, Q1, R3b, R4b, X2, Y2), (A1, B2, M1, N1, P1, Q1, R3b, R4b, X2, Y3), (A1, B2, M1, N1, P1, Q1, R3b, R4c, X1, Y1), (A1, B2, M1, N1, P1, Q1, R3b, R4c, X1, Y2), (A1, B2, M1, N1, P1, Q1, R3b, R4c, X1, Y3), (A1, B2, M1, N1, P1, Q1, R3b, R4c, X2, Y1), (A1, B2, M1, N1, P1, Q1, R3b, R4c, X2, Y2), (A1, B2, M1, N1, P1, Q1, R3b, R4c, X2, Y3), (A1, B2, M1, N1, P1, Q2, R3a, R4a, X1, Y1), (A1, B2, M1, N1, P1, Q2, R3a, R4a, X1, Y2), (A1, B2, M1, N1, P1, Q2, R3a, R4a, X1, Y3), (A1, B2, M1, N1, P1, Q2, R3a, R4a, X2, Y1), (A1, B2, M1, N1, P1, Q2, R3a, R4a, X2, Y2), (A1, B2, M1, N1, P1, Q2, R3a, R4a, X2, Y3), (A1, B2, M1, N1, P1, Q2, R3a, R4b, X1, Y1), (A1, B2, M1, N1, P1, Q2, R3a, R4b, X1, Y2), (A1, B2, M1, N1, P1, Q2, R3a, R4b, X1, Y3), (A1, B2, M1, N1, P1, Q2, R3a, R4b, X2, Y1), (A1, B2, M1, N1, P1, Q2, R3a, R4b, X2, Y2), (A1, B2, M1, N1, P1, Q2, R3a, R4b, X2, Y3), (A1, B2, M1, N1, P1, Q2, R3a, R4c, X1, Y1), B2, M1, N1, P1, Q2, R3a, R4c, X1, Y2), (A1, B2, M1, N1, P1, Q2, R3a, R4c, X1, Y3), (A1, B2, M1, N1, P1, Q2, R3a, R4c, X2, Y1), (A1, B2, M1, N1, P1, Q2, R3a, R4c, X2, Y2), (A1, B2, M1, N1, P1, Q2, R3a, R4c, X2, Y3), (A1, B2, M1, N1, P1, Q2, R3b, R4a, X1, Y1), (A1, B2, M1, N1, P1, Q2, R3b, R4a, X1, Y2), (A1, B2, M1, N1, P1, Q2, R3b, R4a, X1, Y3), (A1, B2, M1, N1, P1, Q2, R3b, R4a, X2, Y1), (A1, B2, M1, N1, P1, Q2, R3b, R4a, X2, Y2), (A1, B2, M1, N1, P1, Q2, R3b, R4a, X2, Y3), (A1, B2, M1, N1, P1, Q2, R3b, R4b, X1, Y1), (A1, B2, M1, N1, P1, Q2, R3b, R4b, X1, Y2), (A1, B2, M1, N1, P1, Q2, R3b, R4b, X1, Y3), (A1, B2, M1, N1, P1, Q2, R3b, R4b, X2, Y1) (A1, B2, M1, N1, P1, Q2, R3b, R4b, X2, Y2), (A1, B2, M1, N1, P1, Q2, R3b, R4b, X2, Y3), (A1, B2, M1, N1, P1, Q2, R3b, R4c, X1, Y1), (A1, B2, M1, N1, P1, Q2, R3b, R4c, X1, Y2), (A1, B2, M1, N1, P1, Q2, R3b, R4c, X1, Y3), (A1, B2, M1, N1, P1, Q2, R3b, R4c, X2, Y1), (A1, B2, M1, N1, P1, Q2, R3b, R4c, X2, Y2), (A1, B2, M1, N1, P1, Q2, R3b, R4c, X2, Y3), (A1, B2, M1, N1, P2, Q1, R3a, R4a, X1, Y1), (A1, B2, M1, N1, P2, Q1, R3a, R4a, X1, Y2), (A1, B2, M1, N1, P2, Q1, R3a, R4a, X1, Y3), (A1, B2, M1, N1, P2, Q1, R3a, R4a, X2, Y1), (A1, B2, M1, N1, P2, Q1, R3a, R4a, X2, Y2), (A1, B2, M1, N1, P2, Q1, R3a, R4a, X2, Y3), (A1, B2, M1, N1, P2, Q1, R3a, R4b, X1, Y1), (A1, B2, M1, N1, P2, Q1, R3a, R4b, X1, Y2), (A1, B2, M1, N1, P2, Q1, R3a, R4b, X1, Y3), (A1, B2, M1, N1, P2, Q1, R3a, R4b, X2, Y1), (A1, B2, M1, N1, P2, Q1, R3a, R4b, X2, Y2), (A1, B2, M1, N1, P2, Q1, R3a, R4b, X2, Y3) (A1, B2, M1, N1, P2, Q1, R3a, R4c, X1, Y1), (A1, B2, M1, N1, P2, Q1, R3a, R4c, X1, Y2), (A1, B2, M1, N1, P2, Q1, R3a, R4c, X1, Y3), (A1, B2, M1, N1, P2, Q1, R3a, R4c, X2, Y1), (A1, B2, M1, N1, P2, Q1, R3a, R4c, X2, Y2), (A1, B2, M1, N1, P2, Q1, R3a, R4c, X2, Y3), (A1, B2, M1, N1, P2, Q1, R3b, R4a, X1, Y1), (A1, B2, M1, N1, P2, Q1, R3b, R4a, X1, Y2), (A1, B2, M1, N1, P2, Q1, R3b, R4a, X1, Y3), (A1, B2, M1, N1, P2, Q1, R3b, R4a, X2, Y1), (A1, B2, M1, N1, P2, Q1, R3b, R4a, X2, Y2), (A1, B2, M1, N1, P2, Q1, R3b, R4a, X2, Y3), (A1, B2, M1, N1, P2, Q1, R3b, R4b, X1, Y1), (A1, B2, M1, N1, P2, Q1, R3b, R4b, X1, Y2), (A1, B2, M1, N1, P2, Q1, R3b, R4b, X1, Y3), (A1, B2, M1, N1, P2, Q1, R3b, R4b, X2, Y1), (A1, B2, M1, N1, P2, Q1, R3b, R4b, X2, Y2), (A1, B2, M1, N1, P2, Q1, R3b, R4b, X2, Y3), (A1, B2, M1, N1, P2, Q1, R3b, R4c, X1, Y1), (A1, B2, M1, N1, P2, Q1, R3b, R4c, X1, Y2), (A1, B2, M1, N1, P2, Q1, R3b, R4c, X1, Y3), (A1, B2, M1, N1, P2, Q1, R3b, R4c, X2, Y1), (A1, B2, M1, N1, P2, Q1, R3b, R4c, X2, Y2), (A1, B2, M1, N1, P2, Q1, R3b, R4c, X2, Y3), (A1, B2, M1, N1, P2, Q2, R3a, R4a, X1, Y1), (A1, B2, M1, N1, P2, Q2, R3a, R4a, X1, Y2), (A1, B2, M1, N1, P2, Q2, R3a, R4a, X1, Y3), (A1, B2, M1, N1, P2, Q2, R3a, R4a, X2, Y1), (A1, B2, M1, N1, P2, Q2, R3a, R4a, X2, Y2), (A1, B2, M1, N1, P2, Q2, R3a, R4a, X2, Y3), (A1, B2, M1, N1, P2, Q2, R3a, R4b, X1, Y1), (A1, B2, M1, N1, P2, Q2, R3a, R4b, X1, Y2), (A1, B2, M1, N1, P2, Q2, R3a, R4b, X1, Y3), (A1, B2, M1, N1, P2, Q2, R3a, R4b, X2, Y1), (A1, B2, M1, N1, P2, Q2, R3a, R4b, X2, Y2), (A1, B2, M1, N1, P2, Q2, R3a, R4b, X2, Y3), (A1, B2, M1, N1, P2, Q2, R3a, R4c, X1, Y1), (A1, B2, M1, N1, P2, Q2, R3a, R4c, X1, Y2), (A1, B2, M1, N1, P2, Q2, R3a, R4c, X1, Y3), (A1, B2, M1, N1, P2, Q2, R3a, R4c, X2, Y1), (A1, B2, M1, N1, P2, Q2, R3a, R4c, X2, Y2), (A1, B2, M1, N1, P2, Q2, R3a, R4c, X2, Y3), (A1, B2, M1, N1, P2, Q2, R3b, R4a, X1, Y1), (A1, B2, M1, N1, P2, Q2, R3b, R4a, X1, Y2), (A1, B2, N1, N1, P2, Q2, R3b, R4a, X1, Y3), (A1, B2, M1, N1, P2, Q2, R3b, R4a, X2, Y1), (A1, B2, M1, N1, P2, Q2, R3b, R4a, X2, Y2), (A1, B2, M1, N1, P2, Q2, R3b, R4a, X2, Y3), (A1, B2, M1, N1, P2, Q2, R3b, R4b, X1, Y1), (A1, B2, M1, N1, P2, Q2, R3b, R4b, X1, Y2), (A1, B2, M1, N1, P2, Q2, R3b, R4b, X1, Y3), (A1, B2, M1, N1, P2, Q2, R3b, R4b, X2, Y1), (A1, B2, M1, N1, P2, Q2, R3b, R4b, X2, Y2), (A1, B2, M1, N1, P2, Q2, R3b, R4b, X2, Y3), (A1, B2, M1, N1, P2, Q2, R3b, R4c, X1, Y1), (A1, B2, M1, N1, P2, Q2, R3b, R4c, X1, Y2), (A1, B2, M1, N1, P2, Q2, R3b, R4c, X1, Y3), (A1, B2, M1, N1, P2, Q2, R3b, R4c, X2, Y1), (A1, B2, M1, N1, P2, Q2, R3b, R4c, X2, Y2), (A1, B2, M1, N1, P2, Q2, R3b, R4c, X2, Y3), (A1, B2, M1, N2, P1, Q1, R3a, R4a, X1, Y1), (A1, B2, M1, N2, P1, Q1, R3a, R4a, X1, Y2), (A1, B2, M1, N2, P1, Q1, R3a, R4a, X1, Y3), (A1, B2, M1, N2, P1, Q1, R3a, R4a, X2, Y1), (A1, B2, M1, N2, P1, Q1, R3a, R4a, X2, Y2), (A1, B2, M1, N2, P1, Q1, R3a, R4a, X2, Y3), (A1, B2, M1, N2, P1, Q1, R3a, R4b, X1, Y1), (A1, B2, M1, N2, P1, Q1, R3a, R4b, X1, Y2), (A1, B2, M1, N2, P1, Q1, R3a, R4b, X1, Y3), (A1, B2, M1, N2, P1, Q1, R3a, R4b, X2, Y1), (A1, B2, M1, N2, P1, Q1, R3a, R4b, X2, Y2), (A1, B2, M1, N2, P1, Q1, R3a, R4b, X2, Y3), (A1, B2, M1, N2, P1, Q1, R3a, R4c, X1, Y1), (A1, B2, M1, N2, P1, Q1, R3a, R4c, X1, Y2), (A1, B2, M1, N2, P1, Q1, R3a, R4c, X1, Y3), (A1, B2, M1, N2, P1, Q1, R3a, R4c, X2, Y1), (A1, B2, M1, N2, P1, Q1, R3a, R4c, X2, Y2), (A1, B2, M1, N2, P1, Q1, R3a, R4c, X2, Y3), (A1, B2, M1, N2, P1, Q1, R3b, R4a, X1, Y1), (A1, B2, M1, N2, P1, Q1, R3b, R4a, X1, Y2), (A1, B2, M1, N2, P1, Q1, R3b, R4a, X1, Y3), (A1, B2, M1, N2, P1, Q1, R3b, R4a, X2, Y1), (A1, B2, M1, N2, P1, Q1, R3b, R4a, X2, Y2), (A1, B2, M1, N2, P1, Q1, R3b, R4a, X2, Y3), (A1, B2, M1, N2, P1, Q1, R3b, R4b, X1, Y1), (A1, B2, M1, N2, P1, Q1, R3b, R4b, X1, Y2), (A1, B2, M1, N2, P1, Q1, R3b, R4b, X1, Y3), (A1, B2, M1, N2, P1, Q1, R3b, R4b, X2, Y1), (A1, B2, M1, N2, P1, Q1, R3b, R4b, X2, Y2), (A1, B2, M1, N2, P1, Q1, R3b, R4b, X2, Y3), (A1, B2, M1, N2, P1, Q1, R3b, R4c, X1, Y1), (A1, B2, M1, N2, P1, Q1, R3b, R4c, X1, Y2), (A1, B2, M1, N2, P1, Q1, R3b, R4c, X1, Y3), (A1, B2, M1, N2, P1, Q1, R3b, R4c, X2, Y1), (A1, B2, M1, N2, P1, Q1, R3b, R4c, X2, Y2), (A1, B2, M1, N2, P1, Q1, R3b, R4c, X2, Y3), (A1, B2, M1, N2, P1, Q2, R3a, R4a, X1, Y1), (A1, B2, M1, N2, P1, Q2, R3a, R4a, X1, Y2), (A1, B2, M1, N2, P1, Q2, R3a, R4a, X1, Y3), (A1, B2, M1, N2, P1, Q2, R3a, R4a, X2, Y1), (A1, B2, M1, N2, P1, Q2, R3a, R4a, X2, Y2), (A1, B2, M1, N2, P1, Q2, R3a, R4a, X2, Y3), (A1, B2, M1, N2, P1, Q2, R3a, R4b, X1, Y1), (A1, B2, M1, N2, P1, Q2, R3a, R4b, X1, Y2), (A1, B2, M1, N2, P1, Q2, R3a, R4b, X1, Y3), (A1, B2, M1, N2, P1, Q2, R3a, R4b, X2, Y1), (A1, B2, M1, N2, P1, Q2, R3a, R4b, X2, Y2), (A1, B2, M1, N2, P1, Q2, R3a, R4b, X2, Y3), (A1, B2, M1, N2, P1, Q2, R3a, R4c, X1, Y1), (A1, B2, M1, N2, P1, Q2, R3a, R4c, X1, Y2), (A1, B2, M1, N2, P1, Q2, R3a, R4c, X1, Y3), (A1, B2, M1, N2, P1, Q2, R3a, R4c, X2, Y1), (A1, B2, M1, N2, P1, Q2, R3a, R4c, X2, Y2), (A1, B2, M1, N2, P1, Q2, R3a, R4c, X2, Y3), (A1, B2, M1, N2, P1, Q2, R3b, R4a, X1, Y1), (A1, B2, M1, N2, P1, Q2, R3b, R4a, X1, Y2), (A1, B2, M1, N2, P1, Q2, R3b, R4a, X1, Y3), (A1, B2, M1, N2, P1, Q2, R3b, R4a, X2, Y1), (A1, B2, M1, N2, P1, Q2, R3b, R4a, X2, Y2), (A1, B2, M1, N2, P1, Q2, R3b, R4a, X2, Y3), (A1, B2, M1, N2, P1, Q2, R3b, R4b, X1, Y1), (A1, B2, M1, N2, P1, Q2, R3b, R4b, X1, Y2), (A1, B2, M1, N2, P1, Q2, R3b, R4b, X1, Y3), (A1, B2, M1, N2, P1, Q2, R3b, R4b, X2, Y1), (A1, B2, M1, N2, P1, Q2, R3b, R4b, X2, Y2), (A1, B2, M1, N2, P1, Q2, R3b, R4b, X2, Y3), (A1, B2, M1, N2, P1, Q2, R3b, R4c, X1, Y1), (A1, B2, M1, N2, P1, Q2, R3b, R4c, X1, Y2), (A1, B2, M1, N2, P1, Q2, R3b, R4c, X1, Y3), (A1, B2, M1, N2, P1, Q2, R3b, R4c, X2, Y1), (A1, B2, M1, N2, P1, Q2, R3b, R4c, X2, Y2), (A1, B2, M1, N2, P1, Q2, R3b, R4c, X2, Y3), (A1, B2, M1, N2, P2, Q1, R3a, R4a, X1, Y1), (A1, B2, M1, N2, P2, Q1, R3a, R4a, X1, Y2), (A1, B2, M1, N2, P2, Q1, R3a, R4a, X1, Y3), (A1, B2, M1, N2, P2, Q1, R3a, R4a, X2, Y1), (A1, B2, M1, N2, P2, Q1, R3a, R4a, X2, Y2), (A1, B2, M1, N2, P2, Q1, R3a, R4a, X2, Y3), (A1, B2, M1, N2, P2, Q1, R3a, R4b, X1, Y1), (A1, B2, M1, N2, P2, Q1, R3a, R4b, X1, Y2), (A1, B2, M1, N2, P2, Q1, R3a, R4b, X1, Y3), (A1, B2, M1, N2, P2, Q1, R3a, R4b, X2, Y1), (A1, B2, M1, N2, P2, Q1, R3a, R4b, X2, Y2), (A1, B2, M1, N2, P2, Q1, R3a, R4b, X2, Y3), (A1, B2, M1, N2, P2, Q1, R3a, R4c, X1, Y1), (A1, B2, M1, N2, P2, Q1, R3a, R4c, X1, Y2), (A1, B2, M1, N2, P2, Q1, R3a, R4c, X1, Y3), (A1, B2, M1, N2, P2, Q1, R3a, R4c, X2, Y1), (A1, B2, M1, N2, P2, Q1, R3a, R4c, X2, Y2), (A1, B2, M1, N2, P2, Q1, R3a, R4c, X2, Y3), (A1, B2, M1, N2, P2, Q1, R3b, R4a, X1, Y1), (A1, B2, M1, N2, P2, Q1, R3b, R4a, X1, Y2), (A1, B2, M1, N2, P2, Q1, R3b, R4a, X1, Y3), (A1, B2, M1, N2, P2, Q1, R3b, R4a, X2, Y1), (A1, B2, M1, N2, P2, Q1, R3b, R4a, X2, Y2), (A1, B2, M1, N2, P2, Q1, R3b, R4a, X2, Y3), (A1, B2, M1, N2, P2, Q1, R3b, R4b, X1, Y1), (A1, B2, M1, N2, P2, Q1, R3b, R4b, X1, Y2), (A1, B2, M1, N2, P2, Q1, R3b, R4b, X1, Y3), (A1, B2, M1, N2, P2, Q1, R3b, R4b, X2, Y1), (A1, B2, M1, N2, P2, Q1, R3b, R4b, X2, Y2), (A1, B2, M1, N2, P2, Q1, R3b, R4b, X2, Y3), (A1, B2, M1, N2, P2, Q1, R3b, R4c, X1, Y1), (A1, B2, M1, N2, P2, Q1, R3b, R4c, X1, Y2), (A1, B2, M1, N2, P2, Q1, R3b, R4c, X1, Y3), (A1, B2, M1, N2, P2, Q1, R3b, R4c, X2, Y1), (A1, B2, M1, N2, P2, Q1, R3b, R4c, X2, Y2), (A1, B2, M1, N2, P2, Q1, R3b, R4c, X2, Y3), (A1, B2, M1, N2, P2, Q2, R3a, R4a, X1, Y1), (A1, B2, M1, N2, P2, Q2, R3a, R4a, X1, Y2), (A1, B2, M1, N2, P2, Q2, R3a, R4a, X1, Y3), (A1, B2, M1, N2, P2, Q2, R3a, R4a, X2, Y1), (A1, B2, M1, N2, P2, Q2, R3a, R4a, X2, Y2), (A1, B2, M1, N2, P2, Q2, R3a, R4a, X2, Y3), (A1, B2, M1, N2, P2, Q2, R3a, R4b, X1, Y1), (A1, B2, M1, N2, P2, Q2, R3a, R4b, X1, Y2), (A1, B2, M1, N2, P2, Q2, R3a, R4b, X1, Y3), (A1, B2, M1, N2, P2, Q2, R3a, R4b, X2, Y1), (A1, B2, M1, N2, P2, Q2, R3a, R4b, X2, Y2), (A1, B2, M1, N2, P2, Q2, R3a, R4b, X2, Y3), (A1, B2, M1, N2, P2, Q2, R3a, R4c, X1, Y1), (A1, B2, M1, N2, P2, Q2, R3a, R4c, X1, Y2), (A1, B2, M1, N2, P2, Q2, R3a, R4c, X1, Y3), (A1, B2, M1, N2, P2, Q2, R3a, R4c, X2, Y1), (A1, B2, M1, N2, P2, Q2, R3a, R4c, X2, Y2), (A1, B2, M1, N2, P2, Q2, R3a, R4c, X2, Y3), (A1, B2, M1, N2, P2, Q2, R3b, R4a, X1, Y1), (A1, B2, M1, N2, P2, Q2, R3b, R4a, X1, Y2), (A1, B2, M1, N2, P2, Q2, R3b, R4a, X1, Y3), (A1, B2, M1, N2, P2, Q2, R3b, R4a, X2, Y1), (A1, B2, M1, N2, P2, Q2, R3b, R4a, X2, Y2), (A1, B2, M1, N2, P2, Q2, R3b, R4a, X2, Y3), (A1, B2, M1, N2, P2, Q2, R3b, R4b, X1, Y1), (A1, B2, M1, N2, P2, Q2, R3b, R4b, X1, Y2), (A1, B2, M1, N2, P2, Q2, R3b, R4b, X1, Y3), (A1, B2, M1, N2, P2, Q2, R3b, R4b, X2, Y1), (A1, B2, M1, N2, P2, Q2, R3b, R4b, X2, Y2), (A1, B2, M1, N2, P2, Q2, R3b, R4b, X2, Y3), (A1, B2, M1, N2, P2, Q2, R3b, R4c, X1, Y1), (A1, B2, M1, N2, P2, Q2, R3b, R4c, X1, Y2), (A1, B2, M1, N2, P2, Q2, R3b, R4c, X1, Y3), (A1, B2, M1, N2, P2, Q2, R3b, R4c, X2, Y1), (A1, B2, M1, N2, P2, Q2, R3b, R4c, X2, Y2), (A1, B2, M1, N2, P2, Q2, R3b, R4c, X2, Y3), (A1, B2, M2, N1, P1, Q1, R3a, R4a, X1, Y1), (A1, B2, M2, N1, P1, Q1, R3a, R4a, X1, Y2), (A1, B2, M2, N1, P1, Q1, R3a, R4a, X1, Y3), (A1, B2, M2, N1, P1, Q1, R3a, R4a, X2, Y1), (A1, B2, M2, N1, P1, Q1, R3a, R4a, X2, Y2), (A1, B2, M2, N1, P1, Q1, R3a, R4a, X2, Y3), (A1, B2, M2, N1, P1, Q1, R3a, R4b, X1, Y1), (A1, B2, M2, N1, P1, Q1, R3a, R4b, X1, Y2), (A1, B2, M2, N1, P1, Q1, R3a, R4b, X1, Y3), (A1, B2, M2, N1, P1, Q1, R3a, R4b, X2, Y1), (A1, B2, M2, N1, P1, Q1, R3a, R4b, X2, Y2), (A1, B2, M2, N1, P1, Q1, R3a, R4b, X2, Y3), (A1, B2, M2, N1, P1, Q1, R3a, R4c, X1, Y1), (A1, B2, M2, N1, P1, Q1, R3a, R4c, X1, Y2), (A1, B2, M2, N1, P1, Q1, R3a, R4c, X1, Y3), (A1, B2, M2, N1, P1, Q1, R3a, R4c, X2, Y1), (A1, B2, M2, N1, P1, Q1, R3a, R4c, X2, Y2), (A1, B2, M2, N1, P1, Q1, R3a, R4c, X2, Y3), (A1, B2, M2, N1, P1, Q1, R3b, R4a, X1, Y1), (A1, B2, M2, N1, P1, Q1, R3b, R4a, X1, Y2), (A1, B2, M2, N1, P1, Q1, R3b, R4a, X1, Y3), (A1, B2, M2, N1, P1, Q1, R3b, R4a, X2, Y1), (A1, B2, M2, N1, P1, Q1, R3b, R4a, X2, Y2), (A1, B2, M2, N1, P1, Q1, R3b, R4a, X2, Y3), (A1, B2, M2, N1, P1, Q1, R3b, R4b, X1, Y1), (A1, B2, M2, N1, P1, Q1, R3b, R4b, X1, Y2), (A1, B2, M2, N1, P1, Q1, R3b, R4b, X1, Y3), (A1, B2, M2, N1, P1, Q1, R3b, R4b, X2, Y1), (A1, B2, M2, N1, P1, Q1, R3b, R4b, X2, Y2), (A1, B2, M2, N1, P1, Q1, R3b, R4b, X2, Y3), (A1, B2, M2, N1, P1, Q1, R3b, R4c, X1, Y1), (A1, B2, M2, N1, P1, Q1, R3b, R4c, X1, Y2), (A1, B2, M2, N1, P1, Q1, R3b, R4c, X1, Y3), (A1, B2, M2, N1, P1, Q1, R3b, R4c, X2, Y1), (A1, B2, M2, N1, P1, Q1, R3b, R4c, X2, Y2), (A1, B2, M2, N1, P1, Q1, R3b, R4c, X2, Y3), (A1, B2, M2, N1, P1, Q2, R3a, R4a, X1, Y1), (A1, B2, M2, N1, P1, Q2, R3a, R4a, X1, Y2), (A1, B2, M2, N1, P1, Q2, R3a, R4a, X1, Y3), (A1, B2, M2, N1, P1, Q2, R3a, R4a, X2, Y1), (A1, B2, M2, N1, P1, Q2, R3a, R4a, X2, Y2), (A1, B2, M2, N1, P1, Q2, R3a, R4a, X2, Y3), (A1, B2, M2, N1, P1, Q2, R3a, R4b, X1, Y1), (A1, B2, M2, N1, P1, Q2, R3a, R4b, X1, Y2), (A1, B2, M2, N1, P1, Q2, R3a, R4b, X1, Y3), (A1, B2, M2, N1, P1, Q2, R3a, R4b, X2, Y1), (A1, B2, M2, N1, P1, Q2, R3a, R4b, X2, Y2), (A1, B2, M2, N1, P1, Q2, R3a, R4b, X2, Y3), (A1, B2, M2, N1, P1, Q2, R3a, R4c, X1, Y1), (A1, B2, M2, N1, P1, Q2, R3a, R4c, X1, Y2), (A1, B2, M2, N1, P1, Q2, R3a, R4c, X1, Y3), (A1, B2, M2, N1, P1, Q2, R3a, R4c, X2, Y1), (A1, B2, M2, N1, P1, Q2, R3a, R4c, X2, Y2), (A1, B2, M2, N1, P1, Q2, R3a, R4c, X2, Y3), (A1, B2, M2, N1, P1, Q2, R3b, R4a, X1, Y1), (A1, B2, M2, N1, P1, Q2, R3b, R4a, X1, Y2), (A1, B2, M2, N1, P1, Q2, R3b, R4a, X1, Y3), (A1, B2, M2, N1, P1, Q2, R3b, R4a, X2, Y1), (A1, B2, M2, N1, P1, Q2, R3b, R4a, X2, Y2), (A1, B2, M2, N1, P1, Q2, R3b, R4a, X2, Y3), (A1, B2, M2, N1, P1, Q2, R3b, R4b, X1, Y1), (A1, B2, M2, N1, P1, Q2, R3b, R4b, X1, Y2), (A1, B2, M2, N1, P1, Q2, R3b, R4b, X1, Y3), (A1, B2, M2, N1, P1, Q2, R3b, R4b, X2, Y1), (A1, B2, M2, N1, P1, Q2, R3b, R4b, X2, Y2), (A1, B2, M2, N1, P1, Q2, R3b, R4b, X2, Y3), (A1, B2, M2, N1, P1, Q2, R3b, R4c, X1, Y1), (A1, B2, M2, N1, P1, Q2, R3b, R4c, X1, Y2), (A1, B2, M2, N1, P1, Q2, R3b, R4c, X1, Y3), (A1, B2, M2, N1, P1, Q2, R3b, R4c, X2, Y1), (A1, B2, M2, N1, P1, Q2, R3b, R4c, X2, Y2), (A1, B2, M2, N1, P1, Q2, R3b, R4c, X2, Y3), (A1, B2, M2, N1, P2, Q1, R3a, R4a, X1, Y1), (A1, B2, M2, N1, P2, Q1, R3a, R4a, X1, Y2), (A1, B2, M2, N1, P2, Q1, R3a, R4a, X1, Y3), (A1, B2, M2, N1, P2, Q1, R3a, R4a, X2, Y1), (A1, B2, M2, N1, P2, Q1, R3a, R4a, X2, Y2), (A1, B2, M2, N1, P2, Q1, R3a, R4a, X2, Y3), (A1, B2, M2, N1, P2, Q1, R3a, R4b, X1, Y1), (A1, B2, M2, N1, P2, Q1, R3a, R4b, X1, Y2), (A1, B2, M2, N1, P2, Q1, R3a, R4b, X1, Y3), (A1, B2, M2, N1, P2, Q1, R3a, R4b, X2, Y1), (A1, B2, M2, N1, P2, Q1, R3a, R4b, X2, Y2), (A1, B2, M2, N1, P2, Q1, R3a, R4b, X2, Y3), (A1, B2, M2, N1, P2, Q1, R3a, R4c, X1, Y1), (A1, B2, M2, N1, P2, Q1, R3a, R4c, X1, Y2), (A1, B2, M2, N1, P2, Q1, R3a, R4c, X1, Y3), (A1, B2, M2, N1, P2, Q1, R3a, R4c, X2, Y1), (A1, B2, M2, N1, P2, Q1, R3a, R4c, X2, Y2), (A1, B2, M2, N1, P2, Q1, R3a, R4c, X2, Y3), (A1, B2, M2, N1, P2, Q1, R3b, R4a, X1, Y1), (A1, B2, M2, N1, P2, Q1, R3b, R4a, X1, Y2), (A1, B2, M2, N1, P2, Q1, R3b, R4a, X1, Y3), (A1, B2, M2, N1, P2, Q1, R3b, R4a, X2, Y1), (A1, B2, M2, N1, P2, Q1, R3b, R4a, X2, Y2), (A1, B2, M2, N1, P2, Q1, R3b, R4a, X2, Y3), (A1, B2, M2, N1, P2, Q1, R3b, R4b, X1, Y1), (A1, B2, M2, N1, P2, Q1, R3b, R4b, X1, Y2), (A1, B2, M2, N1, P2, Q1, R3b, R4b, X1, Y3), (A1, B2, M2, N1, P2, Q1, R3b, R4b, X2, Y1), (A1, B2, M2, N1, P2, Q1, R3b, R4b, X2, Y2), (A1, B2, M2, N1, P2, Q1, R3b, R4b, X2, Y3), (A1, B2, M2, N1, P2, Q1, R3b, R4c, X1, Y1), (A1, B2, M2, N1, P2, Q1, R3b, R4c, X1, Y2), (A1, B2, M2, N1, P2, Q1, R3b, R4c, X1, Y3), (A1, B2, M2, N1, P2, Q1, R3b, R4c, X2, Y1), (A1, B2, M2, N1, P2, Q1, R3b, R4c, X2, Y2), (A1, B2, M2, N1, P2, Q1, R3b, R4c, X2, Y3), (A1, B2, M2, N1, P2, Q2, R3a, R4a, X1, Y1), (A1, B2, M2, N1, P2, Q2, R3a, R4a, X1, Y2), (A1, B2, M2, N1, P2, Q2, R3a, R4a, X1, Y3), (A1, B2, M2, N1, P2, Q2, R3a, R4a, X2, Y1), (A1, B2, M2, N1, P2, Q2, R3a, R4a, X2, Y2), (A1, B2, M2, N1, P2, Q2, R3a, R4a, X2, Y3), (A1, B2, M2, N1, P2, Q2, R3a, R4b, X1, Y1), (A1, B2, M2, N1, P2, Q2, R3a, R4b, X1, Y2), (A1, B2, M2, N1, P2, Q2, R3a, R4b, X1, Y3), (A1, B2, M2, N1, P2, Q2, R3a, R4b, X2, Y1), (A1, B2, M2, N1, P2, Q2, R3a, R4b, X2, Y2), (A1, B2, M2, N1, P2, Q2, R3a, R4b, X2, Y3), (A1, B2, M2, N1, P2, Q2, R3a, R4c, X1, Y1), (A1, B2, M2, N1, P2, Q2, R3a, R4c, X1, Y2), (A1, B2, M2, N1, P2, Q2, R3a, R4c, X1, Y3), (A1, B2, M2, N1, P2, Q2, R3a, R4c, X2, Y1), (A1, B2, M2, N1, P2, Q2, R3a, R4c, X2, Y2), (A1, B2, M2, N1, P2, Q2, R3a, R4c, X2, Y3), (A1, B2, M2, N1, P2, Q2, R3b, R4a, X1, Y1), (A1, B2, M2, N1, P2, Q2, R3b, R4a, X1, Y2), (A1, B2, M2, N1, P2, Q2, R3b, R4a, X1, Y3), (A1, B2, M2, N1, P2, Q2, R3b, R4a, X2, Y1), (A1, B2, M2, N1, P2, Q2, R3b, R4a, X2, Y2), (A1, B2, M2, N1, P2, Q2, R3b, R4a, X2, Y3), (A1, B2, M2, N1, P2, Q2, R3b, R4b, X1, Y1), (A1, B2, M2, N1, P2, Q2, R3b, R4b, X1, Y2), (A1, B2, M2, N1, P2, Q2, R3b, R4b, X1, Y3), (A1, B2, M2, N1, P2, Q2, R3b, R4b, X2, Y1), (A1, B2, M2, N1, P2, Q2, R3b, R4b, X2, Y2), (A1, B2, M2, N1, P2, Q2, R3b, R4b, X2, Y3), (A1, B2, M2, N1, P2, Q2, R3b, R4c, X1, Y1), (A1, B2, M2, N1, P2, Q2, R3b, R4c, X1, Y2), (A1, B2, M2, N1, P2, Q2, R3b, R4c, X1, Y3), (A1, B2, M2, N1, P2, Q2, R3b, R4c, X2, Y1), (A1, B2, M2, N1, P2, Q2, R3b, R4c, X2, Y2), (A1, B2, M2, N1, P2, Q2, R3b, R4c, X2, Y3), (A1, B2, M2, N2, P1, Q1, R3a, R4a, X1, Y1), (A1, B2, M2, N2, P1, Q1, R3a, R4a, X1, Y2), (A1, B2, M2, N2, P1, Q1, R3a, R4a, X1, Y3), (A1, B2, M2, N2, P1, Q1, R3a, R4a, X2, Y1), (A1, B2, M2, N2, P1, Q1, R3a, R4a, X2, Y2), (A1, B2, M2, N2, P1, Q1, R3a, R4a, X2, Y3), (A1, B2, M2, N2, P1, Q1, R3a, R4b, X1, Y1), (A1, B2, M2, N2, P1, Q1, R3a, R4b, X1, Y2), (A1, B2, M2, N2, P1, Q1, R3a, R4b, X1, Y3), (A1, B2, M2, N2, P1, Q1, R3a, R4b, X2, Y1), (A1, B2, M2, N2, P1, Q1, R3a, R4b, X2, Y2), (A1, B2, M2, N2, P1, Q1, R3a, R4b, X2, Y3), (A1, B2, M2, N2, P1, Q1, R3a, R4c, X1, Y1), (A1, B2, M2, N2, P1, Q1, R3a, R4c, X1, Y2), (A1, B2, M2, N2, P1, Q1, R3a, R4c, X1, Y3), (A1, B2, M2, N2, P1, Q1, R3a, R4c, X2, Y1), (A1, B2, M2, N2, P1, Q1, R3a, R4c, X2, Y2), (A1, B2, M2, N2, P1, Q1, R3a, R4c, X2, Y3), (A1, B2, M2, N2, P1, Q1, R3b, R4a, X1, Y1), (A1, B2, M2, N2, P1, Q1, R3b, R4a, X1, Y2), (A1, B2, M2, N2, P1, Q1, R3b, R4a, X1, Y3), (A1, B2, M2, N2, P1, Q1, R3b, R4a, X2, Y1), (A1, B2, M2, N2, P1, Q1, R3b, R4a, X2, Y2), (A1, B2, M2, N2, P1, Q1, R3b, R4a, X2, Y3), (A1, B2, M2, N2, P1, Q1, R3b, R4b, X1, Y1), (A1, B2, M2, N2, P1, Q1, R3b, R4b, X1, Y2), (A1, B2, M2, N2, P1, Q1, R3b, R4b, X1, Y3), (A1, B2, M2, N2, P1, Q1, R3b, R4b, X2, Y1), (A1, B2, M2, N2, P1, Q1, R3b, R4b, X2, Y2), (A1, B2, M2, N2, P1, Q1, R3b, R4b, X2, Y3), (A1, B2, M2, N2, P1, Q1, R3b, R4c, X1, Y1), (A1, B2, M2, N2, P1, Q1, R3b, R4c, X1, Y2), (A1, B2, M2, N2, P1, Q1, R3b, R4c, X1, Y3), (A1, B2, M2, N2, P1, Q1, R3b, R4c, X2, Y1), (A1, B2, M2, N2, P1, Q1, R3b, R4c, X2, Y2), (A1, B2, M2, N2, P1, Q1, R3b, R4c, X2, Y3), (A1, B2, M2, N2, P1, Q2, R3a, R4a, X1, Y1), (A1, B2, M2, N2, P1, Q2, R3a, R4a, X1, Y2), (A1, B2, M2, N2, P1, Q2, R3a, R4a, X1, Y3) (A1, B2, M2, N2, P1, Q2, R3a, R4a, X2, Y1), (A1, B2, M2, N2, P1, Q2, R3a, R4a, X2, Y2), (A1, B2, M2, N2, P1, Q2, R3a, R4a, X2, Y3), (A1, B2, M2, N2, P1, Q2, R3a, R4b, X1, Y1), (A1, B2, M2, N2, P1, Q2, R3a, R4b, X1, Y2), (A1, B2, M2, N2, P1, Q2, R3a, R4b, X1, Y3), (A1, B2, M2, N2, P1, Q2, R3a, R4b, X2, Y1), (A1, B2, M2, N2, P1, Q2, R3a, R4b, X2, Y2), (A1, B2, M2, N2, P1, Q2, R3a, R4b, X2, Y3), (A1, B2, M2, N2, P1, Q2, R3a, R4c, X1, Y1), (A1, B2, M2, N2, P1, Q2, R3a, R4c, X1, Y2), (A1, B2, M2, N2, P1, Q2, R3a, R4c, X1, Y3), (A1, B2, M2, N2, P1, Q2, R3a, R4c, X2, Y1), (A1, B2, M2, N2, P1, Q2, R3a, R4c, X2, Y2), (A1, B2, M2, N2, P1, Q2, R3a, R4c, X2, Y3), (A1, B2, M2, N2, P1, Q2, R3b, R4a, X1, Y1), (A1, B2, M2, N2, P1, Q2, R3b, R4a, X1, Y2), (A1, B2, M2, N2, P1, Q2, R3b, R4a, X1, Y3), (A1, B2, M2, N2, P1, Q2, R3b, R4a, X2, Y1), (A1, B2, M2, N2, P1, Q2, R3b, R4a, X2, Y2), (A1, B2, M2, N2, P1, Q2, R3b, R4a, X2, Y3), (A1, B2, M2, N2, P1, Q2, R3b, R4b, X1, Y1), (A1, B2, M2, N2, P1, Q2, R3b, R4b, X1, Y2), (A1, B2, M2, N2, P1, Q2, R3b, R4b, X1, Y3), (A1, B2, M2, N2, P1, Q2, R3b, R4b, X2, Y1), (A1, B2, M2, N2, P1, Q2, R3b, R4b, X2, Y2), (A1, B2, M2, N2, P1, Q2, R3b, R4b, X2, Y3), (A1, B2, M2, N2, P1, Q2, R3b, R4c, X1, Y1), (A1, B2, M2, N2, P1, Q2, R3b, R4c, X1, Y2), (A1, B2, M2, N2, P1, Q2, R3b, R4c, X1, Y3), (A1, B2, M2, N2, P1, Q2, R3b, R4c, X2, Y1), (A1, B2, M2, N2, P1, Q2, R3b, R4c, X2, Y2), (A1, B2, M2, N2, P1, Q2, R3b, R4c, X2, Y3), (A1, B2, M2, N2, P2, Q1, R3a, R4a, X1, Y1), (A1, B2, M2, N2, P2, Q1, R3a, R4a, X1, Y2), (A1, B2, M2, N2, P2, Q1, R3a, R4a, X1, Y3), (A1, B2, M2, N2, P2, Q1, R3a, R4a, X2, Y1), (A1, B2, M2, N2, P2, Q1, R3a, R4a, X2, Y2), (A1, B2, M2, N2, P2, Q1, R3a, R4a, X2, Y3), (A1, B2, M2, N2, P2, Q1, R3a, R4b, X1, Y1), (A1, B2, M2, N2, P2, Q1, R3a, R4b, X1, Y2), (A1, B2, M2, N2, P2, Q1, R3a, R4b, X1, Y3), (A1, B2, M2, N2, P2, Q1, R3a, R4b, X2, Y1), (A1, B2, M2, N2, P2, Q1, R3a, R4b, X2, Y2), (A1, B2, M2, N2, P2, Q1, R3a, R4b, X2, Y3), (A1, B2, M2, N2, P2, Q1, R3a, R4c, X1, Y1), (A1, B2, M2, N2, P2, Q1, R3a, R4c, X1, Y2), (A1, B2, M2, N2, P2, Q1, R3a, R4c, X1, Y3), (A1, B2, M2, N2, P2, Q1, R3a, R4c, X2, Y1), (A1, B2, M2, N2, P2, Q1, R3a, R4c, X2, Y2), (A1, B2, M2, N2, P2, Q1, R3a, R4c, X2, Y3), (A1, B2, M2, N2, P2, Q1, R3b, R4a, X1, Y1), (A1, B2, M2, N2, P2, Q1, R3b, R4a, X1, Y2), (A1, B2, M2, N2, P2, Q1, R3b, R4a, X1, Y3), (A1, B2, M2, N2, P2, Q1, R3b, R4a, X2, Y1), (A1, B2, M2, N2, P2, Q1, R3b, R4a, X2, Y2), (A1, B2, M2, N2, P2, Q1, R3b, R4a, X2, Y3), (A1, B2, M2, N2, P2, Q1, R3b, R4b, X1, Y1), (A1, B2, M2, N2, P2, Q1, R3b, R4b, X1, Y2), (A1, B2, M2, N2, P2, Q1, R3b, R4b, X1, Y3), (A1, B2, M2, N2, P2, Q1, R3b, R4b, X2, Y1), (A1, B2, M2, N2, P2, Q1, R3b, R4b, X2, Y2), (A1, B2, M2, N2, P2, Q1, R3b, R4b, X2, Y3), (A1, B2, M2, N2, P2, Q1, R3b, R4c, X1, Y1), (A1, B2, M2, N2, P2, Q1, R3b, R4c, X1, Y2), (A1, B2, M2, N2, P2, Q1, R3b, R4c, X1, Y3), (A1, B2, M2, N2, P2, Q1, R3b, R4c, X2, Y1), (A1, B2, M2, N2, P2, Q1, R3b, R4c, X2, Y2), (A1, B2, M2, N2, P2, Q1, R3b, R4c, X2, Y3), (A1, B2, M2, N2, P2, Q2, R3a, R4a, X1, Y1), (A1, B2, M2, N2, P2, Q2, R3a, R4a, X1, Y2), (A1, B2, M2, N2, P2, Q2, R3a, R4a, X1, Y3), (A1, B2, M2, N2, P2, Q2, R3a, R4a, X2, Y1), (A1, B2, M2, N2, P2, Q2, R3a, R4a, X2, Y2), (A1, B2, M2, N2, P2, Q2, R3a, R4a, X2, Y3), (A1, B2, M2, N2, P2, Q2, R3a, R4b, X1, Y1), (A1, B2, M2, N2, P2, Q2, R3a, R4b, X1, Y3), (A1, B2, M2, N2, P2, Q2, R3a, R4b, X2, Y1), (A1, B2, M2, N2, P2, Q2, R3a, R4b, X2, Y2), (A1, B2, M2, N2, P2, Q2, R3a, R4b, X2, Y3), (A1, B2, M2, N2, P2, Q2, R3a, R4c, X1, Y1), (A1, B2, M2, N2, P2, Q2, R3a, R4c, X1, Y2), (A1, B2, M2, N2, P2, Q2, R3a, R4c, X1, Y3), (A1, B2, M2, N2, P2, Q2, R3a, R4c, X2, Y1), (A1, B2, M2, N2, P2, Q2, R3a, R4c, X2, Y2), (A1, B2, M2, N2, P2, Q2, R3a, R4c, X2, Y3), (A1, B2, M2, N2, P2, Q2, R3b, R4a, X1, Y1), (A1, B2, M2, N2, P2, Q2, R3b, R4a, X1, Y2), (A1, B2, M2, N2, P2, Q2, R3b, R4a, X1, Y3), (A1, B2, M2, N2, P2, Q2, R3b, R4a, X2, Y1), (A1, B2, M2, N2, P2, Q2, R3b, R4a, X2, Y2), (A1, B2, M2, N2, P2, Q2, R3b, R4a, X2, Y3), (A1, B2, M2, N2, P2, Q2, R3b, R4b, X1, Y1), (A1, B2, M2, N2, P2, Q2, R3b, R4b, X1, Y2), (A1, B2, M2, N2, P2, Q2, R3b, R4b, X1, Y3), (A1, B2, M2, N2, P2, Q2, R3b, R4b, X2, Y1), (A1, B2, M2, N2, P2, Q2, R3b, R4b, X2, Y2), (A1, B2, M2, N2, P2, Q2, R3b, R4b, X2, Y3), (A1, B2, M2, N2, P2, Q2, R3b, R4c, X1, Y1), (A1, B2, M2, N2, P2, Q2, R3b, R4c, X1, Y2), (A1, B2, M2, N2, P2, Q2, R3b, R4c, X1, Y3), (A1, B2, M2, N2, P2, Q2, R3b, R4c, X2, Y1), (A1, B2, M2, N2, P2, Q2, R3b, R4c, X2, Y2), (A1, B2, M2, N2, P2, Q2, R3b, R4c, X2, Y3), (A1, B3, M1, N1, P1, Q1, R3a, R4a, X1, Y1), (A1, B3, M1, N1, P1, Q1, R3a, R4a, X1, Y2), (A1, B3, M1, N1, P1, Q1, R3a, R4a, X1, Y3), (A1, B3, M1, N1, P1, Q1, R3a, R4a, X2, Y1), (A1, B3, M1, N1, P1, Q1, R3a, R4a, X2, Y2), (A1, B3, M1, N1, P1, Q1, R3a, R4a, X2, Y3), (A1, B3, M1, N1, P1, Q1, R3a, R4b, X1, Y1), (A1, B3, M1, N1, P1, Q1, R3a, R4b, X1, Y2), (A1, B3, M1, N1, P1, Q1, R3a, R4b, X1, Y3), (A1, B3, M1, N1, P1, Q1, R3a, R4b, X2, Y1), (A1, B3, M1, N1, P1, Q1, R3a, R4b, X2, Y2), (A1, B3, M1, N1, P1, Q1, R3a, R4b, X2, Y3), (A1, B3, M1, N1, P1, Q1, R3a, R4c, X1, Y1), (A1, B3, M1, N1, P1, Q1, R3a, R4c, X1, Y2), (A1, B3, M1, N1, P1, Q1, R3a, R4c, X1, Y3), (A1, B3, M1, N1, P1, Q1, R3a, R4c, X2, Y1), (A1, B3, M1, N1, P1, Q1, R3a, R4c, X2, Y2), (A1, B3, M1, N1, P1, Q1, R3a, R4c, X2, Y3), (A1, B3, M1, N1, P1, Q1, R3b, R4a, X1, Y1), (A1, B3, M1, N1, P1, Q1, R3b, R4a, X1, Y2), (A1, B3, M1, N1, P1, Q1, R3b, R4a, X1, Y3), (A1, B3, M1, N1, P1, Q1, R3b, R4a, X2, Y1), (A1, B3, M1, N1, P1, Q1, R3b, R4a, X2, Y2), (A1, B3, M1, N1, P1, Q1, R3b, R4a, X2, Y3), (A1, B3, M1, N1, P1, Q1, R3b, R4b, X1, Y1), (A1, B3, M1, N1, P1, Q1, R3b, R4b, X1, Y2), (A1, B3, M1, N1, P1, Q1, R3b, R4b, X1, Y3), (A1, B3, M1, N1, P1, Q1, R3b, R4b, X2, Y1), (A1, B3, M1, N1, P1, Q1, R3b, R4b, X2, Y2), (A1, B3, M1, N1, P1, Q1, R3b, R4b, X2, Y3), (A1, B3, M1, N1, P1, Q1, R3b, R4c, X1, Y1), (A1, B3, M1, N1, P1, Q1, R3b, R4c, X1, Y2), (A1, B3, M1, N1, P1, Q1, R3b, R4c, X1, Y3), (A1, B3, M1, N1, P1, Q1, R3b, R4c, X2, Y1), (A1, B3, M1, N1, P1, Q1, R3b, R4c, X2, Y2), (A1, B3, M1, N1, P1, Q1, R3b, R4c, X2, Y3), (A1, B3, M1, N1, P1, Q2, R3a, R4a, X1, Y1), (A1, B3, M1, N1, P1, Q2, R3a, R4a, X1, Y2), (A1, B3, M1, N1, P1, Q2, R3a, R4a, X1, Y3), (A1, B3, M1, N1, P1, Q2, R3a, R4a, X2, Y1), (A1, B3, M1, N1, P1, Q2, R3a, R4a, X2, Y2), (A1, B3, M1, N1, P1, Q2, R3a, R4a, X2, Y3), (A1, B3, M1, N1, P1, Q2, R3a, R4b, X1, Y1), (A1, B3, M1, N1, P1, Q2, R3a, R4b, X1, Y2), (A1, B3, M1, N1, P1, Q2, R3a, R4b, X1, Y3), (A1, B3, M1, N1, P1, Q2, R3a, R4b, X2, Y1), (A1, B3, M1, N1, P1, Q2, R3a, R4b, X2, Y2), (A1, B3, M1, N1, P1, Q2, R3a, R4b, X2, Y3), (A1, B3, M1, N1, P1, Q2, R3a, R4c, X1, Y1), (A1, B3, M1, N1, P1, Q2, R3a, R4c, X1, Y2), (A1, B3, M1, N1, P1, Q2, R3a, R4c, X1, Y3), (A1, B3, M1, N1, P1, Q2, R3a, R4c, X2, Y1), (A1, B3, M1, N1, P1, Q2, R3a, R4c, X2, Y2), (A1, B3, M1, N1, P1, Q2, R3a, R4c, X2, Y3), (A1, B3, M1, N1, P1, Q2, R3b, R4a, X1, Y1), (A1, B3, M1, N1, P1, Q2, R3b, R4a, X1, Y2), (A1, B3, M1, N1, P1, Q2, R3b, R4a, X1, Y3), (A1, B3, M1, N1, P1, Q2, R3b, R4a, X2, Y1), (A1, B3, M1, N1, P1, Q2, R3b, R4a, X2, Y2), (A1, B3, M1, N1, P1, Q2, R3b, R4a, X2, Y3), (A1, B3, M1, N1, P1, Q2, R3b, R4b, X1, Y1), (A1, B3, M1, N1, P1, Q2, R3b, R4b, X1, Y2), (A1, B3, M1, N1, P1, Q2, R3b, R4b, X1, Y3), (A1, B3, M1, N1, P1, Q2, R3b, R4b, X2, Y1), (A1, B3, M1, N1, P1, Q2, R3b, R4b, X2, Y2), (A1, B3, M1, N1, P1, Q2, R3b, R4b, X2, Y3), (A1, B3, M1, N1, P1, Q2, R3b, R4c, X1, Y1), (A1, B3, M1, N1, P1, Q2, R3b, R4c, X1, Y2), (A1, B3, M1, N1, P1, Q2, R3b, R4c, X1, Y3), (A1, B3, M1, N1, P1, Q2, R3b, R4c, X2, Y1), (A1, B3, M1, N1, P1, Q2, R3b, R4c, X2, Y2), (A1, B3, M1, N1, P1, Q2, R3b, R4c, X2, Y3), (A1, B3, M1, N1, P2, Q1, R3a, R4a, X1, Y1), (A1, B3, M1, N1, P2, Q1, R3a, R4a, X1, Y2), (A1, B3, M1, N1, P2, Q1, R3a, R4a, X1, Y3), (A1, B3, M1, N1, P2, Q1, R3a, R4a, X2, Y1), (A1, B3, M1, N1, P2, Q1, R3a, R4a, X2, Y2), (A1, B3, M1, N1, P2, Q1, R3a, R4a, X2, Y3), (A1, B3, M1, N1, P2, Q1, R3a, R4b, X1, Y1), (A1, B3, M1, N1, P2, Q1, R3a, R4b, X1, Y2), (A1, B3, M1, N1, P2, Q1, R3a, R4b, X1, Y3), (A1, B3, M1, N1, P2, Q1, R3a, R4b, X2, Y1), (A1, B3, M1, N1, P2, Q1, R3a, R4b, X2, Y2), (A1, B3, M1, N1, P2, Q1, R3a, R4b, X2, Y3), (A1, B3, M1, N1, P2, Q1, R3a, R4c, X1, Y1), (A1, B3, M1, N1, P2, Q1, R3a, R4c, X1, Y2), (A1, B3, M1, N1, P2, Q1, R3a, R4c, X1, Y3),
(A1, B3, M1, N1, P2, Q1, R3a, R4c, X2, Y1), (A1, B3, M1, N1, P2, Q1, R3a, R4c, X2, Y2), (A1, B3, M1, N1, P2, Q1, R3a, R4c, X2, Y3), (A1, B3, M1, N1, P2, Q1, R3b, R4a, X1, Y1), (A1, B3, M1, N1, P2, Q1, R3b, R4a, X1, Y2), (A1, B3, M1, N1, P2, Q1, R3b, R4a, X1, Y3), (A1, B3, M1, N1, P2, Q1, R3b, R4a, X2, Y1), (A1, B3, M1, N1, P2, Q1, R3b, R4a, X2, Y2), (A1, B3, M1, N1, P2, Q1, R3b, R4a, X2, Y3), (A1, B3, M1, N1, P2, Q1, R3b, R4b, X1, Y1), (A1, B3, M1, N1, P2, Q1, R3b, R4b, X1, Y2), (A1, B3, M1, N1, P2, Q1, R3b, R4b, X1, Y3), (A1, B3, M1, N1, P2, Q1, R3b, R4b, X2, Y1), (A1, B3, M1, N1, P2, Q1, R3b, R4b, X2, Y2), (A1, B3, M1, N1, P2, Q1, R3b, R4b, X2, Y3), (A1, B3, M1, N1, P2, Q1, R3b, R4c, X1, Y1), (A1, B3, M1, N1, P2, Q1, R3b, R4c, X1, Y2), (A1, B3, M1, N1, P2, Q1, R3b, R4c, X1, Y3), (A1, B3, M1, N1, P2, Q1, R3b, R4c, X2, Y1), (A1, B3, M1, N1, P2, Q1, R3b, R4c, X2, Y2), (A1, B3, M1, N1, P2, Q1, R3b, R4c, X2, Y3), (A1, B3, M1, N1, P2, Q2, R3a, R4a, X1, Y1), (A1, B3, M1, N1, P2, Q2, R3a, R4a, X1, Y2), (A1, B3, M1, N1, P2, Q2, R3a, R4a, X1, Y3), (A1, B3, M1, N1, P2, Q2, R3a, R4a, X2, Y1), (A1, B3, M1, N1, P2, Q2, R3a, R4a, X2, Y2), (A1, B3, M1, N1, P2, Q2, R3a, R4a, X2, Y3), (A1, B3, M1, N1, P2, Q2, R3a, R4b, X1, Y1), (A1, B3, M1, N1, P2, Q2, R3a, R4b, X1, Y2), (A1, B3, M1, N1, P2, Q2, R3a, R4b, X1, Y3), (A1, B3, M1, N1, P2, Q2, R3a, R4b, X2, Y1), (A1, B3, M1, N1, P2, Q2, R3a, R4b, X2, Y2), (A1, B3, M1, N1, P2, Q2, R3a, R4b, X2, Y3), (A1, B3, M1, N1, P2, Q2, R3a, R4c, X1, Y1), (A1, B3, M1, N1, P2, Q2, R3a, R4c, X1, Y2), (A1, B3, M1, N1, P2, Q2, R3a, R4c, X1, Y3), (A1, B3, M1, N1, P2, Q2, R3a, R4c, X2, Y1), (A1, B3, M1, N1, P2, Q2, R3a, R4c, X2, Y2), (A1, B3, M1, N1, P2, Q2, R3a, R4c, X2, Y3), (A1, B3, M1, N1, P2, Q2, R3b, R4a, X1, Y1), (A1, B3, M1, N1, P2, Q2, R3b, R4a, X1, Y2), (A1, B3, M1, N1, P2, Q2, R3b, R4a, X1, Y3), (A1, B3, M1, N1, P2, Q2, R3b, R4a, X2, Y1), (A1, B3, M1, N1, P2, Q2, R3b, R4a, X2, Y2), (A1, B3, M1, N1, P2, Q2, R3b, R4a, X2, Y3), (A1, B3, M1, N1, P2, Q2, R3b, R4b, X1, Y1), (A1, B3, M1, N1, P2, Q2, R3b, R4b, X1, Y2), (A1, B3, M1, N1, P2, Q2, R3b, R4b, X1, Y3), (A1, B3, M1, N1, P2, Q2, R3b, R4b, X2, Y1), (A1, B3, M1, N1, P2, Q2, R3b, R4b, X2, Y2), (A1, B3, M1, N1, P2, Q2, R3b, R4b, X2, Y3), (A1, B3, M1, N1, P2, Q2, R3b, R4c, X1, Y1), (A1, B3, M1, N1, P2, Q2, R3b, R4c, X1, Y2), (A1, B3, M1, N1, P2, Q2, R3b, R4c, X1, Y3), (A1, B3, M1, N1, P2, Q2, R3b, R4c, X2, Y1), (A1, B3, M1, N1, P2, Q2, R3b, R4c, X2, Y2), (A1, B3, M1, N1, P2, Q2, R3b, R4c, X2, Y3), (A1, B3, M1, N2, P1, Q1, R3a, R4a, X1, Y1), (A1, B3, M1, N2, P1, Q1, R3a, R4a, X1, Y2), (A1, B3, M1, N2, P1, Q1, R3a, R4a, X1, Y3), (A1, B3, M1, N2, P1, Q1, R3a, R4a, X2, Y1), (A1, B3, M1, N2, P1, Q1, R3a, R4a, X2, Y2), (A1, B3, M1, N2, P1, Q1, R3a, R4a, X2, Y3), (A1, B3, M1, N2, P1, Q1, R3a, R4b, X1, Y1), (A1, B3, M1, N2, P1, Q1, R3a, R4b, X1, Y2), (A1, B3, M1, N2, P1, Q1, R3a, R4b, X1, Y3), (A1, B3, M1, N2, P1, Q1, R3a, R4b, X2, Y1), (A1, B3, M1, N2, P1, Q1, R3a, R4b, X2, Y2), (A1, B3, M1, N2, P1, Q1, R3a, R4b, X2, Y3), (A1, B3, M1, N2, P1, Q1, R3a, R4c, X1, Y1), (A1, B3, M1, N2, P1, Q1, R3a, R4c, X1, Y2), (A1, B3, M1, N2, P1, Q1, R3a, R4c, X1, Y3), (A1, B3, M1, N2, P1, Q1, R3a, R4c, X2, Y1), (A1, B3, M1, N2, P1, Q1, R3a, R4c, X2, Y2), (A1, B3, M1, N2, P1, Q1, R3a, R4c, X2, Y3), (A1, B3, M1, N2, P1, Q1, R3b, R4a, X1, Y1), (A1, B3, M1, N2, P1, Q1, R3b, R4a, X1, Y2), (A1, B3, M1, N2, P1, Q1, R3b, R4a, X1, Y3), (A1, B3, M1, N2, P1, Q1, R3b, R4a, X2, Y1), (A1, B3, M1, N2, P1, Q1, R3b, R4a, X2, Y2), (A1, B3, M1, N2, P1, Q1, R3b, R4a, X2, Y3), (A1, B3, M1, N2, P1, Q1, R3b, R4b, X1, Y1), (A1, B3, M1, N2, P1, Q1, R3b, R4b, X1, Y2), (A1, B3, M1, N2, P1, Q1, R3b, R4b, X1, Y3), (A1, B3, M1, N2, P1, Q1, R3b, R4b, X2, Y1), (A1, B3, M1, N2, P1, Q1, R3b, R4b, X2, Y2), (A1, B3, M1, N2, P1, Q1, R3b, R4b, X2, Y3), (A1, B3, M1, N2, P1, Q1, R3b, R4c, X1, Y1), (A1, B3, M1, N2, P1, Q1, R3b, R4c, X1, Y2),
(A1, B3, M1, N2, P1, Q1, R3b, R4c, X1, Y3), (A1, B3, M1, N2, P1, Q1, R3b, R4c, X2, Y1), (A1, B3, M1, N2, P1, Q1, R3b, R4c, X2, Y2), (A1, B3, M1, N2, P1, Q1, R3b, R4c, X2, Y3), (A1, B3, M1, N2, P1, Q2, R3a, R4a, X1, Y1), (A1, B3, M1, N2, P1, Q2, R3a, R4a, X1, Y2), (A1, B3, M1, N2, P1, Q2, R3a, R4a, X1, Y3), (A1, B3, M1, N2, P1, Q2, R3a, R4a, X2, Y1), (A1, B3, M1, N2, P1, Q2, R3a, R4a, X2, Y2), (A1, B3, M1, N2, P1, Q2, R3a, R4a, X2, Y3), (A1, B3, M1, N2, P1, Q2, R3a, R4b, X1, Y1), (A1, B3, M1, N2, P1, Q2, R3a, R4b, X1, Y2), (A1, B3, M1, N2, P1, Q2, R3a, R4b, X1, Y3), (A1, B3, M1, N2, P1, Q2, R3a, R4b, X2, Y1), (A1, B3, M1, N2, P1, Q2, R3a, R4b, X2, Y2), (A1, B3, M1, N2, P1, Q2, R3a, R4b, X2, Y3), (A1, B3, M1, N2, P1, Q2, R3a, R4c, X1, Y1), (A1, B3, M1, N2, P1, Q2, R3a, R4c, X1, Y2), (A1, B3, M1, N2, P1, Q2, R3a, R4c, X1, Y3), (A1, B3, M1, N2, P1, Q2, R3a, R4c, X2, Y1), (A1, B3, M1, N2, P1, Q2, R3a, R4c, X2, Y2), (A1, B3, M1, N2, P1, Q2, R3a, R4c, X2, Y3), (A1, B3, M1, N2, P1, Q2, R3b, R4a, X1, Y1), (A1, B3, M1, N2, P1, Q2, R3b, R4a, X1, Y2), (A1, B3, M1, N2, P1, Q2, R3b, R4a, X1, Y3), (A1, B3, M1, N2, P1, Q2, R3b, R4a, X2, Y1), (A1, B3, M1, N2, P1, Q2, R3b, R4a, X2, Y2), (A1, B3, M1, N2, P1, Q2, R3b, R4a, X2, Y3), (A1, B3, M1, N2, P1, Q2, R3b, R4b, X1, Y1), (A1, B3, M1, N2, P1, Q2, R3b, R4b, X1, Y2), (A1, B3, M1, N2, P1, Q2, R3b, R4b, X1, Y3), (A1, B3, M1, N2, P1, Q2, R3b, R4b, X2, Y1), (A1, B3, M1, N2, P1, Q2, R3b, R4b, X2, Y2), (A1, B3, M1, N2, P1, Q2, R3b, R4b, X2, Y3), (A1, B3, M1, N2, P1, Q2, R3b, R4c, X1, Y1), (A1, B3, M1, N2, P1, Q2, R3b, R4c, X1, Y2), (A1, B3, M1, N2, P1, Q2, R3b, R4c, X1, Y3), (A1, B3, M1, N2, P1, Q2, R3b, R4c, X2, Y1), (A1, B3, M1, N2, P1, Q2, R3b, R4c, X2, Y2), (A1, B3, M1, N2, P1, Q2, R3b, R4c, X2, Y3), (A1, B3, M1, N2, P2, Q1, R3a, R4a, X1, Y1), (A1, B3, M1, N2, P2, Q1, R3a, R4a, X1, Y2), (A1, B3, M1, N2, P2, Q1, R3a, R4a, X1, Y3), (A1, B3, M1, N2, P2, Q1, R3a, R4a, X2, Y1), (A1, B3, M1, N2, P2, Q1, R3a, R4a, X2, Y2), (A1, B3, M1, N2, P2, Q1, R3a, R4a, X2, Y3), (A1, B3, M1, N2, P2, Q1, R3a, R4b, X1, Y1), (A1, B3, M1, N2, P2, Q1, R3a, R4b, X1, Y2), (A1, B3, M1, N2, P2, Q1, R3a, R4b, X1, Y3), (A1, B3, M1, N2, P2, Q1, R3a, R4b, X2, Y1), (A1, B3, M1, N2, P2, Q1, R3a, R4b, X2, Y2), (A1, B3, M1, N2, P2, Q1, R3a, R4b, X2, Y3), (A1, B3, M1, N2, P2, Q1, R3a, R4c, X1, Y1), (A1, B3, M1, N2, P2, Q1, R3a, R4c, X1, Y2), (A1, B3, M1, N2, P2, Q1, R3a, R4c, X1, Y3), (A1, B3, M1, N2, P2, Q1, R3a, R4c, X2, Y1), (A1, B3, M1, N2, P2, Q1, R3a, R4c, X2, Y2), (A1, B3, M1, N2, P2, Q1, R3a, R4c, X2, Y3), (A1, B3, M1, N2, P2, Q1, R3b, R4a, X1, Y1), (A1, B3, M1, N2, P2, Q1, R3b, R4a, X1, Y2), (A1, B3, M1, N2, P2, Q1, R3b, R4a, X1, Y3), (A1, B3, M1, N2, P2, Q1, R3b, R4a, X2, Y1), (A1, B3, M1, N2, P2, Q1, R3b, R4a, X2, Y2), (A1, B3, M1, N2, P2, Q1, R3b, R4a, X2, Y3), (A1, B3, M1, N2, P2, Q1, R3b, R4b, X1, Y1), (A1, B3, M1, N2, P2, Q1, R3b, R4b, X1, Y2), (A1, B3, M1, N2, P2, Q1, R3b, R4b, X1, Y3), (A1, B3, M1, N2, P2, Q1, R3b, R4b, X2, Y1), (A1, B3, M1, N2, P2, Q1, R3b, R4b, X2, Y2), (A1, B3, M1, N2, P2, Q1, R3b, R4b, X2, Y3), (A1, B3, M1, N2, P2, Q1, R3b, R4c, X1, Y1), (A1, B3, M1, N2, P2, Q1, R3b, R4c, X1, Y2), (A1, B3, M1, N2, P2, Q1, R3b, R4c, X1, Y3), (A1, B3, M1, N2, P2, Q1, R3b, R4c, X2, Y1), (A1, B3, M1, N2, P2, Q1, R3b, R4c, X2, Y2), (A1, B3, M1, N2, P2, Q1, R3b, R4c, X2, Y3), (A1, B3, M1, N2, P2, Q2, R3a, R4a, X1, Y1), (A1, B3, M1, N2, P2, Q2, R3a, R4a, X1, Y2), (A1, B3, M1, N2, P2, Q2, R3a, R4a, X1, Y3), (A1, B3, M1, N2, P2, Q2, R3a, R4a, X2, Y1), (A1, B3, M1, N2, P2, Q2, R3a, R4a, X2, Y2), (A1, B3, M1, N2, P2, Q2, R3a, R4a, X2, Y3), (A1, B3, M1, N2, P2, Q2, R3a, R4b, X1, Y1), (A1, B3, M1, N2, P2, Q2, R3a, R4b, X1, Y2), (A1, B3, M1, N2, P2, Q2, R3a, R4b, X1, Y3), (A1, B3, M1, N2, P2, Q2, R3a, R4b, X2, Y1), (A1, B3, M1, N2, P2, Q2, R3a, R4b, X2, Y2), (A1, B3, M1, N2, P2, Q2, R3a, R4b, X2, Y3), (A1, B3, M1, N2, P2, Q2, R3a, R4c, X1, Y1), (A1, B3, M1, N2, P2, Q2, R3a, R4c, X1, Y2), (A1, B3, M1, N2, P2, Q2, R3a, R4c, X1, Y3), (A1, B3, M1, N2, P2, Q2, R3a, R4c, X2, Y1), (A1, B3, M1, N2, P2, Q2, R3a, R4c, X2, Y2), (A1, B3, M1, N2, P2, Q2, R3a, R4c, X2, Y3), (A1, B3, M1, N2, P2, Q2, R3b, R4a, X1, Y1), (A1, B3, M1, N2, P2, Q2, R3b, R4a, X1, Y2), (A1, B3, M1, N2, P2, Q2, R3b, R4a, X1, Y3), (A1, B3, M1, N2, P2, Q2, R3b, R4a, X2, Y1), (A1, B3, M1, N2, P2, Q2, R3b, R4a, X2, Y2), (A1, B3, M1, N2, P2, Q2, R3b, R4a, X2, Y3), (A1, B3, M1, N2, P2, Q2, R3b, R4b, X1, Y1), (A1, B3, M1, N2, P2, Q2, R3b, R4b, X1, Y2), (A1, B3, M1, N2, P2, Q2, R3b, R4b, X1, Y3), (A1, B3, M1, N2, P2, Q2, R3b, R4b, X2, Y1), (A1, B3, M1, N2, P2, Q2, R3b, R4b, X2, Y2), (A1, B3, M1, N2, P2, Q2, R3b, R4b, X2, Y3), (A1, B3, M1, N2, P2, Q2, R3b, R4c, X1, Y1), (A1, B3, M1, N2, P2, Q2, R3b, R4c, X1, Y2), (A1, B3, M1, N2, P2, Q2, R3b, R4c, X1, Y3), (A1, B3, M1, N2, P2, Q2, R3b, R4c, X2, Y1), (A1, B3, M1, N2, P2, Q2, R3b, R4c, X2, Y2), (A1, B3, M1, N2, P2, Q2, R3b, R4c, X2, Y3), (A1, B3, M2, N1, P1, Q1, R3a, R4a, X1, Y1), (A1, B3, M2, N1, P1, Q1, R3a, R4a, X1, Y2), (A1, B3, M2, N1, P1, Q1, R3a, R4a, X1, Y3), (A1, B3, M2, N1, P1, Q1, R3a, R4a, X2, Y1), (A1, B3, M2, N1, P1, Q1, R3a, R4a, X2, Y2), (A1, B3, M2, N1, P1, Q1, R3a, R4a, X2, Y3), (A1, B3, M2, N1, P1, Q1, R3a, R4b, X1, Y1), (A1, B3, M2, N1, P1, Q1, R3a, R4b, X1, Y2), (A1, B3, M2, N1, P1, Q1, R3a, R4b, X1, Y3), (A1, B3, M2, N1, P1, Q1, R3a, R4b, X2, Y1), (A1, B3, M2, N1, P1, Q1, R3a, R4b, X2, Y2), (A1, B3, M2, N1, P1, Q1, R3a, R4b, X2, Y3), (A1, B3, M2, N1, P1, Q1, R3a, R4c, X1, Y1), (A1, B3, M2, N1, P1, Q1, R3a, R4c, X1, Y2), (A1, B3, M2, N1, P1, Q1, R3a, R4c, X1, Y3), (A1, B3, M2, N1, P1, Q1, R3a, R4c, X2, Y1), (A1, B3, M2, N1, P1, Q1, R3a, R4c, X2, Y2), (A1, B3, M2, N1, P1, Q1, R3a, R4c, X2, Y3), (A1, B3, M2, N1, P1, Q1, R3b, R4a, X1, Y1), (A1, B3, M2, N1, P1, Q1, R3b, R4a, X1, Y2), (A1, B3, M2, N1, P1, Q1, R3b, R4a, X1, Y3), (A1, B3, M2, N1, P1, Q1, R3b, R4a, X2, Y1), (A1, B3, M2, N1, P1, Q1, R3b, R4a, X2, Y2), (A1, B3, M2, N1, P1, Q1, R3b, R4a, X2, Y3), (A1, B3, M2, N1, P1, Q1, R3b, R4b, X1, Y1), (A1, B3, M2, N1, P1, Q1, R3b, R4b, X1, Y2), (A1, B3, M2, N1, P1, Q1, R3b, R4b, X1, Y3), (A1, B3, M2, N1, P1, Q1, R3b, R4b, X2, Y1), (A1, B3, M2, N1, P1, Q1, R3b, R4b, X2, Y2), (A1, B3, M2, N1, P1, Q1, R3b, R4b, X2, Y3), (A1, B3, M2, N1, P1, Q1, R3b, R4c, X1, Y1), (A1, B3, M2, N1, P1, Q1, R3b, R4c, X1, Y2), (A1, B3, M2, N1, P1, Q1, R3b, R4c, X1, Y3), (A1, B3, M2, N1, P1, Q1, R3b, R4c, X2, Y1), (A1, B3, M2, N1, P1, Q1, R3b, R4c, X2, Y2), (A1, B3, M2, N1, P1, Q1, R3b, R4c, X2, Y3), (A1, B3, M2, N1, P1, Q2, R3a, R4a, X1, Y1), (A1, B3, M2, N1, P1, Q2, R3a, R4a, X1, Y2), (A1, B3, M2, N1, P1, Q2, R3a, R4a, X1, Y3), (A1, B3, M2, N1, P1, Q2, R3a, R4a, X2, Y1), (A1, B3, M2, N1, P1, Q2, R3a, R4a, X2, Y2), (A1, B3, M2, N1, P1, Q2, R3a, R4a, X2, Y3), (A1, B3, M2, N1, P1, Q2, R3a, R4b, X1, Y1), (A1, B3, M2, N1, P1, Q2, R3a, R4b, X1, Y2) (A1, B3, M2, N1, P1, Q2, R3a, R4b, X1, Y3), (A1, B3, M2, N1, P1, Q2, R3a, R4b, X2, Y1), (A1, B3, M2, N1, P1, Q2, R3a, R4b, X2, Y2), (A1, B3, M2, N1, P1, Q2, R3a, R4b, X2, Y3) (A1, B3, M2, N1, P1, Q2, R3a, R4c, X1, Y1), (A1, B3, M2, N1, P1, Q2, R3a, R4c, X1, Y2), (A1, B3, M2, N1, P1, Q2, R3a, R4c, X1, Y3), (A1, B3, M2, N1, P1, Q2, R3a, R4c, X2, Y1), (A1, B3, M2, N1, P1, Q2, R3a, R4c, X2, Y2), (A1, B3, M2, N1, P1, Q2, R3a, R4c, X2, Y3), (A1, B3, M2, N1, P1, Q2, R3b, R4a, X1, Y1), (A1, B3, M2, N1, P1, Q2, R3b, R4a, X1, Y2), (A1, B3, M2, N1, P1, Q2, R3b, R4a, X1, Y3), (A1, B3, M2, N1, P1, Q2, R3b, R4a, X2, Y1), (A1, B3, M2, N1, P1, Q2, R3b, R4a, X2, Y2) (A1, B3, M2, N1, P1, Q2, R3b, R4a, X2, Y3) (A1, B3, M2, N1, P1, Q2, R3b, R4b, X1, Y1), (A1, B3, M2, N1, P1, Q2, R3b, R4b, X1, Y2), (A1, B3, M2, N1, P1, Q2, R3b, R4b, X1, Y3), (A1, B3, M2, N1, P1, Q2, R3b, R4b, X2, Y1), (A1, B3, M2, N1, P1, Q2, R3b, R4b, X2, Y2), (A1, B3, M2, N1, P1, Q2, R3b, R4b, X2, Y3), (A1, B3, M2, N1, P1, Q2, R3b, R4c, X1, Y1), (A1, B3, M2, N1, P1, Q2, R3b, R4c, X1, Y2), (A1, B3, M2, N1, P1, Q2, R3b, R4c, X1, Y3), (A1, B3, M2, N1, P1, Q2, R3b, R4c, X2, Y1), (A1, B3, M2, N1, P1, Q2, R3b, R4c, X2, Y2), (A1, B3, M2, N1, P1, Q2, R3b, R4c, X2, Y3), (A1, B3, M2, N1, P2, Q1, R3a, R4a, X1, Y1), (A1, B3, M2, N1, P2, Q1, R3a, R4a, X1, Y2), (A1, B3, M2, N1, P2, Q1, R3a, R4a, X1, Y3), (A1, B3, M2, N1, P2, Q1, R3a, R4a, X2, Y1), (A1, B3, M2, N1, P2, Q1, R3a, R4a, X2, Y2), (A1, B3, M2, N1, P2, Q1, R3a, R4a, X2, Y3), (A1, B3, M2, N1, P2, Q1, R3a, R4b, X1, Y1), B3, M2, N1, P2, Q1, R3a, R4b, X1, Y2), (A1, B3, M2, N1, P2, Q1, R3a, R4b, X1, Y3), (A1, B3, M2, N1, P2, Q1, R3a, R4b, X2, Y1), (A1, B3, M2, N1, P2, Q1, R3a, R4b, X2, Y2), (A1, B3, M2, N1, P2, Q1, R3a, R4b, X2, Y3), (A1, B3, M2, N1, P2, Q1, R3a, R4c, X1, Y1), (A1, B3, M2, N1, P2, Q1, R3a, R4c, X1, Y2), (A1, B3, M2, N1, P2, Q1, R3a, R4c, X1, Y3), (A1, B3, M2, N1, P2, Q1, R3a, R4c, X2, Y1), (A1, B3, M2, N1, P2, Q1, R3a, R4c, X2, Y2), (A1, B3, M2, N1, P2, Q1, R3a, R4c, X2, Y3), (A1, B3, M2, N1, P2, Q1, R3b, R4a, X1, Y1), (A1, B3, M2, N1, P2, Q1, R3b, R4a, X1, Y2), (A1, B3, M2, N1, P2, Q1, R3b, R4a, X1, Y3), (A1, B3, M2, N1, P2, Q1, R3b, R4a, X2, Y1), (A1, B3, M2, N1, P2, Q1, R3b, R4a, X2, Y2), (A1, B3, M2, N1, P2, Q1, R3b, R4a, X2, Y3), (A1, B3, M2, N1, P2, Q1, R3b, R4b, X1, Y1), (A1, B3, M2, N1, P2, Q1, R3b, R4b, X1, Y2), (A1, B3, M2, N1, P2, Q1, R3b, R4b, X1, Y3), (A1, B3, M2, N1, P2, Q1, R3b, R4b, X2, Y1), (A1, B3, M2, N1, P2, Q1, R3b, R4b, X2, Y2), (A1, B3, M2, N1, P2, Q1, R3b, R4b, X2, Y3), (A1, B3, M2, N1, P2, Q1, R3b, R4c, X1, Y1), (A1, B3, M2, N1, P2, Q1, R3b, R4c, X1, Y2), (A1, B3, M2, N1, P2, Q1, R3b, R4c, X1, Y3), (A1, B3, M2, N1, P2, Q1, R3b, R4c, X2, Y1), (A1, B3, M2, N1, P2, Q1, R3b, R4c, X2, Y2), (A1, B3, M2, N1, P2, Q1, R3b, R4c, X2, Y3), (A1, B3, M2, N1, P2, Q2, R3a, R4a, X1, Y1), (A1, B3, M2, N1, P2, Q2, R3a, R4a, X1, Y2), (A1, B3, M2, N1, P2, Q2, R3a, R4a, X1, Y3), (A1, B3, M2, N1, P2, Q2, R3a, R4a, X2, Y1), (A1, B3, M2, N1, P2, Q2, R3a, R4a, X2, Y2), (A1, B3, M2, N1, P2, Q2, R3a, R4a, X2, Y3), (A1, B3, M2, N1, P2, Q2, R3a, R4b, X1, Y1), (A1, B3, M2, N1, P2, Q2, R3a, R4b, X1, Y2), (A1, B3, M2, N1, P2, Q2, R3a, R4b, X1, Y3), (A1, B3, M2, N1, P2, Q2, R3a, R4b, X2, Y1), (A1, B3, M2, N1, P2, Q2, R3a, R4b, X2, Y2), (A1, B3, M2, N1, P2, Q2, R3a, R4b, X2, Y3), (A1, B3, M2, N1, P2, Q2, R3a, R4c, X1, Y1), (A1, B3, M2, N1, P2, Q2, R3a, R4c, X1, Y2), (A1, B3, M2, N1, P2, Q2, R3a, R4c, X1, Y3), (A1, B3, M2, N1, P2, Q2, R3a, R4c, X2, Y1), (A1, B3, M2, N1, P2, Q2, R3a, R4c, X2, Y2), (A1, B3, M2, N1, P2, Q2, R3a, R4c, X2, Y3), (A1, B3, M2, N1, P2, Q2, R3b, R4a, X1, Y1), (A1, B3, M2, N1, P2, Q2, R3b, R4a, X1, Y2), (A1, B3, M2, N1, P2, Q2, R3b, R4a, X1, Y3), (A1, B3, M2, N1, P2, Q2, R3b, R4a, X2, Y1), (A1, B3, M2, N1, P2, Q2, R3b, R4a, X2, Y2), (A1, B3, M2, N1, P2, Q2, R3b, R4a, X2, Y3), (A1, B3, M2, N1, P2, Q2, R3b, R4b, X1, Y1), (A1, B3, M2, N1, P2, Q2, R3b, R4b, X1, Y2), (A1, B3, M2, N1, P2, Q2, R3b, R4b, X1, Y3), (A1, B3, M2, N1, P2, Q2, R3b, R4b, X2, Y1), (A1, B3, M2, N1, P2, Q2, R3b, R4b, X2, Y2), (A1, B3, M2, N1, P2, Q2, R3b, R4b, X2, Y3), (A1, B3, M2, N1, P2, Q2, R3b, R4c, X1, Y1), (A1, B3, M2, N1, P2, Q2, R3b, R4c, X1, Y2), (A1, B3, M2, N1, P2, Q2, R3b, R4c, X1, Y3), (A1, B3, M2, N1, P2, Q2, R3b, R4c, X2, Y1), (A1, B3, M2, N1, P2, Q2, R3b, R4c, X2, Y2), (A1, B3, M2, N1, P2, Q2, R3b, R4c, X2, Y3), (A1, B3, M2, N2, P1, Q1, R3a, R4a, X1, Y1), (A1, B3, M2, N2, P1, Q1, R3a, R4a, X1, Y2), (A1, B3, M2, N2, P1, Q1, R3a, R4a, X1, Y3), (A1, B3, M2, N2, P1, Q1, R3a, R4a, X2, Y1), (A1, B3, M2, N2, P1, Q1, R3a, R4a, X2, Y2), (A1, B3, M2, N2, P1, Q1, R3a, R4a, X2, Y3), (A1, B3, M2, N2, P1, Q1, R3a, R4b, X1, Y1), (A1, B3, M2, N2, P1, Q1, R3a, R4b, X1, Y2), (A1, B3, M2, N2, P1, Q1, R3a, R4b, X1, Y3), (A1, B3, M2, N2, P1, Q1, R3a, R4b, X2, Y1) (A1, B3, M2, N2, P1, Q1, R3a, R4b, X2, Y2), (A1, B3, M2, N2, P1, Q1, R3a, R4b, X2, Y3), (A1, B3, M2, N2, P1, Q1, R3a, R4c, X1, Y1), (A1, B3, M2, N2, P1, Q1, R3a, R4c, X1, Y2), (A1, B3, M2, N2, P1, Q1, R3a, R4c, X1, Y3) (A1, B3, M2, N2, P1, Q1, R3a, R4c, X2, Y1), (A1, B3, M2, N2, P1, Q1, R3a, R4c, X2, Y2), (A1, B3, M2, N2, P1, Q1, R3a, R4c, X2, Y3), (A1, B3, M2, N2, P1, Q1, R3b, R4a, X1, Y1), (A1, B3, M2, N2, P1, Q1, R3b, R4a, X1, Y2), (A1, B3, M2, N2, P1, Q1, R3b, R4a, X1, Y3), (A1, B3, M2, N2, P1, Q1, R3b, R4a, X2, Y1), (A1, B3, M2, N2, P1, Q1, R3b, R4a, X2, Y2), (A1, B3, M2, N2, P1, Q1, R3b, R4a, X2, Y3), (A1, B3, M2, N2, P1, Q1, R3b, R4b, X1, Y1), (A1, B3, M2, N2, P1, Q1, R3b, R4b, X1, Y2), (A1, B3, M2, N2, P1, Q1, R3b, R4b, X1, Y3), (A1, B3, M2, N2, P1, Q1, R3b, R4b, X2, Y1), (A1, B3, M2, N2, P1, Q1, R3b, R4b, X2, Y2), (A1, B3, M2, N2, P1, Q1, R3b, R4b, X2, Y3), (A1, B3, M2, N2, P1, Q1, R3b, R4c, X1, Y1), (A1, B3, M2, N2, P1, Q1, R3b, R4c, X1, Y2), (A1, B3, M2, N2, P1, Q1, R3b, R4c, X1, Y3), (A1, B3, M2, N2, P1, Q1, R3b, R4c, X2, Y1), (A1, B3, M2, N2, P1, Q1, R3b, R4c, X2, Y2), (A1, B3, M2, N2, P1, Q1, R3b, R4c, X2, Y3), (A1, B3, M2, N2, P1, Q2, R3a, R4a, X1, Y1), (A1, B3, M2, N2, P1, Q2, R3a, R4a, X1, Y2), (A1, B3, M2, N2, P1, Q2, R3a, R4a, X1, Y3), (A1, B3, M2, N2, P1, Q2, R3a, R4a, X2, Y1), (A1, B3, M2, N2, P1, Q2, R3a, R4a, X2, Y2) (A1, B3, M2, N2, P1, Q2, R3a, R4a, X2, Y3), (A1, B3, M2, N2, P1, Q2, R3a, R4b, X1, Y1), (A1, B3, M2, N2, P1, Q2, R3a, R4b, X1, Y2), (A1, B3, M2, N2, P1, Q2, R3a, R4b, X1, Y3), (A1, B3, M2, N2, P1, Q2, R3a, R4b, X2, Y1), (A1, B3, M2, N2, P1, Q2, R3a, R4b, X2, Y2), (A1, B3, M2, N2, P1, Q2, R3a, R4b, X2, Y3), (A1, B3, M2, N2, P1, Q2, R3a, R4c, X1, Y1), (A1, B3, M2, N2, P1, Q2, R3a, R4c, X1, Y2), (A1, B3, M2, N2, P1, Q2, R3a, R4c, X1, Y3), (A1, B3, M2, N2, P1, Q2, R3a, R4c, X2, Y1), (A1, B3, M2, N2, P1, Q2, R3a, R4c, X2, Y2), (A1, B3, M2, N2, P1, Q2, R3a, R4c, X2, Y3), (A1, B3, M2, N2, P1, Q2, R3b, R4a, X1, Y1), (A1, B3, M2, N2, P1, Q2, R3b, R4a, X1, Y2), (A1, B3, M2, N2, P1, Q2, R3b, R4a, X1, Y3), (A1, B3, M2, N2, P1, Q2, R3b, R4a, X2, Y1), (A1, B3, M2, N2, P1, Q2, R3b, R4a, X2, Y2), (A1, B3, M2, N2, P1, Q2, R3b, R4a, X2, Y3), (A1, B3, M2, N2, P1, Q2, R3b, R4b, X1, Y1), (A1, B3, M2, N2, P1, Q2, R3b, R4b, X1, Y2), (A1, B3, M2, N2, P1, Q2, R3b, R4b, X1, Y3), (A1, B3, M2, N2, P1, Q2, R3b, R4b, X2, Y1), (A1, B3, M2, N2, P1, Q2, R3b, R4b, X2, Y2), (A1, B3, M2, N2, P1, Q2, R3b, R4b, X2, Y3), (A1, B3, M2, N2, P1, Q2, R3b, R4c, X1, Y1), (A1, B3, M2, N2, P1, Q2, R3b, R4c, X1, Y2), (A1, B3, M2, N2, P1, Q2, R3b, R4c, X1, Y3), (A1, B3, M2, N2, P1, Q2, R3b, R4c, X2, Y1), (A1, B3, M2, N2, P1, Q2, R3b, R4c, X2, Y2), (A1, B3, M2, N2, P1, Q2, R3b, R4c, X2, Y3), (A1, B3, M2, N2, P2, Q1, R3a, R4a, X1, Y1), (A1, B3, M2, N2, P2, Q1, R3a, R4a, X1, Y2), (A1, B3, M2, N2, P2, Q1, R3a, R4a, X1, Y3), (A1, B3, M2, N2, P2, Q1, R3a, R4a, X2, Y1), (A1, B3, M2, N2, P2, Q1, R3a, R4a, X2, Y2), (A1, B3, M2, N2, P2, Q1, R3a, R4a, X2, Y3), (A1, B3, M2, N2, P2, Q1, R3a, R4b, X1, Y1), (A1, B3, M2, N2, P2, Q1, R3a, R4b, X1, Y2), (A1, B3, M2, N2, P2, Q1, R3a, R4b, X1, Y3) (A1, B3, M2, N2, P2, Q1, R3a, R4b, X2, Y1), (A1, B3, M2, N2, P2, Q1, R3a, R4b, X2, Y2), (A1, B3, M2, N2, P2, Q1, R3a, R4b, X2, Y3), (A1, B3, M2, N2, P2, Q1, R3a, R4c, X1, Y1), (A1, B3, M2, N2, P2, Q1, R3a, R4c, X1, Y2), (A1, B3, M2, N2, P2, Q1, R3a, R4c, X1, Y3), (A1, B3, M2, N2, P2, Q1, R3a, R4c, X2, Y1), (A1, B3, M2, N2, P2, Q1, R3a, R4c, X2, Y2), (A1, B3, M2, N2, P2, Q1, R3a, R4c, X2, Y3), (A1, B3, M2, N2, P2, Q1, R3b, R4a, X1, Y1), (A1, B3, M2, N2, P2, Q1, R3b, R4a, X1, Y2), (A1, B3, M2, N2, P2, Q1, R3b, R4a, X1, Y3), (A1, B3, M2, N2, P2, Q1, R3b, R4a, X2, Y1), (A1, B3, M2, N2, P2, Q1, R3b, R4a, X2, Y2), (A1, B3, M2, N2, P2, Q1, R3b, R4a, X2, Y3), (A1, B3, M2, N2, P2, Q1, R3b, R4b, X1, Y1), (A1, B3, M2, N2, P2, Q1, R3b, R4b, X1, Y2), (A1, B3, M2, N2, P2, Q1, R3b, R4b, X1, Y3), (A1, B3, M2, N2, P2, Q1, R3b, R4b, X2, Y1), (A1, B3, M2, N2, P2, Q1, R3b, R4b, X2, Y2), (A1, B3, M2, N2, P2, Q1, R3b, R4b, X2, Y3), (A1, B3, M2, N2, P2, Q1, R3b, R4c, X1, Y1), (A1, B3, M2, N2, P2, Q1, R3b, R4c, X1, Y2), (A1, B3, M2, N2, P2, Q1, R3b, R4c, X1, Y3), (A1, B3, M2, N2, P2, Q1, R3b, R4c, X2, Y1), (A1, B3, M2, N2, P2, Q1, R3b, R4c, X2, Y2), (A1, B3, M2, N2, P2, Q1, R3b, R4c, X2, Y3), (A1, B3, M2, N2, P2, Q2, R3a, R4a, X1, Y1), (A1, B3, M2, N2, P2, Q2, R3a, R4a, X1, Y2), (A1, B3, M2, N2, P2, Q2, R3a, R4a, X1, Y3), (A1, B3, M2, N2, P2, Q2, R3a, R4a, X2, Y1), (A1, B3, M2, N2, P2, Q2, R3a, R4a, X2, Y2), (A1, B3, M2, N2, P2, Q2, R3a, R4a, X2, Y3), (A1, B3, M2, N2, P2, Q2, R3a, R4b, X1, Y1), (A1, B3, M2, N2, P2, Q2, R3a, R4b, X1, Y2), (A1, B3, M2, N2, P2, Q2, R3a, R4b, X1, Y3), (A1, B3, M2, N2, P2, Q2, R3a, R4b, X2, Y1), (A1, B3, M2, N2, P2, Q2, R3a, R4b, X2, Y2), (A1, B3, M2, N2, P2, Q2, R3a, R4b, X2, Y3), (A1, B3, M2, N2, P2, Q2, R3a, R4c, X1, Y1), (A1, B3, M2, N2, P2, Q2, R3a, R4c, X1, Y2), (A1, B3, M2, N2, P2, Q2, R3a, R4c, X1, Y3), (A1, B3, M2, N2, P2, Q2, R3a, R4c, X2, Y1), (A1, B3, M2, N2, P2, Q2, R3a, R4c, X2, Y2), (A1, B3, M2, N2, P2, Q2, R3a, R4c, X2, Y3), (A1, B3, M2, N2, P2, Q2, R3b, R4a, X1, Y1), (A1, B3, M2, N2, P2, Q2, R3b, R4a, X1, Y2), (A1, B3, M2, N2, P2, Q2, R3b, R4a, X1, Y3), (A1, B3, M2, N2, P2, Q2, R3b, R4a, X2, Y1), (A1, B3, M2, N2, P2, Q2, R3b, R4a, X2, Y2), (A1, B3, M2, N2, P2, Q2, R3b, R4a, X2, Y3), (A1, B3, M2, N2, P2, Q2, R3b, R4b, X1, Y1), (A1, B3, M2, N2, P2, Q2, R3b, R4b, X1, Y2), (A1, B3, M2, N2, P2, Q2, R3b, R4b, X1, Y3), (A1, B3, M2, N2, P2, Q2, R3b, R4b, X2, Y1), (A1, B3, M2, N2, P2, Q2, R3b, R4b, X2, Y2), (A1, B3, M2, N2, P2, Q2, R3b, R4b, X2, Y3), (A1, B3, M2, N2, P2, Q2, R3b, R4c, X1, Y1), (A1, B3, M2, N2, P2, Q2, R3b, R4c, X1, Y2), (A1, B3, M2, N2, P2, Q2, R3b, R4c, X1, Y3), (A1, B3, M2, N2, P2, Q2, R3b, R4c, X2, Y1), (A1, B3, M2, N2, P2, Q2, R3b, R4c, X2, Y2), (A1, B3, M2, N2, P2, Q2, R3b, R4c, X2, Y3), (A2, B1, M1, N1, P1, Q1, R3a, R4a, X1, Y1), (A2, B1, M1, N1, P1, Q1, R3a, R4a, X1, Y2), (A2, B1, M1, N1, P1, Q1, R3a, R4a, X1, Y3), (A2, B1, M1, N1, P1, Q1, R3a, R4a, X2, Y1), (A2, B1, M1, N1, P1, Q1, R3a, R4a, X2, Y2), (A2, B1, M1, N1, P1, Q1, R3a, R4a, X2, Y3), (A2, B1, M1, N1, P1, Q1, R3a, R4b, X1, Y1), (A2, B1, M1, N1, P1, Q1, R3a, R4b, X1, Y2), (A2, B1, M1, N1, P1, Q1, R3a, R4b, X1, Y3), (A2, B1, M1, N1, P1, Q1, R3a, R4b, X2, Y1), (A2, B1, M1, N1, P1, Q1, R3a, R4b, X2, Y2), (A2, B1, M1, N1, P1, Q1, R3a, R4b, X2, Y3), (A2, B1, M1, N1, P1, Q1, R3a, R4c, X1, Y1), (A2, B1, M1, N1, P1, Q1, R3a, R4c, X1, Y2), (A2, B1, M1, N1, P1, Q1, R3a, R4c, X1, Y3), (A2, B1, M1, N1, P1, Q1, R3a, R4c, X2, Y1), (A2, B1, M1, N1, P1, Q1, R3a, R4c, X2, Y2), (A2, B1, M1, N1, P1, Q1, R3a, R4c, X2, Y3), (A2, B1, M1, N1, P1, Q1, R3b, R4a, X1, Y1), (A2, B1, M1, N1, P1, Q1, R3b, R4a, X1, Y2), (A2, B1, M1, N1, P1, Q1, R3b, R4a, X1, Y3), (A2, B1, M1, N1, P1, Q1, R3b, R4a, X2, Y1), (A2, B1, M1, N1, P1, Q1, R3b, R4a, X2, Y2), (A2, B1, M1, N1, P1, Q1, R3b, R4a, X2, Y3), (A2, B1, M1, N1, P1, Q1, R3b, R4b, X1, Y1), (A2, B1, M1, N1, P1, Q1, R3b, R4b, X1, Y2), (A2, B1, M1, N1, P1, Q1, R3b, R4b, X1, Y3), (A2, B1, M1, N1, P1, Q1, R3b, R4b, X2, Y1), (A2, B1, M1, N1, P1, Q1, R3b, R4b, X2, Y2), (A2, B1, M1, N1, P1, Q1, R3b, R4b, X2, Y3), (A2, B1, M1, N1, P1, Q1, R3b, R4c, X1, Y1), (A2, B1, M1, N1, P1, Q1, R3b, R4c, X1, Y2), (A2, B1, M1, N1, P1, Q1, R3b, R4c, X1, Y3), (A2, B1, M1, N1, P1, Q1, R3b, R4c, X2, Y1), (A2, B1, M1, N1, P1, Q1, R3b, R4c, X2, Y2), (A2, B1, M1, N1, P1, Q1, R3b, R4c, X2, Y3), (A2, B1, M1, N1, P1, Q2, R3a, R4a, X1, Y1), (A2, B1, M1, N1, P1, Q2, R3a, R4a, X1, Y2), (A2, B1, M1, N1, P1, Q2, R3a, R4a, X1, Y3), (A2, B1, M1, N1, P1, Q2, R3a, R4a, X2, Y1), (A2, B1, M1, N1, P1, Q2, R3a, R4a, X2, Y2), (A2, B1, M1, N1, P1, Q2, R3a, R4a, X2, Y3), (A2, B1, M1, N1, P1, Q2, R3a, R4b, X1, Y1), (A2, B1, M1, N1, P1, Q2, R3a, R4b, X1, Y2), (A2, B1, M1, N1, P1, Q2, R3a, R4b, X1, Y3),
(A2, B1, M1, N1, P1, Q2, R3a, R4b, X2, Y1), (A2, B1, M1, N1, P1, Q2, R3a, R4b, X2, Y2), (A2, B1, M1, N1, P1, Q2, R3a, R4b, X2, Y3), (A2, B1, M1, N1, P1, Q2, R3a, R4c, X1, Y1), (A2, B1, M1, N1, P1, Q2, R3a, R4c, X1, Y2), (A2, B1, M1, N1, P1, Q2, R3a, R4c, X1, Y3), (A2, B1, M1, N1, P1, Q2, R3a, R4c, X2, Y1), (A2, B1, M1, N1, P1, Q2, R3a, R4c, X2, Y2), (A2, B1, M1, N1, P1, Q2, R3a, R4c, X2, Y3), (A2, B1, M1, N1, P1, Q2, R3b, R4a, X1, Y1), (A2, B1, M1, N1, P1, Q2, R3b, R4a, X1, Y2), (A2, B1, M1, N1, P1, Q2, R3b, R4a, X1, Y3), (A2, B1, M1, N1, P1, Q2, R3b, R4a, X2, Y1), (A2, B1, M1, N1, P1, Q2, R3b, R4a, X2, Y2), (A2, B1, M1, N1, P1, Q2, R3b, R4a, X2, Y3), (A2, B1, M1, N1, P1, Q2, R3b, R4b, X1, Y1), (A2, B1, M1, N1, P1, Q2, R3b, R4b, X1, Y2), (A2, B1, M1, N1, P1, Q2, R3b, R4b, X1, Y3), (A2, B1, M1, N1, P1, Q2, R3b, R4b, X2, Y1), (A2, B1, M1, N1, P1, Q2, R3b, R4b, X2, Y2), (A2, B1, M1, N1, P1, Q2, R3b, R4b, X2, Y3), (A2, B1, M1, N1, P1, Q2, R3b, R4c, X1, Y1), (A2, B1, M1, N1, P1, Q2, R3b, R4c, X1, Y2), (A2, B1, M1, N1, P1, Q2, R3b, R4c, X1, Y3), (A2, B1, M1, N1, P1, Q2, R3b, R4c, X2, Y1), (A2, B1, M1, N1, P1, Q2, R3b, R4c, X2, Y2), (A2, B1, M1, N1, P1, Q2, R3b, R4c, X2, Y3), (A2, B1, M1, N1, P2, Q1, R3a, R4a, X1, Y1), (A2, B1, M1, N1, P2, Q1, R3a, R4a, X1, Y2), (A2, B1, M1, N1, P2, Q1, R3a, R4a, X1, Y3), (A2, B1, M1, N1, P2, Q1, R3a, R4a, X2, Y1), (A2, B1, M1, N1, P2, Q1, R3a, R4a, X2, Y2), (A2, B1, M1, N1, P2, Q1, R3a, R4a, X2, Y3), (A2, B1, M1, N1, P2, Q1, R3a, R4b, X1, Y1), (A2, B1, M1, N1, P2, Q1, R3a, R4b, X1, Y2), (A2, B1, M1, N1, P2, Q1, R3a, R4b, X1, Y3), (A2, B1, M1, N1, P2, Q1, R3a, R4b, X2, Y1), (A2, B1, M1, N1, P2, Q1, R3a, R4b, X2, Y2), (A2, B1, M1, N1, P2, Q1, R3a, R4b, X2, Y3), (A2, B1, M1, N1, P2, Q1, R3a, R4c, X1, Y1), (A2, B1, M1, N1, P2, Q1, R3a, R4c, X1, Y2), (A2, B1, M1, N1, P2, Q1, R3a, R4c, X1, Y3), (A2, B1, M1, N1, P2, Q1, R3a, R4c, X2, Y1), (A2, B1, M1, N1, P2, Q1, R3a, R4c, X2, Y2), (A2, B1, M1, N1, P2, Q1, R3a, R4c, X2, Y3), (A2, B1, M1, N1, P2, Q1, R3b, R4a, X1, Y1), (A2, B1, M1, N1, P2, Q1, R3b, R4a, X1, Y2), (A2, B1, M1, N1, P2, Q1, R3b, R4a, X1, Y3), (A2, B1, M1, N1, P2, Q1, R3b, R4a, X2, Y1), (A2, B1, M1, N1, P2, Q1, R3b, R4a, X2, Y2), (A2, B1, M1, N1, P2, Q1, R3b, R4a, X2, Y3), (A2, B1, M1, N1, P2, Q1, R3b, R4b, X1, Y1), (A2, B1, M1, N1, P2, Q1, R3b, R4b, X1, Y2), (A2, B1, M1, N1, P2, Q1, R3b, R4b, X1, Y3), (A2, B1, M1, N1, P2, Q1, R3b, R4b, X2, Y1), (A2, B1, M1, N1, P2, Q1, R3b, R4b, X2, Y2), (A2, B1, M1, N1, P2, Q1, R3b, R4b, X2, Y3), (A2, B1, M1, N1, P2, Q1, R3b, R4c, X1, Y1), (A2, B1, M1, N1, P2, Q1, R3b, R4c, X1, Y2), (A2, B1, M1, N1, P2, Q1, R3b, R4c, X1, Y3), (A2, B1, M1, N1, P2, Q1, R3b, R4c, X2, Y1), (A2, B1, M1, N1, P2, Q1, R3b, R4c, X2, Y2), (A2, B1, M1, N1, P2, Q1, R3b, R4c, X2, Y3), (A2, B1, M1, N1, P2, Q2, R3a, R4a, X1, Y1), (A2, B1, M1, N1, P2, Q2, R3a, R4a, X1, Y2), (A2, B1, M1, N1, P2, Q2, R3a, R4a, X1, Y3), (A2, B1, M1, N1, P2, Q2, R3a, R4a, X2, Y1), (A2, B1, M1, N1, P2, Q2, R3a, R4a, X2, Y2), (A2, B1, M1, N1, P2, Q2, R3a, R4a, X2, Y3), (A2, B1, M1, N1, P2, Q2, R3a, R4b, X1, Y1), (A2, B1, M1, N1, P2, Q2, R3a, R4b, X1, Y2), (A2, B1, M1, N1, P2, Q2, R3a, R4b, X1, Y3), (A2, B1, M1, N1, P2, Q2, R3a, R4b, X2, Y1), (A2, B1, M1, N1, P2, Q2, R3a, R4b, X2, Y2), (A2, B1, M1, N1, P2, Q2, R3a, R4b, X2, Y3), (A2, B1, M1, N1, P2, Q2, R3a, R4c, X1, Y1), (A2, B1, M1, N1, P2, Q2, R3a, R4c, X1, Y2), (A2, B1, M1, N1, P2, Q2, R3a, R4c, X1, Y3), (A2, B1, M1, N1, P2, Q2, R3a, R4c, X2, Y1), (A2, B1, M1, N1, P2, Q2, R3a, R4c, X2, Y2), (A2, B1, M1, N1, P2, Q2, R3a, R4c, X2, Y3), (A2, B1, M1, N1, P2, Q2, R3b, R4a, X1, Y1), (A2, B1, M1, N1, P2, Q2, R3b, R4a, X1, Y2), (A2, B1, M1, N1, P2, Q2, R3b, R4a, X1, Y3), (A2, B1, M1, N1, P2, Q2, R3b, R4a, X2, Y1), (A2, B1, M1, N1, P2, Q2, R3b, R4a, X2, Y2), (A2, B1, M1, N1, P2, Q2, R3b, R4a, X2, Y3), (A2, B1, M1, N1, P2, Q2, R3b, R4b, X1, Y1), (A2, B1, M1, N1, P2, Q2, R3b, R4b, X1, Y2),
(A2, B1, M1, N1, P2, Q2, R3b, R4b, X1, Y3), (A2, B1, M1, N1, P2, Q2, R3b, R4b, X2, Y1), (A2, B1, M1, N1, P2, Q2, R3b, R4b, X2, Y2), (A2, B1, M1, N1, P2, Q2, R3b, R4b, X2, Y3), (A2, B1, M1, N1, P2, Q2, R3b, R4c, X1, Y1), (A2, B1, M1, N1, P2, Q2, R3b, R4c, X1, Y2), (A2, B1, M1, N1, P2, Q2, R3b, R4c, X1, Y3), (A2, B1, M1, N1, P2, Q2, R3b, R4c, X2, Y1), (A2, B1, M1, N1, P2, Q2, R3b, R4c, X2, Y2), (A2, B1, M1, N1, P2, Q2, R3b, R4c, X2, Y3), (A2, B1, M1, N2, P1, Q1, R3a, R4a, X1, Y1), (A2, B1, M1, N2, P1, Q1, R3a, R4a, X1, Y2), (A2, B1, M1, N2, P1, Q1, R3a, R4a, X1, Y3), (A2, B1, M1, N2, P1, Q1, R3a, R4a, X2, Y1), (A2, B1, M1, N2, P1, Q1, R3a, R4a, X2, Y2), (A2, B1, M1, N2, P1, Q1, R3a, R4a, X2, Y3), (A2, B1, M1, N2, P1, Q1, R3a, R4b, X1, Y1), (A2, B1, M1, N2, P1, Q1, R3a, R4b, X1, Y2), (A2, B1, M1, N2, P1, Q1, R3a, R4b, X1, Y3), (A2, B1, M1, N2, P1, Q1, R3a, R4b, X2, Y1), (A2, B1, M1, N2, P1, Q1, R3a, R4b, X2, Y2), (A2, B1, M1, N2, P1, Q1, R3a, R4b, X2, Y3), (A2, B1, M1, N2, P1, Q1, R3a, R4c, X1, Y1), (A2, B1, M1, N2, P1, Q1, R3a, R4c, X1, Y2), (A2, B1, M1, N2, P1, Q1, R3a, R4c, X1, Y3), (A2, B1, M1, N2, P1, Q1, R3a, R4c, X2, Y1), (A2, B1, M1, N2, P1, Q1, R3a, R4c, X2, Y2), (A2, B1, M1, N2, P1, Q1, R3a, R4c, X2, Y3), (A2, B1, M1, N2, P1, Q1, R3b, R4a, X1, Y1), (A2, B1, M1, N2, P1, Q1, R3b, R4a, X1, Y2), (A2, B1, M1, N2, P1, Q1, R3b, R4a, X1, Y3), (A2, B1, M1, N2, P1, Q1, R3b, R4a, X2, Y1), (A2, B1, M1, N2, P1, Q1, R3b, R4a, X2, Y2), (A2, B1, M1, N2, P1, Q1, R3b, R4a, X2, Y3), (A2, B1, M1, N2, P1, Q1, R3b, R4b, X1, Y1), (A2, B1, M1, N2, P1, Q1, R3b, R4b, X1, Y2), (A2, B1, M1, N2, P1, Q1, R3b, R4b, X1, Y3), (A2, B1, M1, N2, P1, Q1, R3b, R4b, X2, Y1), (A2, B1, M1, N2, P1, Q1, R3b, R4b, X2, Y2), (A2, B1, M1, N2, P1, Q1, R3b, R4b, X2, Y3), (A2, B1, M1, N2, P1, Q1, R3b, R4c, X1, Y1), (A2, B1, M1, N2, P1, Q1, R3b, R4c, X1, Y2), (A2, B1, M1, N2, P1, Q1, R3b, R4c, X1, Y3), (A2, B1, M1, N2, P1, Q1, R3b, R4c, X2, Y1), (A2, B1, M1, N2, P1, Q1, R3b, R4c, X2, Y2), (A2, B1, M1, N2, P1, Q1, R3b, R4c, X2, Y3), (A2, B1, M1, N2, P1, Q2, R3a, R4a, X1, Y1), (A2, B1, M1, N2, P1, Q2, R3a, R4a, X1, Y2), (A2, B1, M1, N2, P1, Q2, R3a, R4a, X1, Y3), (A2, B1, M1, N2, P1, Q2, R3a, R4a, X2, Y1), (A2, B1, M1, N2, P1, Q2, R3a, R4a, X2, Y2), (A2, B1, M1, N2, P1, Q2, R3a, R4a, X2, Y3), (A2, B1, M1, N2, P1, Q2, R3a, R4b, X1, Y1), (A2, B1, M1, N2, P1, Q2, R3a, R4b, X1, Y2), (A2, B1, M1, N2, P1, Q2, R3a, R4b, X1, Y3), (A2, B1, M1, N2, P1, Q2, R3a, R4b, X2, Y1), (A2, B1, M1, N2, P1, Q2, R3a, R4b, X2, Y2), (A2, B1, M1, N2, P1, Q2, R3a, R4b, X2, Y3), (A2, B1, M1, N2, P1, Q2, R3a, R4c, X1, Y1), (A2, B1, M1, N2, P1, Q2, R3a, R4c, X1, Y2), (A2, B1, M1, N2, P1, Q2, R3a, R4c, X1, Y3), (A2, B1, M1, N2, P1, Q2, R3a, R4c, X2, Y1), (A2, B1, M1, N2, P1, Q2, R3a, R4c, X2, Y2), (A2, B1, M1, N2, P1, Q2, R3a, R4c, X2, Y3), (A2, B1, M1, N2, P1, Q2, R3b, R4a, X1, Y1), (A2, B1, M1, N2, P1, Q2, R3b, R4a, X1, Y2), (A2, B1, M1, N2, P1, Q2, R3b, R4a, X1, Y3), (A2, B1, M1, N2, P1, Q2, R3b, R4a, X2, Y1), (A2, B1, M1, N2, P1, Q2, R3b, R4a, X2, Y2), (A2, B1, M1, N2, P1, Q2, R3b, R4a, X2, Y3), (A2, B1, M1, N2, P1, Q2, R3b, R4b, X1, Y1), (A2, B1, M1, N2, P1, Q2, R3b, R4b, X1, Y2), (A2, B1, M1, N2, P1, Q2, R3b, R4b, X1, Y3), (A2, B1, M1, N2, P1, Q2, R3b, R4b, X2, Y1), (A2, B1, M1, N2, P1, Q2, R3b, R4b, X2, Y2), (A2, B1, M1, N2, P1, Q2, R3b, R4b, X2, Y3), (A2, B1, M1, N2, P1, Q2, R3b, R4c, X1, Y1), (A2, B1, M1, N2, P1, Q2, R3b, R4c, X1, Y2), (A2, B1, M1, N2, P1, Q2, R3b, R4c, X1, Y3), (A2, B1, M1, N2, P1, Q2, R3b, R4c, X2, Y1), (A2, B1, M1, N2, P1, Q2, R3b, R4c, X2, Y2), (A2, B1, M1, N2, P1, Q2, R3b, R4c, X2, Y3), (A2, B1, M1, N2, P2, Q1, R3a, R4a, X1, Y1), (A2, B1, M1, N2, P2, Q1, R3a, R4a, X1, Y2), (A2, B1, M1, N2, P2, Q1, R3a, R4a, X1, Y3), (A2, B1, M1, N2, P2, Q1, R3a, R4a, X2, Y1), (A2, B1, M1, N2, P2, Q1, R3a, R4a, X2, Y2), (A2, B1, M1, N2, P2, Q1, R3a, R4a, X2, Y3), (A2, B1, M1, N2, P2, Q1, R3a, R4b, X1, Y1),
(A2, B1, M1, N2, P2, Q1, R3a, R4b, X1, Y2), (A2, B1, M1, N2, P2, Q1, R3a, R4b, X1, Y3), (A2, B1, M1, N2, P2, Q1, R3a, R4b, X2, Y1), (A2, B1, M1, N2, P2, Q1, R3a, R4b, X2, Y2), (A2, B1, M1, N2, P2, Q1, R3a, R4b, X2, Y3), (A2, B1, M1, N2, P2, Q1, R3a, R4c, X1, Y1) (A2, B1, M1, N2, P2, Q1, R3a, R4c, X1, Y2), (A2, B1, M1, N2, P2, Q1, R3a, R4c, X1, Y3), (A2, B1, M1, N2, P2, Q1, R3a, R4c, X2, Y1), (A2, B1, M1, N2, P2, Q1, R3a, R4c, X2, Y2) (A2, B1, M1, N2, P2, Q1, R3a, R4c, X2, Y3), (A2, B1, M1, N2, P2, Q1, R3b, R4a, X1, Y1), (A2, B1, M1, N2, P2, Q1, R3b, R4a, X1, Y2), (A2, B1, M1, N2, P2, Q1, R3b, R4a, X1, Y3) (A2, B1, M1, N2, P2, Q1, R3b, R4a, X2, Y1), (A2, B1, M1, N2, P2, Q1, R3b, R4a, X2, Y2), (A2, B1, M1, N2, P2, Q1, R3b, R4a, X2, Y3), (A2, B1, M1, N2, P2, Q1, R3b, R4b, X1, Y1), (A2, B1, M1, N2, P2, Q1, R3b, R4b, X1, Y2), (A2, B1, M1, N2, P2, Q1, R3b, R4b, X1, Y3), (A2, B1, M1, N2, P2, Q1, R3b, R4b, X2, Y1), (A2, B1, M1, N2, P2, Q1, R3b, R4b, X2, Y2), (A2, B1, M1, N2, P2, Q1, R3b, R4b, X2, Y3), (A2, B1, M1, N2, P2, Q1, R3b, R4c, X1, Y1), (A2, B1, M1, N2, P2, Q1, R3b, R4c, X1, Y2), (A2, B1, M1, N2, P2, Q1, R3b, R4c, X1, Y3), (A2, B1, M1, N2, P2, Q1, R3b, R4c, X2, Y1), (A2, B1, M1, N2, P2, Q1, R3b, R4c, X2, Y2), (A2, B1, M1, N2, P2, Q1, R3b, R4c, X2, Y3), (A2, B1, M1, N2, P2, Q2, R3a, R4a, X1, Y1), (A2, B1, M1, N2, P2, Q2, R3a, R4a, X1, Y2), (A2, B1, M1, N2, P2, Q2, R3a, R4a, X1, Y3), (A2, B1, M1, N2, P2, Q2, R3a, R4a, X2, Y1), (A2, B1, M1, N2, P2, Q2, R3a, R4a, X2, Y2), (A2, B1, M1, N2, P2, Q2, R3a, R4a, X2, Y3), (A2, B1, M1, N2, P2, Q2, R3a, R4b, X1, Y1), (A2, B1, M1, N2, P2, Q2, R3a, R4b, X1, Y2), (A2, B1, M1, N2, P2, Q2, R3a, R4b, X1, Y3), (A2, B1, M1, N2, P2, Q2, R3a, R4b, X2, Y1), (A2, B1, M1, N2, P2, Q2, R3a, R4b, X2, Y2), (A2, B1, M1, N2, P2, Q2, R3a, R4b, X2, Y3), (A2, B1, M1, N2, P2, Q2, R3a, R4c, X1, Y1), (A2, B1, M1, N2, P2, Q2, R3a, R4c, X1, Y2), (A2, B1, M1, N2, P2, Q2, R3a, R4c, X1, Y3), (A2, B1, M1, N2, P2, Q2, R3a, R4c, X2, Y1), (A2, B1, M1, N2, P2, Q2, R3a, R4c, X2, Y2), (A2, B1, M1, N2, P2, Q2, R3a, R4c, X2, Y3), (A2, B1, M1, N2, P2, Q2, R3b, R4a, X1, Y1), (A2, B1, M1, N2, P2, Q2, R3b, R4a, X1, Y2), (A2, B1, M1, N2, P2, Q2, R3b, R4a, X1, Y3), (A2, B1, M1, N2, P2, Q2, R3b, R4a, X2, Y1), (A2, B1, M1, N2, P2, Q2, R3b, R4a, X2, Y2), (A2, B1, M1, N2, P2, Q2, R3b, R4a, X2, Y3), (A2, B1, M1, N2, P2, Q2, R3b, R4b, X1, Y1), (A2, B1, M1, N2, P2, Q2, R3b, R4b, X1, Y2), (A2, B1, M1, N2, P2, Q2, R3b, R4b, X1, Y3), (A2, B1, M1, N2, P2, Q2, R3b, R4b, X2, Y1), (A2, B1, M1, N2, P2, Q2, R3b, R4b, X2, Y2), (A2, B1, M1, N2, P2, Q2, R3b, R4b, X2, Y3), (A2, B1, M1, N2, P2, Q2, R3b, R4c, X1, Y1), (A2, B1, M1, N2, P2, Q2, R3b, R4c, X1, Y3), (A2, B1, M1, N2, P2, Q2, R3b, R4c, X2, Y1), (A2, B1, M1, N2, P2, Q2, R3b, R4c, X2, Y2), (A2, B1, M1, N2, P2, Q2, R3b, R4c, X2, Y3), (A2, B1, M2, N1, P1, Q1, R3a, R4a, X1, Y1), (A2, B1, M2, N1, P1, Q1, R3a, R4a, X1, Y2), (A2, B1, M2, N1, P1, Q1, R3a, R4a, X1, Y3), (A2, B1, M2, N1, P1, Q1, R3a, R4a, X2, Y1), (A2, B1, M2, N1, P1, Q1, R3a, R4a, X2, Y2), (A2, B1, M2, N1, P1, Q1, R3a, R4a, X2, Y3), (A2, B1, M2, N1, P1, Q1, R3a, R4b, X1, Y1), (A2, B1, M2, N1, P1, Q1, R3a, R4b, X1, Y2), (A2, B1, M2, N1, P1, Q1, R3a, R4b, X1, Y3), (A2, B1, M2, N1, P1, Q1, R3a, R4b, X2, Y1), (A2, B1, M2, N1, P1, Q1, R3a, R4b, X2, Y2), (A2, B1, M2, N1, P1, Q1, R3a, R4b, X2, Y3), (A2, B1, M2, N1, P1, Q1, R3a, R4c, X1, Y1), (A2, B1, M2, N1, P1, Q1, R3a, R4c, X1, Y2), (A2, B1, M2, N1, P1, Q1, R3a, R4c, X1, Y3), (A2, B1, M2, N1, P1, Q1, R3a, R4c, X2, Y1), (A2, B1, M2, N1, P1, Q1, R3a, R4c, X2, Y2), (A2, B1, M2, N1, P1, Q1, R3a, R4c, X2, Y3), (A2, B1, M2, N1, P1, Q1, R3b, R4a, X1, Y1), (A2, B1, M2, N1, P1, Q1, R3b, R4a, X1, Y2), (A2, B1, M2, N1, P1, Q1, R3b, R4a, X1, Y3), (A2, B1, M2, N1, P1, Q1, R3b, R4a, X2, Y1), (A2, B1, M2, N1, P1, Q1, R3b, R4a, X2, Y2), (A2, B1, M2, N1, P1, Q1, R3b, R4a, X2, Y3),
(A2, B1, M2, N1, P1, Q1, R3b, R4b, X1, Y1), (A2, B1, M2, N1, P1, Q1, R3b, R4b, X1, Y2), (A2, B1, M2, N1, P1, Q1, R3b, R4b, X1, Y3), (A2, B1, M2, N1, P1, Q1, R3b, R4b, X2, Y1), (A2, B1, M2, N1, P1, Q1, R3b, R4b, X2, Y2), (A2, B1, M2, N1, P1, Q1, R3b, R4b, X2, Y3), (A2, B1, M2, N1, P1, Q1, R3b, R4c, X1, Y1), (A2, B1, M2, N1, P1, Q1, R3b, R4c, X1, Y2), (A2, B1, M2, N1, P1, Q1, R3b, R4c, X1, Y3), (A2, B1, M2, N1, P1, Q1, R3b, R4c, X2, Y1), (A2, B1, M2, N1, P1, Q1, R3b, R4c, X2, Y2), (A2, B1, M2, N1, P1, Q1, R3b, R4c, X2, Y3), (A2, B1, M2, N1, P1, Q2, R3a, R4a, X1, Y1), (A2, B1, M2, N1, P1, Q2, R3a, R4a, X1, Y2), (A2, B1, M2, N1, P1, Q2, R3a, R4a, X1, Y3), (A2, B1, M2, N1, P1, Q2, R3a, R4a, X2, Y1), (A2, B1, M2, N1, P1, Q2, R3a, R4a, X2, Y2), (A2, B1, M2, N1, P1, Q2, R3a, R4a, X2, Y3), (A2, B1, M2, N1, P1, Q2, R3a, R4b, X1, Y1), (A2, B1, M2, N1, P1, Q2, R3a, R4b, X1, Y2), (A2, B1, M2, N1, P1, Q2, R3a, R4b, X1, Y3), (A2, B1, M2, N1, P1, Q2, R3a, R4b, X2, Y1), (A2, B1, M2, N1, P1, Q2, R3a, R4b, X2, Y2), (A2, B1, M2, N1, P1, Q2, R3a, R4b, X2, Y3), (A2, B1, M2, N1, P1, Q2, R3a, R4c, X1, Y1), (A2, B1, M2, N1, P1, Q2, R3a, R4c, X1, Y2), (A2, B1, M2, N1, P1, Q2, R3a, R4c, X1, Y3), (A2, B1, M2, N1, P1, Q2, R3a, R4c, X2, Y1), (A2, B1, M2, N1, P1, Q2, R3a, R4c, X2, Y2), (A2, B1, M2, N1, P1, Q2, R3a, R4c, X2, Y3), (A2, B1, M2, N1, P1, Q2, R3b, R4a, X1, Y1), (A2, B1, M2, N1, P1, Q2, R3b, R4a, X1, Y2), (A2, B1, M2, N1, P1, Q2, R3b, R4a, X1, Y3), (A2, B1, M2, N1, P1, Q2, R3b, R4a, X2, Y1), (A2, B1, M2, N1, P1, Q2, R3b, R4a, X2, Y2), (A2, B1, M2, N1, P1, Q2, R3b, R4a, X2, Y3), (A2, B1, M2, N1, P1, Q2, R3b, R4b, X1, Y1), (A2, B1, M2, N1, P1, Q2, R3b, R4b, X1, Y2), (A2, B1, M2, N1, P1, Q2, R3b, R4b, X1, Y3), (A2, B1, M2, N1, P1, Q2, R3b, R4b, X2, Y1), (A2, B1, M2, N1, P1, Q2, R3b, R4b, X2, Y2), (A2, B1, M2, N1, P1, Q2, R3b, R4b, X2, Y3), (A2, B1, M2, N1, P1, Q2, R3b, R4c, X1, Y1), (A2, B1, M2, N1, P1, Q2, R3b, R4c, X1, Y2), (A2, B1, M2, N1, P1, Q2, R3b, R4c, X1, Y3), (A2, B1, M2, N1, P1, Q2, R3b, R4c, X2, Y1), (A2, B1, M2, N1, P1, Q2, R3b, R4c, X2, Y2), (A2, B1, M2, N1, P1, Q2, R3b, R4c, X2, Y3), (A2, B1, M2, N1, P2, Q1, R3a, R4a, X1, Y1), (A2, B1, M2, N1, P2, Q1, R3a, R4a, X1, Y2), (A2, B1, M2, N1, P2, Q1, R3a, R4a, X1, Y3), (A2, B1, M2, N1, P2, Q1, R3a, R4a, X2, Y1), (A2, B1, M2, N1, P2, Q1, R3a, R4a, X2, Y2), (A2, B1, M2, N1, P2, Q1, R3a, R4a, X2, Y3), (A2, B1, M2, N1, P2, Q1, R3a, R4b, X1, Y1), (A2, B1, M2, N1, P2, Q1, R3a, R4b, X1, Y2), (A2, B1, M2, N1, P2, Q1, R3a, R4b, X1, Y3), (A2, B1, M2, N1, P2, Q1, R3a, R4b, X2, Y1), (A2, B1, M2, N1, P2, Q1, R3a, R4b, X2, Y2), (A2, B1, M2, N1, P2, Q1, R3a, R4b, X2, Y3), (A2, B1, M2, N1, P2, Q1, R3a, R4c, X1, Y1), (A2, B1, M2, N1, P2, Q1, R3a, R4c, X1, Y2), (A2, B1, M2, N1, P2, Q1, R3a, R4c, X1, Y3), (A2, B1, M2, N1, P2, Q1, R3a, R4c, X2, Y1), (A2, B1, M2, N1, P2, Q1, R3a, R4c, X2, Y2), (A2, B1, M2, N1, P2, Q1, R3a, R4c, X2, Y3), (A2, B1, M2, N1, P2, Q1, R3b, R4a, X1, Y1), (A2, B1, M2, N1, P2, Q1, R3b, R4a, X1, Y2), (A2, B1, M2, N1, P2, Q1, R3b, R4a, X1, Y3), (A2, B1, M2, N1, P2, Q1, R3b, R4a, X2, Y1), (A2, B1, M2, N1, P2, Q1, R3b, R4a, X2, Y2), (A2, B1, M2, N1, P2, Q1, R3b, R4a, X2, Y3), (A2, B1, M2, N1, P2, Q1, R3b, R4b, X1, Y1), (A2, B1, M2, N1, P2, Q1, R3b, R4b, X1, Y2), (A2, B1, M2, N1, P2, Q1, R3b, R4b, X1, Y3), (A2, B1, M2, N1, P2, Q1, R3b, R4b, X2, Y1), (A2, B1, M2, N1, P2, Q1, R3b, R4b, X2, Y2), (A2, B1, M2, N1, P2, Q1, R3b, R4b, X2, Y3), (A2, B1, M2, N1, P2, Q1, R3b, R4c, X1, Y1), (A2, B1, M2, N1, P2, Q1, R3b, R4c, X1, Y2), (A2, B1, M2, N1, P2, Q1, R3b, R4c, X1, Y3), (A2, B1, M2, N1, P2, Q1, R3b, R4c, X2, Y1), (A2, B1, M2, N1, P2, Q1, R3b, R4c, X2, Y2), (A2, B1, M2, N1, P2, Q1, R3b, R4c, X2, Y3), (A2, B1, M2, N1, P2, Q2, R3a, R4a, X1, Y1), (A2, B1, M2, N1, P2, Q2, R3a, R4a, X1, Y2), (A2, B1, M2, N1, P2, Q2, R3a, R4a, X1, Y3), (A2, B1, M2, N1, P2, Q2, R3a, R4a, X2, Y1), (A2, B1, M2, N1, P2, Q2, R3a, R4a, X2, Y2),
(A2, B1, M2, N1, P2, Q2, R3a, R4a, X2, Y3), (A2, B1, M2, N1, P2, Q2, R3a, R4b, X1, Y1), (A2, B1, M2, N1, P2, Q2, R3a, R4b, X1, Y2), (A2, B1, M2, N1, P2, Q2, R3a, R4b, X1, Y3), (A2, B1, M2, N1, P2, Q2, R3a, R4b, X2, Y1), (A2, B1, M2, N1, P2, Q2, R3a, R4b, X2, Y2), (A2, B1, M2, N1, P2, Q2, R3a, R4b, X2, Y3), (A2, B1, M2, N1, P2, Q2, R3a, R4c, X1, Y1), (A2, B1, M2, N1, P2, Q2, R3a, R4c, X1, Y2), (A2, B1, M2, N1, P2, Q2, R3a, R4c, X1, Y3), (A2, B1, M2, N1, P2, Q2, R3a, R4c, X2, Y1), (A2, B1, M2, N1, P2, Q2, R3a, R4c, X2, Y2), (A2, B1, M2, N1, P2, Q2, R3a, R4c, X2, Y3), (A2, B1, M2, N1, P2, Q2, R3b, R4a, X1, Y1), (A2, B1, M2, N1, P2, Q2, R3b, R4a, X1, Y2), (A2, B1, M2, N1, P2, Q2, R3b, R4a, X1, Y3), (A2, B1, M2, N1, P2, Q2, R3b, R4a, X2, Y1), (A2, B1, M2, N1, P2, Q2, R3b, R4a, X2, Y2), (A2, B1, M2, N1, P2, Q2, R3b, R4a, X2, Y3), (A2, B1, M2, N1, P2, Q2, R3b, R4b, X1, Y1), (A2, B1, M2, N1, P2, Q2, R3b, R4b, X1, Y2), (A2, B1, M2, N1, P2, Q2, R3b, R4b, X1, Y3), (A2, B1, M2, N1, P2, Q2, R3b, R4b, X2, Y1), (A2, B1, M2, N1, P2, Q2, R3b, R4b, X2, Y2), (A2, B1, M2, N1, P2, Q2, R3b, R4b, X2, Y3), (A2, B1, M2, N1, P2, Q2, R3b, R4c, X1, Y1), (A2, B1, M2, N1, P2, Q2, R3b, R4c, X1, Y2), (A2, B1, M2, N1, P2, Q2, R3b, R4c, X1, Y3), (A2, B1, M2, N1, P2, Q2, R3b, R4c, X2, Y1), (A2, B1, M2, N1, P2, Q2, R3b, R4c, X2, Y2), (A2, B1, M2, N1, P2, Q2, R3b, R4c, X2, Y3), (A2, B1, M2, N2, P1, Q1, R3a, R4a, X1, Y1), (A2, B1, M2, N2, P1, Q1, R3a, R4a, X1, Y2), (A2, B1, M2, N2, P1, Q1, R3a, R4a, X1, Y3), (A2, B1, M2, N2, P1, Q1, R3a, R4a, X2, Y1), (A2, B1, M2, N2, P1, Q1, R3a, R4a, X2, Y2), (A2, B1, M2, N2, P1, Q1, R3a, R4a, X2, Y3), (A2, B1, M2, N2, P1, Q1, R3a, R4b, X1, Y1), (A2, B1, M2, N2, P1, Q1, R3a, R4b, X1, Y2), (A2, B1, M2, N2, P1, Q1, R3a, R4b, X1, Y3), (A2, B1, M2, N2, P1, Q1, R3a, R4b, X2, Y1), (A2, B1, M2, N2, P1, Q1, R3a, R4b, X2, Y2), (A2, B1, M2, N2, P1, Q1, R3a, R4b, X2, Y3), (A2, B1, M2, N2, P1, Q1, R3a, R4c, X1, Y1), (A2, B1, M2, N2, P1, Q1, R3a, R4c, X1, Y2), (A2, B1, M2, N2, P1, Q1, R3a, R4c, X1, Y3), (A2, B1, M2, N2, P1, Q1, R3a, R4c, X2, Y1), (A2, B1, M2, N2, P1, Q1, R3a, R4c, X2, Y2), (A2, B1, M2, N2, P1, Q1, R3a, R4c, X2, Y3), (A2, B1, M2, N2, P1, Q1, R3b, R4a, X1, Y1), (A2, B1, M2, N2, P1, Q1, R3b, R4a, X1, Y2), (A2, B1, M2, N2, P1, Q1, R3b, R4a, X1, Y3), (A2, B1, M2, N2, P1, Q1, R3b, R4a, X2, Y1), (A2, B1, M2, N2, P1, Q1, R3b, R4a, X2, Y2), (A2, B1, M2, N2, P1, Q1, R3b, R4a, X2, Y3), (A2, B1, M2, N2, P1, Q1, R3b, R4b, X1, Y1), (A2, B1, M2, N2, P1, Q1, R3b, R4b, X1, Y2), (A2, B1, M2, N2, P1, Q1, R3b, R4b, X1, Y3), (A2, B1, M2, N2, P1, Q1, R3b, R4b, X2, Y1), (A2, B1, M2, N2, P1, Q1, R3b, R4b, X2, Y2), (A2, B1, M2, N2, P1, Q1, R3b, R4b, X2, Y3), (A2, B1, M2, N2, P1, Q1, R3b, R4c, X1, Y1), (A2, B1, M2, N2, P1, Q1, R3b, R4c, X1, Y2), (A2, B1, M2, N2, P1, Q1, R3b, R4c, X1, Y3), (A2, B1, M2, N2, P1, Q1, R3b, R4c, X2, Y1), (A2, B1, M2, N2, P1, Q1, R3b, R4c, X2, Y2), (A2, B1, M2, N2, P1, Q1, R3b, R4c, X2, Y3), (A2, B1, M2, N2, P1, Q2, R3a, R4a, X1, Y1), (A2, B1, M2, N2, P1, Q2, R3a, R4a, X1, Y2), (A2, B1, M2, N2, P1, Q2, R3a, R4a, X1, Y3), (A2, B1, M2, N2, P1, Q2, R3a, R4a, X2, Y1), (A2, B1, M2, N2, P1, Q2, R3a, R4a, X2, Y2), (A2, B1, M2, N2, P1, Q2, R3a, R4a, X2, Y3), (A2, B1, M2, N2, P1, Q2, R3a, R4b, X1, Y1), (A2, B1, M2, N2, P1, Q2, R3a, R4b, X1, Y2), (A2, B1, M2, N2, P1, Q2, R3a, R4b, X1, Y3), (A2, B1, M2, N2, P1, Q2, R3a, R4b, X2, Y1), (A2, B1, M2, N2, P1, Q2, R3a, R4b, X2, Y2), (A2, B1, M2, N2, P1, Q2, R3a, R4b, X2, Y3), (A2, B1, M2, N2, P1, Q2, R3a, R4c, X1, Y1), (A2, B1, M2, N2, P1, Q2, R3a, R4c, X1, Y2), (A2, B1, M2, N2, P1, Q2, R3a, R4c, X1, Y3), (A2, B1, M2, N2, P1, Q2, R3a, R4c, X2, Y1), (A2, B1, M2, N2, P1, Q2, R3a, R4c, X2, Y2), (A2, B1, M2, N2, P1, Q2, R3a, R4c, X2, Y3), (A2, B1, M2, N2, P1, Q2, R3b, R4a, X1, Y1), (A2, B1, M2, N2, P1, Q2, R3b, R4a, X1, Y2), (A2, B1, M2, N2, P1, Q2, R3b, R4a, X1, Y3), (A2, B1, M2, N2, P1, Q2, R3b, R4a, X2, Y1),
(A2, B1, M2, N2, P1, Q2, R3b, R4a, X2, Y2), (A2, B1, M2, N2, P1, Q2, R3b, R4a, X2, Y3), (A2, B1, M2, N2, P1, Q2, R3b, R4b, X1, Y1), (A2, B1, M2, N2, P1, Q2, R3b, R4b, X1, Y2), (A2, B1, M2, N2, P1, Q2, R3b, R4b, X1, Y3), (A2, B1, M2, N2, P1, Q2, R3b, R4b, X2, Y1), (A2, B1, M2, N2, P1, Q2, R3b, R4b, X2, Y2), (A2, B1, M2, N2, P1, Q2, R3b, R4b, X2, Y3), (A2, B1, M2, N2, P1, Q2, R3b, R4c, X1, Y1), (A2, B1, M2, N2, P1, Q2, R3b, R4c, X1, Y2), (A2, B1, M2, N2, P1, Q2, R3b, R4c, X1, Y3), (A2, B1, M2, N2, P1, Q2, R3b, R4c, X2, Y1), (A2, B1, M2, N2, P1, Q2, R3b, R4c, X2, Y2), (A2, B1, M2, N2, P1, Q2, R3b, R4c, X2, Y3), (A2, B1, M2, N2, P2, Q1, R3a, R4a, X1, Y1), (A2, B1, M2, N2, P2, Q1, R3a, R4a, X1, Y2), (A2, B1, M2, N2, P2, Q1, R3a, R4a, X1, Y3), (A2, B1, M2, N2, P2, Q1, R3a, R4a, X2, Y1), (A2, B1, M2, N2, P2, Q1, R3a, R4a, X2, Y2), (A2, B1, M2, N2, P2, Q1, R3a, R4a, X2, Y3), (A2, B1, M2, N2, P2, Q1, R3a, R4b, X1, Y1), (A2, B1, M2, N2, P2, Q1, R3a, R4b, X1, Y2), (A2, B1, M2, N2, P2, Q1, R3a, R4b, X1, Y3), (A2, B1, M2, N2, P2, Q1, R3a, R4b, X2, Y1), (A2, B1, M2, N2, P2, Q1, R3a, R4b, X2, Y2), (A2, B1, M2, N2, P2, Q1, R3a, R4b, X2, Y3), (A2, B1, M2, N2, P2, Q1, R3a, R4c, X1, Y1), (A2, B1, M2, N2, P2, Q1, R3a, R4c, X1, Y2), (A2, B1, M2, N2, P2, Q1, R3a, R4c, X1, Y3), (A2, B1, M2, N2, P2, Q1, R3a, R4c, X2, Y1), (A2, B1, M2, N2, P2, Q1, R3a, R4c, X2, Y2), (A2, B1, M2, N2, P2, Q1, R3a, R4c, X2, Y3), (A2, B1, M2, N2, P2, Q1, R3b, R4a, X1, Y1), (A2, B1, M2, N2, P2, Q1, R3b, R4a, X1, Y2), (A2, B1, M2, N2, P2, Q1, R3b, R4a, X1, Y3), (A2, B1, M2, N2, P2, Q1, R3b, R4a, X2, Y1), (A2, B1, M2, N2, P2, Q1, R3b, R4a, X2, Y2), (A2, B1, M2, N2, P2, Q1, R3b, R4a, X2, Y3), (A2, B1, M2, N2, P2, Q1, R3b, R4b, X1, Y1), (A2, B1, M2, N2, P2, Q1, R3b, R4b, X1, Y2), (A2, B1, M2, N2, P2, Q1, R3b, R4b, X1, Y3), (A2, B1, M2, N2, P2, Q1, R3b, R4b, X2, Y1), (A2, B1, M2, N2, P2, Q1, R3b, R4b, X2, Y2), (A2, B1, M2, N2, P2, Q1, R3b, R4b, X2, Y3), (A2, B1, M2, N2, P2, Q1, R3b, R4c, X1, Y1), (A2, B1, M2, N2, P2, Q1, R3b, R4c, X1, Y2), (A2, B1, M2, N2, P2, Q1, R3b, R4c, X1, Y3), (A2, B1, M2, N2, P2, Q1, R3b, R4c, X2, Y1), (A2, B1, M2, N2, P2, Q1, R3b, R4c, X2, Y2), (A2, B1, M2, N2, P2, Q1, R3b, R4c, X2, Y3), (A2, B1, M2, N2, P2, Q2, R3a, R4a, X1, Y1), (A2, B1, M2, N2, P2, Q2, R3a, R4a, X1, Y2), (A2, B1, M2, N2, P2, Q2, R3a, R4a, X1, Y3), (A2, B1, M2, N2, P2, Q2, R3a, R4a, X2, Y1), (A2, B1, M2, N2, P2, Q2, R3a, R4a, X2, Y2), (A2, B1, M2, N2, P2, Q2, R3a, R4a, X2, Y3), (A2, B1, M2, N2, P2, Q2, R3a, R4b, X1, Y1), (A2, B1, M2, N2, P2, Q2, R3a, R4b, X1, Y2), (A2, B1, M2, N2, P2, Q2, R3a, R4b, X1, Y3), (A2, B1, M2, N2, P2, Q2, R3a, R4b, X2, Y1), (A2, B1, M2, N2, P2, Q2, R3a, R4b, X2, Y2), (A2, B1, M2, N2, P2, Q2, R3a, R4b, X2, Y3), (A2, B1, M2, N2, P2, Q2, R3a, R4c, X1, Y1), (A2, B1, M2, N2, P2, Q2, R3a, R4c, X1, Y2), (A2, B1, M2, N2, P2, Q2, R3a, R4c, X1, Y3), (A2, B1, M2, N2, P2, Q2, R3a, R4c, X2, Y1), (A2, B1, M2, N2, P2, Q2, R3a, R4c, X2, Y2), (A2, B1, M2, N2, P2, Q2, R3a, R4c, X2, Y3), (A2, B1, M2, N2, P2, Q2, R3b, R4a, X1, Y1), (A2, B1, M2, N2, P2, Q2, R3b, R4a, X1, Y2), (A2, B1, M2, N2, P2, Q2, R3b, R4a, X1, Y3), (A2, B1, M2, N2, P2, Q2, R3b, R4a, X2, Y1), (A2, B1, M2, N2, P2, Q2, R3b, R4a, X2, Y2), (A2, B1, M2, N2, P2, Q2, R3b, R4a, X2, Y3), (A2, B1, M2, N2, P2, Q2, R3b, R4b, X1, Y1), (A2, B1, M2, N2, P2, Q2, R3b, R4b, X1, Y2), (A2, B1, M2, N2, P2, Q2, R3b, R4b, X1, Y3), (A2, B1, M2, N2, P2, Q2, R3b, R4b, X2, Y1), (A2, B1, M2, N2, P2, Q2, R3b, R4b, X2, Y2), (A2, B1, M2, N2, P2, Q2, R3b, R4b, X2, Y3), (A2, B1, M2, N2, P2, Q2, R3b, R4c, X1, Y1), (A2, B1, M2, N2, P2, Q2, R3b, R4c, X1, Y2), (A2, B1, M2, N2, P2, Q2, R3b, R4c, X1, Y3), (A2, B1, M2, N2, P2, Q2, R3b, R4c, X2, Y1), (A2, B1, M2, N2, P2, Q2, R3b, R4c, X2, Y2), (A2, B1, M2, N2, P2, Q2, R3b, R4c, X2, Y3), (A2, B2, M1, N1, P1, Q1, R3a, R4a, X1, Y1), (A2, B2, M1, N1, P1, Q1, R3a, R4a, X1, Y2), (A2, B2, M1, N1, P1, Q1, R3a, R4a, X1, Y3),
(A2, B2, M1, N1, P1, Q1, R3a, R4a, X2, Y1), (A2, B2, M1, N1, P1, Q1, R3a, R4a, X2, Y2), (A2, B2, M1, N1, P1, Q1, R3a, R4a, X2, Y3), (A2, B2, M1, N1, P1, Q1, R3a, R4b, X1, Y1), (A2, B2, M1, N1, P1, Q1, R3a, R4b, X1, Y2), (A2, B2, M1, N1, P1, Q1, R3a, R4b, X1, Y3), (A2, B2, M1, N1, P1, Q1, R3a, R4b, X2, Y1), (A2, B2, M1, N1, P1, Q1, R3a, R4b, X2, Y2), (A2, B2, M1, N1, P1, Q1, R3a, R4b, X2, Y3), (A2, B2, M1, N1, P1, Q1, R3a, R4c, X1, Y1), (A2, B2, M1, N1, P1, Q1, R3a, R4c, X1, Y2), (A2, B2, M1, N1, P1, Q1, R3a, R4c, X1, Y3), (A2, B2, M1, N1, P1, Q1, R3a, R4c, X2, Y1), (A2, B2, M1, N1, P1, Q1, R3a, R4c, X2, Y2), (A2, B2, M1, N1, P1, Q1, R3a, R4c, X2, Y3), (A2, B2, M1, N1, P1, Q1, R3b, R4a, X1, Y1), (A2, B2, M1, N1, P1, Q1, R3b, R4a, X1, Y2), (A2, B2, M1, N1, P1, Q1, R3b, R4a, X1, Y3), (A2, B2, M1, N1, P1, Q1, R3b, R4a, X2, Y1), (A2, B2, M1, N1, P1, Q1, R3b, R4a, X2, Y2), (A2, B2, M1, N1, P1, Q1, R3b, R4a, X2, Y3), (A2, B2, M1, N1, P1, Q1, R3b, R4b, X1, Y1), (A2, B2, M1, N1, P1, Q1, R3b, R4b, X1, Y2), (A2, B2, M1, N1, P1, Q1, R3b, R4b, X1, Y3), (A2, B2, M1, N1, P1, Q1, R3b, R4b, X2, Y1), (A2, B2, M1, N1, P1, Q1, R3b, R4b, X2, Y2), (A2, B2, M1, N1, P1, Q1, R3b, R4b, X2, Y3), (A2, B2, M1, N1, P1, Q1, R3b, R4c, X1, Y1), (A2, B2, M1, N1, P1, Q1, R3b, R4c, X1, Y2), (A2, B2, M1, N1, P1, Q1, R3b, R4c, X1, Y3), (A2, B2, M1, N1, P1, Q1, R3b, R4c, X2, Y1), (A2, B2, M1, N1, P1, Q1, R3b, R4c, X2, Y2), (A2, B2, M1, N1, P1, Q1, R3b, R4c, X2, Y3), (A2, B2, M1, N1, P1, Q2, R3a, R4a, X1, Y1), (A2, B2, M1, N1, P1, Q2, R3a, R4a, X1, Y2), (A2, B2, M1, N1, P1, Q2, R3a, R4a, X1, Y3), (A2, B2, M1, N1, P1, Q2, R3a, R4a, X2, Y1), (A2, B2, M1, N1, P1, Q2, R3a, R4a, X2, Y2), (A2, B2, M1, N1, P1, Q2, R3a, R4a, X2, Y3), (A2, B2, M1, N1, P1, Q2, R3a, R4b, X1, Y1), (A2, B2, M1, N1, P1, Q2, R3a, R4b, X1, Y2), (A2, B2, M1, N1, P1, Q2, R3a, R4b, X1, Y3), (A2, B2, M1, N1, P1, Q2, R3a, R4b, X2, Y1), (A2, B2, M1, N1, P1, Q2, R3a, R4b, X2, Y2), (A2, B2, M1, N1, P1, Q2, R3a, R4b, X2, Y3), (A2, B2, M1, N1, P1, Q2, R3a, R4c, X1, Y1), (A2, B2, M1, N1, P1, Q2, R3a, R4c, X1, Y2), (A2, B2, M1, N1, P1, Q2, R3a, R4c, X1, Y3), (A2, B2, M1, N1, P1, Q2, R3a, R4c, X2, Y1), (A2, B2, M1, N1, P1, Q2, R3a, R4c, X2, Y2), (A2, B2, N1, N1, P1, Q2, R3a, R4c, X2, Y3), (A2, B2, M1, N1, P1, Q2, R3b, R4a, X1, Y1), (A2, B2, M1, N1, P1, Q2, R3b, R4a, X1, Y2), (A2, B2, M1, N1, P1, Q2, R3b, R4a, X1, Y3), (A2, B2, M1, N1, P1, Q2, R3b, R4a, X2, Y1), (A2, B2, M1, N1, P1, Q2, R3b, R4a, X2, Y2), (A2, B2, M1, N1, P1, Q2, R3b, R4a, X2, Y3), (A2, B2, M1, N1, P1, Q2, R3b, R4b, X1, Y1), (A2, B2, M1, N1, P1, Q2, R3b, R4b, X1, Y2), (A2, B2, M1, N1, P1, Q2, R3b, R4b, X1, Y3), (A2, B2, M1, N1, P1, Q2, R3b, R4b, X2, Y1), (A2, B2, M1, N1, P1, Q2, R3b, R4b, X2, Y2), (A2, B2, M1, N1, P1, Q2, R3b, R4b, X2, Y3), (A2, B2, M1, N1, P1, Q2, R3b, R4c, X1, Y1), (A2, B2, M1, N1, P1, Q2, R3b, R4c, X1, Y2), (A2, B2, M1, N1, P1, Q2, R3b, R4c, X1, Y3), (A2, B2, M1, N1, P1, Q2, R3b, R4c, X2, Y1), (A2, B2, M1, N1, P1, Q2, R3b, R4c, X2, Y2), (A2, B2, M1, N1, P1, Q2, R3b, R4c, X2, Y3), (A2, B2, M1, N1, P2, Q1, R3a, R4a, X1, Y1), (A2, B2, M1, N1, P2, Q1, R3a, R4a, X1, Y2), (A2, B2, M1, N1, P2, Q1, R3a, R4a, X1, Y3), (A2, B2, M1, N1, P2, Q1, R3a, R4a, X2, Y1), (A2, B2, M1, N1, P2, Q1, R3a, R4a, X2, Y2), (A2, B2, M1, N1, P2, Q1, R3a, R4a, X2, Y3), (A2, B2, M1, N1, P2, Q1, R3a, R4b, X1, Y1), (A2, B2, M1, N1, P2, Q1, R3a, R4b, X1, Y2), (A2, B2, M1, N1, P2, Q1, R3a, R4b, X1, Y3), (A2, B2, M1, N1, P2, Q1, R3a, R4b, X2, Y1), (A2, B2, M1, N1, P2, Q1, R3a, R4b, X2, Y2), (A2, B2, M1, N1, P2, Q1, R3a, R4b, X2, Y3), (A2, B2, M1, N1, P2, Q1, R3a, R4c, X1, Y1), (A2, B2, M1, N1, P2, Q1, R3a, R4c, X1, Y2), (A2, B2, M1, N1, P2, Q1, R3a, R4c, X1, Y3), (A2, B2, M1, N1, P2, Q1, R3a, R4c, X2, Y1), (A2, B2, M1, N1, P2, Q1, R3a, R4c, X2, Y2), (A2, B2, M1, N1, P2, Q1, R3a, R4c, X2, Y3), (A2, B2, M1, N1, P2, Q1, R3b, R4a, X1, Y1), (A2, B2, M1, N1, P2, Q1, R3b, R4a, X1, Y2),
(A2, B2, M1, N1, P2, Q1, R3b, R4a, X1, Y3), (A2, B2, M1, N1, P2, Q1, R3b, R4a, X2, Y1), (A2, B2, M1, N1, P2, Q1, R3b, R4a, X2, Y2), (A2, B2, M1, N1, P2, Q1, R3b, R4a, X2, Y3), (A2, B2, M1, N1, P2, Q1, R3b, R4b, X1, Y1), (A2, B2, M1, N1, P2, Q1, R3b, R4b, X1, Y2), (A2, B2, M1, N1, P2, Q1, R3b, R4b, X1, Y3), (A2, B2, M1, N1, P2, Q1, R3b, R4b, X2, Y1), (A2, B2, M1, N1, P2, Q1, R3b, R4b, X2, Y2), (A2, B2, M1, N1, P2, Q1, R3b, R4b, X2, Y3), (A2, B2, M1, N1, P2, Q1, R3b, R4c, X1, Y1), (A2, B2, M1, N1, P2, Q1, R3b, R4c, X1, Y2), (A2, B2, M1, N1, P2, Q1, R3b, R4c, X1, Y3), (A2, B2, M1, N1, P2, Q1, R3b, R4c, X2, Y1), (A2, B2, M1, N1, P2, Q1, R3b, R4c, X2, Y2), (A2, B2, M1, N1, P2, Q1, R3b, R4c, X2, Y3), (A2, B2, M1, N1, P2, Q2, R3a, R4a, X1, Y1), (A2, B2, M1, N1, P2, Q2, R3a, R4a, X1, Y2), (A2, B2, M1, N1, P2, Q2, R3a, R4a, X1, Y3), (A2, B2, M1, N1, P2, Q2, R3a, R4a, X2, Y1), (A2, B2, M1, N1, P2, Q2, R3a, R4a, X2, Y2), (A2, B2, M1, N1, P2, Q2, R3a, R4a, X2, Y3), (A2, B2, M1, N1, P2, Q2, R3a, R4b, X1, Y1), (A2, B2, M1, N1, P2, Q2, R3a, R4b, X1, Y2), (A2, B2, M1, N1, P2, Q2, R3a, R4b, X1, Y3), (A2, B2, M1, N1, P2, Q2, R3a, R4b, X2, Y1), (A2, B2, M1, N1, P2, Q2, R3a, R4b, X2, Y2), (A2, B2, M1, N1, P2, Q2, R3a, R4b, X2, Y3), (A2, B2, M1, N1, P2, Q2, R3a, R4c, X1, Y1), (A2, B2, M1, N1, P2, Q2, R3a, R4c, X1, Y2), (A2, B2, M1, N1, P2, Q2, R3a, R4c, X1, Y3), (A2, B2, M1, N1, P2, Q2, R3a, R4c, X2, Y1), (A2, B2, M1, N1, P2, Q2, R3a, R4c, X2, Y2), (A2, B2, M1, N1, P2, Q2, R3a, R4c, X2, Y3), (A2, B2, M1, N1, P2, Q2, R3b, R4a, X1, Y1), (A2, B2, M1, N1, P2, Q2, R3b, R4a, X1, Y2), (A2, B2, M1, N1, P2, Q2, R3b, R4a, X1, Y3), (A2, B2, M1, N1, P2, Q2, R3b, R4a, X2, Y1), (A2, B2, M1, N1, P2, Q2, R3b, R4a, X2, Y2), (A2, B2, M1, N1, P2, Q2, R3b, R4a, X2, Y3), (A2, B2, M1, N1, P2, Q2, R3b, R4b, X1, Y1), (A2, B2, M1, N1, P2, Q2, R3b, R4b, X1, Y2), (A2, B2, M1, N1, P2, Q2, R3b, R4b, X1, Y3), (A2, B2, M1, N1, P2, Q2, R3b, R4b, X2, Y1), (A2, B2, M1, N1, P2, Q2, R3b, R4b, X2, Y2), (A2, B2, M1, N1, P2, Q2, R3b, R4b, X2, Y3), (A2, B2, M1, N1, P2, Q2, R3b, R4c, X1, Y1), (A2, B2, M1, N1, P2, Q2, R3b, R4c, X1, Y2), (A2, B2, M1, N1, P2, Q2, R3b, R4c, X1, Y3), (A2, B2, M1, N1, P2, Q2, R3b, R4c, X2, Y1), (A2, B2, M1, N1, P2, Q2, R3b, R4c, X2, Y2), (A2, B2, M1, N1, P2, Q2, R3b, R4c, X2, Y3), (A2, B2, M1, N2, P1, Q1, R3a, R4a, X1, Y1), (A2, B2, M1, N2, P1, Q1, R3a, R4a, X1, Y2), (A2, B2, M1, N2, P1, Q1, R3a, R4a, X1, Y3), (A2, B2, M1, N2, P1, Q1, R3a, R4a, X2, Y1), (A2, B2, M1, N2, P1, Q1, R3a, R4a, X2, Y2), (A2, B2, M1, N2, P1, Q1, R3a, R4a, X2, Y3), (A2, B2, M1, N2, P1, Q1, R3a, R4b, X1, Y1), (A2, B2, M1, N2, P1, Q1, R3a, R4b, X1, Y2), (A2, B2, M1, N2, P1, Q1, R3a, R4b, X1, Y3), (A2, B2, M1, N2, P1, Q1, R3a, R4b, X2, Y1), (A2, B2, M1, N2, P1, Q1, R3a, R4b, X2, Y2), (A2, B2, M1, N2, P1, Q1, R3a, R4b, X2, Y3), (A2, B2, M1, N2, P1, Q1, R3a, R4c, X1, Y1), (A2, B2, M1, N2, P1, Q1, R3a, R4c, X1, Y2), (A2, B2, M1, N2, P1, Q1, R3a, R4c, X1, Y3), (A2, B2, M1, N2, P1, Q1, R3a, R4c, X2, Y1), (A2, B2, M1, N2, P1, Q1, R3a, R4c, X2, Y2), (A2, B2, M1, N2, P1, Q1, R3a, R4c, X2, Y3), (A2, B2, M1, N2, P1, Q1, R3b, R4a, X1, Y1), (A2, B2, M1, N2, P1, Q1, R3b, R4a, X1, Y2), (A2, B2, M1, N2, P1, Q1, R3b, R4a, X1, Y3), (A2, B2, M1, N2, P1, Q1, R3b, R4a, X2, Y1), (A2, B2, M1, N2, P1, Q1, R3b, R4a, X2, Y2), (A2, B2, M1, N2, P1, Q1, R3b, R4a, X2, Y3), (A2, B2, M1, N2, P1, Q1, R3b, R4b, X1, Y1), (A2, B2, M1, N2, P1, Q1, R3b, R4b, X1, Y2), (A2, B2, M1, N2, P1, Q1, R3b, R4b, X1, Y3), (A2, B2, M1, N2, P1, Q1, R3b, R4b, X2, Y1), (A2, B2, M1, N2, P1, Q1, R3b, R4b, X2, Y2), (A2, B2, M1, N2, P1, Q1, R3b, R4b, X2, Y3), (A2, B2, M1, N2, P1, Q1, R3b, R4c, X1, Y1), (A2, B2, M1, N2, P1, Q1, R3b, R4c, X1, Y2), (A2, B2, M1, N2, P1, Q1, R3b, R4c, X1, Y3), (A2, B2, M1, N2, P1, Q1, R3b, R4c, X2, Y1), (A2, B2, M1, N2, P1, Q1, R3b, R4c, X2, Y2), (A2, B2, M1, N2, P1, Q1, R3b, R4c, X2, Y3), (A2, B2, M1, N2, P1, Q2, R3a, R4a, X1, Y1),
(A2, B2, M1, N2, P1, Q2, R3a, R4a, X1, Y2), (A2, B2, M1, N2, P1, Q2, R3a, R4a, X1, Y3), (A2, B2, M1, N2, P1, Q2, R3a, R4a, X2, Y1), (A2, B2, M1, N2, P1, Q2, R3a, R4a, X2, Y2), (A2, B2, M1, N2, P1, Q2, R3a, R4a, X2, Y3), (A2, B2, M1, N2, P1, Q2, R3a, R4b, X1, Y1), (A2, B2, M1, N2, P1, Q2, R3a, R4b, X1, Y2), (A2, B2, M1, N2, P1, Q2, R3a, R4b, X1, Y3), (A2, B2, M1, N2, P1, Q2, R3a, R4b, X2, Y1), (A2, B2, M1, N2, P1, Q2, R3a, R4b, X2, Y2), (A2, B2, M1, N2, P1, Q2, R3a, R4b, X2, Y3), (A2, B2, M1, N2, P1, Q2, R3a, R4c, X1, Y1), (A2, B2, M1, N2, P1, Q2, R3a, R4c, X1, Y2), (A2, B2, M1, N2, P1, Q2, R3a, R4c, X1, Y3), (A2, B2, M1, N2, P1, Q2, R3a, R4c, X2, Y1), (A2, B2, M1, N2, P1, Q2, R3a, R4c, X2, Y2), (A2, B2, M1, N2, P1, Q2, R3a, R4c, X2, Y3), (A2, B2, M1, N2, P1, Q2, R3b, R4a, X1, Y1), (A2, B2, M1, N2, P1, Q2, R3b, R4a, X1, Y2), (A2, B2, M1, N2, P1, Q2, R3b, R4a, X1, Y3), (A2, B2, M1, N2, P1, Q2, R3b, R4a, X2, Y1), (A2, B2, M1, N2, P1, Q2, R3b, R4a, X2, Y2), (A2, B2, M1, N2, P1, Q2, R3b, R4a, X2, Y3), (A2, B2, M1, N2, P1, Q2, R3b, R4b, X1, Y1), (A2, B2, M1, N2, P1, Q2, R3b, R4b, X1, Y2), (A2, B2, M1, N2, P1, Q2, R3b, R4b, X1, Y3), (A2, B2, M1, N2, P1, Q2, R3b, R4b, X2, Y1), (A2, B2, M1, N2, P1, Q2, R3b, R4b, X2, Y2), (A2, B2, M1, N2, P1, Q2, R3b, R4b, X2, Y3), (A2, B2, M1, N2, P1, Q2, R3b, R4c, X1, Y1), (A2, B2, M1, N2, P1, Q2, R3b, R4c, X1, Y2), (A2, B2, M1, N2, P1, Q2, R3b, R4c, X1, Y3), (A2, B2, M1, N2, P1, Q2, R3b, R4c, X2, Y1), (A2, B2, M1, N2, P1, Q2, R3b, R4c, X2, Y2), (A2, B2, M1, N2, P1, Q2, R3b, R4c, X2, Y3), (A2, B2, M1, N2, P2, Q1, R3a, R4a, X1, Y1), (A2, B2, M1, N2, P2, Q1, R3a, R4a, X1, Y2), (A2, B2, M1, N2, P2, Q1, R3a, R4a, X1, Y3), (A2, B2, M1, N2, P2, Q1, R3a, R4a, X2, Y1), (A2, B2, M1, N2, P2, Q1, R3a, R4a, X2, Y2), (A2, B2, M1, N2, P2, Q1, R3a, R4a, X2, Y3), (A2, B2, M1, N2, P2, Q1, R3a, R4b, X1, Y1), (A2, B2, M1, N2, P2, Q1, R3a, R4b, X1, Y2), (A2, B2, M1, N2, P2, Q1, R3a, R4b, X1, Y3), (A2, B2, M1, N2, P2, Q1, R3a, R4b, X2, Y1), (A2, B2, M1, N2, P2, Q1, R3a, R4b, X2, Y2), (A2, B2, M1, N2, P2, Q1, R3a, R4b, X2, Y3), (A2, B2, M1, N2, P2, Q1, R3a, R4c, X1, Y1), (A2, B2, M1, N2, P2, Q1, R3a, R4c, X1, Y2), (A2, B2, M1, N2, P2, Q1, R3a, R4c, X1, Y3), (A2, B2, M1, N2, P2, Q1, R3a, R4c, X2, Y1), (A2, B2, M1, N2, P2, Q1, R3a, R4c, X2, Y2), (A2, B2, M1, N2, P2, Q1, R3a, R4c, X2, Y3), (A2, B2, M1, N2, P2, Q1, R3b, R4a, X1, Y1), (A2, B2, M1, N2, P2, Q1, R3b, R4a, X1, Y2), (A2, B2, M1, N2, P2, Q1, R3b, R4a, X1, Y3), (A2, B2, M1, N2, P2, Q1, R3b, R4a, X2, Y1), (A2, B2, M1, N2, P2, Q1, R3b, R4a, X2, Y2), (A2, B2, M1, N2, P2, Q1, R3b, R4a, X2, Y3), (A2, B2, M1, N2, P2, Q1, R3b, R4b, X1, Y1), (A2, B2, M1, N2, P2, Q1, R3b, R4b, X1, Y2), (A2, B2, M1, N2, P2, Q1, R3b, R4b, X1, Y3), (A2, B2, M1, N2, P2, Q1, R3b, R4b, X2, Y1), (A2, B2, M1, N2, P2, Q1, R3b, R4b, X2, Y2), (A2, B2, M1, N2, P2, Q1, R3b, R4b, X2, Y3), (A2, B2, M1, N2, P2, Q1, R3b, R4c, X1, Y1), (A2, B2, M1, N2, P2, Q1, R3b, R4c, X1, Y2), (A2, B2, M1, N2, P2, Q1, R3b, R4c, X1, Y3), (A2, B2, M1, N2, P2, Q1, R3b, R4c, X2, Y1), (A2, B2, M1, N2, P2, Q1, R3b, R4c, X2, Y2), (A2, B2, M1, N2, P2, Q1, R3b, R4c, X2, Y3), (A2, B2, M1, N2, P2, Q2, R3a, R4a, X1, Y1), (A2, B2, M1, N2, P2, Q2, R3a, R4a, X1, Y2), (A2, B2, M1, N2, P2, Q2, R3a, R4a, X1, Y3), (A2, B2, M1, N2, P2, Q2, R3a, R4a, X2, Y1), (A2, B2, M1, N2, P2, Q2, R3a, R4a, X2, Y2), (A2, B2, M1, N2, P2, Q2, R3a, R4a, X2, Y3), (A2, B2, M1, N2, P2, Q2, R3a, R4b, X1, Y1), (A2, B2, M1, N2, P2, Q2, R3a, R4b, X1, Y2), (A2, B2, M1, N2, P2, Q2, R3a, R4b, X1, Y3), (A2, B2, M1, N2, P2, Q2, R3a, R4b, X2, Y1), (A2, B2, M1, N2, P2, Q2, R3a, R4b, X2, Y2), (A2, B2, M1, N2, P2, Q2, R3a, R4b, X2, Y3), (A2, B2, M1, N2, P2, Q2, R3a, R4c, X1, Y1), (A2, B2, M1, N2, P2, Q2, R3a, R4c, X1, Y2), (A2, B2, M1, N2, P2, Q2, R3a, R4c, X1, Y3), (A2, B2, M1, N2, P2, Q2, R3a, R4c, X2, Y1), (A2, B2, M1, N2, P2, Q2, R3a, R4c, X2, Y2), (A2, B2, M1, N2, P2, Q2, R3a, R4c, X2, Y3),
(A2, B2, M1, N2, P2, Q2, R3b, R4a, X1, Y1), (A2, B2, M1, N2, P2, Q2, R3b, R4a, X1, Y2), (A2, B2, M1, N2, P2, Q2, R3b, R4a, X1, Y3), (A2, B2, M1, N2, P2, Q2, R3b, R4a, X2, Y1), (A2, B2, M1, N2, P2, Q2, R3b, R4a, X2, Y2), (A2, B2, M1, N2, P2, Q2, R3b, R4a, X2, Y3), (A2, B2, M1, N2, P2, Q2, R3b, R4b, X1, Y1), (A2, B2, M1, N2, P2, Q2, R3b, R4b, X1, Y2), (A2, B2, M1, N2, P2, Q2, R3b, R4b, X1, Y3), (A2, B2, M1, N2, P2, Q2, R3b, R4b, X2, Y1), (A2, B2, M1, N2, P2, Q2, R3b, R4b, X2, Y2), (A2, B2, M1, N2, P2, Q2, R3b, R4b, X2, Y3), (A2, B2, M1, N2, P2, Q2, R3b, R4c, X1, Y1), (A2, B2, M1, N2, P2, Q2, R3b, R4c, X1, Y2), (A2, B2, M1, N2, P2, Q2, R3b, R4c, X1, Y3), (A2, B2, M1, N2, P2, Q2, R3b, R4c, X2, Y1), (A2, B2, M1, N2, P2, Q2, R3b, R4c, X2, Y2), (A2, B2, M1, N2, P2, Q2, R3b, R4c, X2, Y3), (A2, B2, M2, N1, P1, Q1, R3a, R4a, X1, Y1), (A2, B2, M2, N1, P1, Q1, R3a, R4a, X1, Y2), (A2, B2, M2, N1, P1, Q1, R3a, R4a, X1, Y3), (A2, B2, M2, N1, P1, Q1, R3a, R4a, X2, Y1), (A2, B2, M2, N1, P1, Q1, R3a, R4a, X2, Y2), (A2, B2, M2, N1, P1, Q1, R3a, R4a, X2, Y3), (A2, B2, M2, N1, P1, Q1, R3a, R4b, X1, Y1), (A2, B2, M2, N1, P1, Q1, R3a, R4b, X1, Y2), (A2, B2, M2, N1, P1, Q1, R3a, R4b, X1, Y3), (A2, B2, M2, N1, P1, Q1, R3a, R4b, X2, Y1), (A2, B2, M2, N1, P1, Q1, R3a, R4b, X2, Y2), (A2, B2, M2, N1, P1, Q1, R3a, R4b, X2, Y3), (A2, B2, M2, N1, P1, Q1, R3a, R4c, X1, Y1), (A2, B2, M2, N1, P1, Q1, R3a, R4c, X1, Y2), (A2, B2, M2, N1, P1, Q1, R3a, R4c, X1, Y3), (A2, B2, M2, N1, P1, Q1, R3a, R4c, X2, Y1), (A2, B2, M2, N1, P1, Q1, R3a, R4c, X2, Y2), (A2, B2, M2, N1, P1, Q1, R3a, R4c, X2, Y3), (A2, B2, M2, N1, P1, Q1, R3b, R4a, X1, Y1), (A2, B2, M2, N1, P1, Q1, R3b, R4a, X1, Y2), (A2, B2, M2, N1, P1, Q1, R3b, R4a, X1, Y3), (A2, B2, M2, N1, P1, Q1, R3b, R4a, X2, Y1), (A2, B2, M2, N1, P1, Q1, R3b, R4a, X2, Y2), (A2, B2, M2, N1, P1, Q1, R3b, R4a, X2, Y3), (A2, B2, M2, N1, P1, Q1, R3b, R4b, X1, Y1), (A2, B2, M2, N1, P1, Q1, R3b, R4b, X1, Y2), (A2, B2, M2, N1, P1, Q1, R3b, R4b, X1, Y3), (A2, B2, M2, N1, P1, Q1, R3b, R4b, X2, Y1), (A2, B2, M2, N1, P1, Q1, R3b, R4b, X2, Y2), (A2, B2, M2, N1, P1, Q1, R3b, R4b, X2, Y3), (A2, B2, M2, N1, P1, Q1, R3b, R4c, X1, Y1), (A2, B2, M2, N1, P1, Q1, R3b, R4c, X1, Y2), (A2, B2, M2, N1, P1, Q1, R3b, R4c, X1, Y3), (A2, B2, M2, N1, P1, Q1, R3b, R4c, X2, Y1), (A2, B2, M2, N1, P1, Q1, R3b, R4c, X2, Y2), (A2, B2, M2, N1, P1, Q1, R3b, R4c, X2, Y3), (A2, B2, M2, N1, P1, Q2, R3a, R4a, X1, Y1), (A2, B2, M2, N1, P1, Q2, R3a, R4a, X1, Y2), (A2, B2, M2, N1, P1, Q2, R3a, R4a, X1, Y3), (A2, B2, M2, N1, P1, Q2, R3a, R4a, X2, Y1), (A2, B2, M2, N1, P1, Q2, R3a, R4a, X2, Y2), (A2, B2, M2, N1, P1, Q2, R3a, R4a, X2, Y3), (A2, B2, M2, N1, P1, Q2, R3a, R4b, X1, Y1), (A2, B2, M2, N1, P1, Q2, R3a, R4b, X1, Y2), (A2, B2, M2, N1, P1, Q2, R3a, R4b, X1, Y3), (A2, B2, M2, N1, P1, Q2, R3a, R4b, X2, Y1), (A2, B2, M2, N1, P1, Q2, R3a, R4b, X2, Y2), (A2, B2, M2, N1, P1, Q2, R3a, R4b, X2, Y3), (A2, B2, M2, N1, P1, Q2, R3a, R4c, X1, Y1), (A2, B2, M2, N1, P1, Q2, R3a, R4c, X1, Y2), (A2, B2, M2, N1, P1, Q2, R3a, R4c, X1, Y3), (A2, B2, M2, N1, P1, Q2, R3a, R4c, X2, Y1), (A2, B2, M2, N1, P1, Q2, R3a, R4c, X2, Y2), (A2, B2, M2, N1, P1, Q2, R3a, R4c, X2, Y3), (A2, B2, M2, N1, P1, Q2, R3b, R4a, X1, Y1), (A2, B2, M2, N1, P1, Q2, R3b, R4a, X1, Y2), (A2, B2, M2, N1, P1, Q2, R3b, R4a, X1, Y3), (A2, B2, M2, N1, P1, Q2, R3b, R4a, X2, Y1), (A2, B2, M2, N1, P1, Q2, R3b, R4a, X2, Y2), (A2, B2, M2, N1, P1, Q2, R3b, R4a, X2, Y3), (A2, B2, M2, N1, P1, Q2, R3b, R4b, X1, Y1), (A2, B2, M2, N1, P1, Q2, R3b, R4b, X1, Y2), (A2, B2, M2, N1, P1, Q2, R3b, R4b, X1, Y3), (A2, B2, M2, N1, P1, Q2, R3b, R4b, X2, Y1), (A2, B2, M2, N1, P1, Q2, R3b, R4b, X2, Y2), (A2, B2, M2, N1, P1, Q2, R3b, R4b, X2, Y3), (A2, B2, M2, N1, P1, Q2, R3b, R4c, X1, Y1), (A2, B2, M2, N1, P1, Q2, R3b, R4c, X1, Y2), (A2, B2, M2, N1, P1, Q2, R3b, R4c, X1, Y3), (A2, B2, M2, N1, P1, Q2, R3b, R4c, X2, Y1), (A2, B2, M2, N1, P1, Q2, R3b, R4c, X2, Y2), (A2, B2, M2, N1, P1, Q2, R3b, R4c, X2, Y3), (A2, B2, M2, N1, P2, Q1, R3a, R4a, X1, Y1), (A2, B2, M2, N1, P2, Q1, R3a, R4a, X1, Y2), (A2, B2, M2, N1, P2, Q1, R3a, R4a, X1, Y3), (A2, B2, M2, N1, P2, Q1, R3a, R4a, X2, Y1), (A2, B2, M2, N1, P2, Q1, R3a, R4a, X2, Y2), (A2, B2, M2, N1, P2, Q1, R3a, R4a, X2, Y3), (A2, B2, M2, N1, P2, Q1, R3a, R4b, X1, Y1), (A2, B2, M2, N1, P2, Q1, R3a, R4b, X1, Y2), (A2, B2, M2, N1, P2, Q1, R3a, R4b, X1, Y3), (A2, B2, M2, N1, P2, Q1, R3a, R4b, X2, Y1), (A2, B2, M2, N1, P2, Q1, R3a, R4b, X2, Y2), (A2, B2, M2, N1, P2, Q1, R3a, R4b, X2, Y3), (A2, B2, M2, N1, P2, Q1, R3a, R4c, X1, Y1), (A2, B2, M2, N1, P2, Q1, R3a, R4c, X1, Y2), (A2, B2, M2, N1, P2, Q1, R3a, R4c, X1, Y3), (A2, B2, M2, N1, P2, Q1, R3a, R4c, X2, Y1), (A2, B2, M2, N1, P2, Q1, R3a, R4c, X2, Y2), (A2, B2, M2, N1, P2, Q1, R3a, R4c, X2, Y3), (A2, B2, M2, N1, P2, Q1, R3b, R4a, X1, Y1), (A2, B2, M2, N1, P2, Q1, R3b, R4a, X1, Y2), (A2, B2, M2, N1, P2, Q1, R3b, R4a, X1, Y3), (A2, B2, M2, N1, P2, Q1, R3b, R4a, X2, Y1), (A2, B2, M2, N1, P2, Q1, R3b, R4a, X2, Y2), (A2, B2, M2, N1, P2, Q1, R3b, R4a, X2, Y3), (A2, B2, M2, N1, P2, Q1, R3b, R4b, X1, Y1), (A2, B2, M2, N1, P2, Q1, R3b, R4b, X1, Y2), (A2, B2, M2, N1, P2, Q1, R3b, R4b, X1, Y3), (A2, B2, M2, N1, P2, Q1, R3b, R4b, X2, Y1), (A2, B2, M2, N1, P2, Q1, R3b, R4b, X2, Y2), (A2, B2, M2, N1, P2, Q1, R3b, R4b, X2, Y3), (A2, B2, M2, N1, P2, Q1, R3b, R4c, X1, Y1), (A2, B2, M2, N1, P2, Q1, R3b, R4c, X1, Y2), (A2, B2, M2, N1, P2, Q1, R3b, R4c, X1, Y3), (A2, B2, M2, N1, P2, Q1, R3b, R4c, X2, Y1), (A2, B2, M2, N1, P2, Q1, R3b, R4c, X2, Y2), (A2, B2, M2, N1, P2, Q1, R3b, R4c, X2, Y3), (A2, B2, M2, N1, P2, Q2, R3a, R4a, X1, Y1), (A2, B2, M2, N1, P2, Q2, R3a, R4a, X1, Y2), (A2, B2, M2, N1, P2, Q2, R3a, R4a, X1, Y3), (A2, B2, M2, N1, P2, Q2, R3a, R4a, X2, Y1), (A2, B2, M2, N1, P2, Q2, R3a, R4a, X2, Y2), (A2, B2, M2, N1, P2, Q2, R3a, R4a, X2, Y3), (A2, B2, M2, N1, P2, Q2, R3a, R4b, X1, Y1), (A2, B2, M2, N1, P2, Q2, R3a, R4b, X1, Y2), (A2, B2, M2, N1, P2, Q2, R3a, R4b, X1, Y3), (A2, B2, M2, N1, P2, Q2, R3a, R4b, X2, Y1), (A2, B2, M2, N1, P2, Q2, R3a, R4b, X2, Y2), (A2, B2, M2, N1, P2, Q2, R3a, R4b, X2, Y3), (A2, B2, M2, N1, P2, Q2, R3a, R4c, X1, Y1), (A2, B2, M2, N1, P2, Q2, R3a, R4c, X1, Y2), (A2, B2, M2, N1, P2, Q2, R3a, R4c, X1, Y3), (A2, B2, M2, N1, P2, Q2, R3a, R4c, X2, Y1), (A2, B2, M2, N1, P2, Q2, R3a, R4c, X2, Y2), (A2, B2, M2, N1, P2, Q2, R3a, R4c, X2, Y3), (A2, B2, M2, N1, P2, Q2, R3b, R4a, X1, Y1), (A2, B2, M2, N1, P2, Q2, R3b, R4a, X1, Y2), (A2, B2, M2, N1, P2, Q2, R3b, R4a, X1, Y3), (A2, B2, M2, N1, P2, Q2, R3b, R4a, X2, Y1), (A2, B2, M2, N1, P2, Q2, R3b, R4a, X2, Y2), (A2, B2, M2, N1, P2, Q2, R3b, R4a, X2, Y3), (A2, B2, M2, N1, P2, Q2, R3b, R4b, X1, Y1), (A2, B2, M2, N1, P2, Q2, R3b, R4b, X1, Y3), (A2, B2, M2, N1, P2, Q2, R3b, R4b, X2, Y1), (A2, B2, M2, N1, P2, Q2, R3b, R4b, X2, Y2), (A2, B2, M2, N1, P2, Q2, R3b, R4b, X2, Y3), (A2, B2, M2, N1, P2, Q2, R3b, R4c, X1, Y1), (A2, B2, M2, N1, P2, Q2, R3b, R4c, X1, Y2), (A2, B2, M2, N1, P2, Q2, R3b, R4c, X1, Y3), (A2, B2, M2, N1, P2, Q2, R3b, R4c, X2, Y1), (A2, B2, M2, N1, P2, Q2, R3b, R4c, X2, Y2), (A2, B2, M2, N1, P2, Q2, R3b, R4c, X2, Y3), (A2, B2, M2, N2, P1, Q1, R3a, R4a, X1, Y1), (A2, B2, M2, N2, P1, Q1, R3a, R4a, X1, Y2), (A2, B2, M2, N2, P1, Q1, R3a, R4a, X1, Y3), (A2, B2, M2, N2, P1, Q1, R3a, R4a, X2, Y1), (A2, B2, M2, N2, P1, Q1, R3a, R4a, X2, Y2), (A2, B2, M2, N2, P1, Q1, R3a, R4a, X2, Y3), (A2, B2, M2, N2, P1, Q1, R3a, R4b, X1, Y1), (A2, B2, M2, N2, P1, Q1, R3a, R4b, X1, Y2), (A2, B2, M2, N2, P1, Q1, R3a, R4b, X1, Y3), (A2, B2, M2, N2, P1, Q1, R3a, R4b, X2, Y1), (A2, B2, M2, N2, P1, Q1, R3a, R4b, X2, Y2), (A2, B2, M2, N2, P1, Q1, R3a, R4b, X2, Y3), (A2, B2, M2, N2, P1, Q1, R3a, R4c, X1, Y1) (A2, B2, M2, N2, P1, Q1, R3a, R4c, X1, Y2), (A2, B2, M2, N2, P1, Q1, R3a, R4c, X1, Y3), (A2, B2, M2, N2, P1, Q1, R3a, R4c, X2, Y1), (A2, B2, M2, N2, P1, Q1, R3a, R4c, X2, Y2), (A2, B2, M2, N2, P1, Q1, R3a, R4c, X2, Y3), (A2, B2, M2, N2, P1, Q1, R3b, R4a, X1, Y1), (A2, B2, M2, N2, P1, Q1, R3b, R4a, X1, Y2), (A2, B2, M2, N2, P1, Q1, R3b, R4a, X1, Y3), (A2, B2, M2, N2, P1, Q1, R3b, R4a, X2, Y1), (A2, B2, M2, N2, P1, Q1, R3b, R4a, X2, Y2), (A2, B2, M2, N2, P1, Q1, R3b, R4a, X2, Y3), (A2, B2, M2, N2, P1, Q1, R3b, R4b, X1, Y1), (A2, B2, M2, N2, P1, Q1, R3b, R4b, X1, Y2), (A2, B2, M2, N2, P1, Q1, R3b, R4b, X1, Y3), (A2, B2, M2, N2, P1, Q1, R3b, R4b, X2, Y1), (A2, B2, M2, N2, P1, Q1, R3b, R4b, X2, Y2), (A2, B2, M2, N2, P1, Q1, R3b, R4b, X2, Y3), (A2, B2, M2, N2, P1, Q1, R3b, R4c, X1, Y1), (A2, B2, M2, N2, P1, Q1, R3b, R4c, X1, Y2), (A2, B2, M2, N2, P1, Q1, R3b, R4c, X1, Y3), (A2, B2, M2, N2, P1, Q1, R3b, R4c, X2, Y1), (A2, B2, M2, N2, P1, Q1, R3b, R4c, X2, Y2), (A2, B2, M2, N2, P1, Q1, R3b, R4c, X2, Y3), (A2, B2, M2, N2, P1, Q2, R3a, R4a, X1, Y1), (A2, B2, M2, N2, P1, Q2, R3a, R4a, X1, Y2), (A2, B2, M2, N2, P1, Q2, R3a, R4a, X1, Y3), (A2, B2, M2, N2, P1, Q2, R3a, R4a, X2, Y1), (A2, B2, M2, N2, P1, Q2, R3a, R4a, X2, Y2), (A2, B2, M2, N2, P1, Q2, R3a, R4a, X2, Y3), (A2, B2, M2, N2, P1, Q2, R3a, R4b, X1, Y1), (A2, B2, M2, N2, P1, Q2, R3a, R4b, X1, Y2), (A2, B2, M2, N2, P1, Q2, R3a, R4b, X1, Y3), (A2, B2, M2, N2, P1, Q2, R3a, R4b, X2, Y1), (A2, B2, M2, N2, P1, Q2, R3a, R4b, X2, Y2), (A2, B2, M2, N2, P1, Q2, R3a, R4b, X2, Y3), (A2, B2, M2, N2, P1, Q2, R3a, R4c, X1, Y1), (A2, B2, M2, N2, P1, Q2, R3a, R4c, X1, Y2), (A2, B2, M2, N2, P1, Q2, R3a, R4c, X1, Y3), (A2, B2, M2, N2, P1, Q2, R3a, R4c, X2, Y1), (A2, B2, M2, N2, P1, Q2, R3a, R4c, X2, Y2), (A2, B2, M2, N2, P1, Q2, R3a, R4c, X2, Y3), (A2, B2, M2, N2, P1, Q2, R3b, R4a, X1, Y1), (A2, B2, M2, N2, P1, Q2, R3b, R4a, X1, Y2), (A2, B2, M2, N2, P1, Q2, R3b, R4a, X1, Y3), (A2, B2, M2, N2, P1, Q2, R3b, R4a, X2, Y1), (A2, B2, M2, N2, P1, Q2, R3b, R4a, X2, Y2), (A2, B2, M2, N2, P1, Q2, R3b, R4a, X2, Y3), (A2, B2, M2, N2, P1, Q2, R3b, R4b, X1, Y1), (A2, B2, M2, N2, P1, Q2, R3b, R4b, X1, Y2), (A2, B2, M2, N2, P1, Q2, R3b, R4b, X1, Y3), (A2, B2, M2, N2, P1, Q2, R3b, R4b, X2, Y1), (A2, B2, M2, N2, P1, Q2, R3b, R4b, X2, Y2), (A2, B2, M2, N2, P1, Q2, R3b, R4b, X2, Y3), (A2, B2, M2, N2, P1, Q2, R3b, R4c, X1, Y1), (A2, B2, M2, N2, P1, Q2, R3b, R4c, X1, Y2), (A2, B2, M2, N2, P1, Q2, R3b, R4c, X1, Y3), (A2, B2, M2, N2, P1, Q2, R3b, R4c, X2, Y1), (A2, B2, M2, N2, P1, Q2, R3b, R4c, X2, Y2), (A2, B2, M2, N2, P1, Q2, R3b, R4c, X2, Y3), (A2, B2, M2, N2, P2, Q1, R3a, R4a, X1, Y1), (A2, B2, M2, N2, P2, Q1, R3a, R4a, X1, Y2), (A2, B2, M2, N2, P2, Q1, R3a, R4a, X1, Y3), (A2, B2, M2, N2, P2, Q1, R3a, R4a, X2, Y1), (A2, B2, M2, N2, P2, Q1, R3a, R4a, X2, Y2), (A2, B2, M2, N2, P2, Q1, R3a, R4a, X2, Y3), (A2, B2, M2, N2, P2, Q1, R3a, R4b, X1, Y1), (A2, B2, M2, N2, P2, Q1, R3a, R4b, X1, Y2), (A2, B2, M2, N2, P2, Q1, R3a, R4b, X1, Y3), (A2, B2, M2, N2, P2, Q1, R3a, R4b, X2, Y1), (A2, B2, M2, N2, P2, Q1, R3a, R4b, X2, Y2), (A2, B2, M2, N2, P2, Q1, R3a, R4b, X2, Y3), (A2, B2, M2, N2, P2, Q1, R3a, R4c, X1, Y1), (A2, B2, M2, N2, P2, Q1, R3a, R4c, X1, Y2), (A2, B2, M2, N2, P2, Q1, R3a, R4c, X1, Y3), (A2, B2, M2, N2, P2, Q1, R3a, R4c, X2, Y1), (A2, B2, M2, N2, P2, Q1, R3a, R4c, X2, Y2), (A2, B2, M2, N2, P2, Q1, R3a, R4c, X2, Y3), (A2, B2, M2, N2, P2, Q1, R3b, R4a, X1, Y1), (A2, B2, M2, N2, P2, Q1, R3b, R4a, X1, Y2), (A2, B2, M2, N2, P2, Q1, R3b, R4a, X1, Y3), (A2, B2, M2, N2, P2, Q1, R3b, R4a, X2, Y1), (A2, B2, M2, N2, P2, Q1, R3b, R4a, X2, Y2), (A2, B2, M2, N2, P2, Q1, R3b, R4a, X2, Y3), (A2, B2, M2, N2, P2, Q1, R3b, R4b, X1, Y1), (A2, B2, M2, N2, P2, Q1, R3b, R4b, X1, Y2), (A2, B2, M2, N2, P2, Q1, R3b, R4b, X1, Y3), (A2, B2, M2, N2, P2, Q1, R3b, R4b, X2, Y1), (A2, B2, M2, N2, P2, Q1, R3b, R4b, X2, Y2), (A2, B2, M2, N2, P2, Q1, R3b, R4b, X2, Y3), (A2, B2, M2, N2, P2, Q1, R3b, R4c, X1, Y1), (A2, B2, M2, N2, P2, Q1, R3b, R4c, X1, Y2), (A2, B2, M2, N2, P2, Q1, R3b, R4c, X1, Y3), (A2, B2, M2, N2, P2, Q1, R3b, R4c, X2, Y1), (A2, B2, M2, N2, P2, Q1, R3b, R4c, X2, Y2), (A2, B2, M2, N2, P2, Q1, R3b, R4c, X2, Y3), (A2, B2, M2, N2, P2, Q2, R3a, R4a, X1, Y1), (A2, B2, M2, N2, P2, Q2, R3a, R4a, X1, Y2), (A2, B2, M2, N2, P2, Q2, R3a, R4a, X1, Y3), (A2, B2, M2, N2, P2, Q2, R3a, R4a, X2, Y1), (A2, B2, M2, N2, P2, Q2, R3a, R4a, X2, Y2), (A2, B2, M2, N2, P2, Q2, R3a, R4a, X2, Y3), (A2, B2, M2, N2, P2, Q2, R3a, R4b, X1, Y1), (A2, B2, M2, N2, P2, Q2, R3a, R4b, X1, Y2), (A2, B2, M2, N2, P2, Q2, R3a, R4b, X1, Y3), (A2, B2, M2, N2, P2, Q2, R3a, R4b, X2, Y1), (A2, B2, M2, N2, P2, Q2, R3a, R4b, X2, Y2), (A2, B2, M2, N2, P2, Q2, R3a, R4b, X2, Y3), (A2, B2, M2, N2, P2, Q2, R3a, R4c, X1, Y1), (A2, B2, M2, N2, P2, Q2, R3a, R4c, X1, Y2), (A2, B2, M2, N2, P2, Q2, R3a, R4c, X1, Y3), (A2, B2, M2, N2, P2, Q2, R3a, R4c, X2, Y1), (A2, B2, M2, N2, P2, Q2, R3a, R4c, X2, Y2), (A2, B2, M2, N2, P2, Q2, R3a, R4c, X2, Y3), (A2, B2, M2, N2, P2, Q2, R3b, R4a, X1, Y1), (A2, B2, M2, N2, P2, Q2, R3b, R4a, X1, Y2), (A2, B2, M2, N2, P2, Q2, R3b, R4a, X1, Y3), (A2, B2, M2, N2, P2, Q2, R3b, R4a, X2, Y1), (A2, B2, M2, N2, P2, Q2, R3b, R4a, X2, Y2), (A2, B2, M2, N2, P2, Q2, R3b, R4a, X2, Y3), (A2, B2, M2, N2, P2, Q2, R3b, R4b, X1, Y1), (A2, B2, M2, N2, P2, Q2, R3b, R4b, X1, Y2), (A2, B2, M2, N2, P2, Q2, R3b, R4b, X1, Y3), (A2, B2, M2, N2, P2, Q2, R3b, R4b, X2, Y1), (A2, B2, M2, N2, P2, Q2, R3b, R4b, X2, Y2), (A2, B2, M2, N2, P2, Q2, R3b, R4b, X2, Y3), (A2, B2, M2, N2, P2, Q2, R3b, R4c, X1, Y1), (A2, B2, M2, N2, P2, Q2, R3b, R4c, X1, Y2), (A2, B2, M2, N2, P2, Q2, R3b, R4c, X1, Y3), (A2, B2, M2, N2, P2, Q2, R3b, R4c, X2, Y1), (A2, B2, M2, N2, P2, Q2, R3b, R4c, X2, Y2), (A2, B2, M2, N2, P2, Q2, R3b, R4c, X2, Y3), (A2, B3, M1, N1, P1, Q1, R3a, R4a, X1, Y1), (A2, B3, M1, N1, P1, Q1, R3a, R4a, X1, Y2), (A2, B3, M1, N1, P1, Q1, R3a, R4a, X1, Y3), (A2, B3, M1, N1, P1, Q1, R3a, R4a, X2, Y1), (A2, B3, M1, N1, P1, Q1, R3a, R4a, X2, Y2), (A2, B3, M1, N1, P1, Q1, R3a, R4a, X2, Y3), (A2, B3, M1, N1, P1, Q1, R3a, R4b, X1, Y1), (A2, B3, M1, N1, P1, Q1, R3a, R4b, X1, Y2), (A2, B3, M1, N1, P1, Q1, R3a, R4b, X1, Y3), (A2, B3, M1, N1, P1, Q1, R3a, R4b, X2, Y1), (A2, B3, M1, N1, P1, Q1, R3a, R4b, X2, Y2), (A2, B3, M1, N1, P1, Q1, R3a, R4b, X2, Y3), (A2, B3, M1, N1, P1, Q1, R3a, R4c, X1, Y1), (A2, B3, M1, N1, P1, Q1, R3a, R4c, X1, Y2), (A2, B3, M1, N1, P1, Q1, R3a, R4c, X1, Y3), (A2, B3, M1, N1, P1, Q1, R3a, R4c, X2, Y1), (A2, B3, M1, N1, P1, Q1, R3a, R4c, X2, Y2), (A2, B3, M1, N1, P1, Q1, R3a, R4c, X2, Y3), (A2, B3, M1, N1, P1, Q1, R3b, R4a, X1, Y1), (A2, B3, M1, N1, P1, Q1, R3b, R4a, X1, Y2), (A2, B3, M1, N1, P1, Q1, R3b, R4a, X1, Y3), (A2, B3, M1, N1, P1, Q1, R3b, R4a, X2, Y1), (A2, B3, M1, N1, P1, Q1, R3b, R4a, X2, Y2), (A2, B3, M1, N1, P1, Q1, R3b, R4a, X2, Y3), (A2, B3, M1, N1, P1, Q1, R3b, R4b, X1, Y1), (A2, B3, M1, N1, P1, Q1, R3b, R4b, X1, Y2), (A2, B3, M1, N1, P1, Q1, R3b, R4b, X1, Y3), (A2, B3, M1, N1, P1, Q1, R3b, R4b, X2, Y1), (A2, B3, M1, N1, P1, Q1, R3b, R4b, X2, Y2), (A2, B3, M1, N1, P1, Q1, R3b, R4b, X2, Y3), (A2, B3, M1, N1, P1, Q1, R3b, R4c, X1, Y1), (A2, B3, M1, N1, P1, Q1, R3b, R4c, X1, Y2), (A2, B3, M1, N1, P1, Q1, R3b, R4c, X1, Y3), (A2, B3, M1, N1, P1, Q1, R3b, R4c, X2, Y1), (A2, B3, M1, N1, P1, Q1, R3b, R4c, X2, Y2), (A2, B3, M1, N1, P1, Q1, R3b, R4c, X2, Y3), (A2, B3, M1, N1, P1, Q2, R3a, R4a, X1, Y1), (A2, B3, M1, N1, P1, Q2, R3a, R4a, X1, Y2), (A2, B3, M1, N1, P1, Q2, R3a, R4a, X1, Y3) (A2, B3, M1, N1, P1, Q2, R3a, R4a, X2, Y1), (A2, B3, M1, N1, P1, Q2, R3a, R4a, X2, Y2), (A2, B3, M1, N1, P1, Q2, R3a, R4a, X2, Y3), (A2, B3, M1, N1, P1, Q2, R3a, R4b, X1, Y1), (A2, B3, M1, N1, P1, Q2, R3a, R4b, X1, Y2), (A2, B3, M1, N1, P1, Q2, R3a, R4b, X1, Y3), (A2, B3, M1, N1, P1, Q2, R3a, R4b, X2, Y1), (A2, B3, M1, N1, P1, Q2, R3a, R4b, X2, Y2), (A2, B3, M1, N1, P1, Q2, R3a, R4b, X2, Y3), (A2, B3, M1, N1, P1, Q2, R3a, R4c, X1, Y1), (A2, B3, M1, N1, P1, Q2, R3a, R4c, X1, Y2), (A2, B3, M1, N1, P1, Q2, R3a, R4c, X1, Y3), (A2, B3, M1, N1, P1, Q2, R3a, R4c, X2, Y1), (A2, B3, M1, N1, P1, Q2, R3a, R4c, X2, Y2), (A2, B3, M1, N1, P1, Q2, R3a, R4c, X2, Y3), (A2, B3, M1, N1, P1, Q2, R3b, R4a, X1, Y1), (A2, B3, M1, N1, P1, Q2, R3b, R4a, X1, Y2), (A2, B3, M1, N1, P1, Q2, R3b, R4a, X1, Y3), (A2, B3, M1, N1, P1, Q2, R3b, R4a, X2, Y1), (A2, B3, M1, N1, P1, Q2, R3b, R4a, X2, Y2), (A2, B3, M1, N1, P1, Q2, R3b, R4a, X2, Y3), (A2, B3, M1, N1, P1, Q2, R3b, R4b, X1, Y1), (A2, B3, M1, N1, P1, Q2, R3b, R4b, X1, Y2), (A2, B3, M1, N1, P1, Q2, R3b, R4b, X1, Y3), (A2, B3, M1, N1, P1, Q2, R3b, R4b, X2, Y1), (A2, B3, M1, N1, P1, Q2, R3b, R4b, X2, Y2), (A2, B3, M1, N1, P1, Q2, R3b, R4b, X2, Y3), (A2, B3, M1, N1, P1, Q2, R3b, R4c, X1, Y1), (A2, B3, M1, N1, P1, Q2, R3b, R4c, X1, Y2), (A2, B3, M1, N1, P1, Q2, R3b, R4c, X1, Y3), (A2, B3, M1, N1, P1, Q2, R3b, R4c, X2, Y1) (A2, B3, M1, N1, P1, Q2, R3b, R4c, X2, Y2), (A2, B3, M1, N1, P1, Q2, R3b, R4c, X2, Y3), (A2, B3, M1, N1, P2, Q1, R3a, R4a, X1, Y1), (A2, B3, M1, N1, P2, Q1, R3a, R4a, X1, Y2), (A2, B3, M1, N1, P2, Q1, R3a, R4a, X1, Y3), (A2, B3, M1, N1, P2, Q1, R3a, R4a, X2, Y1), (A2, B3, M1, N1, P2, Q1, R3a, R4a, X2, Y2), (A2, B3, M1, N1, P2, Q1, R3a, R4a, X2, Y3), (A2, B3, M1, N1, P2, Q1, R3a, R4b, X1, Y1), (A2, B3, M1, N1, P2, Q1, R3a, R4b, X1, Y2), (A2, B3, M1, N1, P2, Q1, R3a, R4b, X1, Y3), (A2, B3, M1, N1, P2, Q1, R3a, R4b, X2, Y1), (A2, B3, M1, N1, P2, Q1, R3a, R4b, X2, Y2), (A2, B3, M1, N1, P2, Q1, R3a, R4b, X2, Y3), (A2, B3, M1, N1, P2, Q1, R3a, R4c, X1, Y1), (A2, B3, M1, N1, P2, Q1, R3a, R4c, X1, Y2), (A2, B3, M1, N1, P2, Q1, R3a, R4c, X1, Y3), (A2, B3, M1, N1, P2, Q1, R3a, R4c, X2, Y1), (A2, B3, M1, N1, P2, Q1, R3a, R4c, X2, Y2), (A2, B3, M1, N1, P2, Q1, R3a, R4c, X2, Y3), (A2, B3, M1, N1, P2, Q1, R3b, R4a, X1, Y1), (A2, B3, M1, N1, P2, Q1, R3b, R4a, X1, Y2), (A2, B3, M1, N1, P2, Q1, R3b, R4a, X1, Y3), (A2, B3, M1, N1, P2, Q1, R3b, R4a, X2, Y1), (A2, B3, M1, N1, P2, Q1, R3b, R4a, X2, Y2), (A2, B3, M1, N1, P2, Q1, R3b, R4a, X2, Y3), (A2, B3, M1, N1, P2, Q1, R3b, R4b, X1, Y1), (A2, B3, M1, N1, P2, Q1, R3b, R4b, X1, Y2), (A2, B3, M1, N1, P2, Q1, R3b, R4b, X1, Y3), (A2, B3, M1, N1, P2, Q1, R3b, R4b, X2, Y1), (A2, B3, M1, N1, P2, Q1, R3b, R4b, X2, Y2), (A2, B3, M1, N1, P2, Q1, R3b, R4b, X2, Y3), (A2, B3, M1, N1, P2, Q1, R3b, R4c, X1, Y1), (A2, B3, M1, N1, P2, Q1, R3b, R4c, X1, Y2), (A2, B3, N1, N1, P2, Q1, R3b, R4c, X1, Y3), (A2, B3, M1, N1, P2, Q1, R3b, R4c, X2, Y1), (A2, B3, M1, N1, P2, Q1, R3b, R4c, X2, Y2), (A2, B3, M1, N1, P2, Q1, R3b, R4c, X2, Y3), (A2, B3, M1, N1, P2, Q2, R3a, R4a, X1, Y1), (A2, B3, M1, N1, P2, Q2, R3a, R4a, X1, Y2), (A2, B3, M1, N1, P2, Q2, R3a, R4a, X1, Y3), (A2, B3, M1, N1, P2, Q2, R3a, R4a, X2, Y1), (A2, B3, M1, N1, P2, Q2, R3a, R4a, X2, Y2), (A2, B3, M1, N1, P2, Q2, R3a, R4a, X2, Y3), (A2, B3, M1, N1, P2, Q2, R3a, R4b, X1, Y1), (A2, B3, M1, N1, P2, Q2, R3a, R4b, X1, Y2), (A2, B3, M1, N1, P2, Q2, R3a, R4b, X1, Y3), (A2, B3, M1, N1, P2, Q2, R3a, R4b, X2, Y1), (A2, B3, M1, N1, P2, Q2, R3a, R4b, X2, Y2), (A2, B3, M1, N1, P2, Q2, R3a, R4b, X2, Y3), (A2, B3, M1, N1, P2, Q2, R3a, R4c, X1, Y1), (A2, B3, M1, N1, P2, Q2, R3a, R4c, X1, Y2), (A2, B3, M1, N1, P2, Q2, R3a, R4c, X1, Y3), (A2, B3, M1, N1, P2, Q2, R3a, R4c, X2, Y1), (A2, B3, M1, N1, P2, Q2, R3a, R4c, X2, Y2), (A2, B3, M1, N1, P2, Q2, R3a, R4c, X2, Y3), (A2, B3, M1, N1, P2, Q2, R3b, R4a, X1, Y1), (A2, B3, M1, N1, P2, Q2, R3b, R4a, X1, Y2), (A2, B3, M1, N1, P2, Q2, R3b, R4a, X1, Y3), (A2, B3, M1, N1, P2, Q2, R3b, R4a, X2, Y1), (A2, B3, M1, N1, P2, Q2, R3b, R4a, X2, Y2), (A2, B3, M1, N1, P2, Q2, R3b, R4a, X2, Y3), (A2, B3, M1, N1, P2, Q2, R3b, R4b, X1, Y1), (A2, B3, M1, N1, P2, Q2, R3b, R4b, X1, Y2), (A2, B3, M1, N1, P2, Q2, R3b, R4b, X1, Y3), (A2, B3, M1, N1, P2, Q2, R3b, R4b, X2, Y1), (A2, B3, M1, N1, P2, Q2, R3b, R4b, X2, Y2), (A2, B3, M1, N1, P2, Q2, R3b, R4b, X2, Y3), (A2, B3, M1, N1, P2, Q2, R3b, R4c, X1, Y1), (A2, B3, M1, N1, P2, Q2, R3b, R4c, X1, Y2), (A2, B3, M1, N1, P2, Q2, R3b, R4c, X1, Y3), (A2, B3, M1, N1, P2, Q2, R3b, R4c, X2, Y1), (A2, B3, M1, N1, P2, Q2, R3b, R4c, X2, Y2), (A2, B3, M1, N1, P2, Q2, R3b, R4c, X2, Y3), (A2, B3, M1, N2, P1, Q1, R3a, R4a, X1, Y1), (A2, B3, M1, N2, P1, Q1, R3a, R4a, X1, Y2), (A2, B3, M1, N2, P1, Q1, R3a, R4a, X1, Y3), (A2, B3, M1, N2, P1, Q1, R3a, R4a, X2, Y1), (A2, B3, M1, N2, P1, Q1, R3a, R4a, X2, Y2), (A2, B3, M1, N2, P1, Q1, R3a, R4a, X2, Y3), (A2, B3, M1, N2, P1, Q1, R3a, R4b, X1, Y1), (A2, B3, M1, N2, P1, Q1, R3a, R4b, X1, Y2), (A2, B3, M1, N2, P1, Q1, R3a, R4b, X1, Y3), (A2, B3, M1, N2, P1, Q1, R3a, R4b, X2, Y1), (A2, B3, M1, N2, P1, Q1, R3a, R4b, X2, Y2), (A2, B3, M1, N2, P1, Q1, R3a, R4b, X2, Y3), (A2, B3, M1, N2, P1, Q1, R3a, R4c, X1, Y1), (A2, B3, M1, N2, P1, Q1, R3a, R4c, X1, Y2), (A2, B3, M1, N2, P1, Q1, R3a, R4c, X1, Y3), (A2, B3, M1, N2, P1, Q1, R3a, R4c, X2, Y1), (A2, B3, M1, N2, P1, Q1, R3a, R4c, X2, Y2), (A2, B3, M1, N2, P1, Q1, R3a, R4c, X2, Y3), (A2, B3, M1, N2, P1, Q1, R3b, R4a, X1, Y1), (A2, B3, M1, N2, P1, Q1, R3b, R4a, X1, Y2), (A2, B3, M1, N2, P1, Q1, R3b, R4a, X1, Y3), (A2, B3, M1, N2, P1, Q1, R3b, R4a, X2, Y1), (A2, B3, M1, N2, P1, Q1, R3b, R4a, X2, Y2), (A2, B3, M1, N2, P1, Q1, R3b, R4a, X2, Y3), (A2, B3, M1, N2, P1, Q1, R3b, R4b, X1, Y1), (A2, B3, M1, N2, P1, Q1, R3b, R4b, X1, Y2), (A2, B3, M1, N2, P1, Q1, R3b, R4b, X1, Y3), (A2, B3, M1, N2, P1, Q1, R3b, R4b, X2, Y1), (A2, B3, M1, N2, P1, Q1, R3b, R4b, X2, Y2), (A2, B3, M1, N2, P1, Q1, R3b, R4b, X2, Y3), (A2, B3, M1, N2, P1, Q1, R3b, R4c, X1, Y1), (A2, B3, M1, N2, P1, Q1, R3b, R4c, X1, Y2), (A2, B3, M1, N2, P1, Q1, R3b, R4c, X1, Y3), (A2, B3, M1, N2, P1, Q1, R3b, R4c, X2, Y1), (A2, B3, M1, N2, P1, Q1, R3b, R4c, X2, Y2), (A2, B3, M1, N2, P1, Q1, R3b, R4c, X2, Y3), (A2, B3, M1, N2, P1, Q2, R3a, R4a, X1, Y1), (A2, B3, M1, N2, P1, Q2, R3a, R4a, X1, Y2), (A2, B3, M1, N2, P1, Q2, R3a, R4a, X1, Y3), (A2, B3, M1, N2, P1, Q2, R3a, R4a, X2, Y1), (A2, B3, M1, N2, P1, Q2, R3a, R4a, X2, Y2), (A2, B3, M1, N2, P1, Q2, R3a, R4a, X2, Y3), (A2, B3, M1, N2, P1, Q2, R3a, R4b, X1, Y1), (A2, B3, M1, N2, P1, Q2, R3a, R4b, X1, Y2), (A2, B3, M1, N2, P1, Q2, R3a, R4b, X1, Y3), (A2, B3, M1, N2, P1, Q2, R3a, R4b, X2, Y1), (A2, B3, M1, N2, P1, Q2, R3a, R4b, X2, Y2), (A2, B3, M1, N2, P1, Q2, R3a, R4b, X2, Y3), (A2, B3, M1, N2, P1, Q2, R3a, R4c, X1, Y1), (A2, B3, M1, N2, P1, Q2, R3a, R4c, X1, Y2), (A2, B3, M1, N2, P1, Q2, R3a, R4c, X1, Y3), (A2, B3, M1, N2, P1, Q2, R3a, R4c, X2, Y1), (A2, B3, M1, N2, P1, Q2, R3a, R4c, X2, Y2), (A2, B3, M1, N2, P1, Q2, R3a, R4c, X2, Y3), (A2, B3, M1, N2, P1, Q2, R3b, R4a, X1, Y1), (A2, B3, M1, N2, P1, Q2, R3b, R4a, X1, Y2), (A2, B3, M1, N2, P1, Q2, R3b, R4a, X1, Y3), (A2, B3, M1, N2, P1, Q2, R3b, R4a, X2, Y1), (A2, B3, M1, N2, P1, Q2, R3b, R4a, X2, Y2), (A2, B3, M1, N2, P1, Q2, R3b, R4b, X1, Y1), (A2, B3, M1, N2, P1, Q2, R3b, R4b, X1, Y2), (A2, B3, M1, N2, P1, Q2, R3b, R4b, X1, Y3), (A2, B3, M1, N2, P1, Q2, R3b, R4b, X2, Y1), (A2, B3, M1, N2, P1, Q2, R3b, R4b, X2, Y2), (A2, B3, M1, N2, P1, Q2, R3b, R4b, X2, Y3), (A2, B3, M1, N2, P1, Q2, R3b, R4c, X1, Y1), (A2, B3, M1, N2, P1, Q2, R3b, R4c, X1, Y2), (A2, B3, M1, N2, P1, Q2, R3b, R4c, X1, Y3), (A2, B3, M1, N2, P1, Q2, R3b, R4c, X2, Y1), (A2, B3, M1, N2, P1, Q2, R3b, R4c, X2, Y2), (A2, B3, M1, N2, P1, Q2, R3b, R4c, X2, Y3), (A2, B3, M1, N2, P2, Q1, R3a, R4a, X1, Y1), (A2, B3, M1, N2, P2, Q1, R3a, R4a, X1, Y2), (A2, B3, M1, N2, P2, Q1, R3a, R4a, X1, Y3), (A2, B3, M1, N2, P2, Q1, R3a, R4a, X2, Y1), (A2, B3, M1, N2, P2, Q1, R3a, R4a, X2, Y2), (A2, B3, M1, N2, P2, Q1, R3a, R4a, X2, Y3), (A2, B3, M1, N2, P2, Q1, R3a, R4b, X1, Y1), (A2, B3, M1, N2, P2, Q1, R3a, R4b, X1, Y2), (A2, B3, M1, N2, P2, Q1, R3a, R4b, X1, Y3), (A2, B3, M1, N2, P2, Q1, R3a, R4b, X2, Y1), (A2, B3, M1, N2, P2, Q1, R3a, R4b, X2, Y2), (A2, B3, M1, N2, P2, Q1, R3a, R4b, X2, Y3), (A2, B3, M1, N2, P2, Q1, R3a, R4c, X1, Y1), (A2, B3, M1, N2, P2, Q1, R3a, R4c, X1, Y2), (A2, B3, M1, N2, P2, Q1, R3a, R4c, X1, Y3), (A2, B3, M1, N2, P2, Q1, R3a, R4c, X2, Y1), (A2, B3, M1, N2, P2, Q1, R3a, R4c, X2, Y2), (A2, B3, M1, N2, P2, Q1, R3a, R4c, X2, Y3), (A2, B3, M1, N2, P2, Q1, R3b, R4a, X1, Y1), (A2, B3, M1, N2, P2, Q1, R3b, R4a, X1, Y2), (A2, B3, M1, N2, P2, Q1, R3b, R4a, X1, Y3), (A2, B3, M1, N2, P2, Q1, R3b, R4a, X2, Y1), (A2, B3, M1, N2, P2, Q1, R3b, R4a, X2, Y2), (A2, B3, M1, N2, P2, Q1, R3b, R4a, X2, Y3), (A2, B3, M1, N2, P2, Q1, R3b, R4b, X1, Y1), (A2, B3, M1, N2, P2, Q1, R3b, R4b, X1, Y2), (A2, B3, M1, N2, P2, Q1, R3b, R4b, X1, Y3), (A2, B3, M1, N2, P2, Q1, R3b, R4b, X2, Y1), (A2, B3, M1, N2, P2, Q1, R3b, R4b, X2, Y2), (A2, B3, M1, N2, P2, Q1, R3b, R4b, X2, Y3), (A2, B3, M1, N2, P2, Q1, R3b, R4c, X1, Y1), (A2, B3, M1, N2, P2, Q1, R3b, R4c, X1, Y2), (A2, B3, M1, N2, P2, Q1, R3b, R4c, X1, Y3), (A2, B3, M1, N2, P2, Q1, R3b, R4c, X2, Y1), (A2, B3, M1, N2, P2, Q1, R3b, R4c, X2, Y2), (A2, B3, M1, N2, P2, Q1, R3b, R4c, X2, Y3), (A2, B3, M1, N2, P2, Q2, R3a, R4a, X1, Y1), (A2, B3, M1, N2, P2, Q2, R3a, R4a, X1, Y2), (A2, B3, M1, N2, P2, Q2, R3a, R4a, X1, Y3), (A2, B3, M1, N2, P2, Q2, R3a, R4a, X2, Y1), (A2, B3, M1, N2, P2, Q2, R3a, R4a, X2, Y2), (A2, B3, M1, N2, P2, Q2, R3a, R4a, X2, Y3), (A2, B3, M1, N2, P2, Q2, R3a, R4b, X1, Y1), (A2, B3, M1, N2, P2, Q2, R3a, R4b, X1, Y2), (A2, B3, M1, N2, P2, Q2, R3a, R4b, X1, Y3), (A2, B3, M1, N2, P2, Q2, R3a, R4b, X2, Y1), (A2, B3, M1, N2, P2, Q2, R3a, R4b, X2, Y2), (A2, B3, M1, N2, P2, Q2, R3a, R4b, X2, Y3), (A2, B3, M1, N2, P2, Q2, R3a, R4c, X1, Y1), (A2, B3, M1, N2, P2, Q2, R3a, R4c, X1, Y2), (A2, B3, M1, N2, P2, Q2, R3a, R4c, X1, Y3), (A2, B3, M1, N2, P2, Q2, R3a, R4c, X2, Y1), (A2, B3, M1, N2, P2, Q2, R3a, R4c, X2, Y2), (A2, B3, M1, N2, P2, Q2, R3a, R4c, X2, Y3), (A2, B3, M1, N2, P2, Q2, R3b, R4a, X1, Y1), (A2, B3, M1, N2, P2, Q2, R3b, R4a, X1, Y2), (A2, B3, M1, N2, P2, Q2, R3b, R4a, X1, Y3), (A2, B3, M1, N2, P2, Q2, R3b, R4a, X2, Y1), (A2, B3, M1, N2, P2, Q2, R3b, R4a, X2, Y2), (A2, B3, M1, N2, P2, Q2, R3b, R4a, X2, Y3), (A2, B3, M1, N2, P2, Q2, R3b, R4b, X1, Y1), (A2, B3, M1, N2, P2, Q2, R3b, R4b, X1, Y2), (A2, B3, M1, N2, P2, Q2, R3b, R4b, X1, Y3), (A2, B3, M1, N2, P2, Q2, R3b, R4b, X2, Y1), (A2, B3, M1, N2, P2, Q2, R3b, R4b, X2, Y2), (A2, B3, M1, N2, P2, Q2, R3b, R4b, X2, Y3), (A2, B3, M1, N2, P2, Q2, R3b, R4c, X1, Y1), (A2, B3, M1, N2, P2, Q2, R3b, R4c, X1, Y2), (A2, B3, M1, N2, P2, Q2, R3b, R4c, X1, Y3), (A2, B3, M1, N2, P2, Q2, R3b, R4c, X2, Y1), (A2, B3, M1, N2, P2, Q2, R3b, R4c, X2, Y2), (A2, B3, M1, N2, P2, Q2, R3b, R4c, X2, Y3), (A2, B3, M2, N1, P1, Q1, R3a, R4a, X1, Y1), (A2, B3, M2, N1, P1, Q1, R3a, R4a, X1, Y2), (A2, B3, M2, N1, P1, Q1, R3a, R4a, X1, Y3), (A2, B3, M2, N1, P1, Q1, R3a, R4a, X2, Y1), (A2, B3, M2, N1, P1, Q1, R3a, R4a, X2, Y2), (A2, B3, M2, N1, P1, Q1, R3a, R4a, X2, Y3), (A2, B3, M2, N1, P1, Q1, R3a, R4b, X1, Y1), (A2, B3, M2, N1, P1, Q1, R3a, R4b, X1, Y2), (A2, B3, M2, N1, P1, Q1, R3a, R4b, X1, Y3), (A2, B3, M2, N1, P1, Q1, R3a, R4b, X2, Y1), (A2, B3, M2, N1, P1, Q1, R3a, R4b, X2, Y2), (A2, B3, M2, N1, P1, Q1, R3a, R4b, X2, Y3), (A2, B3, M2, N1, P1, Q1, R3a, R4c, X1, Y1), (A2, B3, M2, N1, P1, Q1, R3a, R4c, X1, Y2), (A2, B3, M2, N1, P1, Q1, R3a, R4c, X1, Y3), (A2, B3, M2, N1, P1, Q1, R3a, R4c, X2, Y1), (A2, B3, M2, N1, P1, Q1, R3a, R4c, X2, Y2), (A2, B3, M2, N1, P1, Q1, R3a, R4c, X2, Y3), (A2, B3, M2, N1, P1, Q1, R3b, R4a, X1, Y1), (A2, B3, M2, N1, P1, Q1, R3b, R4a, X1, Y2), (A2, B3, M2, N1, P1, Q1, R3b, R4a, X1, Y3), (A2, B3, M2, N1, P1, Q1, R3b, R4a, X2, Y1), (A2, B3, M2, N1, P1, Q1, R3b, R4a, X2, Y2), (A2, B3, M2, N1, P1, Q1, R3b, R4a, X2, Y3), (A2, B3, M2, N1, P1, Q1, R3b, R4b, X1, Y1), (A2, B3, M2, N1, P1, Q1, R3b, R4b, X1, Y2), (A2, B3, M2, N1, P1, Q1, R3b, R4b, X1, Y3), (A2, B3, M2, N1, P1, Q1, R3b, R4b, X2, Y1), (A2, B3, M2, N1, P1, Q1, R3b, R4b, X2, Y2),
(A2, B3, M2, N1, P1, Q1, R3b, R4b, X2, Y3), (A2, B3, M2, N1, P1, Q1, R3b, R4c, X1, Y1), (A2, B3, M2, N1, P1, Q1, R3b, R4c, X1, Y2), (A2, B3, M2, N1, P1, Q1, R3b, R4c, X1, Y3), (A2, B3, M2, N1, P1, Q1, R3b, R4c, X2, Y1), (A2, B3, M2, N1, P1, Q1, R3b, R4c, X2, Y2), (A2, B3, M2, N1, P1, Q1, R3b, R4c, X2, Y3), (A2, B3, M2, N1, P1, Q2, R3a, R4a, X1, Y1), (A2, B3, M2, N1, P1, Q2, R3a, R4a, X1, Y2), (A2, B3, M2, N1, P1, Q2, R3a, R4a, X1, Y3), (A2, B3, M2, N1, P1, Q2, R3a, R4a, X2, Y1), (A2, B3, M2, N1, P1, Q2, R3a, R4a, X2, Y2), (A2, B3, M2, N1, P1, Q2, R3a, R4a, X2, Y3), (A2, B3, M2, N1, P1, Q2, R3a, R4b, X1, Y1), (A2, B3, M2, N1, P1, Q2, R3a, R4b, X1, Y2), (A2, B3, M2, N1, P1, Q2, R3a, R4b, X1, Y3), (A2, B3, M2, N1, P1, Q2, R3a, R4b, X2, Y1), (A2, B3, M2, N1, P1, Q2, R3a, R4b, X2, Y2), (A2, B3, M2, N1, P1, Q2, R3a, R4b, X2, Y3), (A2, B3, M2, N1, P1, Q2, R3a, R4c, X1, Y1), (A2, B3, M2, N1, P1, Q2, R3a, R4c, X1, Y2), (A2, B3, M2, N1, P1, Q2, R3a, R4c, X1, Y3), (A2, B3, M2, N1, P1, Q2, R3a, R4c, X2, Y1), (A2, B3, M2, N1, P1, Q2, R3a, R4c, X2, Y2), (A2, B3, M2, N1, P1, Q2, R3a, R4c, X2, Y3), (A2, B3, M2, N1, P1, Q2, R3b, R4a, X1, Y1), (A2, B3, M2, N1, P1, Q2, R3b, R4a, X1, Y2), (A2, B3, M2, N1, P1, Q2, R3b, R4a, X1, Y3), (A2, B3, M2, N1, P1, Q2, R3b, R4a, X2, Y1), (A2, B3, M2, N1, P1, Q2, R3b, R4a, X2, Y2), (A2, B3, M2, N1, P1, Q2, R3b, R4a, X2, Y3), (A2, B3, M2, N1, P1, Q2, R3b, R4b, X1, Y1), (A2, B3, M2, N1, P1, Q2, R3b, R4b, X1, Y2), (A2, B3, M2, N1, P1, Q2, R3b, R4b, X1, Y3), (A2, B3, M2, N1, P1, Q2, R3b, R4b, X2, Y1), (A2, B3, M2, N1, P1, Q2, R3b, R4b, X2, Y2), (A2, B3, M2, N1, P1, Q2, R3b, R4b, X2, Y3), (A2, B3, M2, N1, P1, Q2, R3b, R4c, X1, Y1), (A2, B3, M2, N1, P1, Q2, R3b, R4c, X1, Y2), (A2, B3, M2, N1, P1, Q2, R3b, R4c, X1, Y3), (A2, B3, M2, N1, P1, Q2, R3b, R4c, X2, Y1), (A2, B3, M2, N1, P1, Q2, R3b, R4c, X2, Y2), (A2, B3, M2, N1, P1, Q2, R3b, R4c, X2, Y3), (A2, B3, M2, N1, P2, Q1, R3a, R4a, X1, Y1), (A2, B3, M2, N1, P2, Q1, R3a, R4a, X1, Y2), (A2, B3, M2, N1, P2, Q1, R3a, R4a, X1, Y3), (A2, B3, M2, N1, P2, Q1, R3a, R4a, X2, Y1), (A2, B3, M2, N1, P2, Q1, R3a, R4a, X2, Y2), (A2, B3, M2, N1, P2, Q1, R3a, R4a, X2, Y3), (A2, B3, M2, N1, P2, Q1, R3a, R4b, X1, Y1), (A2, B3, M2, N1, P2, Q1, R3a, R4b, X1, Y2), (A2, B3, M2, N1, P2, Q1, R3a, R4b, X1, Y3), (A2, B3, M2, N1, P2, Q1, R3a, R4b, X2, Y1), (A2, B3, M2, N1, P2, Q1, R3a, R4b, X2, Y2), (A2, B3, M2, N1, P2, Q1, R3a, R4b, X2, Y3), (A2, B3, M2, N1, P2, Q1, R3a, R4c, X1, Y1), (A2, B3, M2, N1, P2, Q1, R3a, R4c, X1, Y2), (A2, B3, M2, N1, P2, Q1, R3a, R4c, X1, Y3), (A2, B3, M2, N1, P2, Q1, R3a, R4c, X2, Y1), (A2, B3, M2, N1, P2, Q1, R3a, R4c, X2, Y2), (A2, B3, M2, N1, P2, Q1, R3a, R4c, X2, Y3), (A2, B3, M2, N1, P2, Q1, R3b, R4a, X1, Y1), (A2, B3, M2, N1, P2, Q1, R3b, R4a, X1, Y2), (A2, B3, M2, N1, P2, Q1, R3b, R4a, X1,
Y3), (A2, B3, M2, N1, P2, Q1, R3b, R4a, X2, Y1), (A2, B3, M2, N1, P2, Q1, R3b, R4a, X2, Y2), (A2, B3, M2, N1, P2, Q1, R3b, R4a, X2, Y3), (A2, B3, M2, N1, P2, Q1, R3b, R4b, X1, Y1), (A2, B3, M2, N1, P2, Q1, R3b, R4b, X1, Y2), (A2, B3, M2, N1, P2, Q1, R3b, R4b, X1, Y3), (A2, B3, M2, N1, P2, Q1, R3b, R4b, X2, Y1), (A2, B3, M2, N1, P2, Q1, R3b, R4b, X2, Y2), (A2, B3, M2, N1, P2, Q1, R3b, R4b, X2, Y3), (A2, B3, M2, N1, P2, Q1, R3b, R4c, X1, Y1), (A2, B3, M2, N1, P2, Q1, R3b, R4c, X1, Y2), (A2, B3, M2, N1, P2, Q1, R3b, R4c, X1, Y3), (A2, B3, M2, N1, P2, Q1, R3b, R4c, X2, Y1), (A2, B3, M2, N1, P2, Q1, R3b, R4c, X2, Y2), (A2, B3, M2, N1, P2, Q1, R3b, R4c, X2, Y3), (A2, B3, M2, N1, P2, Q2, R3a, R4a, X1, Y1), (A2, B3, M2, N1, P2, Q2, R3a, R4a, X1, Y2), (A2, B3, M2, N1, P2, Q2, R3a, R4a, X1, Y3), (A2, B3, M2, N1, P2, Q2, R3a, R4a, X2, Y1), (A2, B3, M2, N1, P2, Q2, R3a, R4a, X2, Y2), (A2, B3, M2, N1, P2, Q2, R3a, R4a, X2, Y3), (A2, B3, M2, N1, P2, Q2, R3a, R4b, X1, Y1), (A2, B3, M2, N1, P2, Q2, R3a, R4b, X1, Y2), (A2, B3, M2, N1, P2, Q2, R3a, R4b, X1, Y3), (A2, B3, M2, N1, P2, Q2, R3a, R4b, X2, Y1),
(A2, B3, M2, N1, P2, Q2, R3a, R4b, X2, Y2), (A2, B3, M2, N1, P2, Q2, R3a, R4b, X2, Y3), (A2, B3, M2, N1, P2, Q2, R3a, R4c, X1, Y1), (A2, B3, M2, N1, P2, Q2, R3a, R4c, X1, Y2), (A2, B3, M2, N1, P2, Q2, R3a, R4c, X1, Y3), (A2, B3, M2, N1, P2, Q2, R3a, R4c, X2, Y1), (A2, B3, M2, N1, P2, Q2, R3a, R4c, X2, Y2), (A2, B3, M2, N1, P2, Q2, R3a, R4c, X2, Y3), (A2, B3, M2, N1, P2, Q2, R3b, R4a, X1, Y1), (A2, B3, M2, N1, P2, Q2, R3b, R4a, X1, Y2), (A2, B3, M2, N1, P2, Q2, R3b, R4a, X1, Y3), (A2, B3, M2, N1, P2, Q2, R3b, R4a, X2, Y1), (A2, B3, M2, N1, P2, Q2, R3b, R4a, X2, Y2), (A2, B3, M2, N1, P2, Q2, R3b, R4a, X2, Y3), (A2, B3, M2, N1, P2, Q2, R3b, R4b, X1, Y1), (A2, B3, M2, N1, P2, Q2, R3b, R4b, X1, Y2), (A2, B3, M2, N1, P2, Q2, R3b, R4b, X1, Y3), (A2, B3, M2, N1, P2, Q2, R3b, R4b, X2, Y1), (A2, B3, M2, N1, P2, Q2, R3b, R4b, X2, Y2), (A2, B3, M2, N1, P2, Q2, R3b, R4b, X2, Y3), (A2, B3, M2, N1, P2, Q2, R3b, R4c, X1, Y1), (A2, B3, M2, N1, P2, Q2, R3b, R4c, X1, Y2), (A2, B3, M2, N1, P2, Q2, R3b, R4c, X1, Y3), (A2, B3, M2, N1, P2, Q2, R3b, R4c, X2, Y1), (A2, B3, M2, N1, P2, Q2, R3b, R4c, X2, Y2), (A2, B3, M2, N1, P2, Q2, R3b, R4c, X2, Y3), (A2, B3, M2, N2, P1, Q1, R3a, R4a, X1, Y1), (A2, B3, M2, N2, P1, Q1, R3a, R4a, X1, Y2), (A2, B3, M2, N2, P1, Q1, R3a, R4a, X1, Y3), (A2, B3, M2, N2, P1, Q1, R3a, R4a, X2, Y1), (A2, B3, M2, N2, P1, Q1, R3a, R4a, X2, Y2), (A2, B3, M2, N2, P1, Q1, R3a, R4a, X2, Y3), (A2, B3, M2, N2, P1, Q1, R3a, R4b, X1, Y1), (A2, B3, M2, N2, P1, Q1, R3a, R4b, X1, Y2), (A2, B3, M2, N2, P1, Q1, R3a, R4b, X1, Y3), (A2, B3, M2, N2, P1, Q1, R3a, R4b, X2, Y1), (A2, B3, M2, N2, P1, Q1, R3a, R4b, X2, Y2), (A2, B3, M2, N2, P1, Q1, R3a, R4b, X2, Y3), (A2, B3, M2, N2, P1, Q1, R3a, R4c, X1, Y1), (A2, B3, M2, N2, P1, Q1, R3a, R4c, X1, Y2), (A2, B3, M2, N2, P1, Q1, R3a, R4c, X1, Y3), (A2, B3, M2, N2, P1, Q1, R3a, R4c, X2, Y1), (A2, B3, M2, N2, P1, Q1, R3a, R4c, X2, Y2), (A2, B3, M2, N2, P1, Q1, R3a, R4c, X2, Y3), (A2, B3, M2, N2, P1, Q1, R3b, R4a, X1, Y1), (A2, B3, M2, N2, P1, Q1, R3b, R4a, X1, Y2), (A2, B3, M2, N2, P1, Q1, R3b, R4a, X1, Y3), (A2, B3, M2, N2, P1, Q1, R3b, R4a, X2, Y1), (A2, B3, M2, N2, P1, Q1, R3b, R4a, X2, Y2), (A2, B3, M2, N2, P1, Q1, R3b, R4a, X2, Y3), (A2, B3, M2, N2, P1, Q1, R3b, R4b, X1, Y1), (A2, B3, M2, N2, P1, Q1, R3b, R4b, X1, Y2), (A2, B3, M2, N2, P1, Q1, R3b, R4b, X1, Y3), (A2, B3, M2, N2, P1, Q1, R3b, R4b, X2, Y1), (A2, B3, M2, N2, P1, Q1, R3b, R4b, X2, Y2), (A2, B3, M2, N2, P1, Q1, R3b, R4b, X2, Y3), (A2, B3, M2, N2, P1, Q1, R3b, R4c, X1, Y1), (A2, B3, M2, N2, P1, Q1, R3b, R4c, X1, Y2), (A2, B3, M2, N2, P1, Q1, R3b, R4c, X1, Y3), (A2, B3, M2, N2, P1, Q1, R3b, R4c, X2, Y1), (A2, B3, M2, N2, P1, Q1, R3b, R4c, X2, Y2), (A2, B3, M2, N2, P1, Q1, R3b, R4c, X2, Y3), (A2, B3, M2, N2, P1, Q2, R3a, R4a, X1, Y1), (A2, B3, M2, N2, P1, Q2, R3a, R4a, X1, Y2), (A2, B3, M2, N2, P1, Q2, R3a, R4a, X1, Y3), (A2, B3, M2, N2, P1, Q2, R3a, R4a, X2,Y1), (A2, B3, M2, N2, P1, Q2, R3a, R4a, X2, Y2), (A2, B3, M2, N2, P1, Q2, R3a, R4b, X1, Y1), (A2, B3, M2, N2, P1, Q2, R3a, R4b, X1, Y2), (A2, B3, M2, N2, P1, Q2, R3a, R4b, X1, Y3), (A2, B3, M2, N2, P1, Q2, R3a, R4b, X2, Y1), (A2, B3, M2, N2, P1, Q2, R3a, R4b, X2, Y2), (A2, B3, M2, N2, P1, Q2, R3a, R4b, X2, Y3), (A2, B3, M2, N2, P1, Q2, R3a, R4c, X1, Y1), (A2, B3, M2, N2, P1, Q2, R3a, R4c, X1, Y2), (A2, B3, M2, N2, P1, Q2, R3a, R4c, X1, Y3), (A2, B3, M2, N2, P1, Q2, R3a, R4c, X2,Y1), (A2, B3, M2, N2, P1, Q2, R3a, R4c, X2, Y2), (A2, B3, M2, N2, P1, Q2, R3a, R4c, X2, Y3), (A2, B3, M2, N2, P1, Q2, R3b, R4a, X1, Y1), (A2, B3, M2, N2, P1, Q2, R3b, R4a, X1, Y2), (A2, B3, M2, N2, P1, Q2, R3b, R4a, X1, Y3), (A2, B3, M2, N2, P1, Q2, R3b, R4a, X2, Y1), (A2, B3, M2, N2, P1, Q2, R3b, R4a, X2, Y2), (A2, B3, M2, N2, P1, Q2, R3b, R4a, X2, Y3), (A2, B3, M2, N2, P1, Q2, R3b, R4b, X1, Y1), (A2, B3, M2, N2, P1, Q2, R3b, R4b, X1, Y2), (A2, B3, M2, N2, P1, Q2, R3b, R4b, X1, Y3), (A2, B3, M2, N2, P1, Q2, R3b, R4b, X2, Y1), (A2, B3, M2, N2, P1, Q2, R3b, R4b, X2, Y2), (A2, B3, M2, N2, P1, Q2, R3b, R4b, X2, Y3), (A2, B3, M2, N2, P1, Q2, R3b, R4c, X1, Y1), (A2, B3, M2, N2, P1, Q2, R3b, R4c, X1, Y2), (A2, B3, M2, N2, P1, Q2, R3b, R4c, X1, Y3), (A2, B3, M2, N2, P1, Q2, R3b, R4c, X2, Y1), (A2, B3, M2, N2, P1, Q2, R3b, R4c, X2, Y2), (A2, B3, M2, N2, P1, Q2, R3b, R4c, X2, Y3), (A2, B3, M2, N2, P2, Q1, R3a, R4a, X1,Y1), (A2, B3, M2, N2, P2, Q1, R3a, R4a, X1, Y2), (A2, B3, M2, N2, P2, Q1, R3a, R4a, X1, Y3), (A2, B3, M2, N2, P2, Q1, R3a, R4a, X2, Y1), (A2, B3, M2, N2, P2, Q1, R3a, R4a, X2,Y2), (A2, B3, M2, N2, P2, Q1, R3a, R4a, X2, Y3), (A2, B3, M2, N2, P2, Q1, R3a, R4b, X1, Y1), (A2, B3, M2, N2, P2, Q1, R3a, R4b, X1, Y2), (A2, B3, M2, N2, P2, Q1, R3a, R4b, X1, Y3), (A2, B3, M2, N2, P2, Q1, R3a, R4b, X2, Y1), (A2, B3, M2, N2, P2, Q1, R3a, R4b, X2, Y2), (A2, B3, M2, N2, P2, Q1, R3a, R4b, X2, Y3), (A2, B3, M2, N2, P2, Q1, R3a, R4c, X1,Y1), (A2, B3, M2, N2, P2, Q1, R3a, R4c, X1, Y2), (A2, B3, M2, N2, P2, Q1, R3a, R4c, X1, Y3), (A2, B3, M2, N2, P2, Q1, R3a, R4c, X2, Y1), (A2, B3, M2, N2, P2, Q1, R3a, R4c, X2, Y2), (A2, B3, M2, N2, P2, Q1, R3a, R4c, X2, Y3), (A2, B3, M2, N2, P2, Q1, R3b, R4a, X1, Y1), (A2, B3, M2, N2, P2, Q1, R3b, R4a, X1, Y2), (A2, B3, M2, N2, P2, Q1, R3b, R4a, X1, Y3), (A2, B3, M2, N2, P2, Q1, R3b, R4a, X2, Y1), (A2, B3, M2, N2, P2, Q1, R3b, R4a, X2, Y2), (A2, B3, M2, N2, P2, Q1, R3b, R4a, X2, Y3), (A2, B3, M2, N2, P2, Q1, R3b, R4b, X1,Y1), (A2, B3, M2, N2, P2, Q1, R3b, R4b, X1, Y2), (A2, B3, M2, N2, P2, Q1, R3b, R4b, X1, Y3), (A2, B3, M2, N2, P2, Q1, R3b, R4b, X2, Y1), (A2, B3, M2, N2, P2, Q1, R3b, R4b, X2,Y2), (A2, B3, M2, N2, P2, Q1, R3b, R4b, X2, Y3), (A2, B3, M2, N2, P2, Q1, R3b, R4c, X1, Y1), (A2, B3, M2, N2, P2, Q1, R3b, R4c, X1, Y2), (A2, B3, M2, N2, P2, Q1, R3b, R4c, X1, Y3), (A2, B3, M2, N2, P2, Q1, R3b, R4c, X2,Y1), (A2, B3, M2, N2, P2, Q1, R3b, R4c, X2, Y2), (A2, B3, M2, N2, P2, Q1, R3b, R4c, X2, Y3), (A2, B3, M2, N2, P2, Q2, R3a, R4a, X1,Y1), (A2, B3, M2, N2, P2, Q2, R3a, R4a, X1, Y2), (A2, B3, M2, N2, P2, Q2, R3a, R4a, X1, Y3), (A2, B3, M2, N2, P2, Q2, R3a, R4a, X2,Y1), (A2, B3, M2, N2, P2, Q2, R3a, R4a, X2,Y2), (A2, B3, M2, N2, P2, Q2, R3a, R4a, X2, Y3), (A2, B3, M2, N2, P2, Q2, R3a, R4b, X1, Y1), (A2, B3, M2, N2, P2, Q2, R3a, R4b, X1, Y2), (A2, B3, M2, N2, P2, Q2, R3a, R4b, X1, Y3), (A2, B3, M2, N2, P2, Q2, R3a, R4b, X2,Y1), (A2, B3, M2, N2, P2, Q2, R3a, R4b, X2, Y2), (A2, B3, M2, N2, P2, Q2, R3a, R4b, X2, Y3), (A2, B3, M2, N2, P2, Q2, R3a, R4c, X1,Y1), (A2, B3, M2, N2, P2, Q2, R3a, R4c, X1, Y2), (A2, B3, M2, N2, P2, Q2, R3a, R4c, X1, Y3), (A2, B3, M2, N2, P2, Q2, R3a, R4c, X2,Y1), (A2, B3, M2, N2, P2, Q2, R3a, R4c, X2,Y2), (A2, B3, M2, N2, P2, Q2, R3a, R4c, X2, Y3), (A2, B3, M2, N2, P2, Q2, R3b, R4a, X1, Y1), (A2, B3, M2, N2, P2, Q2, R3b, R4a, X1, Y2), (A2, B3, M2, N2, P2, Q2, R3b, R4a, X1, Y3), (A2, B3, M2, N2, P2, Q2, R3b, R4a, X2, Y1), (A2, B3, M2, N2, P2, Q2, R3b, R4a, X2, Y2), (A2, B3, M2, N2, P2, Q2, R3b, R4a, X2, Y3), (A2, B3, M2, N2, P2, Q2, R3b, R4b, X1,Y1), (A2, B3, M2, N2, P2, Q2, R3b, R4b, X1, Y2), (A2, B3, M2, N2, P2, Q2, R3b, R4b, X1, Y3), (A2, B3, M2, N2, P2, Q2, R3b, R4b, X2, Y1), (A2, B3, M2, N2, P2, Q2, R3b, R4b, X2,Y2), (A2, B3, M2, N2, P2, Q2, R3b, R4b, X2, Y3), (A2, B3, M2, N2, P2, Q2, R3b, R4c, X1, Y1), (A2, B3, M2, N2, P2, Q2, R3b, R4c, X1, Y2), (A2, B3, M2, N2, P2, Q2, R3b, R4c, X1, Y3), (A2, B3, M2, N2, P2, Q2, R3b, R4c, X2, Y1), (A2, B3, M2, N2, P2, Q2, R3b, R4c, X2, Y2) or (A2, B3, M2, N2, P2, Q2, R3b, R4c, X2, Y3).

Further examples of A include, for example, a group selected from the group consisting of the followings:

[Chemical Formula 17]

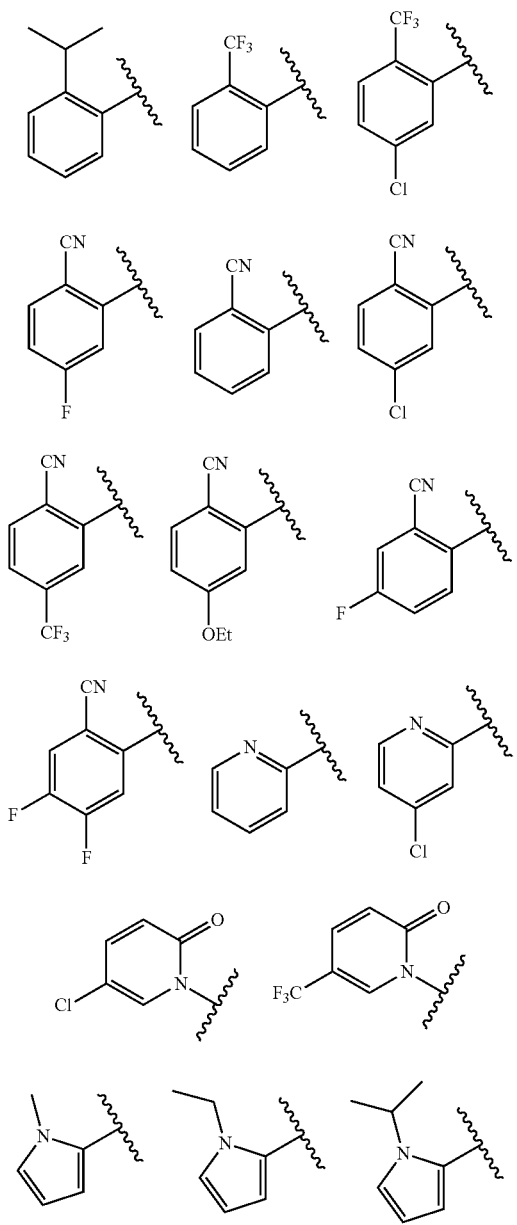

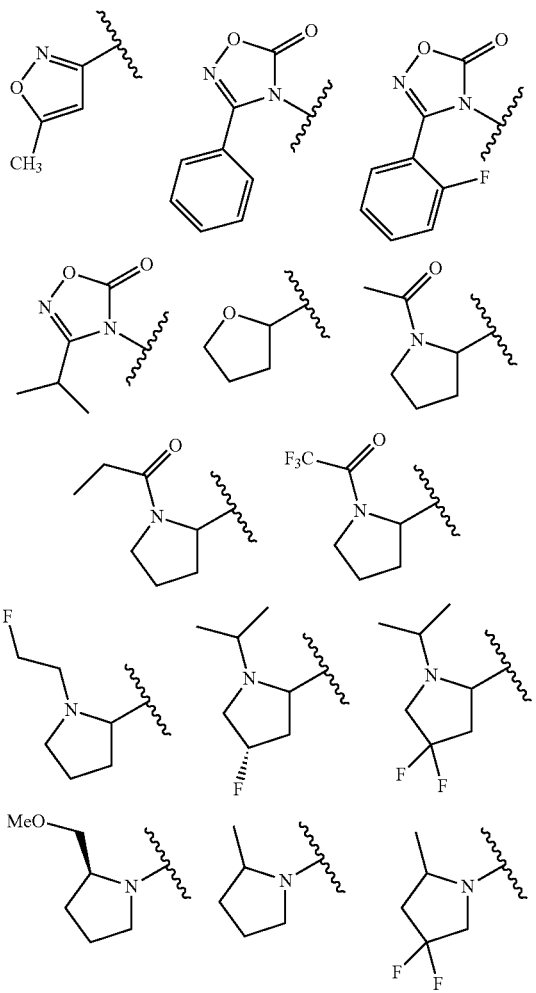

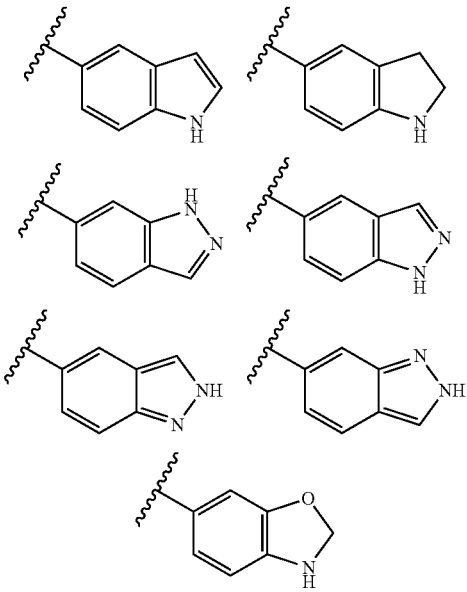

wherein the bond from the groups binds to Y, and each ring is substituted or unsubstituted with m $R^3$s and n $R^4$s.

Further examples of $R^3$ include, for example, a group selected from the group consisting of the followings:

[Chemical Formula 19]

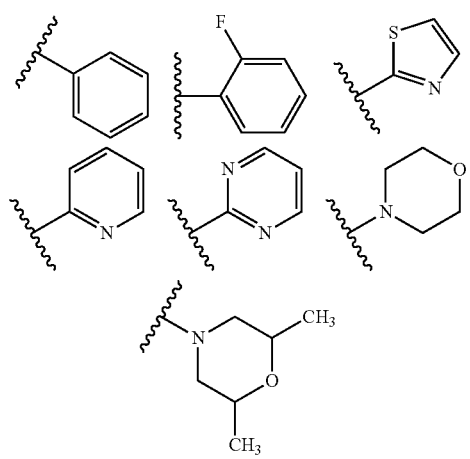

wherein the bond binds to B.

Further examples of $R^4$ include, for example, a group selected from the group consisting of the followings:

[Chemical Formula 20]

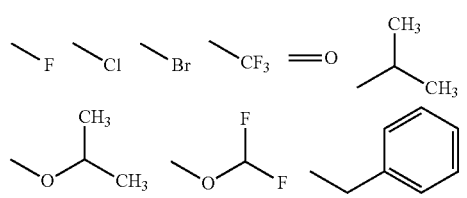

wherein the bond from the groups binds to —C($R^1R^2$)$_p$—.

Further examples of B include, for example, a group selected from the group consisting of the followings:

[Chemical Formula 18]

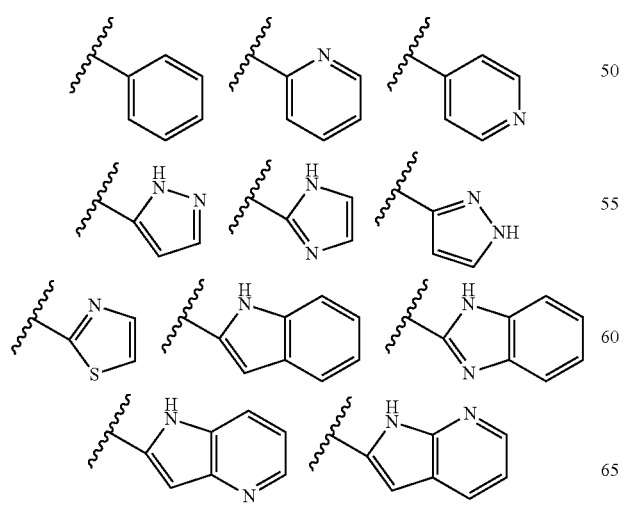

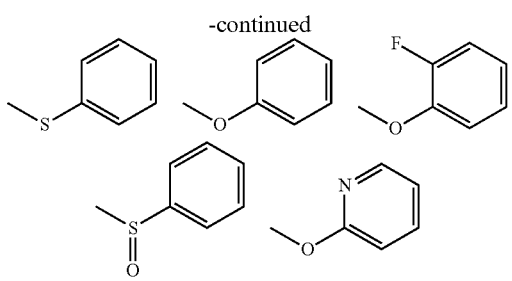

wherein the bond binds to B.

The compound of the formula (I) can be synthesized by the procedure, for example, as described below. If necessary, an amino group or an imino group of the compound may be protected at appropriate stage according to a conventional method, for example, using a protecting group such as Cbz (benzyloxycarbonyl), Fmoc (9-fluororenylmethyloxycarbonyl), Boc (tert-butoxycarbonyl) conventionally used in the art.

Method 1

[Y=$CR^5R^6NR^7$ or C(=O)$NR^7$]

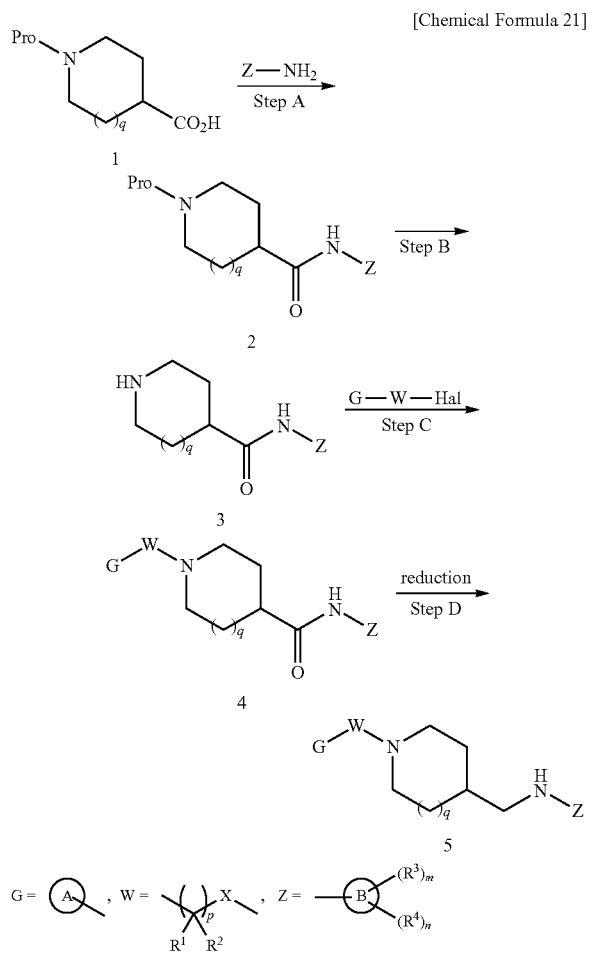

wherein Hal is halogen; G, W and Z are independently a desired substituent; Pro is a protecting group; and the other symbols are as defined above.

Step A

Compound 1 is reacted with an amino compound having a desired substituent Z in a suitable solvent at 0° C. to 50° C. for several minutes to several hours. For the solvent, tetrahydrofuran, dimethylformamide, diethyl ether, dichloromethane, toluene, benzene, xylene, cyclohexane, hexane, chloroform, ethyl acetate, butyl acetate, pentane, heptane, dioxane, acetone, acetonitrile, and a mixture thereof may be used. If necessary, an activator such as thionyl chloride, acid halides, acid anhydrates, activated esters, may be used.

Step B

Compound 2 obtained in Step A is subjected to deprotection by conventional method to give Compound 3.

Step C

Compound 3 obtained in Step B is reacted with halide having a desired substituent G-W— in a suitable solvent at 0° C. to 50° C. for several minutes to several hours. For the solvent, tetrahydrofuran, dimethylformamide, diethyl ether, dichloromethane, toluene, benzene, xylene, cyclohexane, hexane, chloroform, ethyl acetate, butyl acetate, pentane, heptane, dioxane, acetone, acetonitrile, water and a mixture thereof may be used.

Step D

Compound 4 obtained in Step C is treated with reducing agent in a suitable solvent at 0° C. to 100° C. for several minutes to several hours to give Compound 5. For the reducing agent, sodium borohydride, lithium borohydride, lithium aluminum hydride, diborane, etc. For the solvent, tetrahydrofuran, dimethylformamide, dioxane, acetonitrile, methanol, ethanol, propanol and a mixture thereof may be used. If necessary, Compound 5 can be obtained through the intermediate such as acid halide, acid anhydride and activated ester.

Method 2

[Y=single bond, B=indole or azaindole]

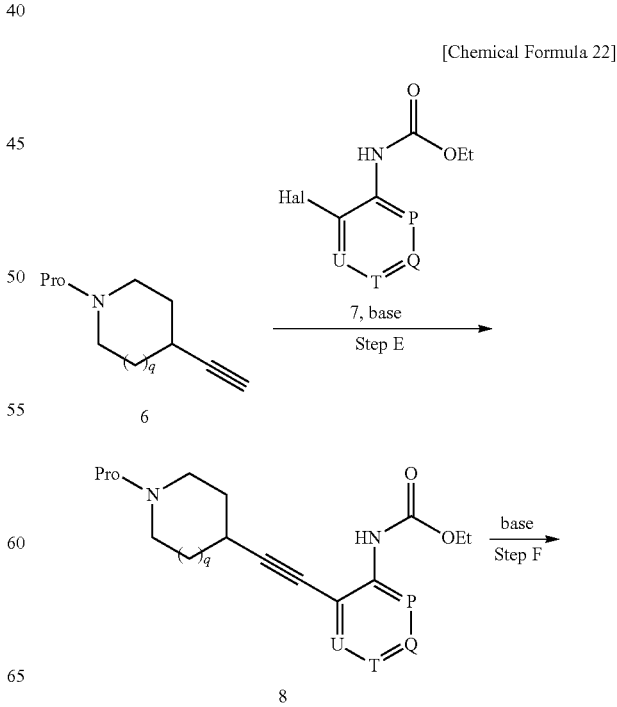

-continued

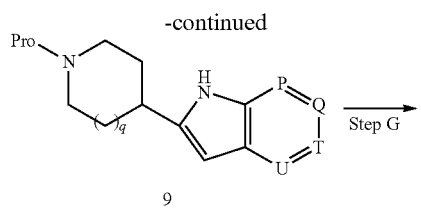
9

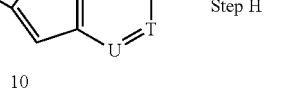 Step G

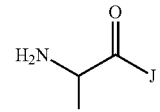 Step H
10

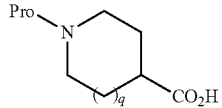
11 wherein P, Q, T and U are independently desired substituent; Hal, G, W and Pro are as defined above.

Step E

Compound 6 is reacted with the halide 7 having a desired substituents P, Q, T, U in a suitable solvent at 0° C. to 100° C. for several minutes to several hours in the presence of a base. For the base, triethylamine, DBU (diazabicycloundecene), sodium carbonate, potassium carbonate, barium hydroxide, sodium hydroxide, potassium hydroxide, etc. may be used. Triethylamine and potassium carbonate are preferable. For the reaction solvent, tetrahydrofuran, dimethylformamide, dimethylacetamide, diethyl ether, dichloromethane, toluene, benzene, xylene, cyclohexane, hexane, chloroform, ethyl acetate, butyl acetate, pentane, heptane, dioxane, acetone, methanol, ethanol, propanol, acetonitrile, water and a mixture thereof may be used. Dimethylformamide is preferable. Examples of the catalyst are Pd (PPh$_3$)$_4$, PdCl$_2$ (PPh$_3$)$_2$, Pd (DBA) (bisdibenzylideneacetonepalladium), copper iodide, DABCO, etc. Dichlorobis(triphenylphosphine)palladium and/or copper iodide are preferable.

Step F

Compound 8 obtained in Step E is treated with a base in an appropriate solvent at 0° C. to 100° C. for several minutes to several hours. For the base, tetrabutylammonium fluoride, triethylamine, pyridine, N-methylmorpholine, dimethylaniline, barium hydroxide, sodium hydroxide, potassium hydroxide, potassium carbonate, sodium carbonate, hydrazine, propanethiol lithium salt, etc. may be used. Tetrabutylammonium fluoride is preferable. For the reaction solvent, tetrahydrofuran, dimethylformamide, diethylether, dichloromethane, toluene, benzene, xylene, cyclohexane, hexane, chloroform, ethyl acetate, butyl acetate, pentane, heptane, dioxane, acetone, methanol, ethanol, acetonitrile, water and a mixture thereof, etc. Tetrahydrofuran is preferable.

Step G

Compound 9 obtained in Step F is subjected to deprotection by conventional method to give Compound 10.

Step H

Compound 10 obtained in Step G is reacted with halide having a desired substituent G-W— in a suitable solvent at 0° C. to 50° C. for several minutes to several hours to give Compound 11. For the solvent, tetrahydrofuran, dimethylformamide, diethylether, dichloromethane, toluene, benzene, xylene, cyclohexane, hexane, chloroform, ethyl acetate, butyl acetate, pentane, heptane, dioxane, acetone, acetonitrile, water and a mixture thereof, etc. may be used.

Method 3

[Y=single bond, B=imidazole]

[Chemical Formula 23]

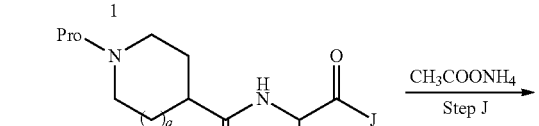

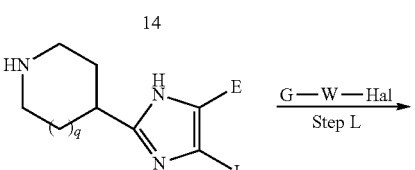
14

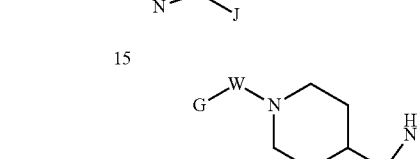
15

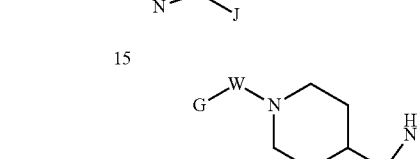
16 wherein E and J are independently desired substituent; Hal, G, W and Pro are as defined above.

Step I

Compound 1 is reacted with the amino compound 12 having the desired substituents E and J in a suitable solvent at 0° C. to 50° C. for several minutes to several hours. For the solvent, tetrahydrofuran, dimethylformamide, diethylether, dichloromethane, toluene, benzene, xylene, cyclohexane, hexane, chloroform, ethyl acetate, butyl acetate, pentane, heptane, dioxane, acetone, acetonitrile and a mixture thereof, etc. may be used; and if necessary, an activator such as thionyl chloride, acid halides, acid anhydrides, activated ester may be used.

Step J

Compound 13 obtained in Step I is reacted with ammonium acetate in a suitable solvent at room temperature to 150° C. for several minutes to several hours. For the reaction solvent, acetic acid, methylene chloride, tetrahydrofuran, dimethylformamide, dimethylacetamide, N-methylpyrrolidone, diethylether, diisopropyl ether, 1,2-dichloroethane, toluene, benzene, xylene, cyclohexane, hexane, chloroform, ethyl acetate, butyl acetate, pentane, heptane, dioxane, acetone, methanol, ethanol, propanol, acetonitrile, water and a mixture thereof, etc. may be used. Acetic acid is preferable.

Step K

Compound 14 obtained in Step J is subjected to deprotection by conventional method to give Compound 15.

Step L

Compound 15 obtained in Step K is reacted with halide having the desired substituents G and W in a suitable solvent at 0° C. to 50° C. for several minutes to several hours to give Compound 16. For the solvent, tetrahydrofuran, dimethylformamide, diethylether, dichloromethane, toluene, benzene, xylene, cyclohexane, hexane, chloroform, ethyl acetate, butyl acetate, pentane, heptane, dioxane, acetone, acetonitrile, water and a mixture thereof, etc. may be used.

Method 4

[Y=single bond, B=benzimidazole]

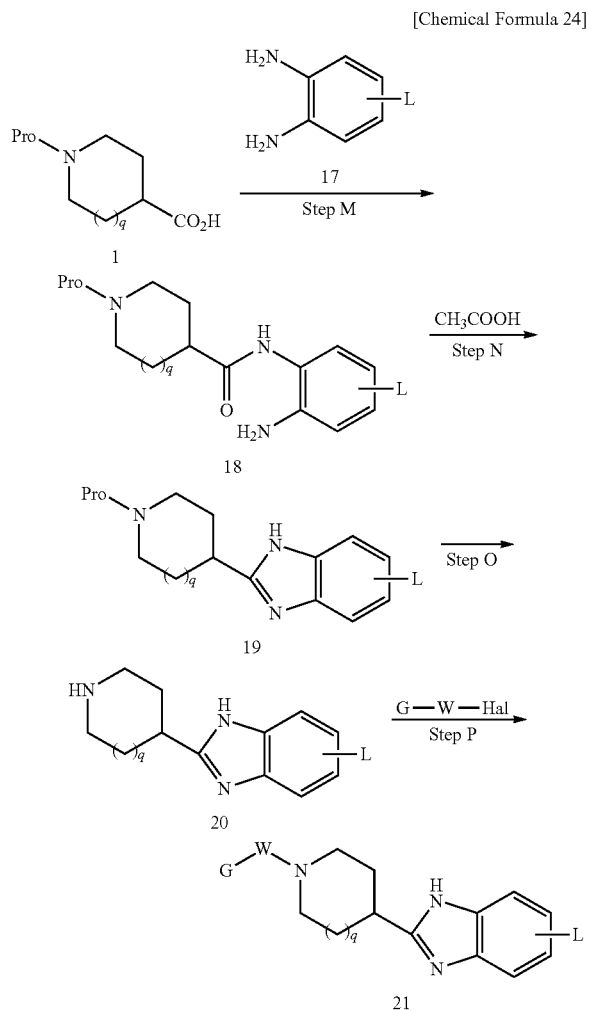

wherein L is a desired substituent; Hal, G, W and Pro are as defined above.

Step M

Compound 1 is reacted with Compound 17 having a desired substituent L in a suitable solvent at 0° C. to 50° C. for several minutes to several hours. For the solvent, tetrahydrofuran, dimethylformamide, diethylether, dichloromethane, toluene, benzene, xylene, cyclohexane, hexane, chloroform, ethyl acetate, butyl acetate, pentane, heptane, dioxane, acetone, acetonitrile and a mixture thereof, etc. may be used; and if necessary, an activator such as thionyl chloride, acid halides, acid anhydrides, activated ester may be used.

Step N

Compound 18 obtained in Step M is reacted with acetic acid in a suitable solvent at room temperature to 150° C. for several minutes to several hours. For the reaction solvent, acetic acid, methylene chloride, tetrahydrofuran, dimethylformamide, dimethylacetamide, N-methylpyrrolidone, diethylether, diisopropyl ether, 1,2-dichloroethane, toluene, benzene, xylene, cyclohexane, hexane, chloroform, ethyl acetate, butyl acetate, pentane, heptane, dioxane, acetone, methanol, ethanol, propanol, acetonitrile, water and a mixture thereof, etc. may be used. Acetic acid is preferable.

Step O

Compound 19 obtained in Step N is subjected to deprotection by conventional method to give Compound 20.

Step P

Compound 20 obtained in Step O is reacted with halide having the desired substituents G and W in a suitable solvent at 0° C. to 50° C. for several minutes to several hours to give Compound 21. For the solvent, tetrahydrofuran, dimethylformamide, diethylether, dichloromethane, toluene, benzene, xylene, cyclohexane, hexane, chloroform, ethyl acetate, butyl acetate, pentane, heptane, dioxane, acetone, acetonitrile, water and a mixture thereof, etc. may be used.

Method 6

[Y=single bond, B=pyrazole]

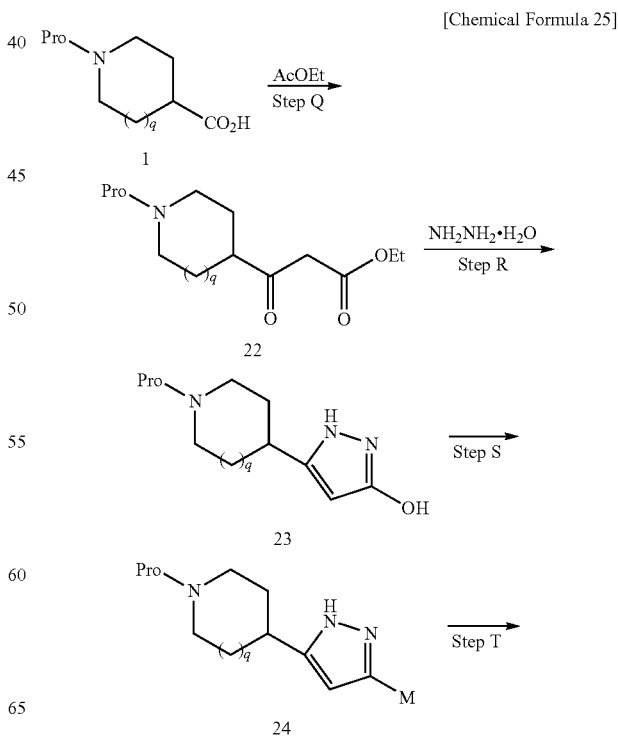

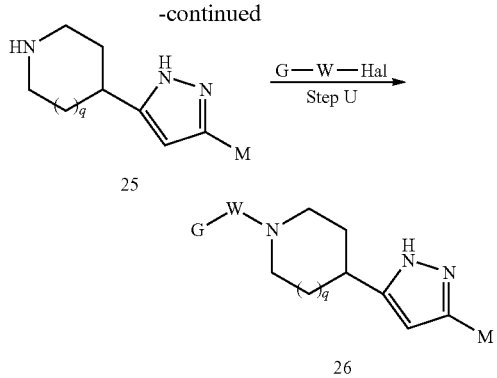

wherein M is a desired substituent; Hal, G, W and Pro are as defined above.

Step Q

Compound 1 is treated with a dehydrating agent containing chlorine atom in a suitable solvent at 0° C. to 50° C. for several minutes to several hours to give acid halide. For the dehydrating agent, oxalyl chloride, thionyl chloride, phosphorous pentachloride, phosphorous oxychloride, acetic anhydride, methanesulfonyl chloride, ethyl chlorocarbonate, etc. Oxalyl chloride is preferable. The dehydrating agent is preferably used in an amount of 1 to 5 equivalents per Compound 1. In addition, dimethylformamide may be added as a catalyst. For the reaction solvent, methylene chloride, tetrahydrofuran, dimethylformamide, dimethylacetamide, N-methylpyrrolidone, diethylether, 1,2-dichloroethane, toluene, benzene, xylene, cyclohexane, hexane, chloroform, ethyl acetate, butyl acetate, pentane, heptane, dioxane, acetone, methanol, ethanol, acetonitrile and a mixture thereof, etc. may be used. Methylene chloride and/or dimethylformamide are preferable.

Obtained acid halide is reacted with ethyl acetate in a suitable solvent, in the presence of a Lewis acid and N-alkylimidazole, at −100° C. to 0° C., for several minutes to several hours, and followed by addition of a base to give Compound 22. For the Lewis acid, titanium tetrachloride, tin tetrachloride, aluminum trichloride, boron trifluoride-ether complex, boron trichloride, trimethylsilyltrifluoromethanesulfonate (TMSOTf), zinc dichloride, etc. may be used. Titanium tetrachloride is preferable. For the N-alkylimidazole, N-methylimidazole, N-ethylimidazole, etc. may be used. N-methylimidazole is preferable. For the base, N,N'-diisopropylethylamine, diethylamine, triethylamine, pyridine, N-methylmorpholine, dimethylaniline, barium hydroxide, sodium hydroxide, potassium hydroxide, etc. may be used. N,N'-diisopropylethylamine is preferable. For the reaction solvent, methylene chloride, tetrahydrofuran, dimethylformamide, diethylether, dichloromethane, toluene, benzene, xylene, cyclohexane, hexane, chloroform, ethyl acetate, butyl acetate, pentane, heptane, dioxane, acetone, methanol, ethanol, acetonitrile, water and a mixture thereof, etc. may be used. Methylene chloride and/or ethyl acetate are preferable.

Step R

Compound 22 obtained in Step Q is reacted with hydrazine (e.g., hydrazine monohydrate) in a suitable solvent, at 0° C. to 100° C. for several minutes to several hours. For the reaction solvent, methylene chloride, tetrahydrofuran, dimethylformamide, diethylether, dichloromethane, toluene, benzene, xylene, cyclohexane, hexane, chloroform, ethyl acetate, butyl acetate, pentane, heptane, dioxane, acetone, methanol, ethanol, acetonitrile, water and a mixture thereof, etc. may be used. Methanol is preferable.

Optionally, the formula $NH_2NHR^5$, wherein $R^5$ is $R^3$ or $R^4$, or a group that can give $R^3$ or $R^4$, may be used instead of hydrazine to introduce $R^5$, simultaneously with a hydroxy group, into B (pyrazole).

Step S

A desired substituent M is attached to Compound 23 obtained in Step R by conventional method to give Compound 24.

Step T

Compound 24 obtained in Step S is subjected to deprotection by conventional method to give Compound 25.

Step U

Compound 25 obtained in Step T is reacted with halide having the desired substituents G and W in a suitable solvent at 0° C. to 50° C. for several minutes to several hours to give Compound 26. For the solvent, tetrahydrofuran, dimethylformamide, diethylether, dichloromethane, toluene, benzene, xylene, cyclohexane, hexane, chloroform, ethyl acetate, butyl acetate, pentane, heptane, dioxane, acetone, acetonitrile, water and a mixture thereof, etc. may be used.

Also, one skilled in the art can prepare a compound wherein Y is a single bond but B is not the ring as exemplified above.

When administering a compound of the present invention as a pharmaceutical composition, it can be administered orally or parenterally. For oral administration, the compound of the present invention can be used in any form of usual formulations, for example, tablets, granules, powders, capsules, pills, solutions, syrup, buccals, sublingual tablets or the like which are made by the usual procedure. For parenteral administration, the compound of the present invention can be used in any form of usual formulations, for example, injections such as intramuscular administration and intravenous administration, suppository, transdermal therapeutic agent, insufflation or the like. A compound of the present invention can be preferably used as an oral formulation because it has high oral bioavailability.

The pharmaceutical formulation according to the present invention may be manufactured by combining a therapeutically effective amount of a compound of the present invention with various pharmaceutically acceptable excipients, binder, moistening agent, disintegrating agents, lubricant, diluent and the like. When it is an injectable formulation, the compound of the present invention may be subjected to sterilization treatment together with an appropriate carrier to obtain such formulation.

Specifically, the excipient includes lactose, saccharose, glucose, starch, calcium carbonate, crystalline cellulose and the like. The binder includes methylcellulose, carboxymethylcellulose, hydroxypropylcellulose, gelatin, polyvinylpyrrolidone and the like. The disintegrating agent includes carboxymethylcellulose, sodium carboxymethylcellulose, starch, sodium alginate, powdered agar, sodium lauryl sulfate and the like. The lubricant includes talc, magnesium stearate, macrogol and the like. As a basis for suppository, cocoa butter, macrogol, methyl cellulose and the like can be used. When the present invention is manufactured as an injectable formulation of liquid, emulsion or suspension, conventionally used solubilizing agent, suspending agent, emulsifying agent, stabilizing agent, preservatives, isotonic agent and the like may be appropriately added. In case of oral formulation, sweetening agent, flavoring agent and the like may be added.

The dose of a compound of the present invention is preferably determined depending on age, body weight, type and severity of disease of the patient, administration route, and the like. In case of oral administration for an adult, it is usually 0.05 to 100 mg/kg/day and preferably 0.1 to 10 mg/kg/day. In case of parenteral administration, although it is very different depending on route of administration, it is usually 0.005 to 10 mg/kg/day and preferably 0.01 to 1 mg/kg/day. The dose may be administrated at once or divided to several times a day.

The pharmaceutical composition of the present invention can be used in combination with other anti-obesity agent (agents that can be used in obesity and weight control in obesity). Also, the administration regimen of the pharmaceutical composition of the invention may be combined with diet, drug therapy, exercise, etc.

The present invention is further explained by the following Examples, which are not intended to limit the scope of the present invention.

The abbreviations used in the following Examples have the following meanings.
EDC: 1-ethyl-3-(3-dimethylaminopropyl)carbodiimide
HOBt: 1-hydroxybenztriazole
Boc: tert-butoxycarbonyl
WSCD: 1-ethyl-3-(3-dimethylamino) carbodiimide
TBAF: tetra-N-butylammonium fluoride
DMF: N,N-dimethylformamide Example 1

Synthesis of compound Ia-1

Step 1

[Chemical Formula 26]

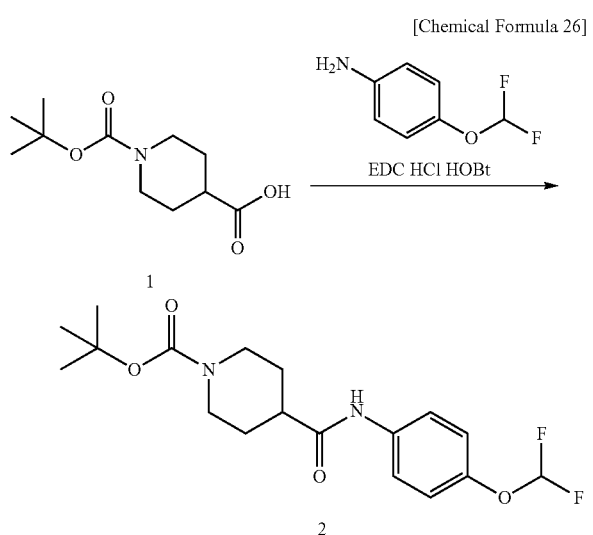

Compound 1 (3.44 g, 15.0 mmol) in N,N'-dimethylformamide (20 mL) at room temperature was added with 4-difluoromethoxyaniline (2.23 mL, 18.0 mmol), HOBt (2.63 g, 19.5 mmol) and EDC hydrochloride (3.45 g, 18.0 mmol). The mixture was stirred overnight at room temperature. The reaction mixture was poured into 0.05 N hydrochloride and extracted with ethyl acetate. The organic layer was washed with saturated aqueous sodium bicarbonate, and dried over magnesium sulfate, and then, the solvent was removed in vacuo. The residue was added with ethyl acetate and hexanes, and the precipitated crystals were collected by filtration to give the desired amide compound 2 (3.88 g, yield 70%).

Step 2

[Chemical Formula 27]

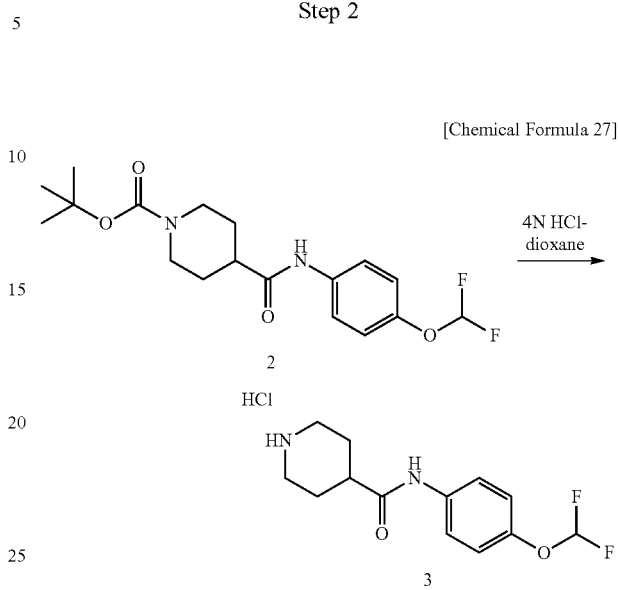

Compound 2 (3.88 g) obtained in Step 1 at room temperature was added with 4N-hydrochloride-dioxane solution (30 mL), and the mixture was stirred for 1 hour. The solution was then concentrated to give the desired amine hydrochloride 3 (3.39 g) as a crude product.

$^1$H-NMR (DMSO-$d_6$) δ ppm: 1.76-1.91 (m, 2H), 1.91-2.03 (m, 2H), 2.69 (m, 1H), 2.81-2.97 (m, 2H), 3.22-3.36 (m, 2H), 7.13 (d, 2H, J=9.3 Hz), 7.14 (t, 1H, J=74.1 Hz), 7.67 (d, 2H, J=9.3 Hz), 8.34 (br.s, 1H), 9.19 (br.s, 1H), 10.3 (br.s, 1H).

Step 3

[Chemical Formula 28]

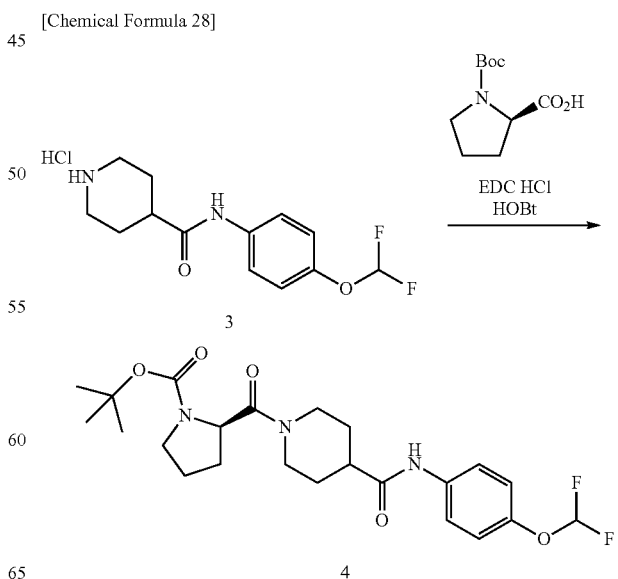

The amine hydrochloride 3 (613 mg, 2.00 mmol) obtained in Step 2 in N,N'-dimethylformamide (5 mL), at room temperature, was added with Boc-D-proline (517 mg, 2.40 mmol), HOBt (54 mg, 0.40 mmol), EDC hydrochloride (497 mg, 2.60 mmol). The mixture was stirred overnight at room temperature. The solution was poured into 3% citric acid, and extracted with ethyl acetate. The organic layer was washed with saturated aqueous sodium bicarbonate, and dried over magnesium sulfate. The solvent was removed in vacuo, and the residue was purified by silica gel (110 g) column chromatography (chloroform:methanol=97:3→90:10) to yield the desired amide compound 4 (818 mg, yield 88%).

$^1$H-NMR (DMSO-$d_6$) δ ppm: 1.23-1.61 (m, 12H), 1.61-1.90 (m, 5H), 2.20 (m, 1H), 2.53-2.74 (m, 2H), 3.04 (m, 1H), 3.29-3.40 (m, 2H), 4.01 (m, 1H), 4.29-4.47 (m, 1H), 4.55-4.69 (m, 1H), 7.13 (t, 1H, J=74.1 Hz), 7.19 (d, 2H, J=8.6 Hz), 7.57-7.67 (m, 2H), 9.99-10.0 (m, 1H).

Step 4

[Chemical Formula 29]

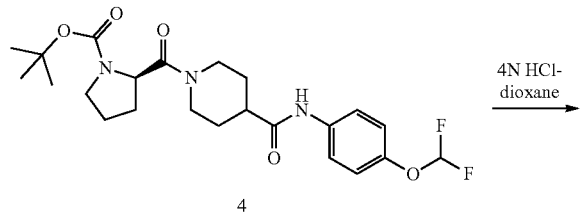

The amide compound 4 (511 mg) obtained in Step 3, at room temperature, was added with 4N-hydrochloride-dioxane solution (5 mL). The mixture was stirred for 1 hour. The solution was concentrated to afford the desired amine hydrochloride 5 (520 mg) as a crude product.

$^1$H-NMR (DMSO-$d_6$) δ ppm: (observed as 1:1 mixture of two rotamers) 1.45-1.71 (m, 2H), 1.71-2.02 (m, 5H), 2.40 (m, 1H), 2.65-2.87 (m, 2H), 3.07-3.32 (m, 3H), 3.86-3.97 (m, 1H), 4.33-4.43 (m, 1H), 4.54 (m, 0.5H), 4.62 (m, 0.5H), 7.12 (d, 2H, J=8.6 Hz), 7.14 (t, 1H, J=74.5 Hz), 7.67 (d, 2H, J=8.6 Hz), 8.44 (br.s, 1H), 10.0 (br.s, 0.5H), 10.2 (br.s, 0.5H), 10.30 (s, 0.5H), 10.31 (s, 0.5H).

Step 5

[Chemical Formula 30]

The amine hydrochloride 5 obtained in Step 4 (85% purity, 185 mg, ca. 0.389 mmol) in methylene chloride (3 mL), at room temperature, was added with triethylamine (217 μL, 1.56 mmol) and acetyl chloride (55 μL, 1.56 mmol). The mixture was stirred for 1 hour at room temperature. The solution was poured into 1% hydrochloride, and extracted with ethyl acetate. The organic layer was washed with brine, and dried over magnesium sulfate. The solvent was removed in vacuo, and the residue was recrystallized from a mixed solvent of chloroform and n-hexane to afford the desired compound 6 (58 mg) as a colorless solid.

$^1$H-NMR (DMSO-$d_6$) δ ppm: 1.35-2.03 (m, 11H), 2.04-2.36 (m, 1H), 2.54-2.70 (m, 2H), 3.12 (m, 1H), 3.51 (m, 1H), 4.04 (m, 1H), 4.28-4.48 (m, 1H), 4.71-4.99 (m, 1H), 7.12 (d, 2H, J=8.3 Hz), 7.13 (t, 1H, J=74.4 Hz), 7.64 (d, 2H, J=8.3 Hz), 9.99-10.01 (m, 1H).

Example 2

Synthesis of compound Ia-24

Step 1

[Chemical Formula 31]

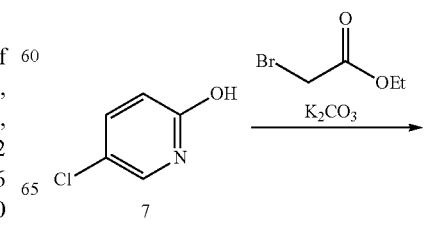

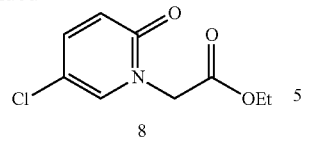

5-chloro-2-hydroxypyridine 7 (4.00 g, 30.9 mmol) was suspended in acetonitrile (61 mL), and added with potassium carbonate (8.53 g, 61.7 mmol) and ethyl bromoacetate (5.14 ml, 46.4 mmol), and the mixture was stirred for 1 hour and 15 minutes with heating at 50° C. The reaction mixture was poured into brine, and extracted with ethyl acetate. The organic layer was washed with brine, dried over anhydrous magnesium sulfate. The solvent was removed under reduced pressure, and the residue was purified using silica gel chromatography to yield the desired ester 8 (6.000 g, yield 90%).

$^1$H-NMR (d$_5$-DMSO) δ ppm: 1.21 (t, 3H, J=7.2 Hz), 4.15 (q, 2H, J=7.2 Hz), 4.66 (s, 2H), 6.47 (d, 1H, J=9.9 Hz), 7.55 (dd, 1H, J=3.0 Hz and 9.9 Hz), 7.98 (d, 1H, J=3.0 Hz).

Step 2

[Chemical Formula 32]

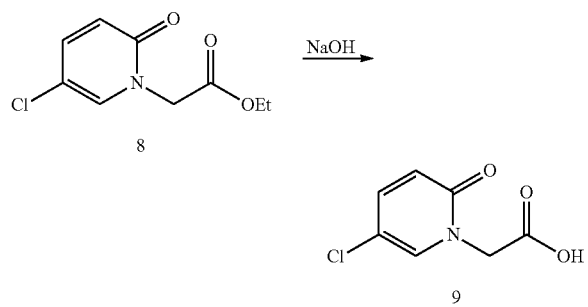

The ester 8 obtained in Step 1 (5.73 g, 24.9 mmol) was dissolved in tetrahydrofuran (18 mL) and methanol (18 mL), and added with 4 N sodium hydroxide (19.94 ml, 80 mmol) and the mixture was stirred for 1 hour and 30 minutes at room temperature. The reaction mixture was concentrated in vacuo, and then poured into water (60 mL), and 6N hydrochloride (14 mL) was added to acidify. The crystals thus precipitated were collected by filtration, washed with water, and dried under reduced pressure to yield the desired pyridone acetic acid 9 (4.667 g, yield 94%).

$^1$H-NMR (d$_6$-DMSO) δ ppm: 4.58 (s, 2H), 6.46 (d, 1H, J=9.9 Hz), 7.53 (dd, 1H, J=3.0 Hz and 9.9 Hz), 7.97 (d, 1H, J=3.0 Hz), 13.13 (brs, 1H).

Step 3

[Chemical Formula 33]

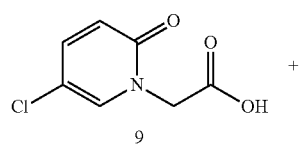

+

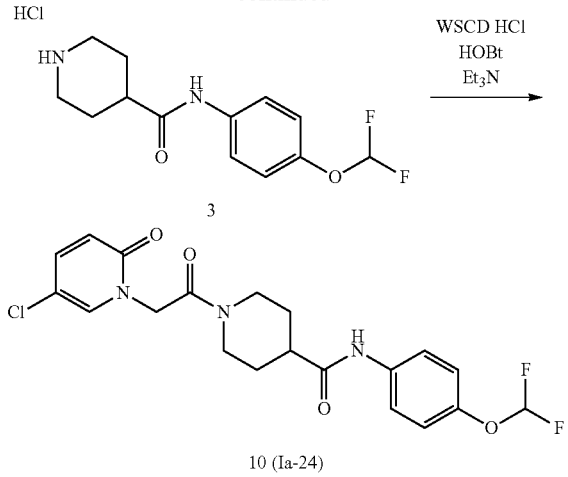

The carboxylic acid 9 obtained in Step 2 (300 mg, 1.599 mmol) and piperidine amine hydrochloride 3 (490 mg, 1.597 mmol) were dissolved in N,N'-dimethylformamide (5 mL), and added with WSCD hydrochloride (337 mg, 1.758 mmol), N-hydroxybenztriazole (43 mg, 0.318 mmol) and triethylamine (0.45 ml, 3.226 mmol), and the mixture was stirred for 24 hours at room temperature. The reaction mixture was poured into diluted hydrochloric acid to acidify, and extracted with ethyl acetate. The organic layer was washed with water, saturated aqueous sodium bicarbonate, and water, and dried over anhydrous magnesium sulfate. The solvent was removed under reduced pressure, and the residue was purified using silica gel chromatography, and recrystallization from ethyl acetate-methanol to yield the desired product 10 (132 mg, yield 19%).

$^1$H-NMR (d$_6$-DMSO) δ ppm: 1.49 (m, 1H), 1.62-1.94 (m, 3H), 2.56-2.76 (m, 2H), 3.14 (m, 1H), 3.97 (m, 1H), 4.34 (m, 1H), 4.81 (dd, 2H, J=15.9 Hz and 21.9 Hz), 6.43 (d, 1H, J=9.9 Hz), 7.13 (d, 2H, J=9.0 Hz), 7.14 (t, 1H, J=74 Hz), 7.51 (dd, 1H, J=9.9 Hz and 3.0 Hz), 7.64 (d, 2H, J=9.0 Hz), 7.88 (d, 1H, J=3.0 Hz), 10.05 (s, 1H).

Example 3

Synthesis of Compound Ia-33

[Chemical Formula 34]

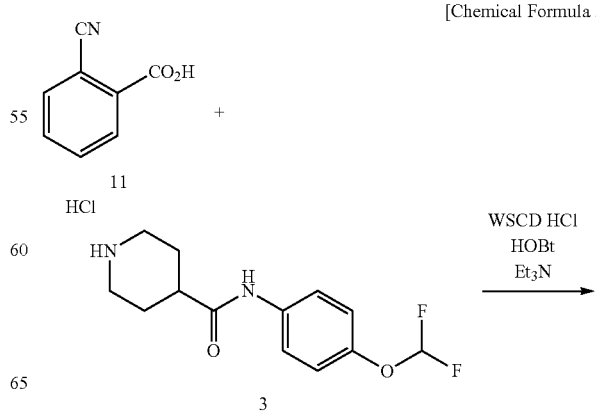

-continued

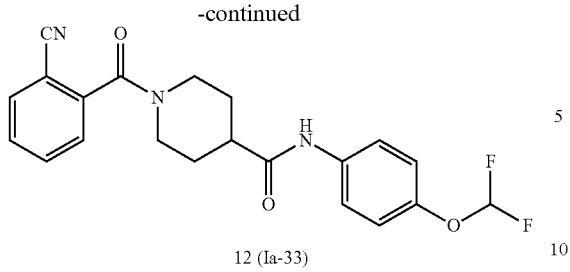

12 (Ia-33)

2-cyanobenzoic acid 11 (1.3 g, 8.97 mmol), piperidine amine hydrochloride 3 (2.5 g, 8.15 mmol) and HOBt (132 mg, 0.98 mmol) were dissolved in DMF (20 ml), and triethylamine (1.2 mL, 8.56 mmol), WSCD hydrochloride (2.0 g, 10.6 mmol) were added. The mixture was stirred at room temperature for 50 minutes. The reaction mixture was poured into water and extracted with ethyl acetate. The organic layer was washed with water and dried over anhydrous magnesium sulfate. The filtrate was concentrated under reduced pressure, and the resultant crude crystals were added with methanol (42 ml) and heated to dissolve. The solution was added with water (42 ml) and stirred at room temperature for 30 min. The crystals thus precipitated were collected by filtration and dried in vacuo to yield the desired product 12 (2.1 g, 64%) as a white solid.

$^1$H-NMR (DMSO-$d_6$) δ ppm: 1.62-1.97 (m, 4H), 2.61-2.68 (m, 1H), 2.94 (t, 1H, J=9.9 Hz), 3.18 (t, 1H, J=11.1 Hz), 3.40 (d, 1H, J=12.9 Hz), 4.56 (d, 1H, J=9.3 Hz), 7.13 (d, 1H, J=75.0 Hz), 7.12 (d, 2H, J=8.4 Hz), 7.38-7.67 (m, 4H), 7.80 (td, 1H, J=7.8, 1.2 Hz), 7.96 (d, 1H, J=7.8, 0.6 Hz), 10.03 (s, 1H).

Example 4

Synthesis of Compound Ia-79

Step 1

[Chemical Formula 35]

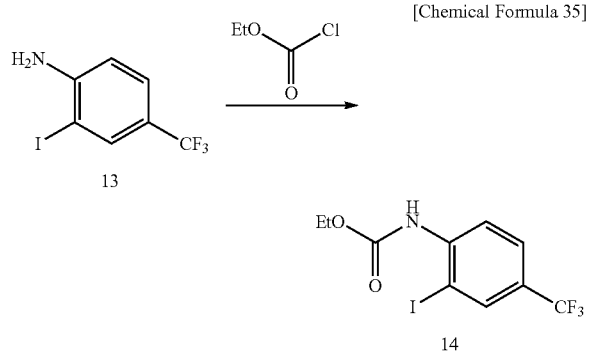

4-amino-3-iodobenzotrifluoride 13 (6.000 g, 20.90 mmol) was added with ethyl chlorocarbonate (10.0 ml, 104.6 mmol), and the mixture was heated to reflux for 1 hour and 30 minutes. Ethyl chlorocarbonate was removed under ambient pressure from the reaction mixture, and the residue was added with n-hexane to crystallize. The crystals thus precipitated was collected by filtration, washed with n-hexane, and dried under reduced pressure to yield the desired ethoxycarbonyl 14 (6.742 g, yield 90%).

$^1$H-NMR ($d_5$-DMSO) δ ppm: 1.26 (t, 3H, J=7.2 Hz), 4.15 (q, 2H, J=7.2 Hz), 7.68 (d, 1H, J=8.7 Hz), 7.75 (dd, 1H, J=2.4 Hz and 6.3 Hz), 8.16 (s, 1H), 9.00 (s, 1H).

Step 2

[Chemical Formula 36]

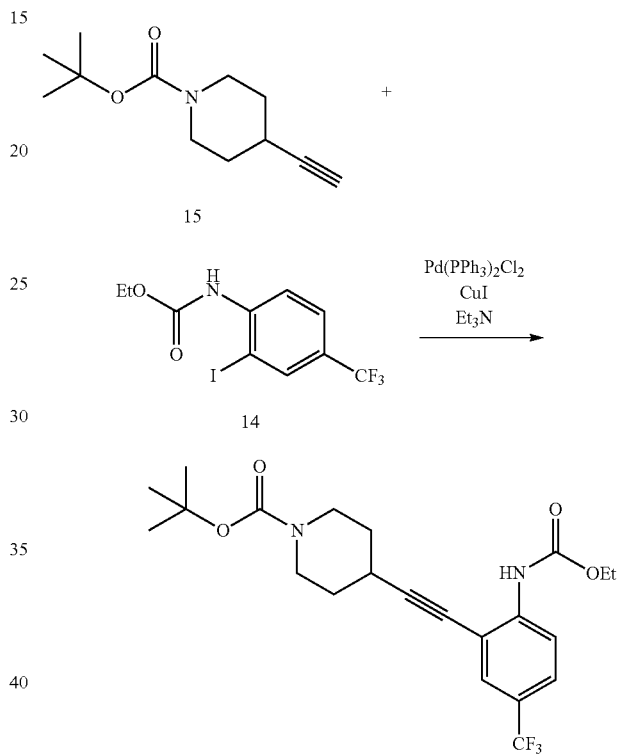

Compound 14 obtained in Step 1 (4.736 g, 13.189 mmol) and 1-t-butyloxycarbonyl-4-ethynylpiperidine 15 (3.036 g, 14.507 mmol) were dissolved in N,N'-dimethylformamide (47 mL), and dichlorobistriphenylphosphine palladium (268 mg, 0.382 mmol), copper iodide (133 mg, 0.698 mmol) and triethylamine (5.52 ml, 39.575 mmol) were added. After degassing, the mixture was stirred for 2 hours and 20 minutes with heating at 80° C. The reaction mixture was poured into saturated aqueous ammonium chloride, and extracted with ethyl acetate. The organic layer was washed with water and brine, and dried over anhydrous magnesium sulfate. The solvent was removed under reduced pressure, and the residue was purified using silica gel chromatography to yield the desired compound 16 (6.010 g) quantitatively.

$^1$H-NMR ($d_6$-DMSO) δ ppm: 1.25 (t, 3H, J=7.2 Hz), 1.40 (s, 9H), 1.42-1.65 (m, 2H), 1.76-1.88 (m, 2H), 2.95 (m, 1H), 3.16-3.28 (m, 2H), 3.55-3.67 (m, 2H), 4.16 (q, 2H, J=7.2 Hz), 7.65-7.75 (m, 2H), 7.91 (d, 2H, J=8.4 Hz), 8.87 (s, 1H).

Step 3

[Chemical Formula 37]

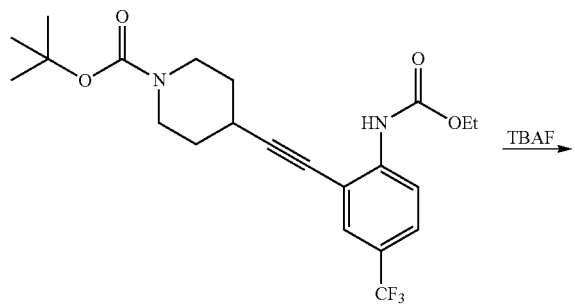

Compound 16 obtained in Step 2 (5.998 g, 13.162 mmol) was dissolved in tetrahydrofuran (60 mL). 1.0 M tetrabutylammoniumfluoride-tetrahydrofuran solution (24.2 ml, 24.2 mmol) was added, and the mixture was heated to reflux for 2 hours. The reaction mixture was poured into water, and extracted with ethyl acetate. The organic layer was washed with brine and dried over anhydrous magnesium sulfate. The solvent was concentrated under reduced pressure, and n-hexane was added to crystallize to yield the desired compound 17 (4.237 g, yield 87%).

$^1$H-NMR (d$_6$-DMSO) δ ppm: 1.42 (s, 9H), 1.46-1.64 (m, 2H), 1.92-2.03 (m, 2H), 2.75-3.02 (m, 3H), 3.98-4.13 (m, 2H), 6.34 (s, 1H), 7.30 (d, 1H, J=8.4 Hz), 7.46 (d, 1H, J=8.4 Hz), 7.81 (s, 1H), 11.44 (s, 1H).

Step 4

[Chemical Formula 38]

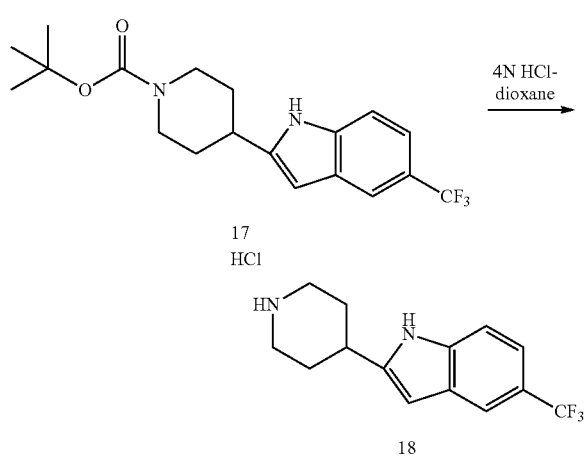

Compound 17 obtained in Step 3 (4.232 g, 11.488 mmol) was added with 4N hydrochloride-dioxane solution (11.5 ml, 46=1) to dissolve, and the solution was stirred for 50 minutes at room temperature. Dioxane was removed from the solution under reduced pressure, and the residue was added with ethyl acetate. The ethyl acetate was removed under reduced pressure, and the residue was dried under reduced pressure to yield the desired piperidine amine hydrochloride 18 (4.053 g) quantitatively.

$^1$H-NMR (d$_5$-DMSO) δ ppm: 1.78-1.95 (m, 2H), 2.17-2.29 (m, 2H), 2.98-3.17 (m, 4H), 3.38 (m, 1H), 6.36 (s, 1H), 7.32 (d, 1H, J=8.4 Hz), 7.50 (d, 1H, J=8.4 Hz), 7.85 (s, 1H), 8.90 (brs, 2H), 11.59 (s, 1H).

Step 5

[Chemical Formula 39]

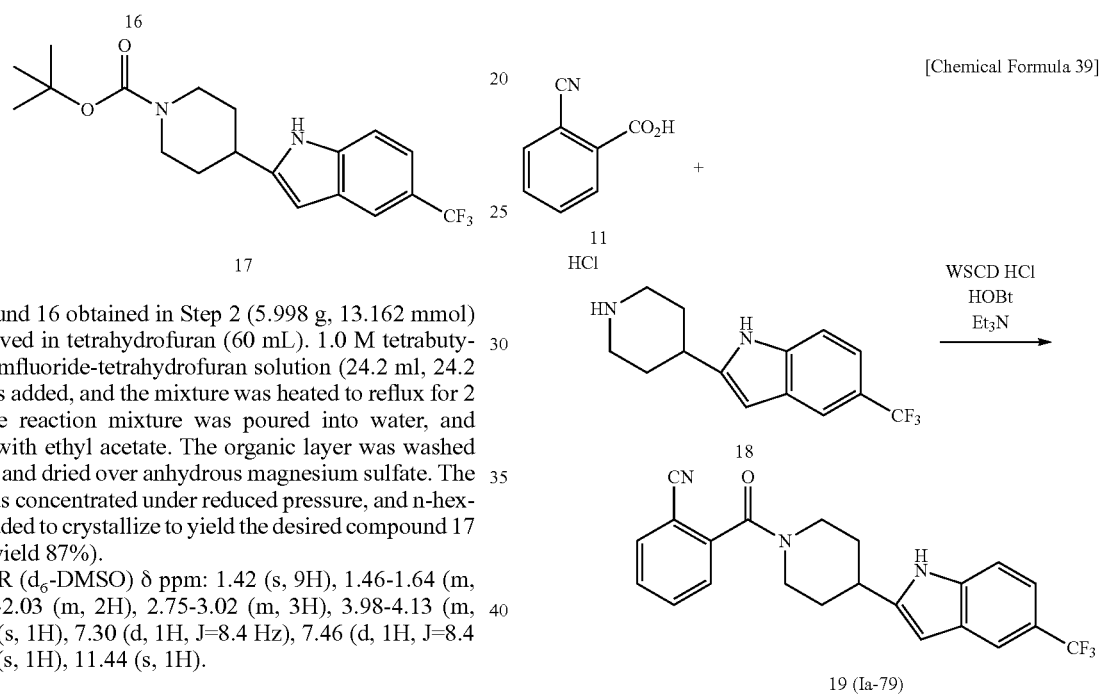

The piperidine amine hydrochloride 18 obtained in Step 4 (343 mg, 0.972 mmol) was added with N,N'-dimethylformamide (5 mL) to dissolve, and 2-cyanobenzoic acid 11 (150 mg, 1.020 mmol), WSCD hydrochloride (242 mg, 1.262 mmol), N-hydroxybenztriazole (26 mg, 0.192 mmol) and triethylamine (0.27 ml, 1.936 mmol) were added. The mixture was stirred for 1 hour and 30 minutes at room temperature. The reaction mixture was poured into diluted hydrochloric acid to acidify, and extracted with ethyl acetate. The organic layer was washed with water, saturated aqueous sodium bicarbonate, and water, and dried over anhydrous magnesium sulfate. The solvent was removed under reduced pressure, and the residue was purified using silica gel chromatography to yield the desired product 19 (242 mg, yield 63%).

$^1$H-NMR (d$_6$-DMSO) δ ppm: 1.59-1.80 (m, 2H), 1.99 (m, 1H), 2.18 (m, 1H), 2.98-3.20 (m, 2H), 3.22-3.50 (m, 2H), 4.64 (m, 1H), 6.36 (s, 1H), 7.31 (d, 1H, J=8.4 Hz), 7.48 (d, 1H, J=8.4 Hz), 7.62 (d, 1H, J=7.8 Hz), 7.67 (d, 1H, J=7.8 Hz), 7.78-7.86 (m, 2H), 7.97 (d, 1H, J=7.8 Hz), 11.48 (s, 1H).

The following compounds were synthesized in similar manner as described above. The structural formula and Physical properties of these compounds are as follows.

Compound Ia-2

[Chemical Formula 40]

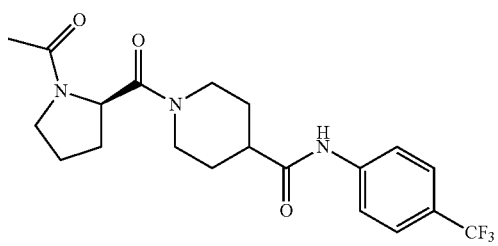

$^1$H-NMR (DMSO-d$_6$) δ: 1.35-1.98 (m, 11H), 2.00-2.35 (m, 1H), 2.48-2.71 (m, 2H), 3.10 (m, 1H), 3.51 (m, 1H), 4.04 (m, 1H), 4.38 (m, 1H), 4.71-4.98 (m, 1H), 7.66 (d, 2H, J=8.0 Hz), 7.82 (d, 2H, J=8.0 Hz), 10.03 (s, 1H).

Compound Ia-3

[Chemical Formula 41]

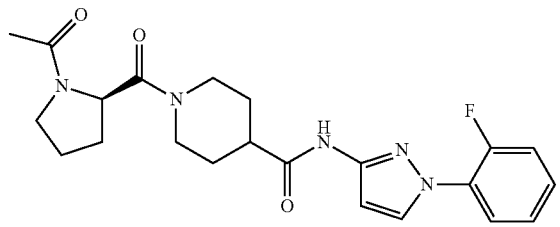

$^1$H-NMR (DMSO-d$_6$) δ: 1.31-2.01 (m, 11H), 2.01-2.39 (m, 1H), 2.50-2.68 (m, 2H), 3.08 (m, 1H), 3.54 (m, 1H), 4.02 (m, 1H), 4.35 (m, 1H), 4.70-4.99 (m, 1H), 6.82 (s, 1H), 7.26-7.52 (m, 3H), 7.73 (m, 1H), 8.01 (s, 1H), 10.08 (s, 1H).

[Chemical Formula 42]

Compound Ia-4

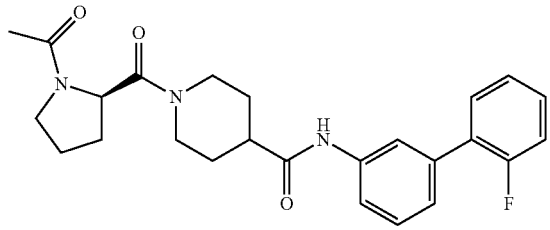

$^1$H-NMR (DMSO-d$_6$) δ: 1.35-2.00 (m, 11H), 2.00-2.35 (m, 1H), 2.52-2.80 (m, 2H), 3.10 (m, 1H), 3.51 (m, 1H), 4.04 (m, 1H), 4.35 (m, 1H), 4.72-4.98 (m, 1H), 7.21 (d, 1H, J=8.0 Hz), 7.22-7.35 (m, 2H), 7.35-7.55 (m, 3H), 7.63 (m, 1H), 7.85 (s, 1H), 10.07 (s, 1H).

Compound Ia-5

[Chemical Formula 43]

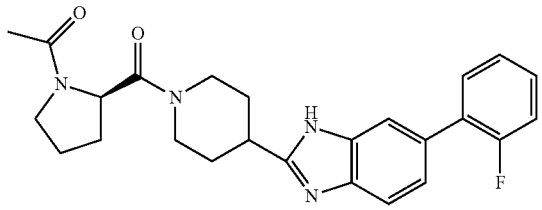

$^1$H-NMR (CD$_3$OD) δ: 1.74-2.38 (m, 7H), 2.11 (s, 3H), 2.92 (m, 1H), 3.55-3.72 (m, 2H), 4.21 (m, 1H), 4.61 (m, 1H), 4.97 (m, 1H), 7.13-7.28 (m, 2H), 7.33 (m, 1H), 7.40 (d, 1H, J=8.4 Hz), 7.50 (m, 1H), 7.51 (m, 1H), 7.67 (m, 1H).

Compound Ia-6

[Chemical Formula 44]

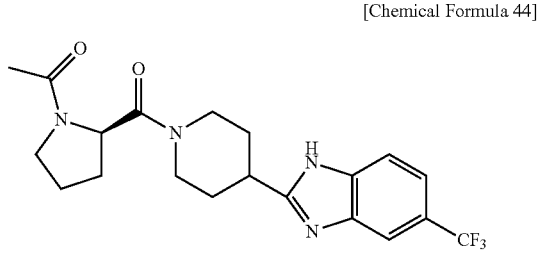

$^1$H-NMR (DMSO-d$_6$) δ: 1.54-2.37 (m, 6H), 1.95 (s, 3H), 2.81 (m, 1H), 3.14-3.45 (m, 5H), 3.52 (t, 1H, J=6.6 Hz), 4.19 (m, 1H), 4.37 (m, 1H), 4.81 (m, 0.6H), 4.96 (m, 0.4H), 7.46 (d, 1H, J=8.7 Hz), 7.68 (d, 1H, J=8.7 Hz), 7.85 (s, 1H), 12.68 (brs, 1H).

Compound Ia-7

[Chemical Formula 45]

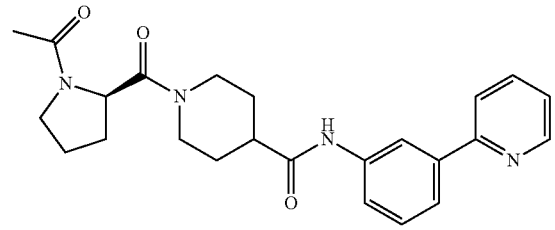

$^1$H-NMR (DMSO-d$_6$) δ: 1.35-2.01 (m, 11H), 2.01-2.40 (m, 1H), 2.55-2.72 (m, 2H), 3.13 (m, 1H), 3.50 (m, 1H), 4.03 (m, 1H), 4.39 (m, 1H), 4.72-4.98 (m, 1H), 7.39-7.49 (m, 2H), 7.62-7.79 (m, 2H), 7.82-7.95 (m, 2H), 8.37 (s, 1H), 8.65 (s, 1H), 10.09 (s, 1H).

Compound Ia-8

[Chemical Formula 46]

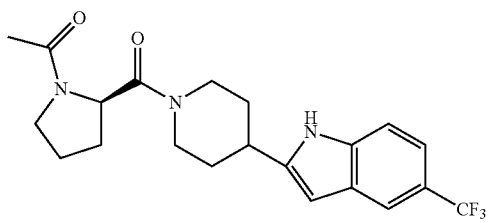

¹H-NMR (DMSO-d₆) δ: 1.44-2.40 (m, 7H), 1.96 (s, 3H), 2.78 (m, 1H), 2.98-3.45 (m, 4H), 3.52 (t, 1H, J=6.6 Hz), 4.09 (m, 1H), 4.46 (m, 1H), 4.82 (m, 0.6H), 4.96 (m, 0.4H), 6.34 (s, 1H), 7.31 (d, 1H, J=8.7 Hz), 7.47 (d, 1H, J=8.7 Hz), 7.82 (s, 1H), 11.46 (s, 1H).

Compound Ia-9

[Chemical Formula 47]

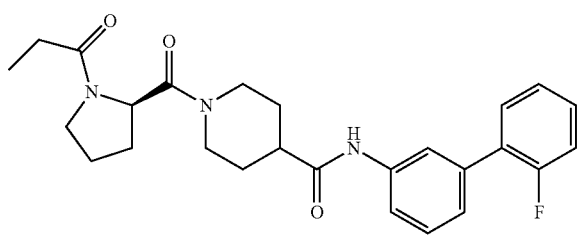

¹H-NMR (DMSO-d₆) δ: 0.88-1.02 (m, 3H), 1.35-2.00 (m, 8H), 2.01-2.35 (m, 3H), 2.55-2.72 (m, 2H), 3.10 (m, 1H), 3.49 (m, 1H), 4.05 (m, 1H), 4.36 (m, 1H), 4.72-4.98 (m, 1H), 7.21 (d, 1H, J=8.0 Hz), 7.24-7.36 (m, 2H), 7.36-7.52 (m, 3H), 7.63 (m, 1H), 7.85 (s, 1H), 10.07 (s, 1H).

Compound Ia-10

[Chemical Formula 48]

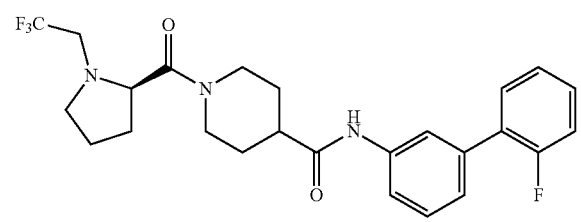

¹H-NMR (DMSO-d₆) δ: 1.42-1.82 (m, 6H), 2.08-2.15 (m, 2H), 2.61 (t, 2H, J=11.7 Hz), 2.80-2.89 (m, 1H), 3.02-3.07 (m, 1H), 3.35-3.43 (m, 2H), 3.99-4.02 (m, 2H), 4.41 (d, 1H, J=13.2 Hz), 7.20 (d, 1H, J=6.6 Hz), 7.28-7.51 (m, 5H), 7.63 (d, 1H, J=9.3 Hz), 7.85 (s, 1H), 10.06 (s, 1H).

Compound Ia-11

[Chemical Formula 49]

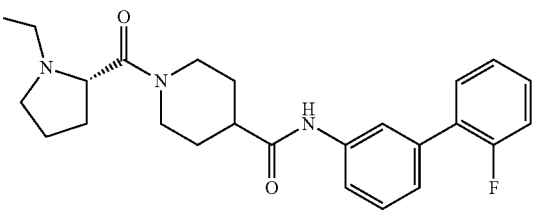

¹H-NMR (DMSO-d₆) δ: 1.82-1.99 (m, 7H), 2.17-2.27 (m, 1H), 2.47-2.50 (m, 1H), 2.72 (brs, 1H), 2.88-2.96 (m, 1H), 3.07-3.37 (m, 4H), 3.86 (brs, 2H), 4.09 (t, 1H, J=14.7 Hz), 4.60 (d, 1H, J=13.6 Hz), 7.11-7.22 (m, 2H), 7.28-7.34 (m, 2H), 7.40-7.46 (m, 3H), 7.56 (d, 1H, J=7.45 Hz), 7.69 (s, 1H).

[Chemical Formula 50]

Compound Ia-12

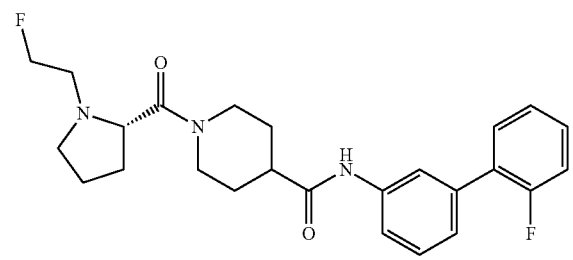

¹H-NMR (DMSO-d₆) δ: 1.28-1.62 (m, 6H), 1.76-1.79 (m, 1H), 2.16-2.85 (m, 9H), 3.25-3.32 (m, 1H), 3.94-4.18 (m, 1H), 4.18 (brs, 2H), 4.34 (brs, 1H), 6.97 (d, 1H, J=8.1 Hz), 7.05-7.11 (m, 2H), 7.19-7.28 (m, 3H), 7.39 (d, 1H, J=7.8 Hz), 7.62 (s, 1H), 9.82 (s, 1H).

Compound Ia-13

[Chemical Formula 51]

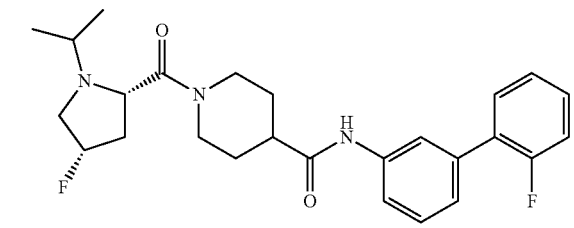

¹H-NMR (DMSO-d₆) δ: 090-1.09 (m, 6H), 1.38-1.67 (m, 2H), 1.76-1.96 (m, 2H), 2.52-2.60 (m, 2H), 2.78 (m, 1H), 3.02 (m, 1H), 3.15 (m, 1H), 3.56 (m, 1H), 4.43 (m, 1H), 4.54-4.72 (m, 1H), 5.10-5.24 (m, 1H), 7.21 (d, 1H, J=7.6 Hz), 7.29 (d, 1H, J=7.6 Hz), 7.32 (m, 1H), 7.40 (dd, 1H, J=7.6, 7.6 Hz), 7.42 (m, 1H), 7.49 (dd, 1H, J=7.6, 7.6 Hz), 7.62 (d, 1H, J=7.6 Hz), 7.86 (s, 1H), 10.05 (s, 1H).

Compound Ia-14

[Chemical Formula 52]

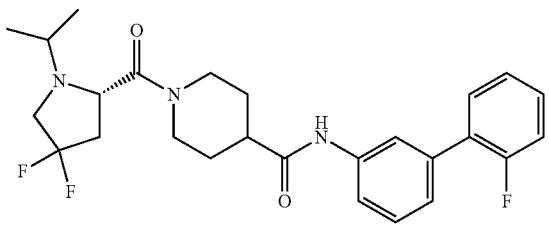

¹H-NMR (DMSO-d₆) δ: 090-1.03 (m, 6H), 1.349-1.54 (m, 2H), 1.80-1.90 (m, 2H), 2.20 (m, 1H), 2.57-2.71 (m, 3H), 2.89-3.13 (m, 3H), 4.04-4.47 (m, 3H), 7.21 (d, 1H, J=8.0 Hz), 7.30 (dd, 1H, J=8.0, 8.0 Hz), 7.32 (m, 1H), 7.40 (dd, 1H, J=8.0, 8.0 Hz), 7.43 (m, 1H), 7.50 (dd, 1H, J=8.0, 8.0 Hz), 7.62 (d, 1H, J=8.0 Hz), 7.85 (s, 1H), 10.05 (s, 1H).

Compound Ia-15

[Chemical Formula 53]

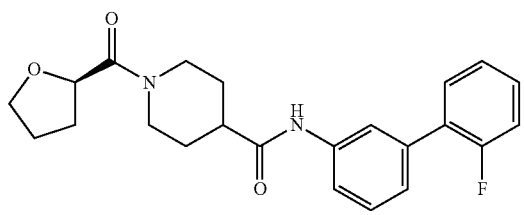

¹H-NMR (DMSO-d₆) δ: 1.44-1.63 (m, 2H), 1.80-1.85 (m, 3H), 1.99-2.06 (m, 2H), 2.58-2.73 (m, 2H), 3.00-3.13 (m, 2H), 3.73-3.80 (m, 2H), 4.07 (d, 1H, J=12.6 Hz), 4.38 (d, 1H, J=11.1 Hz), 4.67 (t, 1H, J=6.9 Hz), 7.21 (d, 1H, J=7.5 Hz), 7.28-7.34 (m, 2H), 7.43-7.51 (m, 3H), 7.63 (d, 1H, J=7.8 Hz), 7.84 (s, 1H), 10.05 (s, 1H).

Compound Ia-16

[Chemical Formula 54]

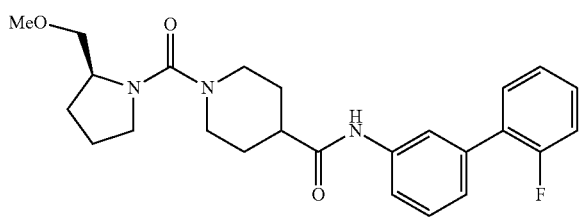

¹H-NMR (DMSO-d₆) δ: 1.50 (m, 1H), 1.53-1.87 (m, 6H), 1.96 (m, 1H), 2.53 (m, 1H), 2.67 (m, 1H), 2.78 (m, 1H), 3.15 (m, 1H), 3.24 (s, 1H), 3.20-3.50 (m, 3H), 3.63-3.77 (m, 2H), 4.05 (m, 1H), 7.20 (m, 1H), 7.26-7.36 (m, 2H), 7.36-7.53 (m, 3H), 7.63 (d, 1H, J=8.0 Hz), 7.85 (s, 1H), 10.08 (s, 1H).

Compound Ia-17

[Chemical Formula 55]

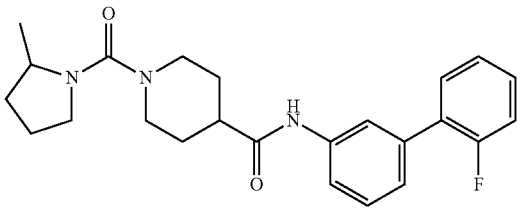

¹H-NMR (DMSO-d₆) δ: 1.08 (d, 3H, J=6.0 Hz), 1.36 (m, 1H), 1.50 (m, 1H), 1.56-1.71 (m, 2H), 1.71-1.84 (m, 2H), 2.02 (m, 1H), 2.67 (m, 1H), 2.76 (m, 1H), 3.20-3.42 (m, 2H), 3.60-3.80 (m, 2H), 4.04 (m, 1H), 7.20 (d, 1H, J=7.2 Hz), 7.30 (d, 1H, J=8.0 Hz), 7.32 (m, 2H), 7.40 (m, 1H), 7.63 (m, 1H), 7.85 (s, 1H), 10.02 (s, 1H).

Compound Ia-18

[Chemical Formula 56]

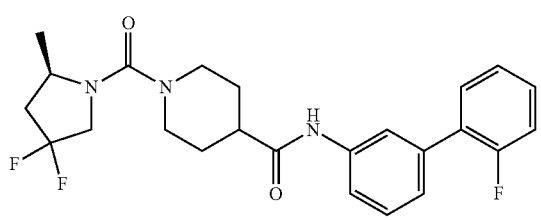

¹H-NMR (DMSO-d₆) δ: 1.07-1.20 (m, 3H), 1.51 (m, 1H), 1.56-1.87 (m, 4H), 2.05 (m, 1H), 2.73 (m, 1H), 2.83 (m, 1H), 3.48-3.61 (m, 2H), 3.61-3.80 (m, 2H), 3.90 (m, 1H), 4.15 (m, 1H), 7.20 (m, 1H), 7.26-7.35 (m, 2H), 7.35-7.45 (m, 2H), 7.49 (m, 1H), 7.63 (d, 1H, J=8.0 Hz), 7.84 (s, 1H), 10.03 (s, 1H).

Compound Ia-19

[Chemical Formula 57]

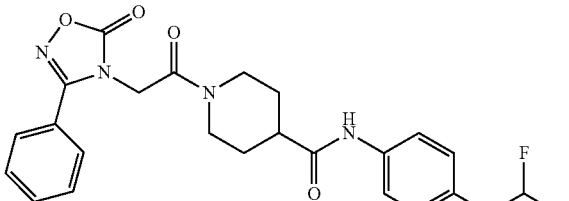

¹H-NMR (DMSO-d₆) δ: 1.30-1.38 (1H, m), 1.48-1.56 (1H, m), 1.76-1.80 (2H, m), 2.55-2.58 (1H, m), 2.63-2.72 (1H, m), 3.02-3.10 (1H, m), 3.82-3.86 (1H, m), 4.22-4.27 (1H, m), 4.68 (2H, dd, J=35.8, 17.4 Hz), 7.12 (2H, d, J=9.2 Hz), 7.13 (1H, t, J=74.6 Hz), 7.60-7.68 (7H, m), 10.00 (1H, s).

Compound Ia-20

[Chemical Formula 58]

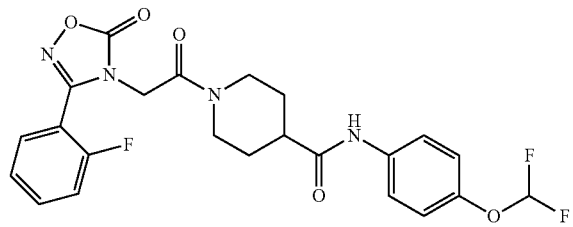

¹H-NMR (DMSO-d$_6$) δ: 1.26-1.34 (1H, m), 1.42-1.51 (1H, m), 1.72-1.77 (2H, m), 2.54-2.58 (1H, m), 2.60-2.68 (1H, m), 2.98-3.06 (1H, m), 3.78-3.82 (1H, m), 4.19-4.24 (1H, m), 4.59 (2H, dd, J=31.7, 17.5 Hz), 7.10-7.14 (2H, m), 7.12 (1H, t, J=74.7 Hz), 7.41-7.53 (2H, m), 7.58-7.62 (3H, m), 7.71-7.78 (1H, m), 9.98 (1H, s).

Compound Ia-21

[Chemical Formula 59]

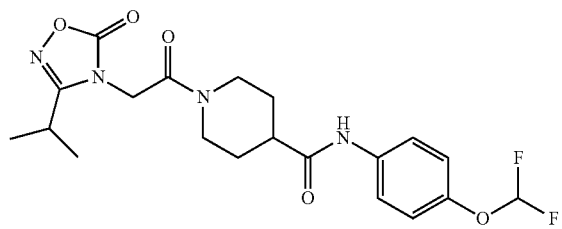

¹H-NMR (DMSO-d$_6$) δ: 1.17-1.21 (6H, m), 1.42-1.52 (1H, m), 1.66-1.76 (1H, m), 1.81-1.88 (2H, m), 2.57-2.65 (1H, m), 2.69-2.77 (1H, m), 2.80-2.89 (1H, m), 3.10-3.18 (1H, m), 3.89-3.93 (1H, m), 4.31-4.35 (1H, m), 4.65 (2H, dd, J=41.3, 17.6 Hz), 7.11-7.14 (2H, m), 7.13 (1H, t, J=74.7 Hz), 7.62-7.65 (2H, m), 10.03 (1H, s).

[Chemical Formula 60]

Compound Ia-22

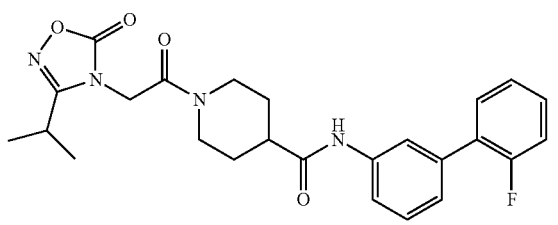

¹H-NMR (DMSO-d$_6$) δ: 1.18-1.21 (6H, m), 1.45-1.53 (1H, m), 1.68-1.76 (1H, m), 1.84-1.90 (2H, m), 2.65-2.76 (2H, m), 2.81-2.90 (1H, m), 3.12-3.19 (1H, m), 3.91-3.95 (1H, m), 4.32-4.36 (1H, m), 4.66 (2H, dd, J=42.7, 17.4 Hz), 7.22 (1H, d, J=7.7 Hz), 7.29-7.34 (2H, m), 7.41-7.49 (3H, m), 7.64 (1H, d, J=7.7 Hz), 7.86 (1H, s), 10.07 (1H, s).

Compound Ia-23

[Chemical Formula 61]

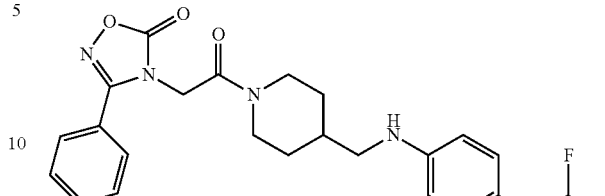

¹H-NMR (DMSO-d$_6$) δ: 0.84-0.88 (2H, m), 1.69-1.77 (3H, m), 2.54-2.58 (1H, m), 2.83-2.87 (2H, m), 2.92-3.00 (1H, m), 3.74-3.81 (1H, m), 4.16-4.23 (1H, m), 4.63 (2H, dd, J=26.9, 16.8 Hz), 6.59 (2H, d, J=8.9 Hz), 6.92 (2H, d, J=8.9 Hz), 6.93 (1H, s), 7.59-7.66 (5H, m).

Compound Ia-25

[Chemical Formula 62]

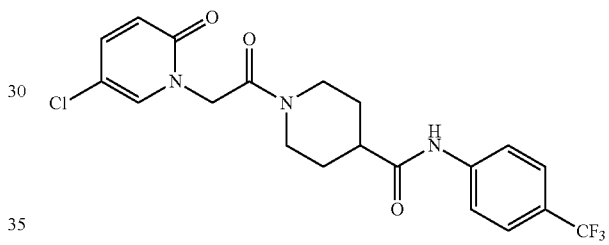

¹H-NMR (DMSO-d$_6$) δ: 1.52 (m, 1H), 1.73 (m, 1H), 1.80-1.96 (m, 2H), 2.58-2.78 (m, 2H), 3.15 (m, 1H), 3.97 (m, 1H), 4.35 (m, 1H), 4.82 (dd, 2H, J=15.9 Hz and 21.9 Hz), 6.43 (d, 1H, J=9.6 Hz), 7.51 (dd, 1H, J=2.7 Hz and 9.6 Hz), 7.67 (d, 2H, J=8.7 Hz), 7.83 (d, 2H, J=8.7 Hz), 7.88 (d, 1H, J=2.7 Hz), 10.34 (s, 1H).

[Chemical Formula 63]

Compound Ia-26

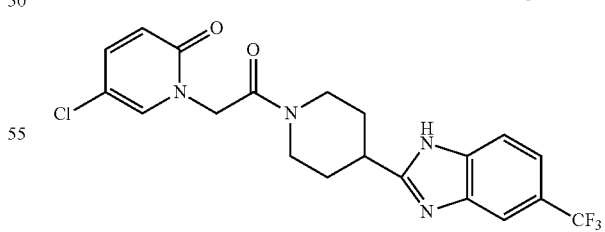

¹H-NMR (DMSO-d$_6$) δ: 1.72 (m, 1H), 1.93 (m, 1H), 2.02-2.18 (m, 2H), 2.91 (m, 1H), 3.16-3.40 (m, 2H), 4.01 (m, 1H), 4.34 (m, 1H), 4.84 (s, 2H), 6.44 (d, 1H, J=9.9 Hz), 7.47 (d, 1H, J=10.2 Hz), 7.51 (dd, 1H, J=.2.4 Hz and 9.9 Hz), 7.68 (d, 1H, J=8.1 Hz), 7.72-7.91 (m, 2H), 12.72 (brs, 1H).

[Chemical Formula 64]

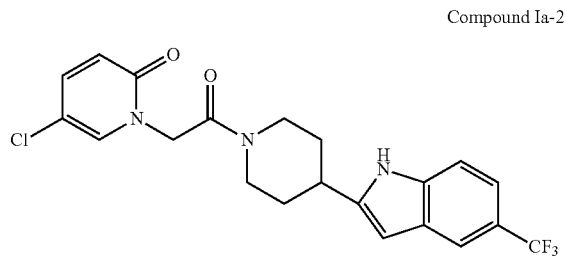

Compound Ia-27

$^1$H-NMR (DMSO-d$_6$) δ: 1.58 (m, 1H), 1.76 (m, 1H), 2.00-2.16 (m, 2H), 2.81 (m, 1H), 3.08 (m, 1H), 3.26 (m, 1H), 4.02 (m, 1H), 4.41 (m, 1H), 4.84 (s, 2H), 6.36 (s, 1H), 6.44 (d, 1H, J=9.6 Hz), 7.31 (d, 1H, J=9.3 Hz), 7.46-7.54 (m, 2H), 7.84 (d, 1H, J=7.5 Hz), 7.86 (d, 1H, J=2.7 Hz), 11.48 (s, 1H).

[Chemical Formula 65]

Compound Ia-28

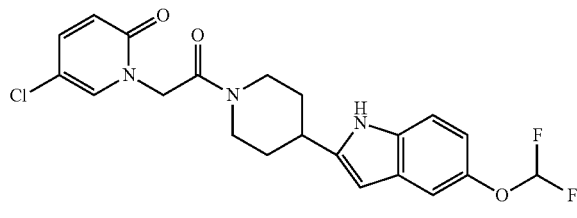

$^1$H-NMR (DMSO-d$_6$) δ: 1.46-1.80 (m, 2H), 1.97-2.13 (m, 2H), 2.79 (m, 1H), 3.03 (m, 1H), 3.24 (m, 1H), 4.01 (m, 1H), 4.39 (m, 1H), 4.83 (s, 2H), 6.19 (s, 1H), 6.43 (d, 1H, J=9.6 Hz), 6.84 (dd, 1H, J=8.7, 2.4 Hz), 7.04 (t, 1H, J=75.3 Hz), 7.22 (d, 1H, J=2.4 Hz), 7.29 (d, 1H, J=8.7 Hz), 7.50 (dd, 1H, J=9.6, 3.0 Hz), 7.85 (d, 1H, J=3.0 Hz), 11.13 (s, 1H).

[Chemical Formula 66]

Compound Ia-29

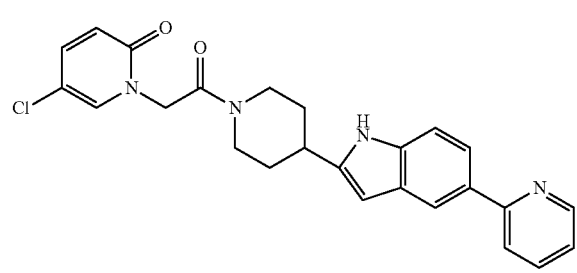

$^1$H-NMR (DMSO-d$_6$) δ: 1.48-1.83 (m, 2H), 2.01-2.17 (m, 2H), 2.81 (m, 1H), 3.05 (m, 1H), 3.28 (m, 1H), 4.02 (m, 1H), 4.41 (m, 1H), 4.84 (s, 2H), 6.26 (s, 1H), 6.43 (d, 1H, J=9.9 Hz), 7.23 (ddd, 1H, J=7.8, 4.8, 0.9 Hz), 7.36 (d, 1H, J=8.7 Hz), 7.45 (dd, 1H, J=9.9, 3.0 Hz), 7.77-7.91 (m, 4H), 8.18 (d, 1H, J=1.2 Hz), 8.59 (ddd, 1H, J=4.8, 1.8, 0.9 Hz), 11.12 (s, 1H).

[Chemical Formula 67]

Compound Ia-30

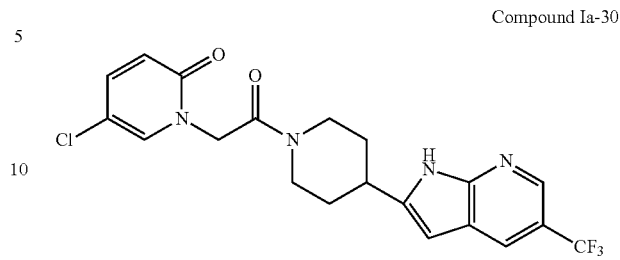

$^1$H-NMR (DMSO-d$_6$) δ: 1.59 (m, 1H), 1.74 (m, 1H), 2.02-2.20 (m, 2H), 2.80 (m, 1H), 3.10 (m, 1H), 3.26 (m, 1H), 4.03 (m, 1H), 4.42 (m, 1H), 4.84 (s, 2H), 6.38 (s, 1H), 6.44 (d, 1H, J=9.6 Hz), 7.51 (dd, 1H, J=3.0 Hz and 9.6 Hz), 7.86 (d, 1H, J=3.0 Hz), 8.25 (d, 1H, J=2.1 Hz), 8.47 (d, 1H, J=1.5 Hz), 12.13 (s, 1H).

[Chemical Formula 68]

Compound Ia-31

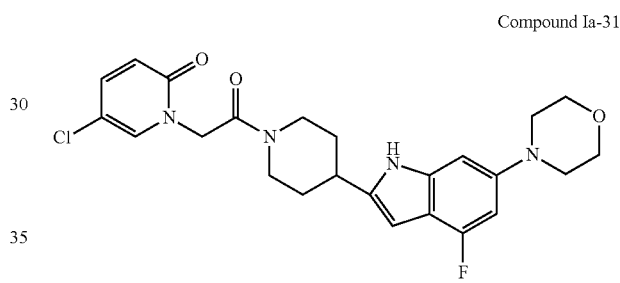

$^1$H-NMR (DMSO-d$_6$) δ: 1.54 (m, 1H), 1.73 (m, 1H), 1.96-2.14 (m, 2H), 2.79 (m, 1H), 2.98 (m, 1H), 3.00-3.10 (m, 4H), 3.23 (m, 1H), 3.71-3.80 (m, 4H), 4.02 (m, 1H), 4.39 (m, 1H), 4.83 (s, 2H), 6.07 (s, 1H), 6.44 (d, 1H, J=9.6 Hz), 6.51-6.60 (m, 2H), 7.51 (dd, 1H, J=3.0 Hz and 9.6 Hz), 7.86 (d, 1H, J=3.0 Hz), 10.99 (s, 1H).

[Chemical Formula 69]

Compound Ia-32

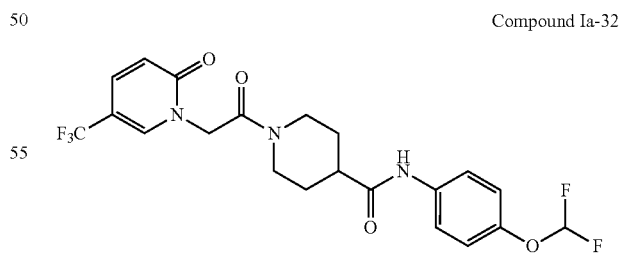

$^1$H-NMR (DMSO-d$_6$) δ: 1.51 (m, 1H), 1.64-1.94 (m, 3H), 2.56-2.78 (m, 2H), 3.15 (m, 1H), 3.97 (m, 1H), 4.34 (m, 1H), 4.92 (dd, 2H, J=15 Hz and 22 Hz), 6.55 (d, 1H, J=9.6 Hz), 7.13 (d, 2H, J=9.0 Hz), 7.14 (t, 1H, J=74 Hz), 7.64 (d, 2H, J=9.0 Hz), 7.70 (dd, 1H, J=2.7 Hz and 9.6 Hz), 8.31 (s, 1H), 10.06 (s, 1H).

[Chemical Formula 70]

Compound Ia-34

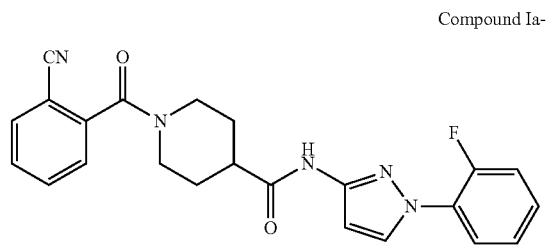

¹H-NMR (DMSO-d₆) δ: 1.68-1.76 (m, 3H), 2.72-2.74 (m, 2H), 2.92-2.96 (m, 2H), 3.12-3.16 (m, 1H), 4.54-4.58 (m, 1H), 6.85 (d, 1H, J=2.7 Hz), 7.36-7.85 (m, 7H), 7.98 (d, 1H, J=7.6 Hz), 8.12 (t, 1H, J=2.6 Hz), 10.81 (s, 1H).

[Chemical Formula 71]

Compound Ia-35

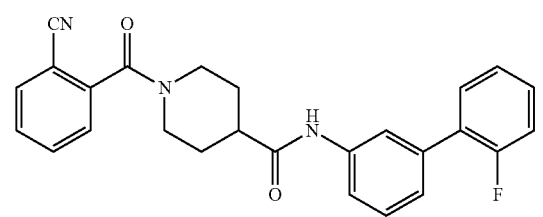

¹H-NMR (DMSO-d₆) δ: 1.63-1.83 (m, 3H), 1.99-2.06 (m, 1H), 2.68-2.72 (m, 1H), 2.95-2.99 (m, 1H), 3.15-3.19 (m, 1H), 3.41-3.45 (m, 1H), 4.56-4.61 (m, 1H), 7.34-7.43 (m, 6H), 7.59-7.70 (m, 3H), 7.82-7.85 (m, 2H), 7.98 (d, 1H, J=7.7 Hz), 10.10 (s, 1H).

[Chemical Formula 72]

Compound Ia-36

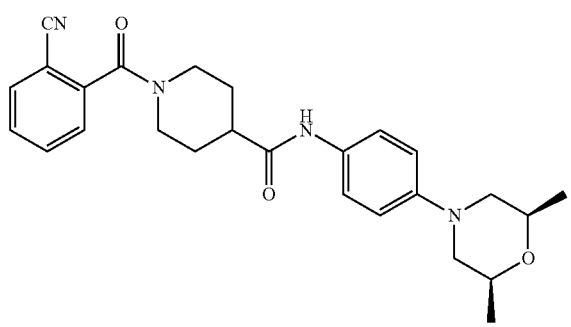

¹H-NMR (DMSO-d₆) δ: 1.16 (d, 6H, J=6.2 Hz), 1.60-1.78 (m, 4H), 1.93-1.97 (m, 1H), 2.20 (t, 2H, J=11.1 Hz), 2.58-2.61 (m, 1H), 2.93-2.97 (m, 1H), 3.13-3.17 (m, 1H), 3.49-3.53 (m, 2H), 3.69-3.71 (m, 2H), 4.55-4.60 (m, 1H), 6.90 (d, 2H, J=8.9 Hz), 7.46 (d, 2H, J=8.7 Hz), 7.59-7.69 (m, 2H), 7.82 (t, 1H, J=7.6 Hz), 7.98 (d, 1H, J=7.9 Hz), 9.74 (s, 1H).

[Chemical Formula 73]

Compound Ia-37

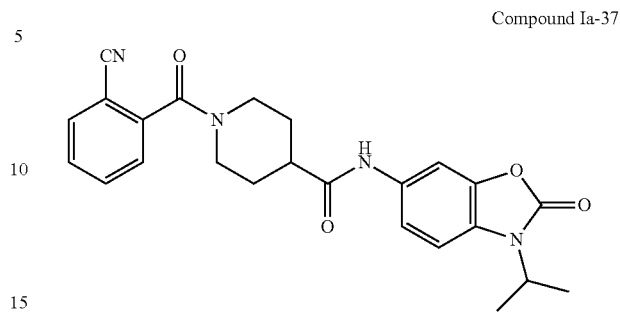

¹H-NMR (DMSO-d₆) δ: 1.46 (d, 6H, J=7.1 Hz), 1.67-1.80 (m, 3H), 1.96-2.01 (m, 1H), 2.65-2.68 (m, 1H), 2.95-2.98 (m, 1H), 3.16-3.20 (m, 1H), 3.40-3.45 (m, 1H), 4.46-4.48 (m, 1H), 4.56-4.60 (m, 1H), 7.31-7.37 (m, 2H), 7.59-7.70 (m, 2H), 7.76-7.85 (m, 2H), 7.98 (d, 1H, J=7.7 Hz), 10.08 (s, 1H)

[Chemical Formula 74]

Compound Ia-38

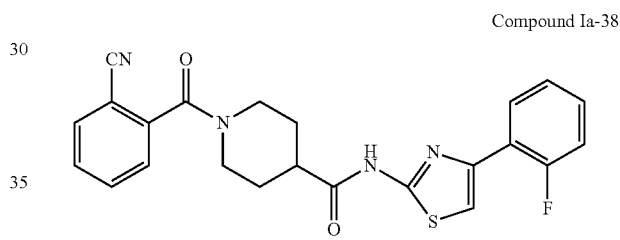

¹H-NMR (DMSO-d₆) δ: 1.61-1.68 (m, 2H), 1.77 (d, 1H, J=12.8 Hz), 1.94-1.99 (m, 1H), 2.62-2.68 (m, 1H), 2.94 (t, 1H, J=11.6 Hz), 3.14 (t, 1H, J=12.0 Hz), 3.41 (d, 1H, J=12.8 Hz), 4.56 (d, 1H, J=7.6 Hz), 7.12 (d, 2H, J=6.8 Hz), 7.13 (d, 1H, J=32.4 Hz), 7.58 (d, 1H, J=7.6 Hz), 7.62-7.66 (m, 3H), 7.80 (t, 1H, J=8.0 Hz), 7.96 (d, 1H, J=7.6 Hz), 10.03 (s, 1H).

Compound Ia-39

[Chemical Formula 75]

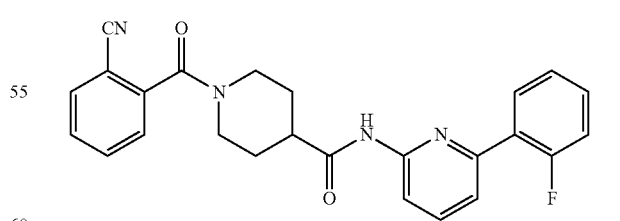

¹H-NMR (CDCl₃) δ: 1.88-2.07 (m, 4H), 2.56 (brs, 1H), 3.02-3.10 (m, 1H), 3.21 (brs, 1H), 3.58 (d, 1H, J=10.8 Hz), 4.73 (d, 1H, J=12.0 Hz), 7.13-7.20 (m, 1H), 7.38-7.40 (m, 1H), 7.48-7.55 (m, 3H), 7.65-7.87 (m, 4H), 8.16 (brs, 2H).

[Chemical Formula 76]

Compound Ia-40

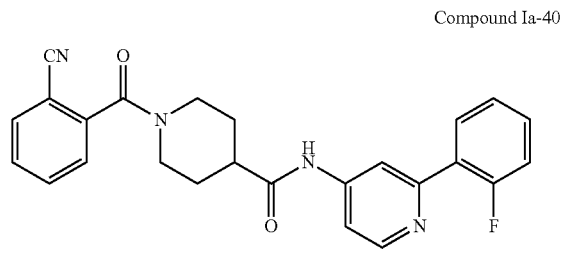

¹H-NMR (CDCl₃) δ: 1.87 (brs, 5H), 2.62 (brs, 1H), 3.00 (brs, 1H), 3.16-3.59 (m, 1H), 3.57 (d, 1H, J=12.0 Hz), 4.70 (d, 1H, J=12.6 Hz), 7.14 (dd, 1H, J=11.1, 7.8 Hz), 7.23 (d, 1H, J=7.8 Hz), 7.34-7.40 (m, 1H), 7.44-7.54 (m, 3H), 7.62-7.73 (m, 3H), 7.81 (s, 1H), 7.92 (t, 1H, J=6.0 Hz), 8.58 (d, 1H, J=5.7 Hz).

[Chemical Formula 77]

Compound Ia-41

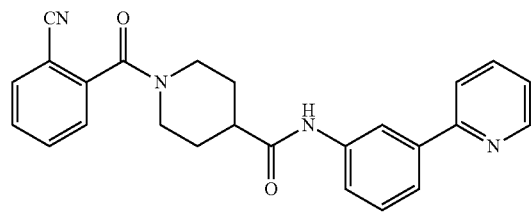

¹H-NMR (DMSO-d₆) δ: 1.62-1.82 (m, 3H), 1.96 (brs, 1H), 2.65-2.73 (m, 1H), 2.92-3.00 (m, 1H), 3.15 (t, 1H, J=11.4 Hz), 3.38-3.43 (m, 1H), 4.56 (d, J=13.2 Hz), 7.35-7.43 (m, 2H), 7.57-7.73 (m, 4H), 7.80 (t, 1H, J=7.5 Hz), 7.88-7.89 (m, 2H), 7.96 (d, 1H, J=7.5 Hz), 8.38 (s, 1H), 8.66 (d, 1H, J=4.8 Hz), 10.09 (s, 1H).

[Chemical Formula 78]

Compound Ia-42

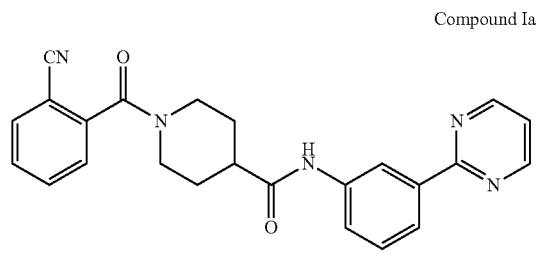

¹H-NMR (CDCl₃) δ: 1.83-2.04 (m, 3H), 2.04-2.17 (m, 1H), 2.59 (m, 1H), 3.07 (m, 1H), 3.22 (m, 1H), 3.59 (brd, 1H, J=13.5 Hz), 4.75 (brd, 1H, J=14.0 Hz), 7.20 (t, 1H, J=4.9 Hz), 7.42-7.55 (m, 3H), 7.59 (brs, 1H), 7.63-7.75 (m, 2H), 7.86 (m, 1H), 8.19 (m, 1H), 8.42 (m, 1H), 8.80 (d, 2H, J=4.9 Hz).

[Chemical Formula 79]

Compound Ia-43

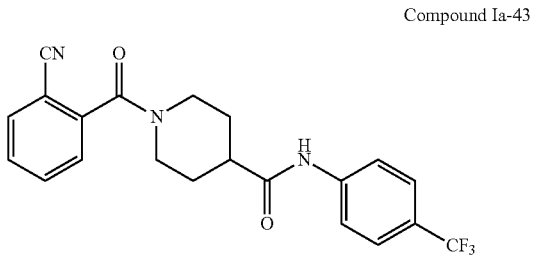

¹H-NMR (DMSO-d₆) δ: 1.62-1.82 (m, 3H), 1.96 (brs, 1H), 2.65-2.73 (m, 1H), 2.92-3.00 (m, 1H), 3.15 (t, 1H, J=11.4 Hz), 3.38-3.43 (m, 1H), 4.56 (d, J=13.2 Hz), 7.35-7.43 (m, 2H), 7.57-7.73 (m, 4H), 7.80 (t, 1H, J=7.5 Hz), 7.88-7.89 (m, 2H), 7.96 (d, 1H, J=7.5 Hz), 8.38 (s, 1H), 8.66 (d, 1H, J=4.8 Hz), 10.09 (s, 1H).

Compound Ia-44

[Chemical Formula 80]

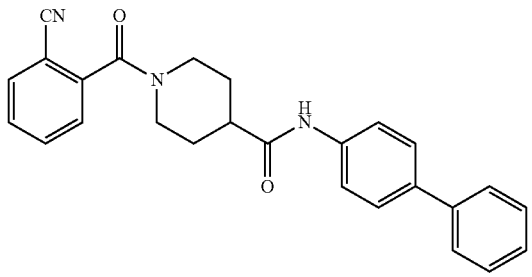

¹H-NMR (CDCl₃) δ: 1.83-2.05 (m, 3H), 2.07-2.19 (m, 1H), 2.60 (m, 1H), 3.06 (m, 1H), 3.22 (m, 1H), 3.59 (brd, 1H, J=13.1 Hz), 4.77 (brd, 1H, J=13.0 Hz), 7.26-7.62 (m, 12H), 7.67 (dt, 1H, J=1.2, 7.8 Hz), 7.72 (m, 1H).

Compound Ia-45

[Chemical Formula 81]

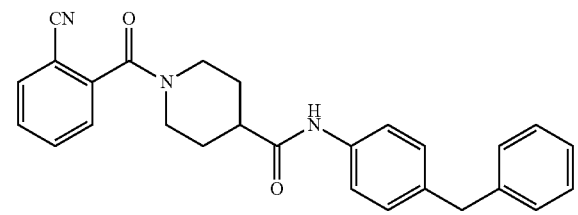

¹H-NMR (CDCl₃) δ: 1.80-2.01 (m, 3H), 2.02-2.15 (m, 1H), 2.54 (m, 1H), 3.03 (m, 1H), 3.20 (m, 1H), 3.57 (brd, 1H, J=13.4 Hz), 3.94 (s, 2H), 4.74 (brd, 1H, J=13.1 Hz), 7.09-7.21 (m, 5H), 7.22-7.30 (m, 2H), 7.32 (brs, 1H), 7.38-7.55 (m, 4H), 7.66 (dt, 1H, J=1.2, 7.8 Hz), 7.71 (m, 1H).

Compound Ia-46

[Chemical Formula 82]

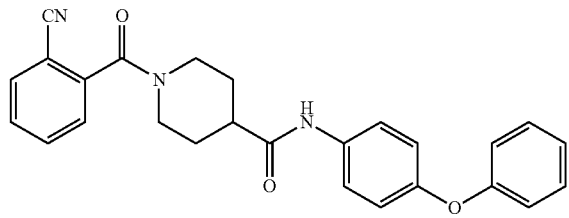

$^1$H-NMR (CDCl$_3$) δ: 1.79-2.02 (m, 3H), 2.06-2.17 (m, 1H), 2.57 (m, 1H), 3.05 (m, 1H), 3.22 (m, 1H), 3.58 (brd, 1H, J=13.1 Hz), 4.76 (brd, 1H, J=13.3 Hz), 6.93-7.00 (m, 4H), 7.08 (m, 1H), 7.31 (m, 2H), 7.35 (brs, 1H), 7.43-7.55 (m, 4H), 7.67 (dt, 1H, J=1.2, 7.8 Hz), 7.72 (m, 1H).

Compound Ia-47

[Chemical Formula 83]

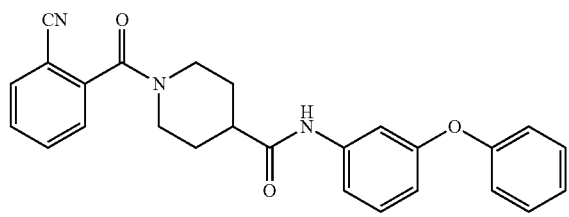

$^1$H-NMR (CDCl$_3$) δ: 1.78-2.00 (m, 3H), 2.02-2.13 (m, 1H), 2.54 (m, 1H), 3.03 (m, 1H), 3.19 (m, 1H), 3.57 (brd, 1H, J=13.1 Hz), 4.74 (brd, 1H, J=13.1 Hz), 6.75 (m, 1H), 6.98-7.04 (m, 2H), 7.10 (m, 1H), 7.21 (m, 1H), 7.23-7.27 (m, 2H), 7.29-7.37 (m, 3H), 7.47 (m, 1H), 7.51 (dt, 1H, J=1.2, 7.8 Hz), 7.66 (dt, 1H, J=1.2, 7.8 Hz), 7.71 (m, 1H).

Compound Ia-48

[Chemical Formula 84]

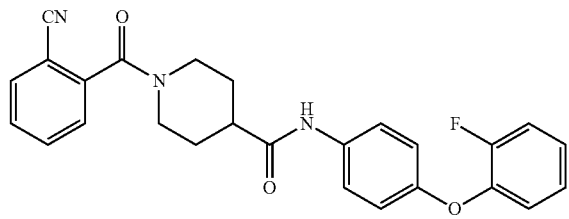

$^1$H-NMR (CDCl$_3$) δ: 1.82-2.03 (m, 3H), 2.04-2.18 (m, 1H), 2.56 (m, 1H), 3.04 (m, 1H), 3.21 (m, 1H), 3.58 (brd, 1H, J=13.2 Hz), 4.76 (brd, 1H, J=13.0 Hz), 6.91-6.97 (m, 2H), 6.97-7.20 (m, 4H), 7.32 (brs, 1H), 7.42-7.56 (m, 4H), 7.67 (dt, 1H, J=1.2, 7.6 Hz), 7.72 (m, 1H).

Compound Ia-49

[Chemical Formula 85]

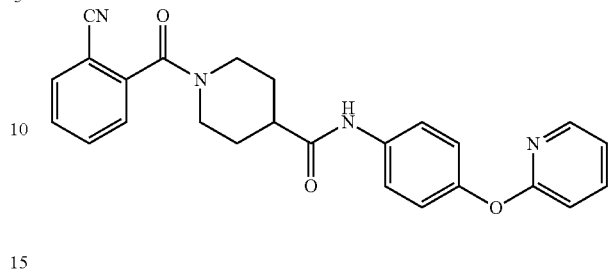

$^1$H-NMR (CDCl$_3$) δ: 1.81 (bs, 3H), 2.10 (bs, 1H), 2.52-2.60 (m, 1H), 3.03 (t, 1H, J=11.7 Hz), 3.19 (bs, 1H), 3.57 (d, 1H, J=12.3 Hz), 4.64 (d, 1H, J=13.2 Hz), 6.88 (d, 1H, J=8.4 Hz), 6.98 (t, 1H, J=7.2 Hz), 7.08 (d, 2H, J=9.0 Hz), 7.47-7.55 (m, 4H), 7.65-7.73 (m, 4H), 8.16 (dd, 1H, J=4.8, 1.5 Hz).

Compound Ia-50

[Chemical Formula 86]

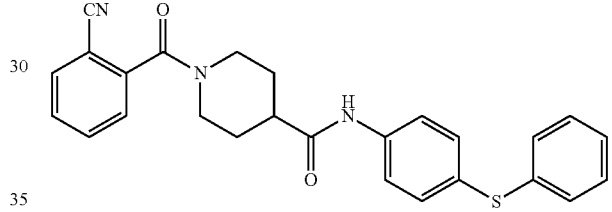

$^1$H-NMR (CDCl$_3$) δ: 1.80-2.02 (m, 3H), 2.03-2.16 (m, 1H), 2.57 (m, 1H), 3.04 (m, 1H), 3.21 (m, 1H), 3.58 (brd, 1H, J=13.2 Hz), 4.75 (brd, 1H, J=13.1 Hz), 7.15-7.22 (m, 1H), 7.22-7.28 (m, 3H), 7.31-7.38 (m, 2H), 7.42 (brs, 1H), 7.45-7.56 (m, 5H), 7.67 (dt, 1H, J=1.2, 7.7 Hz), 7.72 (m, 1H).

Compound Ia-51

[Chemical Formula 87]

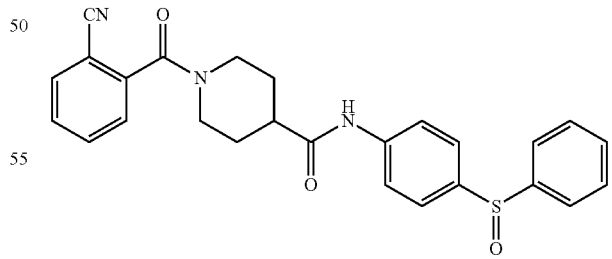

$^1$H-NMR (DMSO-d$_6$) δ: 1.50-1.69 (m, 2H), 1.69-1.81 (m, 1H), 1.87-2.00 (m, 1H), 2.65 (m, 1H), 2.92 (m, 1H), 3.12 (m, 1H), 3.38-3.43 (m, 1H), 4.53 (d, 1H, J=13.0 Hz), 7.45-7.58 (m, 4H), 7.59-7.68 (m, 5H), 7.70-7.82 (m, 3H), 7.94 (d, 1H, J=7.5 Hz), 10.23 (s, 1H).

Compound Ia-52

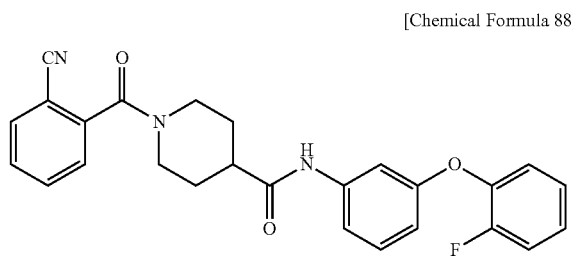

[Chemical Formula 88]

¹H-NMR (CDCl₃) δ: 1.78-1.99 (m, 3H), 2.02-2.13 (m, 1H), 2.54 (m, 1H), 3.01 (m, 1H), 3.19 (m, 1H), 3.56 (brd, 1H, J=13.3 Hz), 4.73 (brd, 1H, J=13.0 Hz), 6.67-6.73 (m, 1H), 7.03-7.16 (m, 3H), 7.16-7.28 (m, 4H), 7.41 (brs, 1H), 7.46 (m, 1H), 7.51 (dt, 1H, J=1.2, 7.7 Hz), 7.66 (dt, 1H, J=1.2, 7.7 Hz), 7.71 (m, 1H).

Compound Ia-53

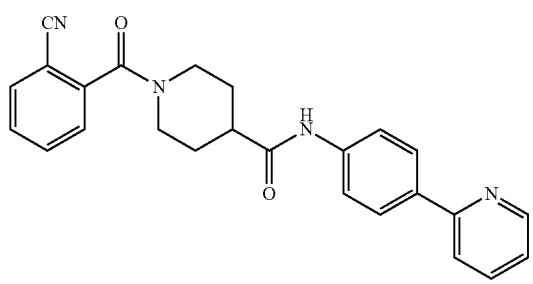

[Chemical Formula 89]

¹H-NMR (CDCl₃) δ: 1.82-2.05 (m, 3H), 2.07-2.19 (m, 1H), 2.60 (m, 1H), 3.06 (m, 1H), 3.22 (m, 1H), 3.59 (brd, 1H, J=13.1 Hz), 4.76 (brd, 1H, J=13.1 Hz), 7.21 (ddd, 1H, J=1.7, 4.9, 6.7 Hz), 7.49 (m, 1H), 7.51 (brs, 1H), 7.53 (dt, 1H, J=1.2, 7.7 Hz), 7.64 (m, 1H), 7.66 (dt, 1H, J=1.2, 7.7 Hz), 7.68-7.78 (m, 4H), 7.94-8.00 (m, 2H), 8.66 (m, 1H).

Compound Ia-54

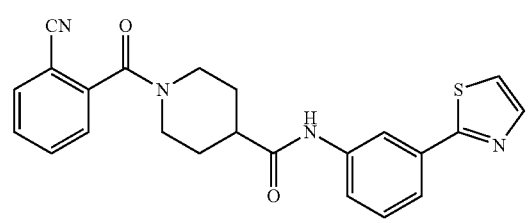

[Chemical Formula 90]

¹H-NMR (DMSO-d₆) δ: 1.65-1.69 (m, 2H), 1.80 (d, 1H, J=12.4 Hz), 1.97-1.99 (m, 1H), 2.65-2.73 (m, 1H), 2.96 (t, 1H, J=11.4 Hz), 3.12 (t, 1H, J=12.0 Hz), 3.40-3.44 (m, 1H), 4,57 (d, 1H, J=11.7 Hz), 7.43 (t, 1H, J=8.1 Hz), 7.58-7.70 (m, 3H), 7.79-7.80 (m, 2H), 7.93-7.98 (m, 2H), 8.33 (s, 1H), 10.17 (s, 1H).

Compound Ia-55

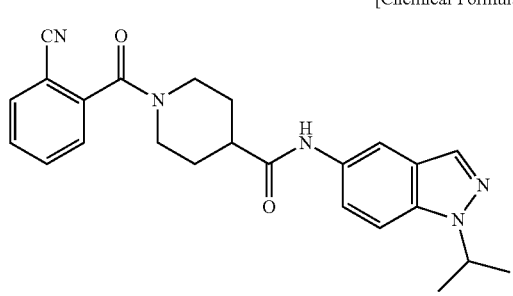

[Chemical Formula 91]

¹H-NMR (DMSO-d₆) δ: 1.46 (d, 6H, J=6.6 Hz), 1.65-1.80 (m, 3H), 1.95-1.99 (m, 1H), 2.63-2.67 (m, 1H), 2.95 (t, 1H, J=12.6 Hz), 3.15 (t, 1H, J=13.2 Hz), 3.44 (brs, 1H), 4.58 (d, 1H, J=13.2 Hz), 4.88-4.97 (m, 1H), 7.43 (d, 1H, J=9.0 Hz), 7.57-7.67 (m, 3H), 7.39-7.43 (m, 2H), 7.80 (d, 1H, J=7.5 Hz), 7.97 (d, 1H, J=10.5 Hz), 7.98 (s, 1H), 8.09 (s, 1H), 9.95 (s, 1H).

Compound Ia-56

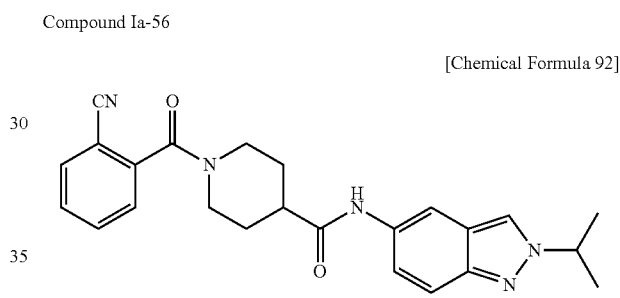

[Chemical Formula 92]

¹H-NMR (CDCl₃) δ: 1.64 (d, 6H, J=6.9 Hz), 1.89 (brs, 3H), 2.08 (brs, 1H), 2.54-2.57 (m, 1H), 3.03 (t, 1H, J=11.4 Hz), 3.20 (brs, 1H), 3.58 (d, 1H, J=13.2 Hz), 4.72-4.80 (m, 2H), 7.07 (dd, 1H, J=9.0, 1.8 Hz), 7.47-7.54 (m, 2H), 7.63-7.74 (m, 4H), 7.88 (s, 1H), 8.15 (s, 1H).

Compound Ia-57

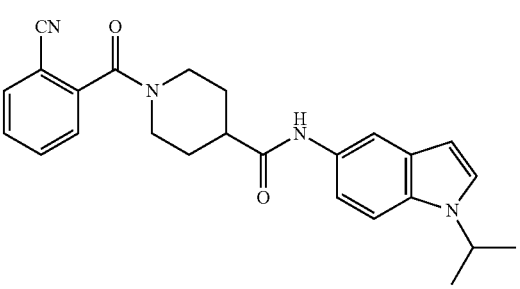

[Chemical Formula 93]

¹H-NMR (DMSO-d₆) δ: 1.43 (d, 6H, J=6.6 Hz), 1.61-1.65 (m, 3H), 1.94 (bs, 1H), 2.63-2.70 (m, 1H), 2.94 (t, 1H, J=12.0 Hz), 3.14 (t, 1H, J=11.7 Hz), 3.39 (t, 1H, J=12.6 Hz), 4.57 (d, 1H, J=12.9 Hz), 4.65-4.73 (m, 1H), 6.38 (d, J=3.0 Hz), 7.24 (dd, 1H, J=9.0, 1.8 Hz), 7.39-7.43 (m, 2H), 7.57-7.67 (m, 2H), 7.80 (t, 1H, J=7.5 Hz), 7.86 (d, 1H, J=2.1 Hz), 7.96 (d, 1H, J=7.2 Hz), 9.76 (s, 1H).

Compound Ia-58

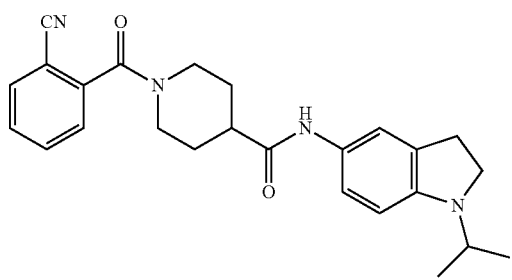

[Chemical Formula 94]

$^1$H-NMR (CDCl$_3$) δ: 1.13 (d, 6H, J=6.9 Hz), 1.63 (brs, 1H), 1.87 (brs, 2H), 2.87 (brs, 1H), 2.45-2.54 (m, 1H), 2.87-2.95 (m, 2H), 3.04 (t, 1H, J=11.1 Hz), 3.19 (t, 1H, J=10.8 Hz), 3.31 (t, 1H, J=8.4 Hz), 3.56 (d, 1H, J=12.9 Hz), 3.73-3.82 (m, 1H), 4.73 (d, 1H, J=13.2 Hz), 6.33 (d, 1H, J=8.1 Hz), 7.03 (dd, 1H, J=8.7, 1.5 Hz), 7.17 (brs, 1H), 7.46-7.54 (m, 2H), 7.63-7.72 (m, 2H).

Compound Ia-59

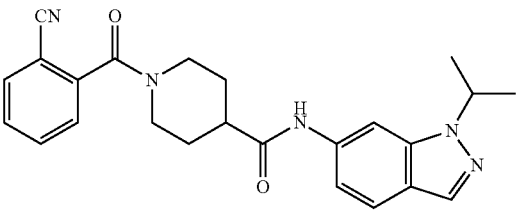

[Chemical Formula 95]

$^1$H-NMR (DMSO-d$_6$) δ: 1.56 (d, 6H, J=6.9 Hz), 1.93 (brs, 4H), 2.56-2.62 (brs, 1H), 3.03-3.10 (m, 1H), 3.22 (brs, 1H), 3.56 (d, 1H, J=13.2 Hz), 4.75-4.86 (m, 2H), 6.80 (dd, 1H, J=8.7, 1.8 Hz), 7.47-7.74 (m, 6H), 7.92 (s, 1H), 8.24 (s, 1H)

Compound Ia-60

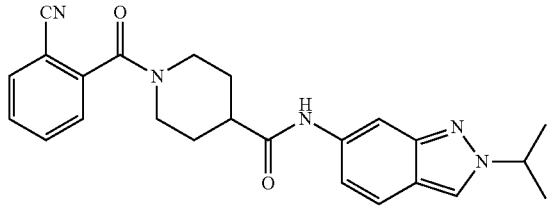

[Chemical Formula 96]

$^1$H-NMR (CDCl$_3$) δ: 1.64 (d, 6H, J=6.6 Hz), 1.90 (brs, 4H), 2.09 (brs, 1H), 2.55-2.58 (m, 1H), 3.02 (brs, 1H), 3.19 (brs, 1H), 3.57 (d, 1H, J=13.2 Hz), 4.72-4.81 (m, 2H), 7.16 (d, 1H, J=9.0 Hz), 7.49 (t, 2H, J=7.2 Hz), 7.57 (t, 2H, J=7.2 Hz), 7.65 (d, 1H, J=7.8 Hz), 7.72 (d, 1H, J=7.8 Hz), 7.90 (s, 1H), 7.95 (s, 1H)

Compound Ia-61

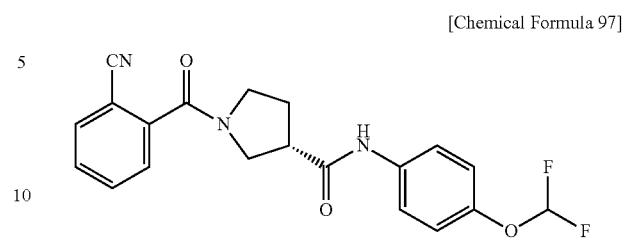

[Chemical Formula 97]

$^1$H-NMR (DMSO-d$_6$) δ: 2.08-2.28 (m, 2H), 3.16-3.89 (m, 5H), 6.88-7.39 (m, 3H), 7.52-7.66 (m, 4H), 8.05-8.09 (m, 1H), 10.16 (br-s, 1H).

Compound Ia-62

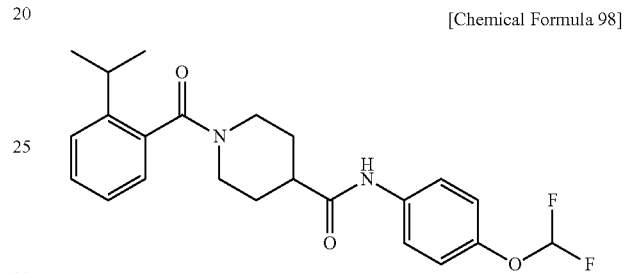

[Chemical Formula 98]

$^1$H-NMR (DMSO-d$_6$) δ: 1.15-1.21 (6H, m), 1.48-1.62 (2H, m), 1.66-1.75 (1H, m), 1.90-1.94 (1H, m), 2.58-2.63 (1H, m), 2.81-2.94 (2H, m), 3.00-3.05 (1H, m), 3.37-3.41 (1H, m), 4.58-4.62 (1H, m), 7.07-7.15 (3H, m), 7.13 (1H, t, J=74.5 Hz), 7.21-7.27 (1H, m), 7.34-7.44 (2H, m), 7.62 (2H, dd, J=9.1, 2.9 Hz), 10.03 (1H, d, J=9.6 Hz).

[Chemical Formula 99]

Compound Ia-63

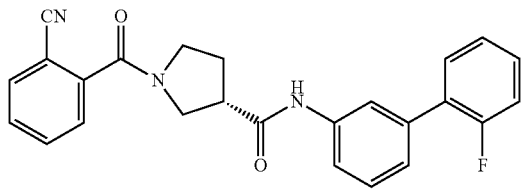

$^1$H-NMR (DMSO-d$_6$) δ: 2.08-2.28 (m, 2H), 3.16-3.89 (m, 5H), 7.22-7.56 (m, 6H), 7.57-7.75 (m, 3H), 7.79-7.96 (m, 3H), 10.14 (s, ½H) and 10.26 (s, ½H).

[Chemical Formula 100]

Compound Ia-64

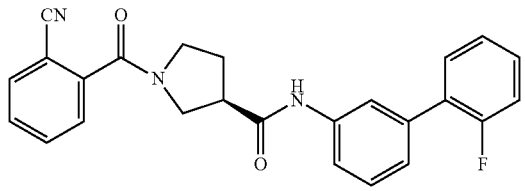

¹H-NMR (CDCl₃) δ: 2.15-2.45 (m, 2H), 3.21 (m, 1H), 3.38-3.76 (m, 3H), 3.92 (m, 1H), 7.09-7.72 (m, 12H), 8.15 (br-s, 1H)

Compound Ia-65

[Chemical Formula 101]

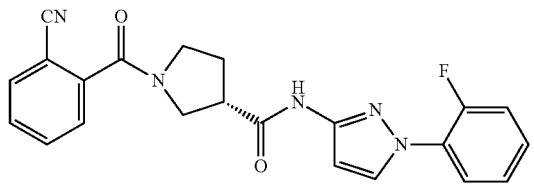

¹H-NMR (DMSO-d₆) δ: 2.08-2.63 (m, 2H), 3.22-3.87 (m, 5H), 6.83 (dd, J=2.4, 18.9 Hz), 7.35-7.49 (m, 3H), 7.63-7.82 (m, 4H), 7.94-7.97 (m, 1H), 8.04-8.13 (m, 1H), 10.86 (s, ½H) and 10.99 (s, ½H).

[Chemical Formula 102]

Compound Ia-66

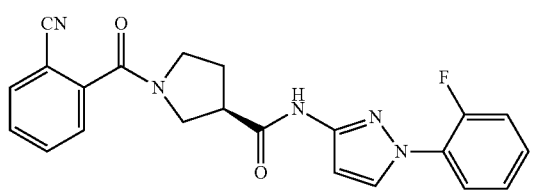

¹H-NMR (DMSO-d₆) δ: 2.10-2.35 (m, 2H), 3.09 (m, 1H), 3.40-3.74 (m, 3H), 3.98 (m, 1H), 6.93 (d, 1H, J=19.8 Hz), 7.19-7.24 (m, 3H), 7.47-7.55 (m, 2H), 7.62-7.75 (m, 3H), 7.88 (1H,).

[Chemical Formula 103]

Compound Ia-67

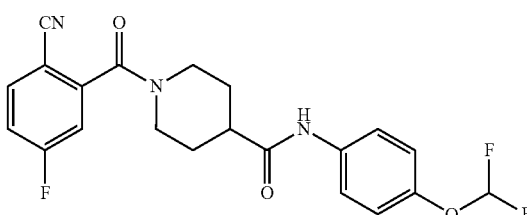

¹H-NMR (CDCl₃) δ: 1.64 (d, 6H, J=6.6 Hz), 1.90 (brs, 4H), 2.09 (brs, 1H), 2.55-2.58 (m, 1H), 3.02 (brs, 1H), 3.19 (brs, 1H), 3.57 (d, 1H, J=13.2 Hz), 4.72-4.81 (m, 2H), 7.16 (d, 1H, J=9.0 Hz), 7.49 (t, 2H, J=7.2 Hz), 7.57 (t, 2H, J=7.2 Hz), 7.65 (d, 1H, J=7.8 Hz), 7.72 (d, 1H, J=7.8 Hz), 7.90 (s, 1H), 7.95 (s, 1H)

Compound Ia-68

[Chemical Formula 104]

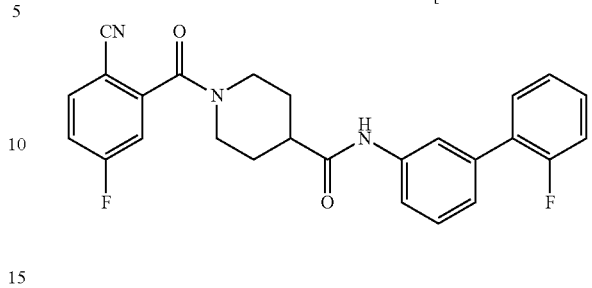

¹H-NMR (DMSO-d₆) δ: 1.63-1.77 (m, 4H), 1.95 (brs, 1H), 2.67 (brs, 1H), 2.94 (t, 1H, J=11.1 Hz), 3.15 (t, 1H, J=11.4 Hz), 3.43 (d, 1H, J=13.5 Hz), 4.54 (d, 1H, J=12.6 Hz), 7.21 (d, 1H, J=7.5 Hz), 76.28-7.33 (m, 2H), 7.38-7.64 (m, 6H), 7.85 (s, 1H), 8.09 (dd, 1H, J=8.7, 5.4 Hz), 10.08 (s, 1H).

[Chemical Formula 105]

Compound Ia-69

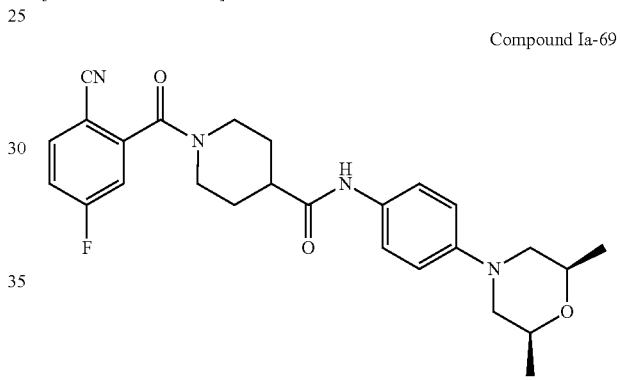

¹H-NMR (DMSO-d₆) δ: 1.16 (d, 6H, J=5.9 Hz), 1.70-1.93 (m, 4H), 2.20 (t, 2H, J=11.1 Hz), 2.60-2.63 (m, 1H), 2.93-2.96 (m, 1H), 3.13-3.16 (m, 1H), 3.43-3.50 (m, 3H), 3.68-3.72 (m, 2H), 4.52-4.57 (m, 1H), 6.89 (d, 2H, J=8.9 Hz), 7.48-7.58 (m, 4H), 8.08-8.10 (m, 1H), 9.73 (s, 1H).

[Chemical Formula 106]

Compound Ia-70

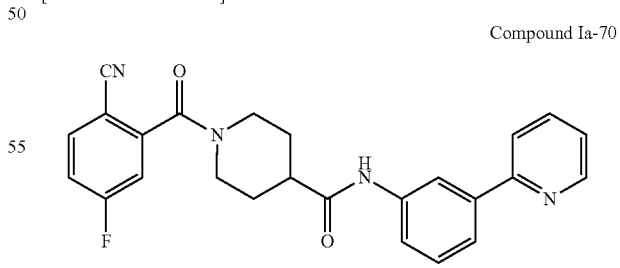

¹H-NMR (CDCl₃) δ: 1.83-2.02 (m, 3H), 2.04-2.16 (m, 1H), 2.57 (m, 1H), 3.06 (m, 1H), 3.22 (m, 1H), 3.57 (brd, 1H, J=13.3 Hz), 4.70 (brd, 1H, J=13.4 Hz), 7.17-7.22 (m, 2H), 7.23-7.28 (m, 1H), 7.43 (t, 1H, J=7.6 Hz), 7.66 (brs, 1H), 7.68-7.81 (m, 5H), 8.11 (m, 1H), 8.66 (m, 1H).

[Chemical Formula 107]

Compound Ia-71

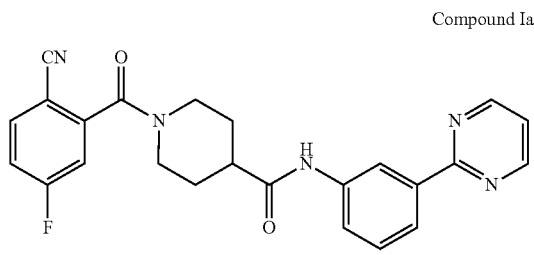

$^1$H-NMR (CDCl$_3$) δ: 1.83-2.05 (m, 3H), 2.07-2.19 (m, 1H), 2.60 (m, 1H), 3.11 (m, 1H), 3.25 (m, 1H), 3.59 (brd, 1H, J=13.4 Hz), 4.71 (brd, 1H, J=13.3 Hz), 7.17-7.25 (m, 3H), 7.46 (brs, 1H), 7.47 (t, 1H, J=7.9 Hz), 7.74 (m, 1H), 7.87 (m, 1H), 8.20 (m, 1H), 8.40 (m, 1H), 8.80 (d, 2H, J=7.9 Hz).

[Chemical Formula 108]

Compound Ia-72

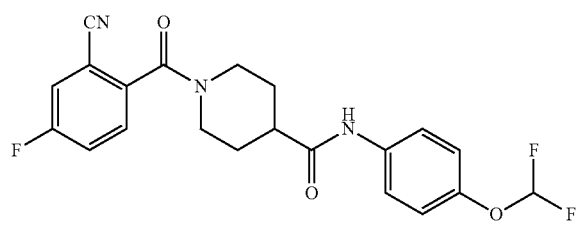

$^1$H-NMR (DMSO-d$_6$) δ: 1.54-1.73 (m, 2H), 1.73-1.84 (m, 1H), 1.91-2.02 (m, 1H), 2.66 (m, 1H), 2.95 (m, 1H), 3.15 (m, 1H), 3.42 (m, 1H), 4.54 (d, 1H, J=12.1 Hz), 6.91 (d, 0.3H, J=1.37 Hz), 7.11-7.18 (m, 2.6H), 7.40 (d, 0.3H, J=1.37 Hz), 7.62-7.75 (m, 4H), 8.01 (d, 1H, J=8.79 Hz), 10.02 (s, 1H).

[Chemical Formula 109]

Compound Ia-73

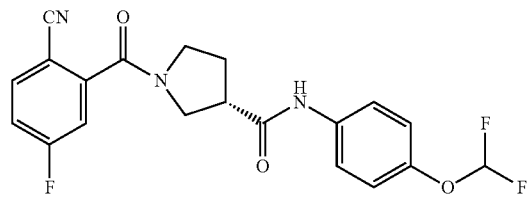

$^1$H-NMR (DMSO-d$_6$) δ: 2.08-2.28 (m, 2H), 3.16-3.89 (m, 5H), 6.88-7.39 (m, 3H), 7.52-7.66 (m, 4H), 8.05-8.09 (m, 1H), 10.11 (s, ½H), and 10.22 (s, ½H).

[Chemical Formula 110]

Compound Ia-74

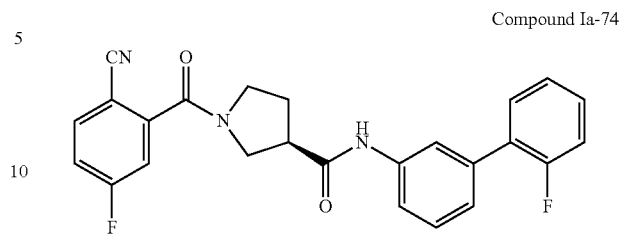

$^1$H-NMR (DMSO-d$_6$) δ: 2.10-2.28 (m, 2H), 3.15-3.89 (m, 4H), 7.20-7.56 (m, 6H), 7.60-7.75 (m, 3H), 7.79-7.96 (m, 3H), 10.2 (br-s, 1H).

[Chemical Formula 111]

Compound Ia-75

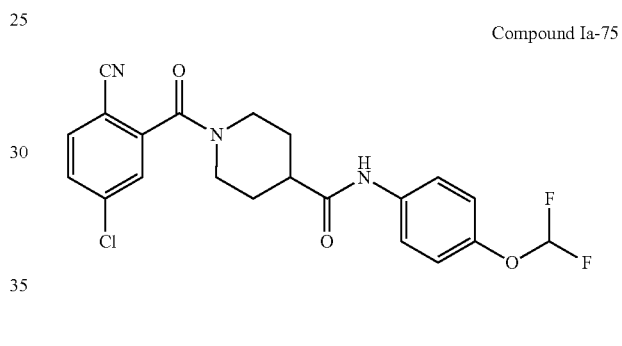

$^1$H-NMR (DMSO-d$_6$) δ: 1.58-1.83 (m, 3H), 1.94-1.99 (m, 1H), 2.62-2.64 (m, 1H), 2.85-2.97 (m, 1H), 3.04-3.15 (m, 1H), 3.43 (d, 1H, J=10.2 Hz), 4.53 (d, 1H, J=12.3 Hz), 7.11 (s, 2H), 7.13 (t, 1H, J=74.0 Hz), 7.43 (d, 1H, J=8.4 Hz), 7.56-7.77 (m, 3H), 8.00 (d, 1H, J=8.4 Hz).

[Chemical Formula 112]

Compound Ia-76

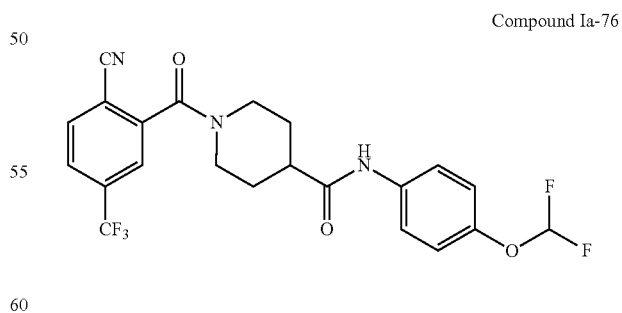

$^1$H-NMR (DMSO-d$_6$) δ: 1.62-1.74 (m, 3H), 1.94-1.98 (m, 1H), 2.61-2.64 (m, 1H), 2.92-2.99 (m, 1H), 3.38-3.54 (m, 1H), 4.55 (d, 1H, J=13.8 Hz), 7.13 (t, 1H, J=74.4 Hz), 7.12 (d, 1H, J=8.7 Hz), 7.63 (d, 2H, J=9.0 Hz), 8.03-8.07 (m, 2H), 8.23 (d, 1H, J=8.1 Hz), 10.04 (s, 1H).

[Chemical Formula 113]

Compound Ia-77

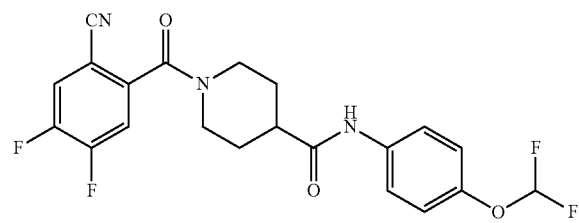

¹H-NMR (DMSO-d₆) δ: 1.62-1.78 (m, 3H), 1.92-1.97 (m, 1H), 2.64 (brs, 1H), 2.89-2.97 (m, 1H), 3.13 (t, 1H, J=8.4 Hz), 3.47 (d, 1H, J=14.4 Hz), 4.51 (1H, J=12.9 Hz), 7.12 (d, 1H, J=7.8 Hz), 7.13 (t, 1H, J=74, 1 Hz), 7.63 (d, 1H, J=8.4 Hz), 7.86 (t, 1H, J=8.4 Hz), 8.30 (t, 1H, J=9.0 Hz), 10.03 (s, 1H).

[Chemical Formula 114]

Compound Ia-78

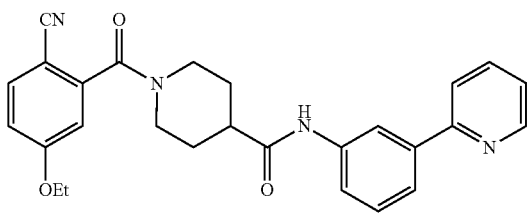

¹H-NMR (CDCl₃) δ: 1.45 (t, 3H, J=6.7 Hz), 1.85-2.03 (m, 3H), 2.06-2.18 (m, 1H), 2.59 (m, 1H), 3.06 (m, 1H), 3.23 (m, 1H), 3.62 (brd, 1H, J=13.2 Hz), 4.11 (q, 2H, J=6.7 Hz), 4.76 (brd, 1H, J=13.2 Hz), 6.90-6.99 (m, 2H), 7.23-7.28 (m, 1H), 7.44 (m, 2H), 7.62 (d, 1H, J=7.5 Hz), 7.68-7.79 (m, 4H), 8.11 (m, 1H), 8.68 (m, 1H).

Compound Ia-80

[Chemical Formula 115]

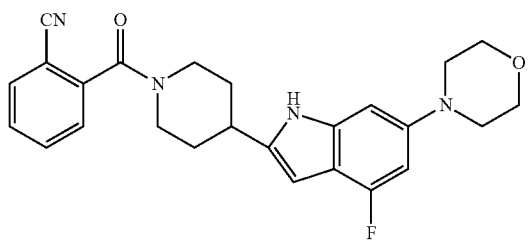

¹H-NMR (DMSO-d₆) δ: 1.56-1.76 (m, 2H), 1.96 (m, 1H), 2.14 (m, 1H), 2.92-3.12 (m, 6H), 3.20-3.47 (m, 2H), 3.72-3.82 (m, 4H), 4.61 (m, 1H), 6.07 (s, 1H), 6.51-6.60 (m, 2H), 7.61 (dd, 1H, J=7.5 Hz), 7.66 (dd, 1H, J=0.9 Hz and 7.5 Hz), 7.81 (t-d, 1H, J=0.9 Hz and 7.5 Hz), 7.96 (dd, 1H, J=0.9 Hz and 7.5 Hz), 10.98 (s, 1H).

[Chemical Formula 116]

Compound Ia-81

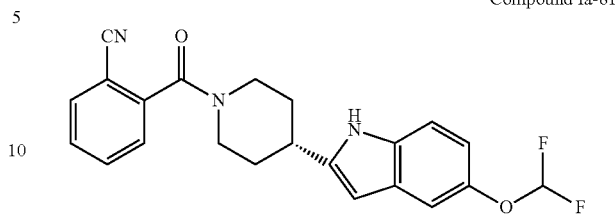

¹H-NMR (DMSO-d₆) δ: 1.57-1.77 (m, 2H), 1.88-2.19 (m, 2H), 2.96-3.12 (m, 2H), 3.19-3.46 (m, 2H), 4.61 (m, 1H), 6.19 (s, 1H), 6.84 (dd, 1H, J=8.7, 2.4 Hz), 7.04 (t, 1H, J=75.0 Hz), 7.22 (d, 1H, J=2.4 Hz), 7.29 (d, 1H, J=8.7 Hz), 7.57-7.67 (m, 2H), 7.80 (m, 1H), 7.95 (m, 1H), 11.12 (s, 1H).

[Chemical Formula 117]

Compound Ia-82

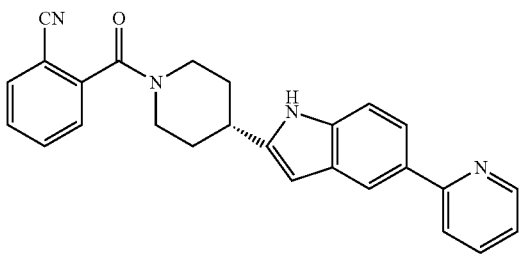

¹H-NMR (DMSO-d₆) δ: 1.60-1.81 (m, 2H), 1.92-2.24 (m, 2H), 2.97-3.15 (m, 2H), 3.21-3.48 (m, 2H), 4.63 (m, 1H), 6.26 (s, 1H), 7.22 (ddd, 1H, J=7.2, 4.8, 0.9 Hz), 7.36 (d, 1H, J=8.7 Hz), 7.58-7.68 (m, 2H), 7.75-7.84 (m, 3H), 7.90 (m, 1H), 7.96 (m, 1H), 8.17 (d, 1H, J=1.2 Hz), 8.59 (ddd, 1H, J=4.8, 1.8, 0.9 Hz), 11.11 (s, 1H).

[Chemical Formula 118]

Compound Ia-83

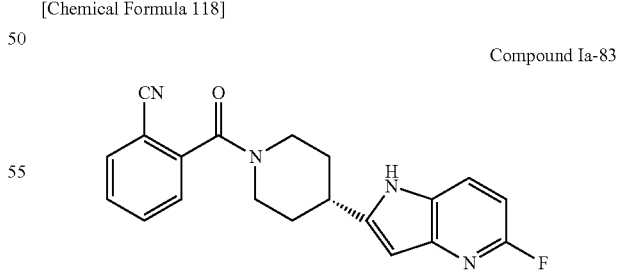

¹H-NMR (DMSO-d₆) δ: 1.59-1.80 (m, 2H), 1.97 (brd, 1H, J=12.4 Hz), 2.15 (brd, 1H, J=12.4 Hz), 2.95-3.18 (m, 2H), 3.20-3.47 (m, 2H), 4.62 (brd, 1H, J=13.1 Hz), 6.25 (s, 1H), 6.72 (dd, 1H, J=1.5, 8.5 Hz), 7.58-7.68 (m, 2H), 7.76-7.83 (m, 2H), 7.96 (m, 1H), 11.45 (brs, 1H).

[Chemical Formula 119]

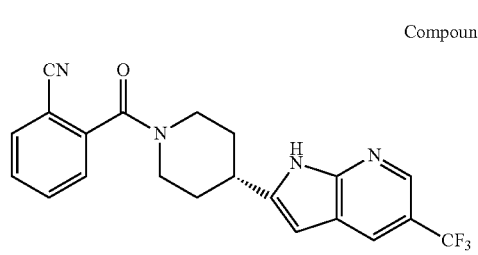

Compound Ia-84

¹H-NMR (DMSO-d₆) δ: 1.62-1.82 (m, 2H), 2.01 (m, 1H), 2.18 (m, 1H), 2.96-3.20 (m, 2H), 3.22-3.50 (m, 2H), 4.64 (m, 1H), 6.38 (s, 1H), 7.60-7.69 (m, 2H), 7.80 (m, 1H), 7.97 (m, 1H), 8.25 (m, 1H), 8.47 (m, 1H), 12.13 (s, 1H).

[Chemical Formula 120]

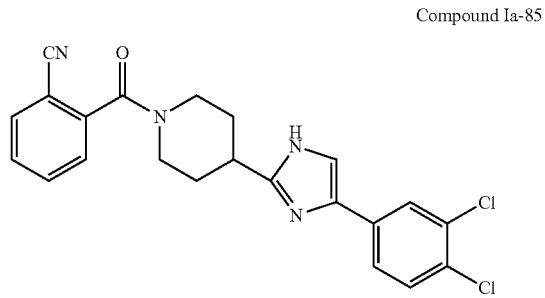

Compound Ia-85

¹H-NMR (DMSO-d₆) δ: 1.73 (brs, 2H), 1.92 (brs, H), 2.09 (brs, 1H), 3.07 (d, 2H, J=10.8 Hz), 3.20-3.26 (m, 2H), 4.46-4.58 (m, 1H), 7.55-7.89 (m, 6H), 7.96 (brs, 2H), 12.05 (s, 1H).

[Chemical Formula 121]

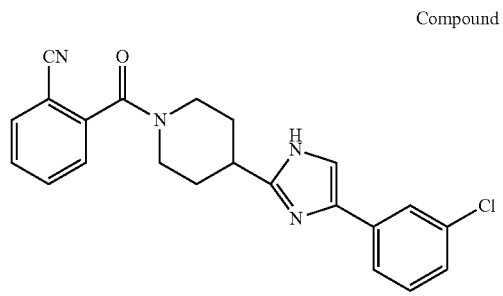

Compound Ia-86

¹H-NMR (CDCl₃) δ: 1.95-2.21 (m, 4H), 3.01-3.30 (m, 3H), 3.55-3.63 (m, 1H), 4.83 (m, 1H), 7.16-7.18 (m, 1), 7.19 (s, 1H), 7.23 (t, 1H, J=6.6 Hz), 7.47-7.55 (m, 3H), 7.65-7.75 (m, 3H).

[Chemical Formula 122]

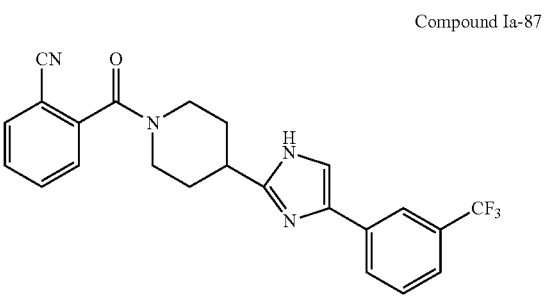

Compound Ia-87

¹¹H-NMR (CDCl₃) δ: 1.92-2.20 (m, 5H), 3.04 (t, 1H, J=11.4 Hz), 3.20-3.30 (m, 1H), 3.56-3.60 (m, 1H), 4.84 (d, 1H, J=12.9 Hz), 7.43-7.50 (m, 3H), 7.54 (d, 1H, J=7.8 Hz), 7.66 (d, 1H, J=7.8 Hz), 7.73 (d, 1H, J=7.8 Hz), 7.85 (brs, 1H), 7.94 (brs, 1H), 10.00 (brs, 1H).

[Chemical Formula 123]

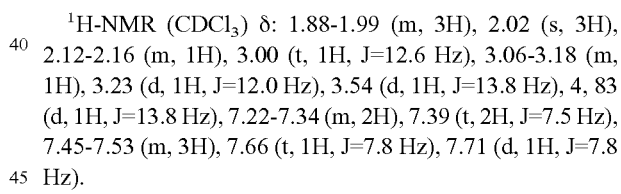

Compound Ia-88

¹H-NMR (CDCl₃) δ: 1.88-1.99 (m, 3H), 2.02 (s, 3H), 2.12-2.16 (m, 1H), 3.00 (t, 1H, J=12.6 Hz), 3.06-3.18 (m, 1H), 3.23 (d, 1H, J=12.0 Hz), 3.54 (d, 1H, J=13.8 Hz), 4, 83 (d, 1H, J=13.8 Hz), 7.22-7.34 (m, 2H), 7.39 (t, 2H, J=7.5 Hz), 7.45-7.53 (m, 3H), 7.66 (t, 1H, J=7.8 Hz), 7.71 (d, 1H, J=7.8 Hz).

[Chemical Formula 124]

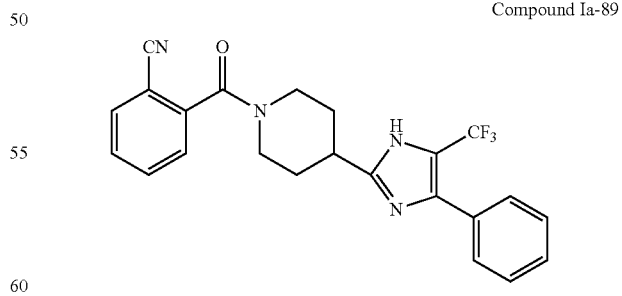

Compound Ia-89

¹H-NMR (DMSO-d₆) δ: 1.71-1.78 (m, 2H), 1.92-1.99 (m, 1H), 2.10-2.14 (m, 1H), 3.02-3.09 (m, 2H), 3.18-3.27 (m, 1H), 4.54 (d, 1H, J=12.9 Hz), 7.42-7.48 (m, 5H), 7.60 (d, 1H, J=7.8 Hz), 7.66 (d, 1H, J=7.8 Hz), 7.80 (t, 1H, J=7.8 Hz), 7.96 (d, 1H, J=7.8 Hz), 12.68 (brs, 1H).

[Chemical Formula 125]

Compound Ia-90

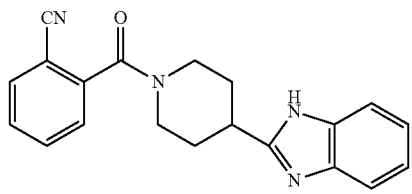

$^{1}$H-NMR (DMSO-d$_{6}$) δ: 1.62-2.18 (m, 4H), 3.00-3.42 (m, 4H), 4.55 (d, 1H, J=13.5 Hz), 6.97 (t, 1H, J=8.4 Hz), 7.29 (d, 1H, J=9.0 Hz), 7.46 (m, 2H), 7.55-7.70 (m, 2H), 7.81 (t, 1H, J=7.8 Hz), 12.4 (br-s, 1H).

[Chemical Formula 126]

Compound Ia-91

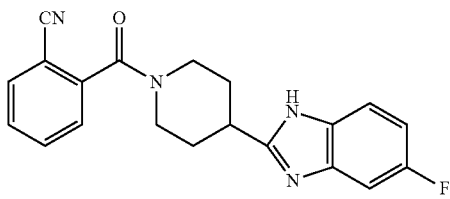

$^{1}$H-NMR (DMSO-d$_{6}$) δ: 1.63-2.21 (m, 4H), 3.04-3.36 (m, 4H), 4.53 (d, 1H, J=13.8 Hz), 6.97 (t, 1H, J=8.1 Hz), 7.28 (d, 1H, J=9.3 Hz), 7.46 (m, 1H), 7.59-7.68 (m, 2H), 7.79 (t, 1H, J=7.8 Hz), 7.95 (d, 1H, J=7.5 Hz), 12.37 (br-s, 1H).

[Chemical Formula 127]

Compound Ia-92

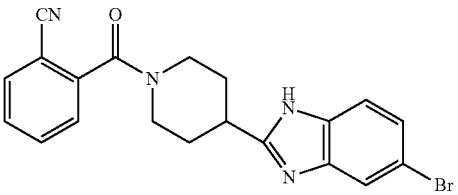

$^{1}$H-NMR (DMSO-d$_{6}$) δ: 1.61-2.20 (m, 4H), 3.01-3.40 (m, 4H), 4.54 (d, 1H, J=13.5 Hz), 6.99 (t, 1H, J=8.4 Hz), 7.26 (d, 1H, J=9.0 Hz), 7.46 (m, 1H), 7.55-7.70 (m, 2H), 7.81 (t, 1H, J=7.8 Hz), 7.96 (d, 1H, J=7.5 Hz), 12.4 (br-s, 1H).

[Chemical Formula 128]

Compound Ia-93

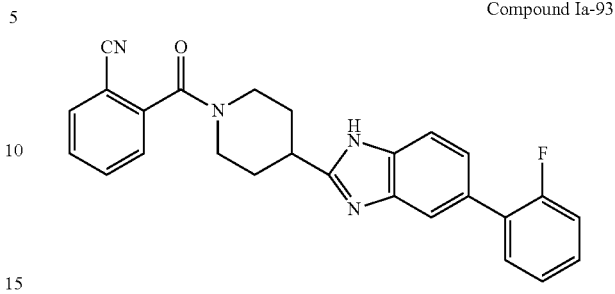

$^{1}$H-NMR (DMSO-d$_{6}$) δ: 1.76-1.93 (m, 2H), 2.00 (m, 1H), 2.18 (m, 1H), 3.1-3.55 (m, 4H), 4.55 (1H, d, J=12.9 Hz), 7.26-7.43 (m, 4H), 7.50-7.74 (m, 5H), 7.84 (m, 1H), 7.97 (d, 1H, J=7.5 Hz), 12.38 (br-s, 1H).

Compound Ia-94

[Chemical Formula 129]

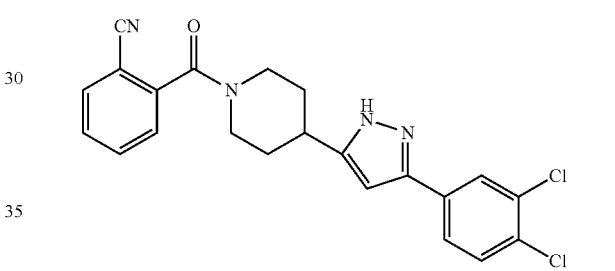

$^{1}$H-NMR (DMSO-d$_{6}$) δ: 1.53-1.71 (m, 2H), 1.92 (m, 1H), 2.09 (m, 1H), 2.95-3.09 (m, 2H), 3.15-3.30 (m, 2H), 4.55 (m, 1H), 6.67 (s, 1H), 7.59 (d, 1H, J=7.6 Hz), 7.61-7.68 (m, 2H), 7.75 (m, 1H), 7.80 (dd, 1H, J=7.6, 7.6 Hz), 7.69 (d, 1H, J=7.6 Hz), 7.99 (s 1H), 12.88 (s, 1H).

[Chemical Formula 130]

Compound Ia-95

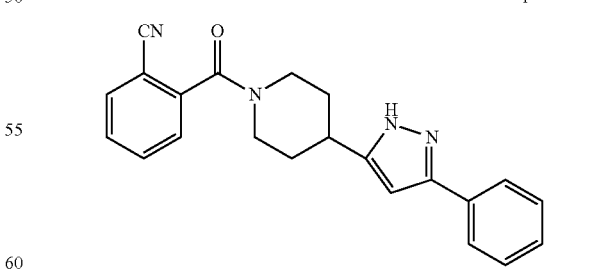

$^{1}$H-NMR (DMSO-d$_{6}$) δ: 1.55-1.75 (m, 2H), 1.92 (m, 1H), 2.10 (m, 1H), 2.90-3.10 (m, 2H), 3.16-3.39 (m, 2H), 4.56 (m, 1H), 6.52 (s, 1H), 7.28 (m, 1H), 7.32-7.48 (m, 2H), 7.61 (dd, 1H, J=7.6, 7.6 Hz), 7.64 (dd, 1H, J=7.6, 7.6 Hz), 7.69 (d, 1H, J=7.6 Hz), 12.69 (s, 1H×⅔), 12.97 (s, 1H×⅓).

[Chemical Formula 131]

Compound Ia-96

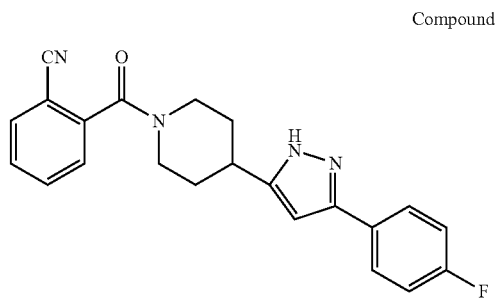

¹H-NMR (DMSO-d₆) δ: 1.53-1.74 (m, 2H), 1.84-2.14 (m, 2H), 2.87-3.10 (m, 2H), 3.18-3.43 (m, 2H), 4.56 (m, 1H), 6.52 (s, 1H), 7.17-7.31 (m, 2H), 7.59-7.66 (m, 2H), 7.74-7.83 (m, 3H), 7.96 (d, 1H, J=7.8 Hz), 12.69 (s, 1H×⅔), 12.95 (s, 1H×⅓).

[Chemical Formula 132]

Compound Ia-97

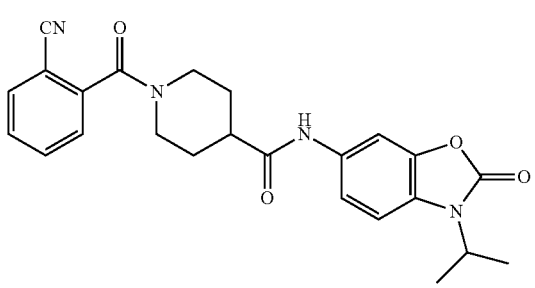

¹H-NMR (DMSO-d₆) δ: 1.43 (s, 3H), 1.49 (s, 3H), 1.58-1.80 (m, 4H), 2.08 (t, 2H, J=10.39 Hz), 2.32 (s, 1H), 2.86 (d, 2H, J=11.15 Hz), 3.64 (s, 2H), 4.44 (t, 1H, J=6.84 Hz), 7.26-7.35 (m, 2H), 7.47 (t, 1H, J=7.60 Hz), 7.60 (d, 1H, J=7.60 Hz), 7.68 (t, 1H, J=3.80 Hz), 7.74 (d, 1H, J=1.52 Hz), 7.81 (d, 1H, J=7.60 Hz), 9.95 (s, 1H).

Compound Ia-98

[Chemical Formula 133]

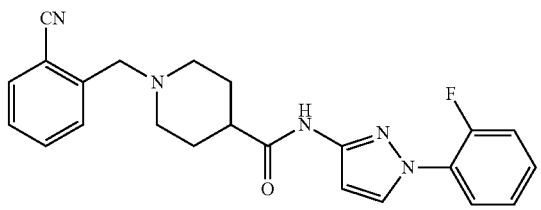

¹H-NMR (DMSO-d₆) δ: 1.85-2.12 (m, 4H), 3.15-3.24 (m, 1H), 3.25-3.40 (m, 2H), 3.43-3.55 (m, 2H), 4.51 (t, 2H, J=1.77 Hz), 6.81 (d, 1H, J=2.53 Hz), 7.35-7.46 (m, 3H), 7.72 (dd, 2H, J=7.86, 2.28 Hz), 7.86 (d, 1H, J=1.01 Hz), 7.97 (t, 2H, J=12.67 Hz), 8.10 (t, 1H, J=2.28 Hz), 10.90 (s, 1H).

Compound Ia-99

[Chemical Formula 134]

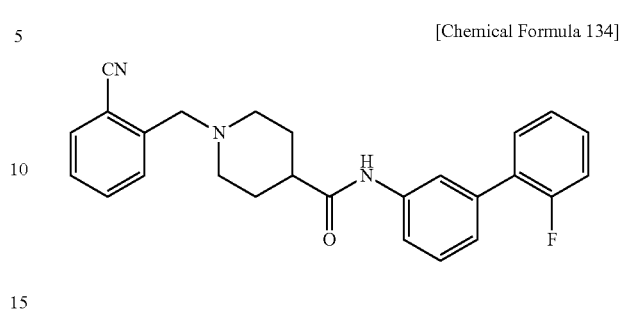

¹H-NMR (DMSO-d₆) δ: 1.94-2.10 (m, 2H), 2.63-2.75 (m, 1H), 3.10-3.23 (m, 2H), 3.27-3.35 (m, 2H), 3.45-3.57 (m, 2H), 4.51 (d, 2H, J=4.06 Hz), 7.22 (d, 1H, J=7.10 Hz), 7.29-7.33 (m, 2H), 7.39-7.44 (m, 2H), 7.45-7.52 (m, 1H), 7.60-7.67 (m, 1H), 7.70 (s, 1H), 7.80-7.90 (m, 2H), 7.95-8.05 (m, 2H), 10.23 (s, 1H).

Compound Ia-100

[Chemical Formula 135]

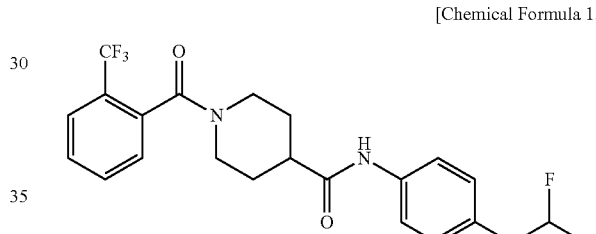

¹H-NMR (DMSO-d₆) δ: 1.38-1.78 (m, 3H), 1.88-2.00 (m, 1H), 2.56-2.71 (m, 1H), 2.78-3.20 (m, 2H), 3.23-3.34 (m, 1H), 4.52-4.63 (m, 1H), 6.91 (s, 0.3H), 7.10-7.18 (m, 2.6H), 7.40 (s, 0.3H), 7.47 (d, 0.5H, J=7.42 Hz), 7.54 (d, 0.5H, J=7.42 Hz), 7.61-7.72 (m, 3H), 7.73-7.88 (m, 2H), 10.06 (d, 1H, J=2.75 Hz).

Compound Ia-101

[Chemical Formula 136]

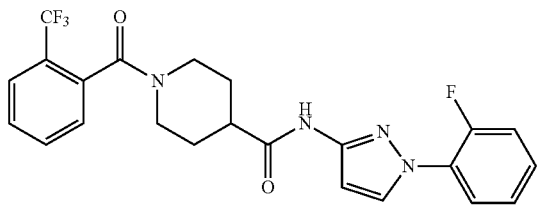

¹H-NMR (DMSO-d₆) δ: 1.57-1.74 (m, 3H), 1.92-1.96 (m, 1H), 2.76-2.85 (m, 3H), 3.25-3.30 (m, 1H), 4.54-4.58 (m, 1H), 6.85 (t, 1H, J=2.1 Hz), 7.37-7.56 (m, 4H), 7.71-7.79 (m, 4H), 8.10-8.13 (m, 1H), 10.80 (d, 1H, J=4.9 Hz).

Compound Ia-102

[Chemical Formula 137]

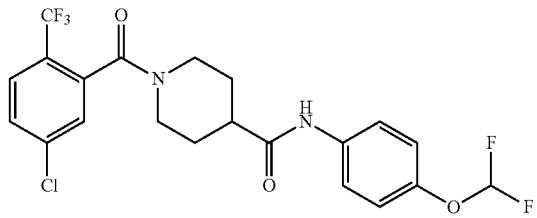

¹H-NMR (DMSO-d₆) δ: 1.42-1.52 (1H, m), 1.65-1.73 (2H, m), 1.89-1.95 (1H, m), 2.58-2.64 (1H, m), 2.89-3.12 (2H, m), 3.27-3.30 (1H, m), 4.49-4.52 (1H, m), 7.10-7.15 (2H, m), 7.13 (1H, t, J=74.7 Hz), 7.61-7.77 (4H, m), 7.86 (1H, dd, J=8.9, 3.5 Hz), 10.02 (1H, d, J=8.4 Hz).

Compound Ia-103

[Chemical Formula 138]

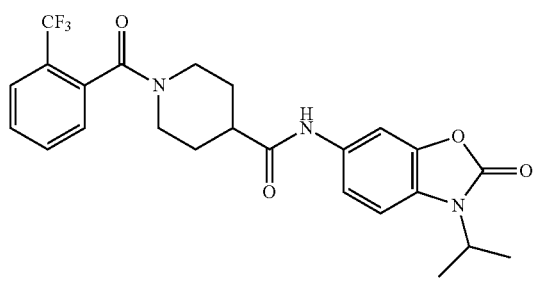

¹H-NMR (DMSO-d₆) δ: 1.43 (s, 3H), 1.45 (s, 3H), 1.55-1.76 (m, 1H), 1.82-1.97 (m, 1H), 2.59-2.63 (m, 1H), 2.85-2.98 (m, 2H), 3.07-3.15 (m, 1H), 3.20-3.35 (m, 2H), 4.37-4.48 (m, 1H), 4.54-4.58 (m, 1H), 7.28 (dd, 1H, J=6.84, 1.77 Hz), 7.34 (dd, 1H, J=8.36, 1.77 Hz), 7.40-7.55 (m, 1H), 7.65 (t, 1H, J=7.86 Hz), 7.73-7.77 (m, 2H), 7.82 (dd, 1H, J=7.86, 3.30 Hz), 10.03 (d, 1H, J=4.56 Hz).

Compound Ia-104

[Chemical Formula 139]

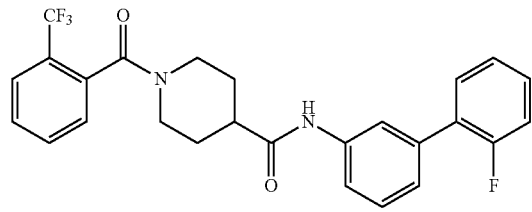

¹H-NMR (DMSO-d₆) δ: 1.59-1.68 (m, 3H), 1.95-2.01 (m, 1H), 2.67-2.68 (m, 1H), 2.89-3.12 (m, 2H), 3.28-3.31 (m, 1H), 4.56-4.60 (m, 1H), 7.31-7.46 (m, 7H), 7.63-7.69 (m, 2H), 7.75-7.87 (m, 3H), 10.10 (d, 1H, J=5.0 Hz).

Compound Ia-105

[Chemical Formula 140]

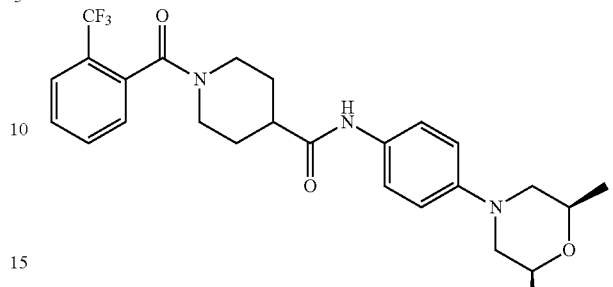

¹H-NMR (DMSO-d₆) δ: 1.16 (d, 6H, J=6.2 Hz), 1.68-1.72 (m, 3H), 2.20 (t, 2H, J=11.1 Hz), 2.56-2.58 (m, 1H), 2.86-2.90 (m, 3H), 3.26-3.29 (m, 1H), 3.51 (d, 2H, J=11.6 Hz), 3.69-3.71 (m, 2H), 4.53 (m, 1H), 6.89 (d, 2H, J=8.9 Hz), 7.46-7.53 (m, 3H), 7.71-7.82 (m, 3H), 9.74 (s, 1H).

Compound Ia-106

[Chemical Formula 141]

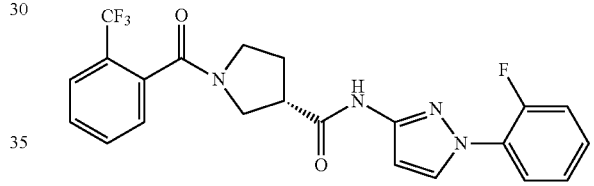

¹H-NMR (DMSO-d₆) δ: 1.99-2.25 (m, 2H), 3.12-3.83 (m, 5H), 6.82 (dd, J=2.4, 18.9 Hz, 1H), 7.33-7.54 (m, 4H), 7.62-7.83 (m, 4H), 8.08-8.11 (m, 1H), 10.84 (s, ½H) and 10.98 (s, ½H).

Compound Ia-107

[Chemical Formula 142]

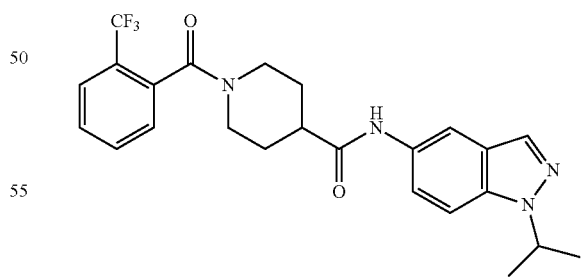

¹H-NMR (DMSO-d₆) δ: 1.44 (d, 6H, J=6.6 Hz), 1.51-1.75 (m, 2H), 1.91 (brs, 1H), 2.61 (brs, 1H), 2.86 (d, 1H, J=12.9 Hz), 2.93-3.13 (m, 2H), 3.20-3.28 (m, 1H), 4.55 (d, 1H, J=8.7 Hz), 4.86-4.95 (m, 1H), 7.39-7.42 (m, 2H), 7.50 (d, 1H, J=7.5 Hz), 7.59 (d, 1H, J=9.0 Hz), 7.64 (d, 1H, J=7.2 Hz), 7.73 (t, 1H, J=6.9 Hz), 7.80 (d, 1H, J=6.6 Hz), 7.96 (d, 1H, J=2.4 Hz), 8.06 (s, 1H), 9.92 (d, 1H, J=3.3 Hz).

Compound Ia-108

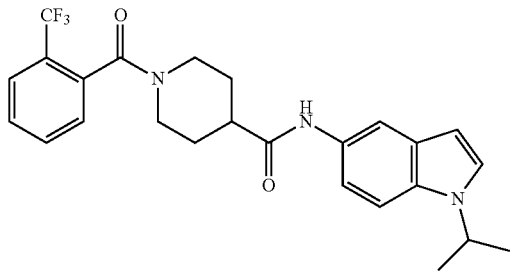

[Chemical Formula 143]

$^1$H-NMR (DMSO-d$_6$) δ: 1.43 (d, 6H, J=6.6 Hz), 1.44-1.78 (m, 3H), 1.92 (brs, 1H), 2.61 (brs, 1H), 2.81-3.13 (m, 3H), 4.56 (d, 1H, J=9.0 Hz), 4.64-4.73 (m, 1H), 6.37 (t, 1H, J=2.7 Hz), 7.22 (d, 1H, J=9.0 Hz), 7.38-7.45 (m, 2H), 7.51 (d, 1H, J=6.6 Hz), 7.65 (t, 1H, J=7.5 Hz), 7.74 (d, 1H, J=6.6 Hz), 7.80-7.84 (m, 2H), 9.73 (d, 1H, J=3.9 Hz).

Compound Ia-109

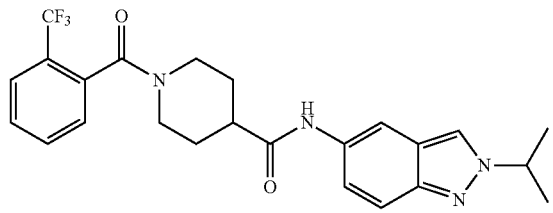

[Chemical Formula 144]

$^1$H-NMR (DMSO-d$_6$) δ: 1.52 (d, 6H, J=6.6 Hz), 1.59-1.71 (m, 3H), 1.90 (brs, 1H), 2.61 (brs, 1H), 2.79-3.12 (m, 3H), 4.50 (d, 1H, J=10.2 Hz), 4.70-4.79 (m, 1H), 7.18-7.23 (m, 1H), 7.43 (d, 1H, J=7.5 Hz), 7.51 (d, 1H, J=9.6 Hz), 7.63 (t, 1H, J=7.8 Hz), 7.73 (t, 1H, J=6.9 Hz), 7.80 (d, 1H, J=7.2 Hz), 8.09 (s, 1H), 8.27 (s, 1H), 9.83 (d, 1H, J=3.3 Hz).

Compound Ia-110

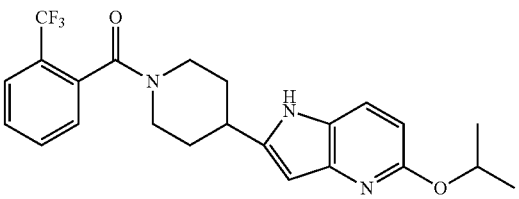

[Chemical Formula 145]

$^1$H-NMR (DMSO-d$_6$) δ: 1.26 (d, 3H, J=6.2 Hz), 1.27 (d, 3H, J=6.2 Hz), 1.35-1.81 (m, 2H), 1.81-1.96 (m, 1H), 2.03-2.16 (m, 1H), 2.86-3.15 (m, 2H), 3.15-3.35 (m, 2H), 4.59 (m, 1H), 5.24 (m, 1H), 6.14 (dd, 1H, J=1.2, 16.0 Hz), 6.37 (dd, 1H, J=1.4, 8.7 Hz), 7.42-7.58 (m, 2H), 7.60-7.69 (m, 1H), 7.71-7.80 (m, 1H), 7.80-7.85 (m, 1H), 11.00 (brs, 1H).

Compound Ia-111

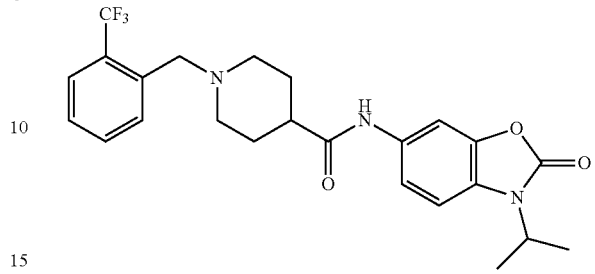

[Chemical Formula 146]

$^1$H-NMR (DMSO-d$_6$) δ: 1.43 (s, 3H), 1.45 (s, 3H), 1.67-1.78 (m, 4H), 1.99-2.07 (m, 2H), 2.34 (s, 1H), 2.85 (d, 2H, J=11.66 Hz), 3.62 (s, 2H), 4.38-4.50 (m, 1H), 7.27-7.37 (m, 2H), 7.46 (t, 1H, J=7.60 Hz), 7.63-7.71 (m, 2H), 7.73-7.77 (m, 1H), 7.81 (d, 1H, J=8.11 Hz), 9.98 (s, 1H).

Compound Ia-112

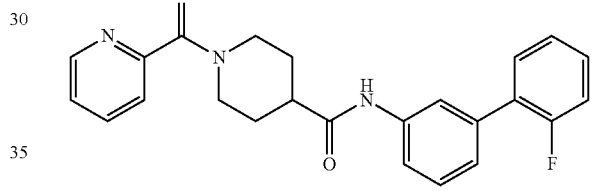

[Chemical Formula 147]

$^1$H-NMR (DMSO-d$_6$) δ: 1.56-1.71 (m, 2H), 1.78 (m, 1H), 1.94 (m, 1H), 2.67 (m, 1H), 2.90 (m, 1H), 3.11 (m, 1H), 3.73 (m, 1H), 4.55 (m, 1H), 7.21 (d, 1H, J=7.6 Hz), 7.26-7.35 (m, 2H), 7.37-7.52 (m, 4H), 7.56 (d, 1H, J=7.6 Hz), 7.64 (d, 1H, J=7.6 Hz), 7.84 (s, 1H), 7.93 (dd, 1H, J=7.6, 7.6 Hz), 8.59 (m, 1H), 10.06 (s, 1H).

Compound Ia-113

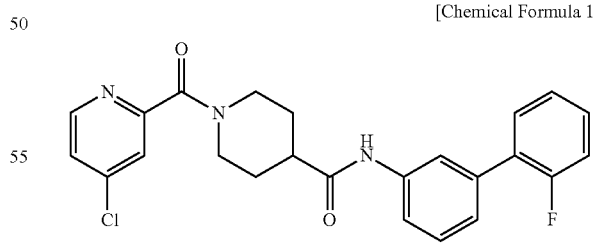

[Chemical Formula 148]

$^1$H-NMR (DMSO-d$_6$) δ: 1.58-1.72 (m, 2H), 1.79 (m, 1H), 1.95 (m, 1H), 2.68 (m, 1H), 2.91 (m, 1H), 3.12 (m, 1H), 3.69 (m, 1H), 4.52 (m, 1H), 7.21 (d, 1H, J=7.6 Hz), 7.30 (d, 1H, J=7.6 Hz), 7.32 (m, 1H), 7.40 (dd, 1H, J=7.6, 7.6 Hz), 7.42 (m, 1H), 7.51 (dd, 1H, J=7.6, 7.6 Hz), 7.60-7.67 (m, 2H), 7.72 (s, 1H), 7.85 (s, 1H), 8.58 (d, 1H, J=5.6 Hz), 10.06 (s, 1H).

Compound Ia-114

[Chemical Formula 149]

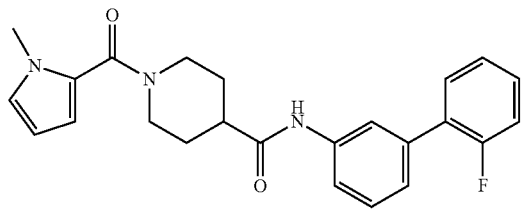

¹H-NMR (DMSO-d₆) δ: 1.60 (qd, 2H, J=12.9, 2.7 Hz), 1.87 (d, 2H, J=11.1 Hz), 2.63-2.70 (m, 1H), 30.1 (t, 1H, J=12.3 Hz), 4.35 (d, 1H, J=12.3 Hz), 6.03 (t, 1H, J=3.0 Hz), 6.30 (t, 1H, J=3.0 Hz), 6.89 (t, 1H, J=3.3 Hz), 7.21 (d, 1H, J=6.9 Hz), 7.31-7.38 (m, 2H), 7.41-7.49 (m, 3H), 7.64 (d, 1H, J=9.3 Hz), 7.86 (s, 1H), 10.08 (s, 1H).

Compound Ia-115

[Chemical Formula 150]

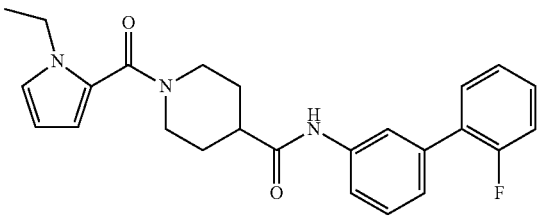

¹H-NMR (DMSO-d₆) δ: 1.39 (t, 3H, J=7.5 Hz), 1.77-1.96 (m, 4H), 2.55 (brs, 1H), 2.95 (brs, 2H), 3.88 (q, 2H, J=7.2 Hz), 4.56 (d, 1H, J=12.6 Hz), 6.26 (s, 1H), 6.58 (t, 1H, J=2.7 Hz), 7.02 (s, 1H), 7.10-7.45 (m, 6H), 7.60 (d, 1H, J=7.2 Hz), 7.74 (s, 1H), 8.04 (s, 1H).

Compound Ia-116

[Chemical Formula 151]

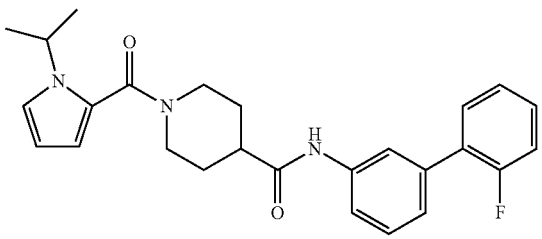

¹H-NMR (CDCl₃) δ: 1.40 (d, 6H, J=6.6 Hz), 1.76-1.95 (m, 4H), 2.51 (brs, 1H), 2.98 (t, 1H, J=11.7 Hz), 4.51 (d, 1H, J=12.9 Hz), 4.76-4.85 (m, 1H), 6.11 (s, 1H), 6.25 (s, 1H), 7.09-7.20 (m, 2H), 7.26-7.44 (m, 4H), 7.55 (d, 1H, J=8.1 Hz), 7.72 (s, 1H), 7.79 (s, 1H).

Compound Ia-117

[Chemical Formula 152]

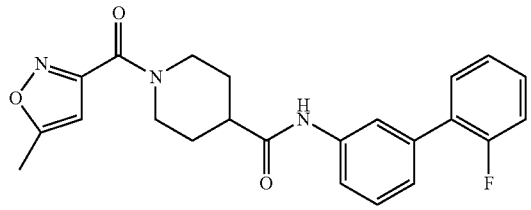

¹H-NMR (DMSO-d₆) δ: 1.51-1.69 (m, 2H), 1.77-1.99 (m, 2H), 2.43 (s, 3H), 2.67 (m, 1H), 2.90 (m, 1H), 3.17 (m, 1H), 3.97 (m, 1H), 4.48 (m, 1H), 6.34 (s, 1H), 7.13-7.53 (m, 6H), 7.61 (m, 1H), 7.82 (s, 1H), 10.05 (s, 1H).

Test Example 1-1

Affinity for NPY Y5 receptor cDNA sequence encoding mouse NPY Y5 receptor (Biochem. Biophys. Acta 1328: 83-89, 1997) was cloned in the expression vector (pME18S, Takebe et al. Mol. Cell. Biol. 8, 466-472). The obtained expression vector was transfected into CHO cells as a host according to the instruction manual using Lipofectamine reagent (Trademark, Gibco BRL Co., Ltd.). The cells that stably express NPY Y5 receptor were obtained.

The membrane samples prepared from the CHO cells expressing NPY Y5 receptor, the compound of the invention and 30,000 cpm ¹²⁵I peptide YY (60 pM of final concentration: Amersham) were incubated in the assay buffer (20 mM HEPES-Hanks buffer containing 0.1% bovine serum albumin, pH 7.4) at 25° C. for 2 hours. The membrane samples were then filtered from the mixture through a glassfilter (GF/C) presoaked with 1% polyethyleneimine. After washing with 50 mM Tris-HCl buffer (pH 7.4), radioactivity retained on the filters was determined using gamma counter. Non-specific binding was determined in the presence of 200 nM of peptide YY and calculated the 50% inhibitory concentration ($IC_{50}$ value) of the test compound for specific peptide YY binding (Inui, A. et al. Endocrinology 131, 2090-2096 (1992)). The results are shown in Table 1.

The compounds of the present invention inhibited the binding of peptide YY (homologue of NPY) to NPY Y5 receptor, indicating that the compounds of the present invention have an affinity for the NPY Y5 receptor.

TABLE 1

| Compound No. | Binding $IC_{50}$ (nM) |
|---|---|
| Ia-4 | 0.47 |
| Ia-5 | 0.28 |
| Ia-18 | 1.56 |
| Ia-19 | 0.29 |
| Ia-22 | 0.22 |
| Ia-28 | 0.96 |
| Ia-29 | 0.97 |
| Ia-34 | 0.59 |
| Ia-35 | 0.26 |
| Ia-40 | 0.27 |
| Ia-41 | 0.31 |
| Ia-44 | 0.26 |
| Ia-47 | 0.38 |
| Ia-52 | 0.28 |

TABLE 1-continued

| Compound No. | Binding IC$_{50}$ (nM) |
|---|---|
| Ia-54 | 0.39 |
| Ia-57 | 0.23 |
| Ia-62 | 1.77 |
| Ia-63 | 0.33 |
| Ia-65 | 0.25 |
| Ia-68 | 0.20 |
| Ia-70 | 0.18 |
| Ia-71 | 0.37 |
| Ia-85 | 0.12 |
| Ia-87 | 0.17 |
| Ia-88 | 0.35 |
| Ia-93 | 0.19 |
| Ia-94 | 0.30 |
| Ia-99 | 0.64 |
| Ia-104 | 2.00 |
| Ia-106 | 1.50 |
| Ia-108 | 0.48 |
| Ia-113 | 4.28 |
| Ia-116 | 1.43 |

Test Example 1-2

Affinity for NPY Y5 receptor cDNA sequence encoding human NPY Y5 receptor (WO96/16542) was cloned in the expression vector (pME18S, Takebe et al. Mol. Cell. Biol. 8, 466-472). The obtained expression vector was transfected into CHO cells as a host according to the instruction manual using Lipofect AMINE reagent (Trademark, Gibco BRL Co., Ltd.). The cells that stably express NPY Y5 receptor were obtained.

The membrane samples prepared from the CHO cells expressing NPY Y5 receptor, the compound of the invention and 30,000 cpm $^{125}$I peptide YY (60 pM of final concentration: Amersham) were incubated in the assay buffer (20 mM HEPES-Hanks buffer containing 0.1% bovine serum albumin, pH 7.4) at 25° C. for 2 hours. The membrane samples were then filtered from the mixture through a glassfilter (GF/C) presoaked with 1% polyethyleneimine. After washing with 50 mM Tris-HCl buffer (pH 7.4), radioactivity retained on the filters was determined using gamma counter. Non-specific binding was determined in the presence of 200 nM of peptide YY, and the 50% inhibitory concentration (IC$_{50}$ value) of the test compound for specific peptide YY binding was calculated (Inui, A. et al. Endocrinology 131, 2090-2096 (1992)).

The compounds of the present invention inhibited the binding of peptide YY (homologue of NPY) to NPY Y5 receptor, indicating that the compounds of the present invention have an affinity for NPY Y5 receptor (data not shown).

Test Example 2

Transportability Through the Blood-Brain Barrier and Drug-Drug Interactions Through P-gp To evaluate transportability of the compound of the invention through the blood-brain barrier (blood-brain partition coefficient; Kp), the concentrations of the compounds in plasma and brain after intravenous administration of the compounds (0.5 mg/2 mL/kg) were determined in mice (Jcl; C57BL/6J mice, male, 7 weeks) (data not shown). The results indicated that the compounds of the invention showed high transportability through the blood-brain barrier.

To evaluate the drug-drug interactions through P-gp in vivo, the brain Kp value of the compounds in the presence of P-gp inhibitor cyclosporin A (20 mg/kg) was determined (Kp$_{CSA}$), and the value was compared with that of control group (Kp$_{cont}$) (data not shown). The results indicated that the compound of the invention has no significant potential for drug-drug interactions through P-gp.

Test Example 3

NPY Y5 Receptor Selectivity

Using the membrane samples prepared from Y1-expression cells (human neuroblastoma, SK-N-MC) and the membrane samples prepared from Y2-expression cells (human neuroblastoma, SMS-KAN), the experiments were carried out in a similar manner as described in Test Example 1-2 to determine the affinity of the compounds of the invention for NPY Y1 and NPY Y2 receptor (data not shown). The results indicate that the compounds of the invention have high selectivity for NPY Y5 receptor.

Formulation Example 1

Tablets

Compound of the invention 15 mg
Starch 15 mg
Lactose 15 mg
Crystalline cellulose 19 mg
Polyvinyl alcohol 3 mg
Distilled water 30 ml
Calcium stearate 3 mg The above ingredients except calcium stearate are uniformly mixed and milled to granulate, and dried to obtain a suitable size of granules. Then, the granules are added with calcium stearate and compressed to form a tablet.

Formulation Example 2

Capsules

Compound of the invention 10 mg
Magnesium stearate 10 mg
Lactose 80 mg

The above ingredients are mixed uniformly to obtain powders or fine granules, which are then filled in a capsule.

Formulation Example 3

Granules

Compound of the invention 30 g
Lactose 265 g
Magnesium Stearate 5 g

The above ingredients are mixed uniformly, and the mixture was compressed. The compressed matters are milled, granulated and sieved to obtain the desired size of granules.

INDUSTRIAL APPLICABILITY

As shown in the above experiments, the compounds of the present invention have a NPY Y5 receptor antagonistic activity. Therefore, the compound of the present invention is useful as a medicament for diseases involved in NPY Y5 receptor such as obesity.

The invention claimed is:

1. A pharmaceutical composition, comprising a compound of the formula (I), and/or a pharmaceutically acceptable salt or solvate thereof:

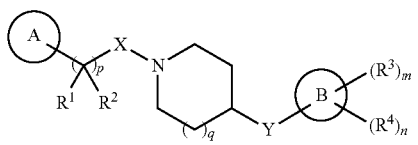
(I)

wherein:
A is selected from the group consisting of:

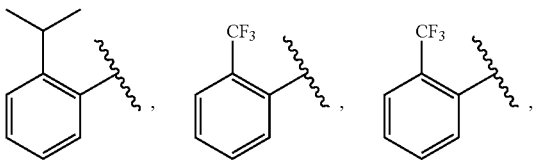

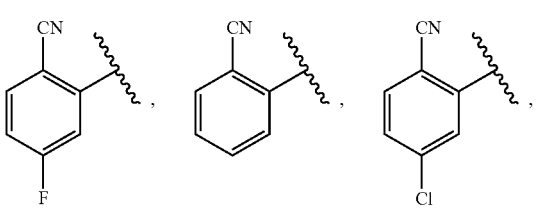

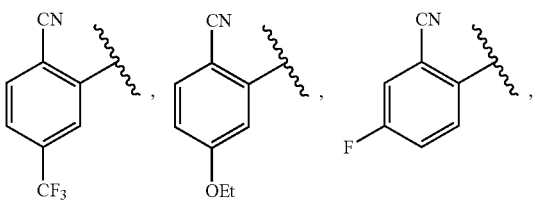

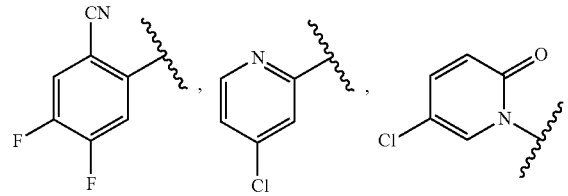

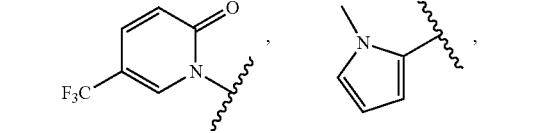

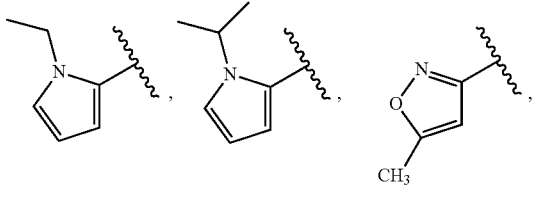

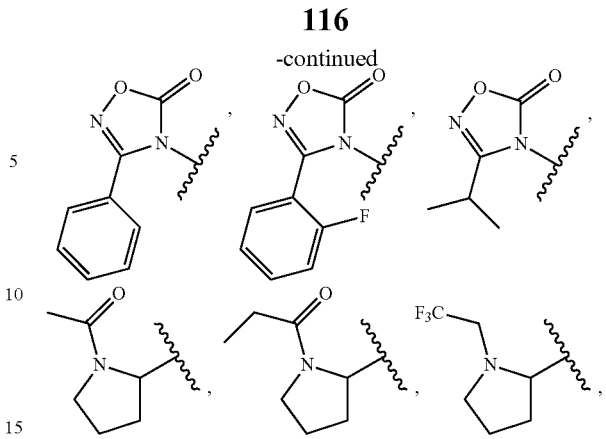

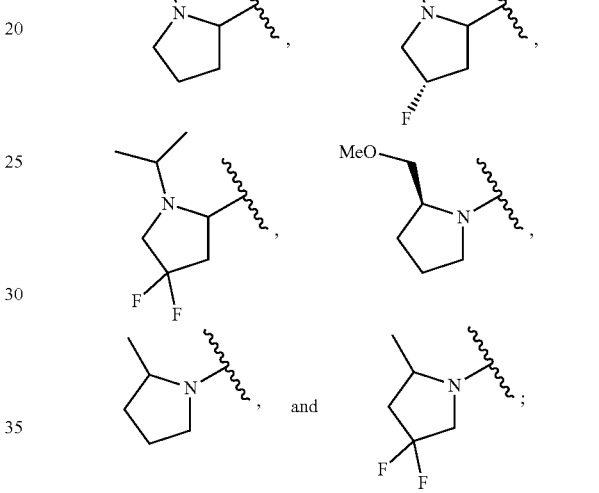

X is C(=O);
the group of the formula (II)

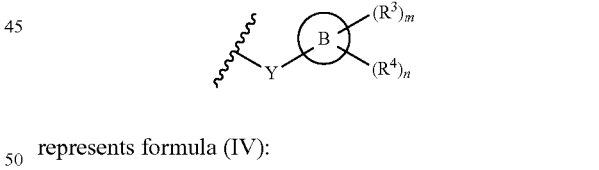
(II)

represents formula (IV):

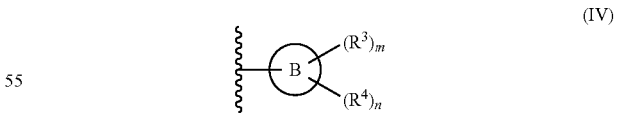
(IV)

wherein:
R⁵, R⁶ and R⁷ are independently hydrogen or substituted or unsubstituted alkyl;
R¹ and R² are independently hydrogen or substituted or unsubstituted alkyl;
R³ is substituted or unsubstituted phenyl, substituted or unsubstituted thiazolyl, substituted or unsubstituted pyridyl, substituted or unsubstituted pyrimidyl, or substituted or unsubstituted morpholino;

$R^4$ is each independently selected from the group consisting of:

halogen, cyano, nitro, nitroso, azido, oxo, substituted or unsubstituted alkyl, substituted or unsubstituted alkenyl, substituted or unsubstituted alkynyl, substituted or unsubstituted cycloalkyl;

hydroxy, substituted or unsubstituted alkoxy, substituted or unsubstituted alkenyloxy, substituted or unsubstituted cycloalkyloxy, substituted or unsubstituted cycloalkenyloxy, substituted or unsubstituted aryloxy, substituted or unsubstituted heterocyclyloxy;

mercapto, substituted or unsubstituted alkylthio, substituted or unsubstituted alkenylthio, substituted or unsubstituted cycloalkylthio, substituted or unsubstituted cycloalkenylthio, substituted or unsubstituted arylthio, substituted or unsubstituted heterocyclylthio;

formyl, substituted or unsubstituted alkylcarbonyl, substituted or unsubstituted alkenylcarbonyl, substituted or unsubstituted cycloalkylcarbonyl, substituted or unsubstituted cycloalkenylcarbonyl, substituted or unsubstituted arylcarbonyl, substituted or unsubstituted heterocyclylcarbonyl;

sulfino, sulfo, substituted or unsubstituted alkylsulfonyl, substituted or unsubstituted alkenylsulfonyl, substituted or unsubstituted cycloalkylsulfonyl, substituted or unsubstituted cycloalkenylsulfonyl, substituted or unsubstituted arylsulfonyl, substituted or unsubstituted heterocyclylsulfonyl, substituted or unsubstituted alkylsulfinyl, substituted or unsubstituted alkenylsulfinyl, substituted or unsubstituted cycloalkylsulfinyl, substituted or unsubstituted cycloalkenylsulfinyl, substituted or unsubstituted arylsulfinyl, substituted or unsubstituted heterocyclylsulfinyl, substituted or unsubstituted sulfamoyl; and substituted or unsubstituted amino;

p is 0 q is 0 or 1;

m is 1;

n is an integer of 0 to 5;

B is benzene, pyrazole, imidazole, pyridine, benzimidazole, indole, pyrrolopyridine, indazole, dihydrobenzoxazole or indoline; and the pharmaceutical composition has NPY Y5 receptor antagonist activity.

2. The pharmaceutical composition of claim 1, wherein the pharmaceutical composition is suitable for preventing or treating obesity or obesity-related diseases, or weight control in obesity.

\* \* \* \* \*